US010240152B2

(12) United States Patent
Sah et al.

(10) Patent No.: US 10,240,152 B2
(45) Date of Patent: *Mar. 26, 2019

(54) COMPOSITIONS AND METHODS FOR INHIBITING EXPRESSION OF TRANSTHYRETIN

(71) Applicant: Alnylam Pharmaceuticals, Inc., Cambridge, MA (US)

(72) Inventors: Dinah Wen-Yee Sah, Boston, MA (US); Gregory Hinkle, Plymouth, MA (US); Rene Alvarez, Boxborough, MA (US); Stuart Milstein, Cambridge, MA (US); Qingmin Chen, Lincoln, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,571

(22) Filed: Dec. 15, 2016

(65) Prior Publication Data

US 2017/0321213 A1    Nov. 9, 2017

Related U.S. Application Data

(63) Continuation of application No. 14/965,825, filed on Dec. 10, 2015, now abandoned, which is a continuation of application No. 14/220,829, filed on Mar. 20, 2014, now Pat. No. 9,234,196, which is a continuation of application No. 13/410,262, filed on Mar. 1, 2012, now Pat. No. 8,741,866, which is a continuation of application No. 12/582,669, filed on Oct. 20, 2009, now Pat. No. 8,168,775.

(60) Provisional application No. 61/106,956, filed on Oct. 20, 2008, provisional application No. 61/115,738, filed on Nov. 18, 2008, provisional application No. 61/156,670, filed on Mar. 2, 2009, provisional application No. 61/185,545, filed on Jun. 9, 2009, provisional application No. 61/242,783, filed on Sep. 15, 2009, provisional application No. 61/244,794, filed on Sep. 22, 2009.

(51) Int. Cl.
| | |
|---|---|
| *A61K 48/00* | (2006.01) |
| *C07H 21/04* | (2006.01) |
| *C12N 15/113* | (2010.01) |
| *C12N 15/11* | (2006.01) |
| *A61K 9/00* | (2006.01) |
| *A61K 31/713* | (2006.01) |

(52) U.S. Cl.
CPC .......... *C12N 15/113* (2013.01); *A61K 9/0019* (2013.01); *A61K 31/713* (2013.01); *C12N 15/111* (2013.01); *C12N 2310/14* (2013.01); *C12N 2310/315* (2013.01); *C12N 2310/321* (2013.01); *C12N 2310/335* (2013.01); *C12N 2310/3515* (2013.01); *C12N 2320/30* (2013.01); *C12N 2320/32* (2013.01)

(58) Field of Classification Search
CPC .... C12N 15/113; C12N 15/111; A61K 31/713
See application file for complete search history.

(56) References Cited

U.S. PATENT DOCUMENTS

| | | | |
|---|---|---|---|
| 7,250,496 | B2 | 7/2007 | Bentwich |
| 7,427,605 | B2 | 9/2008 | Davis et al. |
| 7,718,629 | B2 | 5/2010 | Bumcrot et al. |
| 7,834,170 | B2 | 11/2010 | Khvorova et al. |
| 8,168,775 | B2 | 5/2012 | Sah et al. |
| 8,741,866 | B2 | 6/2014 | Sah et al. |
| 2003/0072794 | A1 | 4/2003 | Boulikas |
| 2003/0143732 | A1 | 7/2003 | Fosnaugh et al. |
| 2003/0170891 | A1 | 9/2003 | McSwiggen |
| 2003/0229037 | A1 | 12/2003 | Massing et al. |
| 2004/0259247 | A1 | 12/2004 | Tuschl et al. |
| 2005/0244869 | A1 | 11/2005 | Brown-Driver |
| 2005/0276804 | A1 | 12/2005 | Smith et al. |
| 2006/0008910 | A1 | 1/2006 | MacLachlan et al. |
| 2006/0083780 | A1 | 4/2006 | Heyes et al. |
| 2006/0240093 | A1 | 10/2006 | MacLachlan et al. |
| 2006/0263435 | A1 | 11/2006 | Davis et al. |
| 2007/0004664 | A1 | 1/2007 | McSwiggen et al. |
| 2007/0031844 | A1 | 2/2007 | Khvorova et al. |
| 2007/0135372 | A1 | 6/2007 | MacLachlan et al. |
| 2007/0207974 | A1 | 9/2007 | Khvorova et al. |
| 2007/0281899 | A1 | 12/2007 | Bumcrot et al. |
| 2008/0188675 | A1 | 8/2008 | Chen et al. |
| 2009/0023215 | A1 | 1/2009 | Jessee et al. |
| 2009/0023673 | A1 | 1/2009 | Manoharan et al. |
| 2009/0082300 | A1 | 3/2009 | Brown-Driver et al. |
| 2009/0149403 | A1 | 6/2009 | MacLachlan |
| 2009/0247608 | A1 | 10/2009 | Manoharan et al. |

(Continued)

FOREIGN PATENT DOCUMENTS

| EP | 2344639 A1 | 7/2011 |
|---|---|---|
| WO | WO 2004/045543 | 6/2004 |

(Continued)

OTHER PUBLICATIONS

Morsles, S., "Collagen gel contraction by ARPE-19 cells is mediated by a FAK-Src dependent pathway," Experimental Eye Research, 2007, pp. 790-798, vol. 85.

Adams, D et al., "FAP Neuropathy and Emerging Treatments," Current Neurology and Neuroscience Reports, Feb. 1, 2014. vol. 14, No. 3, pp. 1-12.

Agrawal, S., et al., "Antisense oligonucleotides: towards clinical trials." Trends in Biotechnology. Oct. 1996, vol. 14, pp. 376-387.

Akinc, A., et al., "A combinatorial library of lipid-like materials for delivery of RNAi therapeutics." Nature Biotechnology, 2008, vol. 26, pp. 561-569.

(Continued)

*Primary Examiner* — Amy H Bowman
(74) *Attorney, Agent, or Firm* — Fenwick & West LLP

(57) ABSTRACT

The invention relates to a double-stranded ribonucleic acid (dsRNA) targeting a transthyretin (TTR) gene, and methods of using the dsRNA to inhibit expression of TTR.

53 Claims, 23 Drawing Sheets

Specification includes a Sequence Listing.

(56) References Cited

U.S. PATENT DOCUMENTS

| | | |
|---|---|---|
| 2009/0291131 A1 | 11/2009 | MacLachlan et al. |
| 2010/0120893 A1 | 5/2010 | Sah et al. |
| 2010/0130588 A1 | 5/2010 | Yaworski |
| 2010/0324120 A1 | 12/2010 | Chen et al. |
| 2011/0015250 A1 | 1/2011 | Bumcrot et al. |
| 2011/0237646 A1 | 9/2011 | Smith et al. |
| 2011/0294868 A1 | 12/2011 | Monia |
| 2012/0149109 A1 | 6/2012 | Brown-Driver et al. |
| 2012/0225927 A1 | 9/2012 | Sah et al. |
| 2012/0244207 A1 | 9/2012 | Fitzgerald et al. |
| 2012/0294905 A1 | 11/2012 | Sah |

FOREIGN PATENT DOCUMENTS

| | | |
|---|---|---|
| WO | WO 2004/080406 | 9/2004 |
| WO | WO 2004/090108 | 10/2004 |
| WO | WO 2005/120152 | 12/2005 |
| WO | WO 2007/012191 | 2/2007 |
| WO | WO 2008/042973 | 4/2008 |
| WO | WO 2009/086558 | 7/2009 |
| WO | WO 2009/127060 | 10/2009 |
| WO | WO 2010/042877 | 4/2010 |
| WO | WO 2010/053572 | 5/2010 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/147992 | 12/2010 |

OTHER PUBLICATIONS

Ando, Y., et al., "Pathogenesis and Therapy for Transthyretin Related Amyloidosis," Rinsho byori (The Japanese Journal of Clinical Pathology), Feb. 2008, vol. 56, pp. 114-120 (With English Abstract).
Bass, B., "The short answer," Nature, May 24, 2001, pp. 428-429, vol. 411.
Benson, M., et al., "Targeted suppression of an amyloidogenic transthyretin with antisense oligonucleotides", Muscle & Nerve, Jan. 18, 2006, pp. 609-618, vol. 33, No. 5.
Communication pursuant to Article 94(3) EPC for European Patent Application No. 09 810 834.3, Feb. 15, 2012, 6 pages.
Communication Pursuant to Article 94(3) EPC for European Patent Application No. EP 09810834.3, Nov. 9, 2012, 4 pages.
Elbashir, S., et al., "Analysis of gene function in somatic mammalian cells using small interfering RNAs," Methods, 2002, pp. 199-213, vol. 26.
Elbashir, S., et al., "Duplexes of 21-nucleotide RNAs mediate RNA interference in mammalian cell culture," Nature, May 24, 2001, p. 494-498, vol. 411.
Elbashir, S., et al., "Functional Anatomy of siRNAs for Mediating Efficient RNAi in Drosophila melanogaster Embryo Lysate", The EMBO Journal, 2001, pp. 6877-6888, vol. 20, No. 23.
Elbashir, S., et al., "RNA Interference is Mediated by 21-and 22 Nucleotide RNAs," Genes & Development, 2001, pp. 188-200, vol. 15.
Examination Report dated Jun. 14, 2011, for New Zealand Patent Application No. 592867, 2 Pages.
Fire, A., "RNA-triggered Gene Silencing," Trends in Genetics, Sep. 1999, pp. 358-363, vol. 15, No. 9.
Fire, A., et al., "Potent and Specific Genetic Interference by Double Stranded RNA in Caenorhabditis elegans," Nature, Feb. 19, 1998, pp. 806-811, vol. 391.
Heyes, J., et al., "Cationic lipid saturation influences intracellular delivery of encapsulated nucleic acids," Journal of Controlled Release, vol. 107, pp. 276-287, 2005.
Kurosawa, T., et al., "Selective silencing of a mutant transthyretin allele by small interfering RNAs" Biochem Biophys Res Commun., Nov. 25, 2005, vol. 337, No. 3, pp. 1012-1018.
Love, K., et al., "Lipid-like materials for low-dose, in vivo gene silencing," PNAS, Feb. 2, 2010, pp. 1864-1869, vol. 107, No. 5.
Morrissey, D., et al., "Potent and persistent in vivo anti-HBV activity of chemically modified siRNAs," Nature Biotechnology, vol. 23, pp. 1002-1007, Aug. 2005.
Notification of the First Office Action for Chinese Patent Application No. 200980141740.4, dated Jun. 5, 2012, 6 pages.
Office Action for Australian Patent Application No. AU 2009307677, dated May 27, 2014, 6 Pages.
Office Action for Japanese Patent Application No. JP 2011-533279, dated Apr. 22, 2014, 9 Pages.
Office Action for Japanese Patent Application No. JP 2013-502765, dated Mar. 17, 2015, 5 Pages.
Office Action for U.S. Appl. No. 12/582,669, dated Dec. 14, 2010, 10 Pages.
Office Action for U.S. Appl. No. 12/582,669, dated Jul. 28, 2011, 13 Pages.
Office Action for U.S. Appl. No. 13/410,262, dated Feb. 6, 2013, 10 Pages.
Office Action for U.S. Appl. No. 14/789,378, dated Jan. 12, 2016, 6 pages.
Office Action for U.S. Appl. No. 14/807,852, dated Jan. 6, 2016, 10 pages.
Palaninathan, S.K. et al., "*Homo sapiens* transthyretin (TTR), mRNA," Database GenBank [online], Accession No. NM_000371.2, NCBI, Oct. 5, 2008, 3 pages, [online] [Retrieved on Apr. 15, 2014] Retrieved from the internet <URL:http://www.ncbi.nlm.nih.gov/nuccore/1677363u3?sat=12&satkey=8748419>.
PCT International Search Report and Written Opinion for PCT/US15/47185, dated Feb. 9, 2016, 12 Pages.
PCT International Search Report and Written Opinion, PCT/US2009/061381, dated Jul. 26, 2010, 15 pages.
PCT International Search Report and Written Opinion, PCT/US2010/055311, dated Mar. 2, 2011, 12 pages.
PCT Invitation to Pay Additional Fees and, Where Applicable, Protest Fee, PCT/US2009/061381, dated Apr. 27, 2010, 7 Pages.
Reynolds, et al. (2004) "Rational siRNA design for RNA interference," Nature Biotechnology, vol. 22, No. 3, pp. 326-330.
Robbins, M., et al., "Stable expression of shRNAs in human CD34+ progenitor cells can avoid induction of interferon responses to siRNAs in vitro," Nature Biotechnology, May 2006, pp. 566-571, vol. 24, No. 5.
Rose, S., et al., "Functional polarity is introduced by Dicer processing of short substrate RNAs," Nucleic Acids Research, 2005, pp. 4140-4156, vol. 33, No. 13.
Santos, A. L. Gomes Dos, et al., "Intraocular Delivery of Oligonucleotides," Current Pharmaceutical Biotechnology, 2005, pp. 7-15, vol. 6.
Second Office Action for Chinese Patent Application No. CN 2009801417404, dated Mar. 1, 2013, 8 Pages.
Sekijima, Y., "Recent Progress in the Understanding and Treatment of Transthyretin Amyloidosis," Journal of Clinical Pharmacy and Therapeutics, Jun. 2014. vol. 39, No. 3, pp. 225-233.
Sekijima, Y., et al., "Pathogenesis of and Therapeutic Strategies to Ameliorate the Transthyretin Amyloidoses", Current Pharmaceutical Design, Jan. 1, 2008, pp. 3219-3230, vol. 14, No. 30.
Stein, T., et al., "Neutralization of transthyretin reverses the neuroprotective effects of secreted amyloid precursor protein (APP) in $APP_{sw}$ mice resulting in Tau phosphorylation and loss of Hippocampal neurons: support for the amyloid hypothesis." The Journal of Neuroscience, Sep. 1, 2004, vol. 24, No. 35, p. 7707-7717.
Supplementary European Search Report for European Patent Application No. EP 10829034, dated Aug. 30, 2013, 10 Pages.
Tomi, M., "Drug Delivery Targeting the Retina," Journal of Pharmaceutical Science and Technology, Japan, 2003, pp. 193-196, vol. 63, No. 4.
Tuschl T., "RNA Interference and Small Interfering RNAs" Chembiochem, 2001, pp. 239-245, vol. 2.
Tuschl, T., "Expanding small RNA interference," Nature Biotechnology, May 2002, pp. 446-448, vol. 20.
Tuschl, T., "Functional genomics: RNA sets the standard," Nature, Jan. 16, 2003, vol. 421, No. 6920, pp. 220-221.

(56) References Cited

OTHER PUBLICATIONS

Tuschl, T., "Mammalian RNA Interference," RNAi, A Guide to Gene Silencing, Chapter 13, G.J. Hannon (ed,), 2003, pp. 265-295.

Tuschl, T., et al., "Small Interfering RNAs: A Revolutionary Tool for the Analysis of Gene Function and Gene Therapy," Molecular Interventions, 2002, pp. 158-167, vol. 2, No. 3.

Tuschl, T., et al., "Targeted mRNA Degradation by Double-Stranded RNA In Vitro," Genes & Development, 1999, pp. 3191-3197, vol. 13.

Vickers, T., et al., "Efficient Reduction of Target RNAs by Small Interfering RNA and RNase H-dependent Antisense Agents," The Journal of Biological Chemistry, Feb. 28, 2003, pp. 7108-7118, vol. 278, No. 9.

Weil, et al (2002) "Targeting the Kinesin Eg5 to Monitor siRNA Transfection in Mammalian Cells," *Biotechniques* 33(6):1244-1248.

Yasukawa, T., "New Ocular Drug Delivery Systems," Journal of the Eye, 2010, pp. 1377-1384, vol. 27, No. 10.

Zimmerman, et al. (2006) "RNAi-mediated gene silencing in non-human primates," *Nature*, vol. 441, May 4: 111-114.

Hornung, V., et al., "Sequence-specific potent induction of IFN-α by short interfering RNA in plasmacytoid dendritic cells throughTLR7," Nature Medicine, Mar. 2005, pp. 263-270, vol. 11, No. 3.

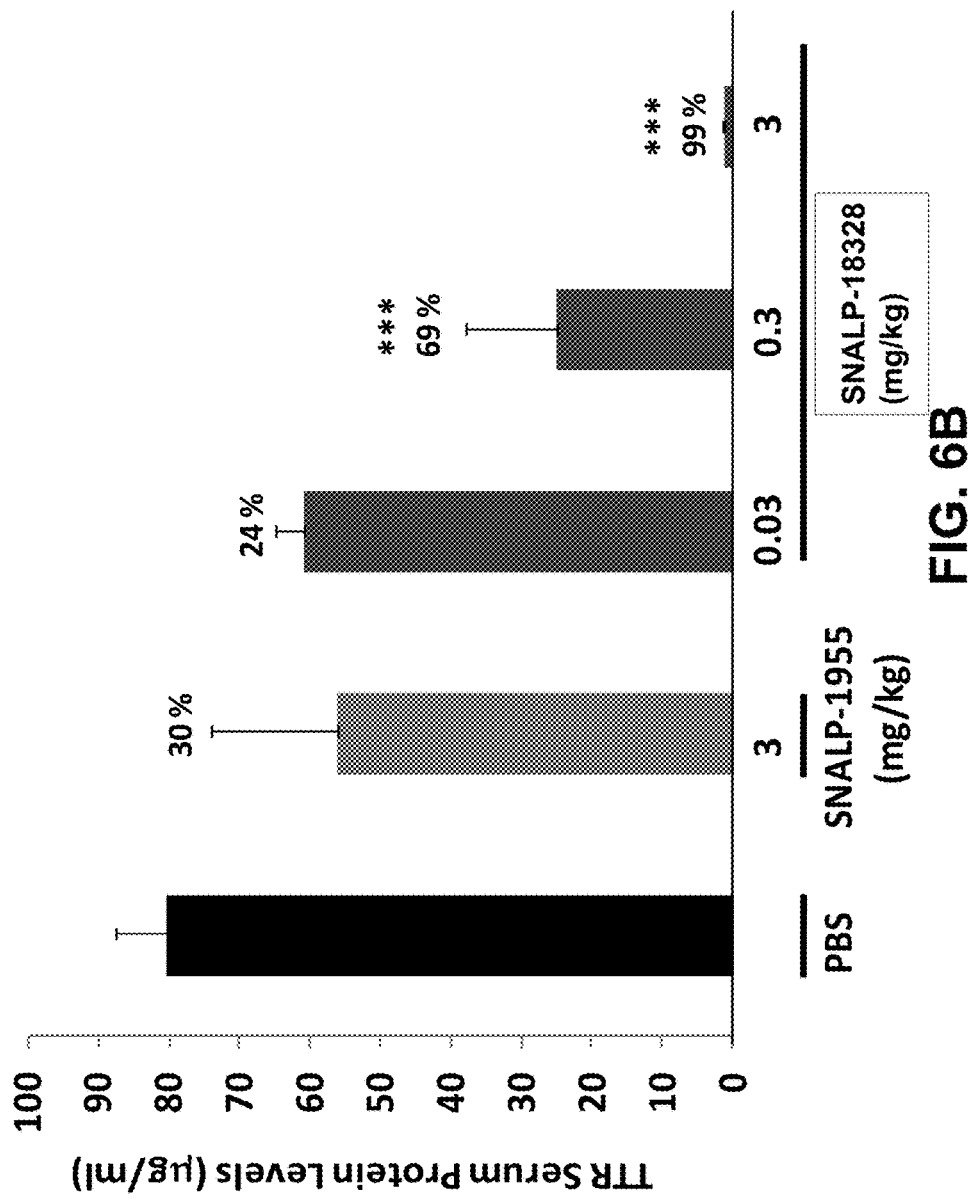

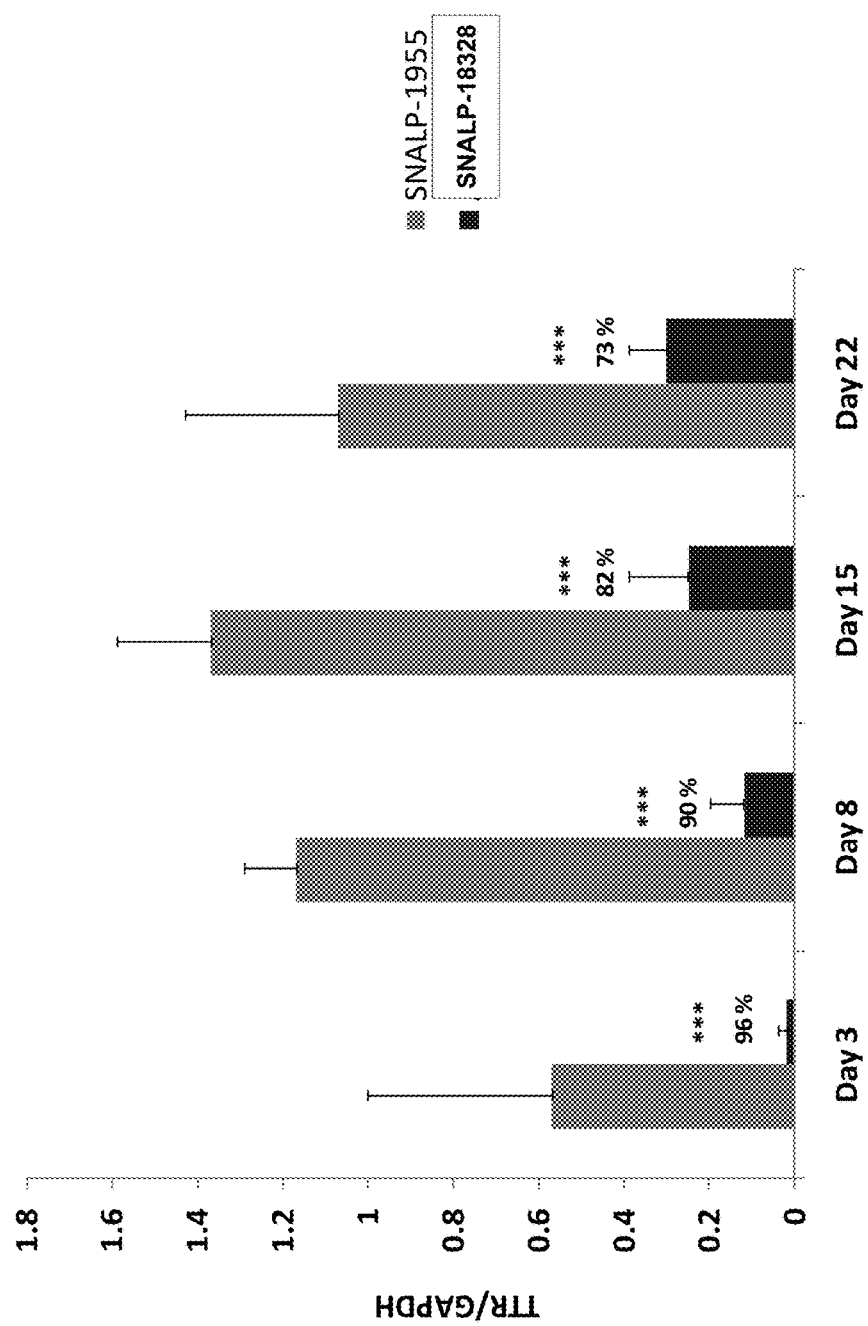

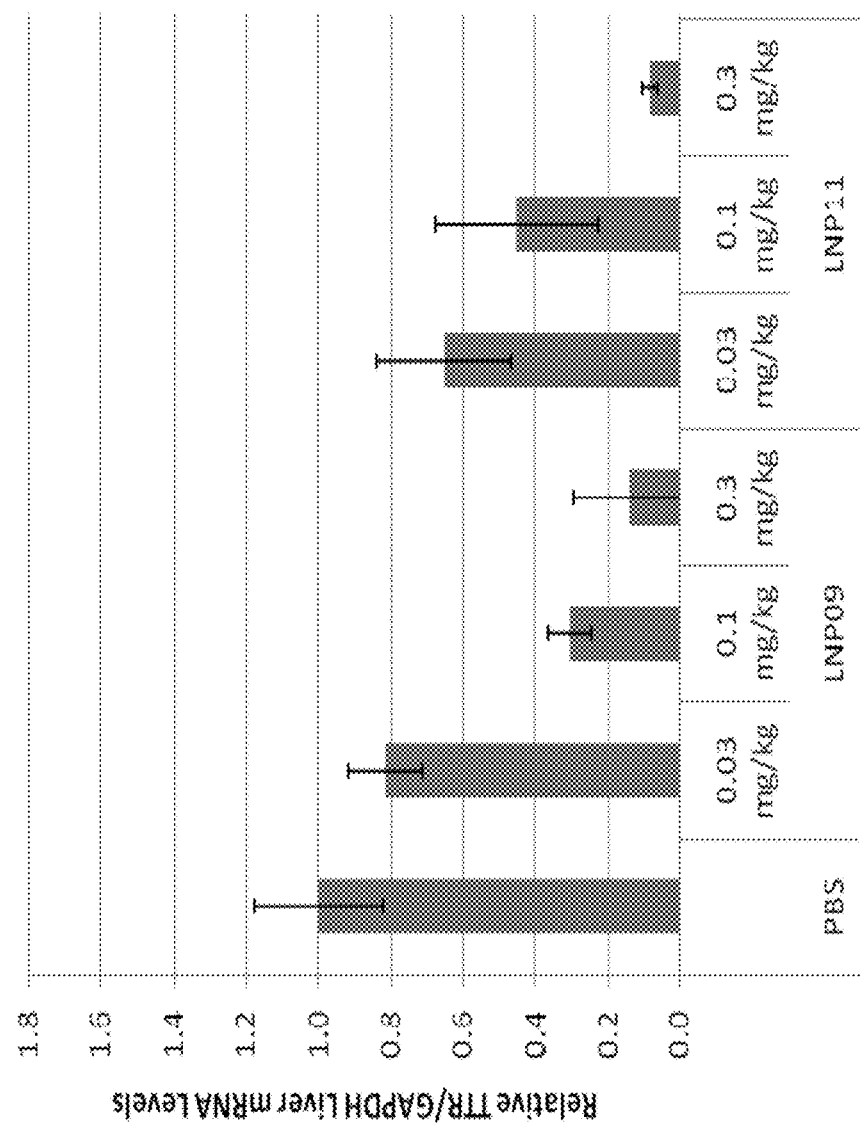

gttgactaag tcaataatca gaatcagcag
gtttgcagtc agattggcag ggataagcag
cctagctcag gagaagtgag tataaaagcc
ccaggctggg agcagccatc acagaagtcc
actcattctt ggcaggatgg cttctcatcg
tctgctcctc ctctgccttg ctggactggt
atttgtgtct gaggctggcc ctacgggcac
cggtgaatcc aagtgtcctc tgatggtcaa
agttctagat gctgtccgag gcagtcctgc
catcaatgtg gccgtgcatg tgttcagaaa
ggctgctgat gacacctggg agccatttgc
ctctgggaaa accagtgagt ctggagagct
gcatgggctc acaactgagg aggaatttgt
agaaggata tacaaagtgg aaatagacac
caaatcttac tggaaggcac ttggcatctc
cccattccat gagcatgcag aggtggtatt
cacagccaac gactccggcc cccgccgcta
caccattgcc gccctgctga gcccctactc
ctattccacc acggctgtcg tcaccaatcc
caaggaatga gggacttctc ctccagtgga
cctgaaggac gagggatggg atttcatgta
accaagagta ttccattttt actaaagcag
tgttttcacc tcatatgcta tgttagaagt
ccaggcagag acaataaaac attcctgtga
aaggcacttt tcattccact ttaacttgat
tttttaaatt cccttattgt cccttccaaa
aaaaagagaa tcaaattt acaaagaatc
aaggaattc tagaaagtat ctgggcagaa
cgctaggaga gatccaaatt tccattgtct
tgcaagcaaa gcacgtatta aatatgatct
gcagccatta aaaagacaca ttctgtaaaa
aaaaaaaa (SEQ ID NO: 1331)

ACAGAAGTCCACTCATTCTTGGCAGGATGGCTTCTCATCGTCTGCTCCTCCT
CTGCCTTGCTGGACTGGTATTTGTGTCTGAGGCTGGCCCTACGGGCACCGGT
GAATCCAAGTGTCCTCTGATGGTCAAAGTTCTAGATGCTGTCCGAGGCAGTC
CTGCCATCAATGTGGCCGTGCATGTGTTCAGAAAGGCTGCTGATGACACCTG
GGAGCCATTTGCCTCTGGGAAAACCAGTGAGTCTGGAGAGCTGCATGGGCTC
ACAACTGAGGAGGAATTTGTAGAAGGATATACAAAGTGGAAATAGACACCA
AATCTTACTGGAAGGCACTTGGCATCTCCCCATTCCATGAGCATGCAGAGGT
GGTATTCACAGCCAACGACTCCGGCCCCGCCGCTACACCATTGCCGCCCTG
CTGAGCCCCTACTCCTATTCCACCACGGCTGTCGTCACCAATCCCAAGGAAT
GAGGGACTTCTCCTCCAGTGGACCTGAAGGACGAGGGATGGGATTTCATGTA
ACCAAGAGTATTCCATTTTTACTAAAGCAGTGTTTTCACCTCATATGCTATG
TTAGAAGTCCAGGCAGAGACAATAAAACATTCCTGTGAAAGGCACTTTTCAT
TCCAAAAAAAAAAAAAAAAAAAAAAA     (SEQ ID NO:1329)

FIG. 13B

CCTGACAGGATGGCTTCCCTTCGCCTGTTCCTCCTCTGCCTCGCTGGACTGA
TATTTGCGTCTGAAGCTGGCCCTGGGGGTGCTGGAGAATCCAAGTGTCCTCT
GATGGTCAAAGTCCTGGATGCTGTCCGAGGCAGCCCTGCTGTCGATGTGGCC
GTGAAAGTGTTCAAAAGGACTGCAGACGGAAGCTGGGAGCCGTTTGCCTCTG
GAAGACCGCCGAGTCTGGAGAGCTGCACGGGCTCACCACAGATGAGAAGTT
CACGGAAGGGGTGTACAGGGTAGAACTGGACACCAAATCATACTGGAAGGCT
CTTGGCATTTCCCCATTCCATGAATACGCAGAGGTGGTTTTCACAGCCAATG
ACTCTGGTCATCGCCACTACACCATCGCAGCCCTGCTCAGCCCGTACTCCTA
CAGCACCACTGCTGTCGTCAGTAACCCCAGAACTGAGGGACCCAGCCCACG
AGGACCAAGATCTTGCCAAAGCAGTAGCTCCCATTTGTACTGAAACAGTGTT
CTTGCTCTATAAACCGTGTTAGCAACTCGGGAAGATGCCGTGAAACGTTCTT
ATTAAACCACCTTTATTTCATTC
(SEQ ID NO:1330)

FIG. 14

| Phenotype | Features | Genotypes (associated mutation in TTR) | | |
|---|---|---|---|---|
| Familial amyloidotic neuropathy (FAP) | Early: Impotence<br>Sensorimotor polyneuropathy of the legs<br>Carpal tunnel syndrome<br>Autonomic dysfunction<br>Constipation/diarrhea<br>Late: Cardiomyopathy<br>Vitreous opacities<br>Nephropathy | V28M<br>L58H V30M<br>L58R<br>K70N<br>Y78F<br>I84S<br>Y114H<br>V30A<br>K35N<br>G47V<br>S50R<br>T60A<br>Y114C | | |
| Familial amyloidotic cardiomyopathy (FAC) | Cardiomegaly<br>Congestive heart failure<br>Conduction abnormalities, arrhythmias<br>Angina<br>Sudden death | D18N D18E V20I<br>P24S<br>E42D A45T T49P<br>S50I<br>H56R I68L A81T<br>Q92K<br>R103S L111M V122I<br>T60A | | |
| CNS amyloidosis (CNSA) | Dementia, ataxia, spasticity, seizures, hemorrhage (intracerebellar and/or subarachnoid), psychosis, hydrocephalus | L12P D18G A25T<br>V30G A36P G53E<br>F64S Y69H Y114C | | |

FIG. 15

SEQUENCE LISTING

<160> NUMBER OF SEQ ID NOS: 1410

<210> SEQ ID NO 1
<211> LENGTH: 19
<212> TYPE: RNA
<213> ORGANISM: Homo sapiens

<400> SEQUENCE: 1
ccggugaauc caagugucc                                                19

<210> SEQ ID NO 2
<211> LENGTH: 19
<212> TYPE: RNA
<213> ORGANISM: Homo sapiens

<400> SEQUENCE: 2
ggacacuugg auucaccgg                                                19

<210> SEQ ID NO 3
<211> LENGTH: 19
<212> TYPE: RNA
<213> ORGANISM: Homo sapiens

<400> SEQUENCE: 3
acucauucuu ggcaggaug                                                19

<210> SEQ ID NO 4
<211> LENGTH: 19
<212> TYPE: RNA
<213> ORGANISM: Homo sapiens

<400> SEQUENCE: 4
cauccugcca agaaugagu                                                19

<210> SEQ ID NO 5
<211> LENGTH: 19
<212> TYPE: RNA
<213> ORGANISM: Homo sapiens

<400> SEQUENCE: 5
aaguguccuc ugaugguca                                                19

<210> SEQ ID NO 6
<211> LENGTH: 19
<212> TYPE: RNA
<213> ORGANISM: Homo sapiens

<400> SEQUENCE: 6
ugaccaucag aggacacuu                                                19

<210> SEQ ID NO 7
<211> LENGTH: 19
<212> TYPE: RNA
<213> ORGANISM: Homo sapiens

<400> SEQUENCE: 7
ucauucuugg caggauggc                                                19

<210> SEQ ID NO 8
<211> LENGTH: 19
<212> TYPE: RNA
<213> ORGANISM: Homo sapiens

<400> SEQUENCE: 8
gccauccugc caagaauga                                              19

<210> SEQ ID NO 9
<211> LENGTH: 19
<212> TYPE: RNA
<213> ORGANISM: Homo sapiens

<400> SEQUENCE: 9
aaguucuaga ugcuguccg                                              19

<210> SEQ ID NO 10
<211> LENGTH: 19
<212> TYPE: RNA
<213> ORGANISM: Homo sapiens

<400> SEQUENCE: 10
cggacagcau cuagaacuu                                              19

<210> SEQ ID NO 11
<211> LENGTH: 19
<212> TYPE: RNA
<213> ORGANISM: Homo sapiens

<400> SEQUENCE: 11
guucuagaug cuguccgag                                              19

<210> SEQ ID NO 12
<211> LENGTH: 19
<212> TYPE: RNA
<213> ORGANISM: Homo sapiens

<400> SEQUENCE: 12
cucggacagc aucuagaac                                              19

<210> SEQ ID NO 13
<211> LENGTH: 19
<212> TYPE: RNA
<213> ORGANISM: Homo sapiens

<400> SEQUENCE: 13
cuagaugcug uccgaggca                                              19

<210> SEQ ID NO 14
<211> LENGTH: 19
<212> TYPE: RNA
<213> ORGANISM: Homo sapiens

<400> SEQUENCE: 14
ugccucggac agcaucuag                                              19

<210> SEQ ID NO 15
<211> LENGTH: 19
<212> TYPE: RNA
<213> ORGANISM: Homo sapiens

<400> SEQUENCE: 15
gaugcugucc gaggcaguc                                              19

<210> SEQ ID NO 16
<211> LENGTH: 19
<212> TYPE: RNA
<213> ORGANISM: Homo sapiens

```
<400> SEQUENCE: 16
gacugccucg gacagcauc                                                19

<210> SEQ ID NO 17
<211> LENGTH: 19
<212> TYPE: RNA
<213> ORGANISM: Homo sapiens

<400> SEQUENCE: 17
cauucuuggc aggauggcu                                                19

<210> SEQ ID NO 18
<211> LENGTH: 19
<212> TYPE: RNA
<213> ORGANISM: Homo sapiens

<400> SEQUENCE: 18
agccauccug ccaagaaug                                                19

<210> SEQ ID NO 19
<211> LENGTH: 19
<212> TYPE: RNA
<213> ORGANISM: Homo sapiens

<400> SEQUENCE: 19
ugcuguccga ggcaguccu                                                19

<210> SEQ ID NO 20
<211> LENGTH: 19
<212> TYPE: RNA
<213> ORGANISM: Homo sapiens

<400> SEQUENCE: 20
aggacugccu cggacagca                                                19

<210> SEQ ID NO 21
<211> LENGTH: 19
<212> TYPE: RNA
<213> ORGANISM: Homo sapiens

<400> SEQUENCE: 21
ccgaggcagu ccugccauc                                                19

<210> SEQ ID NO 22
<211> LENGTH: 19
<212> TYPE: RNA
<213> ORGANISM: Homo sapiens

<400> SEQUENCE: 22
gauggcagga cugccucgg                                                19

<210> SEQ ID NO 23
<211> LENGTH: 19
<212> TYPE: RNA
<213> ORGANISM: Homo sapiens

<400> SEQUENCE: 23
caguccugcc aucaaugug                                                19

<210> SEQ ID NO 24
<211> LENGTH: 19
<212> TYPE: RNA
<213> ORGANISM: Homo sapiens
```

```
<400> SEQUENCE: 24
cacauugaug gcaggacug                                              19

<210> SEQ ID NO 25
<211> LENGTH: 19
<212> TYPE: RNA
<213> ORGANISM: Homo sapiens

<400> SEQUENCE: 25 caaugug gcc gugcaugug                                             19

<210> SEQ ID NO 26
<211> LENGTH: 19
<212> TYPE: RNA
<213> ORGANISM: Homo sapiens

<400> SEQUENCE: 26
cacaugcacg gccacauug                                              19

<210> SEQ ID NO 27
<211> LENGTH: 19
<212> TYPE: RNA
<213> ORGANISM: Homo sapiens

<400> SEQUENCE: 27
auguguucag aaaggcugc                                              19

<210> SEQ ID NO 28
<211> LENGTH: 19
<212> TYPE: RNA
<213> ORGANISM: Homo sapiens

<400> SEQUENCE: 28
gcagccuuuc ugaacacau                                              19

<210> SEQ ID NO 29
<211> LENGTH: 19
<212> TYPE: RNA
<213> ORGANISM: Homo sapiens

<400> SEQUENCE: 29
cagaagucca cucauucuu                                              19

<210> SEQ ID NO 30
<211> LENGTH: 19
<212> TYPE: RNA
<213> ORGANISM: Homo sapiens

<400> SEQUENCE: 30
aagaaugagu ggacuucug                                              19

<210> SEQ ID NO 31
<211> LENGTH: 19
<212> TYPE: RNA
<213> ORGANISM: Homo sapiens

<400> SEQUENCE: 31
ggcaggaugg cuucucauc                                              19

<210> SEQ ID NO 32
<211> LENGTH: 19
<212> TYPE: RNA
```

<213> ORGANISM: Homo sapiens

<400> SEQUENCE: 32
gaugagaagc cauccugcc                                            19

<210> SEQ ID NO 33
<211> LENGTH: 19
<212> TYPE: RNA
<213> ORGANISM: Homo sapiens

<400> SEQUENCE: 33
gagccauuug ccucuggga                                            19

<210> SEQ ID NO 34
<211> LENGTH: 19
<212> TYPE: RNA
<213> ORGANISM: Homo sapiens

<400> SEQUENCE: 34
ucccagaggc aaauggcuc                                            19

<210> SEQ ID NO 35
<211> LENGTH: 19
<212> TYPE: RNA
<213> ORGANISM: Homo sapiens

<400> SEQUENCE: 35
caggauggcu ucucaucgu                                            19

<210> SEQ ID NO 36
<211> LENGTH: 19
<212> TYPE: RNA
<213> ORGANISM: Homo sapiens

<400> SEQUENCE: 36
acgaugagaa gccauccug                                            19

<210> SEQ ID NO 37
<211> LENGTH: 19
<212> TYPE: RNA
<213> ORGANISM: Homo sapiens

<400> SEQUENCE: 37
aggauggcuu cucaucguc                                            19

<210> SEQ ID NO 38
<211> LENGTH: 19
<212> TYPE: RNA
<213> ORGANISM: Homo sapiens

<400> SEQUENCE: 38
gacgaugaga agccauccu                                            19

<210> SEQ ID NO 39
<211> LENGTH: 19
<212> TYPE: RNA
<213> ORGANISM: Homo sapiens

<400> SEQUENCE: 39
agagcugcau gggcucaca                                            19

<210> SEQ ID NO 40
<211> LENGTH: 19

<212> TYPE: RNA
<213> ORGANISM: Homo sapiens

<400> SEQUENCE: 40
ugugagccca ugcagcucu                                          19

<210> SEQ ID NO 41
<211> LENGTH: 19
<212> TYPE: RNA
<213> ORGANISM: Homo sapiens

<400> SEQUENCE: 41
gcugcauggg cucacaacu                                          19

<210> SEQ ID NO 42
<211> LENGTH: 19
<212> TYPE: RNA
<213> ORGANISM: Homo sapiens

<400> SEQUENCE: 42
aguugugagc ccaugcagc                                          19

<210> SEQ ID NO 43
<211> LENGTH: 19
<212> TYPE: RNA
<213> ORGANISM: Homo sapiens

<400> SEQUENCE: 43
ggauggcuuc ucaucgucu                                          19

<210> SEQ ID NO 44
<211> LENGTH: 19
<212> TYPE: RNA
<213> ORGANISM: Homo sapiens

<400> SEQUENCE: 44
agacgaugag aagccaucc                                          19

<210> SEQ ID NO 45
<211> LENGTH: 19
<212> TYPE: RNA
<213> ORGANISM: Homo sapiens

<400> SEQUENCE: 45
gcaugggcuc acaacugag                                          19

<210> SEQ ID NO 46
<211> LENGTH: 19
<212> TYPE: RNA
<213> ORGANISM: Homo sapiens

<400> SEQUENCE: 46
cucaguugug agcccaugc                                          19

<210> SEQ ID NO 47
<211> LENGTH: 19
<212> TYPE: RNA
<213> ORGANISM: Homo sapiens

<400> SEQUENCE: 47
augggcucac aacugagga                                          19

<210> SEQ ID NO 48

```
<211> LENGTH: 19
<212> TYPE: RNA
<213> ORGANISM: Homo sapiens

<400> SEQUENCE: 48
uccucaguug ugagcccau                                                    19

<210> SEQ ID NO 49
<211> LENGTH: 19
<212> TYPE: RNA
<213> ORGANISM: Homo sapiens

<400> SEQUENCE: 49
ugggcucaca acugaggag                                                    19

<210> SEQ ID NO 50
<211> LENGTH: 19
<212> TYPE: RNA
<213> ORGANISM: Homo sapiens

<400> SEQUENCE: 50
cuccucaguu gugagccca                                                    19

<210> SEQ ID NO 51
<211> LENGTH: 19
<212> TYPE: RNA
<213> ORGANISM: Homo sapiens

<400> SEQUENCE: 51
gaggaauuug uagaaggga                                                    19

<210> SEQ ID NO 52
<211> LENGTH: 19
<212> TYPE: RNA
<213> ORGANISM: Homo sapiens

<400> SEQUENCE: 52
ucccuucuac aaauuccuc                                                    19

<210> SEQ ID NO 53
<211> LENGTH: 19
<212> TYPE: RNA
<213> ORGANISM: Homo sapiens

<400> SEQUENCE: 53
uuuguagaag ggauauaca                                                    19

<210> SEQ ID NO 54
<211> LENGTH: 19
<212> TYPE: RNA
<213> ORGANISM: Homo sapiens

<400> SEQUENCE: 54
uguauauccc uucuacaaa                                                    19

<210> SEQ ID NO 55
<211> LENGTH: 19
<212> TYPE: RNA
<213> ORGANISM: Homo sapiens

<400> SEQUENCE: 55
uuguagaagg gauauacaa                                                    19
```

```
<210> SEQ ID NO 56
<211> LENGTH: 19
<212> TYPE: RNA
<213> ORGANISM: Homo sapiens

<400> SEQUENCE: 56
uuguauaucc cuucuacaa                                                        19

<210> SEQ ID NO 57
<211> LENGTH: 19
<212> TYPE: RNA
<213> ORGANISM: Homo sapiens

<400> SEQUENCE: 57
uguagaaggg auauacaaa                                                        19

<210> SEQ ID NO 58
<211> LENGTH: 19
<212> TYPE: RNA
<213> ORGANISM: Homo sapiens

<400> SEQUENCE: 58
uuuguauauc ccuucuaca                                                        19

<210> SEQ ID NO 59
<211> LENGTH: 19
<212> TYPE: RNA
<213> ORGANISM: Homo sapiens

<400> SEQUENCE: 59
agaagggaua uacaaagug                                                        19

<210> SEQ ID NO 60
<211> LENGTH: 19
<212> TYPE: RNA
<213> ORGANISM: Homo sapiens

<400> SEQUENCE: 60
cacuuuguau aucccuucu                                                        19

<210> SEQ ID NO 61
<211> LENGTH: 19
<212> TYPE: RNA
<213> ORGANISM: Homo sapiens

<400> SEQUENCE: 61
aaguggaaau agacaccaa                                                        19

<210> SEQ ID NO 62
<211> LENGTH: 19
<212> TYPE: RNA
<213> ORGANISM: Homo sapiens

<400> SEQUENCE: 62
uuggugucua uuuccacuu                                                        19

<210> SEQ ID NO 63
<211> LENGTH: 19
<212> TYPE: RNA
<213> ORGANISM: Homo sapiens

<400> SEQUENCE: 63
ggaaauagac accaaaucu                                                        19
```

```
<210> SEQ ID NO 64
<211> LENGTH: 19
<212> TYPE: RNA
<213> ORGANISM: Homo sapiens

<400> SEQUENCE: 64 agauuggug ucuauuucc                                                   19

<210> SEQ ID NO 65
<211> LENGTH: 19
<212> TYPE: RNA
<213> ORGANISM: Homo sapiens

<400> SEQUENCE: 65
gaaauagaca ccaaaucuu                                                  19

<210> SEQ ID NO 66
<211> LENGTH: 19
<212> TYPE: RNA
<213> ORGANISM: Homo sapiens

<400> SEQUENCE: 66
aagauuuggu gucuauuuc                                                  19

<210> SEQ ID NO 67
<211> LENGTH: 19
<212> TYPE: RNA
<213> ORGANISM: Homo sapiens

<400> SEQUENCE: 67
auagacacca aaucuuacu                                                  19

<210> SEQ ID NO 68
<211> LENGTH: 19
<212> TYPE: RNA
<213> ORGANISM: Homo sapiens

<400> SEQUENCE: 68
aguaagauuu ggugucuau                                                  19

<210> SEQ ID NO 69
<211> LENGTH: 19
<212> TYPE: RNA
<213> ORGANISM: Homo sapiens

<400> SEQUENCE: 69
uagacaccaa aucuuacug                                                  19

<210> SEQ ID NO 70
<211> LENGTH: 19
<212> TYPE: RNA
<213> ORGANISM: Homo sapiens

<400> SEQUENCE: 70
caguaagauu uggugucua                                                  19

<210> SEQ ID NO 71
<211> LENGTH: 19
<212> TYPE: RNA
<213> ORGANISM: Homo sapiens

<400> SEQUENCE: 71
agacaccaaa ucuuacugg                                                  19
```

```
<210> SEQ ID NO 72
<211> LENGTH: 19
<212> TYPE: RNA
<213> ORGANISM: Homo sapiens

<400> SEQUENCE: 72
ccaguaagau uggugucu                                                 19

<210> SEQ ID NO 73
<211> LENGTH: 19
<212> TYPE: RNA
<213> ORGANISM: Homo sapiens

<400> SEQUENCE: 73
uuacuggaag gcacuuggc                                                19

<210> SEQ ID NO 74
<211> LENGTH: 19
<212> TYPE: RNA
<213> ORGANISM: Homo sapiens

<400> SEQUENCE: 74
gccaagugcc uuccaguaa                                                19

<210> SEQ ID NO 75
<211> LENGTH: 19
<212> TYPE: RNA
<213> ORGANISM: Homo sapiens

<400> SEQUENCE: 75
uucucaucgu cugcuccuc                                                19

<210> SEQ ID NO 76
<211> LENGTH: 19
<212> TYPE: RNA
<213> ORGANISM: Homo sapiens

<400> SEQUENCE: 76
gaggagcaga cgaugagaa                                                19

<210> SEQ ID NO 77
<211> LENGTH: 19
<212> TYPE: RNA
<213> ORGANISM: Homo sapiens

<400> SEQUENCE: 77
ggaaggcacu uggcaucuc                                                19

<210> SEQ ID NO 78
<211> LENGTH: 19
<212> TYPE: RNA
<213> ORGANISM: Homo sapiens

<400> SEQUENCE: 78
gagaugccaa gugccuucc                                                19

<210> SEQ ID NO 79
<211> LENGTH: 19
<212> TYPE: RNA
<213> ORGANISM: Homo sapiens

<400> SEQUENCE: 79
```
ggcacuuggc aucuccccca    19

<210> SEQ ID NO 80
<211> LENGTH: 19
<212> TYPE: RNA
<213> ORGANISM: Homo sapiens

<400> SEQUENCE: 80 ugggagaug ccaagugcc    19

<210> SEQ ID NO 81
<211> LENGTH: 19
<212> TYPE: RNA
<213> ORGANISM: Homo sapiens

<400> SEQUENCE: 81
ggcaucuccc cauuccaug    19

<210> SEQ ID NO 82
<211> LENGTH: 20
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 82
auggaauggg gagaugccttt    20

<210> SEQ ID NO 83
<211> LENGTH: 19
<212> TYPE: RNA
<213> ORGANISM: Homo sapiens

<400> SEQUENCE: 83 gcaucuccc auuccauga    19

<210> SEQ ID NO 84
<211> LENGTH: 19
<212> TYPE: RNA
<213> ORGANISM: Homo sapiens

<400> SEQUENCE: 84
ucauggaaug gggagaugc    19

<210> SEQ ID NO 85
<211> LENGTH: 19
<212> TYPE: RNA
<213> ORGANISM: Homo sapiens

<400> SEQUENCE: 85
caucucccca uuccaugag    19

<210> SEQ ID NO 86
<211> LENGTH: 19
<212> TYPE: RNA
<213> ORGANISM: Homo sapiens

<400> SEQUENCE: 86
cucauggaau ggggagaug    19

<210> SEQ ID NO 87
<211> LENGTH: 19
<212> TYPE: RNA

```
<213> ORGANISM: Homo sapiens

<400> SEQUENCE: 87
aucuccccau uccaugagc                                                    19

<210> SEQ ID NO 88
<211> LENGTH: 19
<212> TYPE: RNA
<213> ORGANISM: Homo sapiens

<400> SEQUENCE: 88
gcucauggaa ugggagau                                                     19

<210> SEQ ID NO 89
<211> LENGTH: 19
<212> TYPE: RNA
<213> ORGANISM: Homo sapiens

<400> SEQUENCE: 89
cuccccauuc caugagcau                                                    19

<210> SEQ ID NO 90
<211> LENGTH: 19
<212> TYPE: RNA
<213> ORGANISM: Homo sapiens

<400> SEQUENCE: 90
augcucaugg aaugggag                                                     19

<210> SEQ ID NO 91
<211> LENGTH: 19
<212> TYPE: RNA
<213> ORGANISM: Homo sapiens

<400> SEQUENCE: 91
cccauuccau gagcaugca                                                    19

<210> SEQ ID NO 92
<211> LENGTH: 19
<212> TYPE: RNA
<213> ORGANISM: Homo sapiens

<400> SEQUENCE: 92
ugcaugcuca uggaauggg                                                    19

<210> SEQ ID NO 93
<211> LENGTH: 19
<212> TYPE: RNA
<213> ORGANISM: Homo sapiens

<400> SEQUENCE: 93
ccaugagcau gcagaggug                                                    19

<210> SEQ ID NO 94
<211> LENGTH: 19
<212> TYPE: RNA
<213> ORGANISM: Homo sapiens

<400> SEQUENCE: 94
caccucugca ugcucaugg                                                    19

<210> SEQ ID NO 95
<211> LENGTH: 19
```

```
<212> TYPE: RNA
<213> ORGANISM: Homo sapiens

<400> SEQUENCE: 95
agcaugcaga ggugguauu                                               19

<210> SEQ ID NO 96
<211> LENGTH: 19
<212> TYPE: RNA
<213> ORGANISM: Homo sapiens

<400> SEQUENCE: 96
aauaccaccu cugcaugcu                                               19

<210> SEQ ID NO 97
<211> LENGTH: 19
<212> TYPE: RNA
<213> ORGANISM: Homo sapiens

<400> SEQUENCE: 97
caugcagagg ugguauuca                                               19

<210> SEQ ID NO 98
<211> LENGTH: 19
<212> TYPE: RNA
<213> ORGANISM: Homo sapiens

<400> SEQUENCE: 98
ugaauaccac cucugcaug                                               19

<210> SEQ ID NO 99
<211> LENGTH: 19
<212> TYPE: RNA
<213> ORGANISM: Homo sapiens

<400> SEQUENCE: 99
augcagaggu gguauucac                                               19

<210> SEQ ID NO 100
<211> LENGTH: 19
<212> TYPE: RNA
<213> ORGANISM: Homo sapiens

<400> SEQUENCE: 100
gugaauacca ccucugcau                                               19

<210> SEQ ID NO 101
<211> LENGTH: 19
<212> TYPE: RNA
<213> ORGANISM: Homo sapiens

<400> SEQUENCE: 101
ggugguauuc acagccaac                                               19

<210> SEQ ID NO 102
<211> LENGTH: 19
<212> TYPE: RNA
<213> ORGANISM: Homo sapiens

<400> SEQUENCE: 102
guuggcugug aauaccacc                                               19

<210> SEQ ID NO 103
```

```
<211> LENGTH: 19
<212> TYPE: RNA
<213> ORGANISM: Homo sapiens

<400> SEQUENCE: 103
gugguauuca cagccaacg                                                      19

<210> SEQ ID NO 104
<211> LENGTH: 19
<212> TYPE: RNA
<213> ORGANISM: Homo sapiens

<400> SEQUENCE: 104
cguuggcugu gaauaccac                                                      19

<210> SEQ ID NO 105
<211> LENGTH: 19
<212> TYPE: RNA
<213> ORGANISM: Homo sapiens

<400> SEQUENCE: 105
ugguauucac agccaacga                                                      19

<210> SEQ ID NO 106
<211> LENGTH: 19
<212> TYPE: RNA
<213> ORGANISM: Homo sapiens

<400> SEQUENCE: 106
ucguuggcug ugaauacca                                                      19

<210> SEQ ID NO 107
<211> LENGTH: 19
<212> TYPE: RNA
<213> ORGANISM: Homo sapiens

<400> SEQUENCE: 107
gguauucaca gccaacgac                                                      19

<210> SEQ ID NO 108
<211> LENGTH: 19
<212> TYPE: RNA
<213> ORGANISM: Homo sapiens

<400> SEQUENCE: 108
gucguuggcu gugaauacc                                                      19

<210> SEQ ID NO 109
<211> LENGTH: 19
<212> TYPE: RNA
<213> ORGANISM: Homo sapiens

<400> SEQUENCE: 109
guauucacag ccaacgacu                                                      19

<210> SEQ ID NO 110
<211> LENGTH: 19
<212> TYPE: RNA
<213> ORGANISM: Homo sapiens

<400> SEQUENCE: 110
agucguuggc ugugaauac                                                      19
```

```
<210> SEQ ID NO 111
<211> LENGTH: 19
<212> TYPE: RNA
<213> ORGANISM: Homo sapiens

<400> SEQUENCE: 111
uauucacagc caacgacuc                                              19

<210> SEQ ID NO 112
<211> LENGTH: 19
<212> TYPE: RNA
<213> ORGANISM: Homo sapiens

<400> SEQUENCE: 112
gagucguugg cugugaaua                                              19

<210> SEQ ID NO 113
<211> LENGTH: 19
<212> TYPE: RNA
<213> ORGANISM: Homo sapiens

<400> SEQUENCE: 113
ucacagccaa cgacuccgg                                              19

<210> SEQ ID NO 114
<211> LENGTH: 19
<212> TYPE: RNA
<213> ORGANISM: Homo sapiens

<400> SEQUENCE: 114
ccggagucgu uggcuguga                                              19

<210> SEQ ID NO 115
<211> LENGTH: 19
<212> TYPE: RNA
<213> ORGANISM: Homo sapiens

<400> SEQUENCE: 115
ccccgccgcu acaccauug                                              19

<210> SEQ ID NO 116
<211> LENGTH: 19
<212> TYPE: RNA
<213> ORGANISM: Homo sapiens

<400> SEQUENCE: 116
caauggugua gcggcgggg                                              19

<210> SEQ ID NO 117
<211> LENGTH: 19
<212> TYPE: RNA
<213> ORGANISM: Homo sapiens

<400> SEQUENCE: 117
gaaguccacu cauucuugg                                              19

<210> SEQ ID NO 118
<211> LENGTH: 19
<212> TYPE: RNA
<213> ORGANISM: Homo sapiens

<400> SEQUENCE: 118
ccaagaauga guggacuuc                                              19
```

<210> SEQ ID NO 119
<211> LENGTH: 19
<212> TYPE: RNA
<213> ORGANISM: Homo sapiens

<400> SEQUENCE: 119
cccugcugag ccccuacuc                                                    19

<210> SEQ ID NO 120
<211> LENGTH: 19
<212> TYPE: RNA
<213> ORGANISM: Homo sapiens

<400> SEQUENCE: 120
gaguaggggc ucagcaggg                                                    19

<210> SEQ ID NO 121
<211> LENGTH: 19
<212> TYPE: RNA
<213> ORGANISM: Homo sapiens

<400> SEQUENCE: 121
cugagccccu acuccuauu                                                    19

<210> SEQ ID NO 122
<211> LENGTH: 19
<212> TYPE: RNA
<213> ORGANISM: Homo sapiens

<400> SEQUENCE: 122
aauaggagua ggggcucag                                                    19

<210> SEQ ID NO 123
<211> LENGTH: 19
<212> TYPE: RNA
<213> ORGANISM: Homo sapiens

<400> SEQUENCE: 123
ugagccccua cuccuauuc                                                    19

<210> SEQ ID NO 124
<211> LENGTH: 19
<212> TYPE: RNA
<213> ORGANISM: Homo sapiens

<400> SEQUENCE: 124
gaauaggagu aggggcuca                                                    19

<210> SEQ ID NO 125
<211> LENGTH: 19
<212> TYPE: RNA
<213> ORGANISM: Homo sapiens

<400> SEQUENCE: 125
ccccuacucc uauuccacc                                                    19

<210> SEQ ID NO 126
<211> LENGTH: 19
<212> TYPE: RNA
<213> ORGANISM: Homo sapiens

<400> SEQUENCE: 126
gguggaauag gaguagggg                                                    19

<210> SEQ ID NO 127
<211> LENGTH: 19
<212> TYPE: RNA
<213> ORGANISM: Homo sapiens

<400> SEQUENCE: 127
cuacuccuau uccaccacg                                               19

<210> SEQ ID NO 128
<211> LENGTH: 19
<212> TYPE: RNA
<213> ORGANISM: Homo sapiens

<400> SEQUENCE: 128
cgugguggaa uaggaguag                                               19

<210> SEQ ID NO 129
<211> LENGTH: 19
<212> TYPE: RNA
<213> ORGANISM: Homo sapiens

<400> SEQUENCE: 129
uacuccuauu ccaccacgg                                               19

<210> SEQ ID NO 130
<211> LENGTH: 19
<212> TYPE: RNA
<213> ORGANISM: Homo sapiens

<400> SEQUENCE: 130
ccguggugga auaggagua                                               19

<210> SEQ ID NO 131
<211> LENGTH: 19
<212> TYPE: RNA
<213> ORGANISM: Homo sapiens

<400> SEQUENCE: 131
acuccuauuc caccacggc                                               19

<210> SEQ ID NO 132
<211> LENGTH: 19
<212> TYPE: RNA
<213> ORGANISM: Homo sapiens

<400> SEQUENCE: 132
gccguggugg aauaggagu                                               19

<210> SEQ ID NO 133
<211> LENGTH: 19
<212> TYPE: RNA
<213> ORGANISM: Homo sapiens

<400> SEQUENCE: 133
uccuauucca ccacggcug                                               19

<210> SEQ ID NO 134
<211> LENGTH: 19
<212> TYPE: RNA
<213> ORGANISM: Homo sapiens

<400> SEQUENCE: 134
cagccguggu ggaauagga                                                    19

<210> SEQ ID NO 135
<211> LENGTH: 19
<212> TYPE: RNA
<213> ORGANISM: Homo sapiens

<400> SEQUENCE: 135
uauuccacca cggcugucg                                                    19

<210> SEQ ID NO 136
<211> LENGTH: 19
<212> TYPE: RNA
<213> ORGANISM: Homo sapiens

<400> SEQUENCE: 136
cgacagccgu gguggaaua                                                    19

<210> SEQ ID NO 137
<211> LENGTH: 19
<212> TYPE: RNA
<213> ORGANISM: Homo sapiens

<400> SEQUENCE: 137
auuccaccac ggcugucgu                                                    19

<210> SEQ ID NO 138
<211> LENGTH: 19
<212> TYPE: RNA
<213> ORGANISM: Homo sapiens

<400> SEQUENCE: 138
acgacagccg ugguggaau                                                    19

<210> SEQ ID NO 139
<211> LENGTH: 19
<212> TYPE: RNA
<213> ORGANISM: Homo sapiens

<400> SEQUENCE: 139
caccacggcu gucgucacc                                                    19

<210> SEQ ID NO 140
<211> LENGTH: 19
<212> TYPE: RNA
<213> ORGANISM: Homo sapiens

<400> SEQUENCE: 140
ggugacgaca gccguggug                                                    19

<210> SEQ ID NO 141
<211> LENGTH: 19
<212> TYPE: RNA
<213> ORGANISM: Homo sapiens

<400> SEQUENCE: 141
accacggcug ucgucacca                                                    19

<210> SEQ ID NO 142
<211> LENGTH: 19
<212> TYPE: RNA
<213> ORGANISM: Homo sapiens

<400> SEQUENCE: 142
uggugacgac agccguggu                                            19

<210> SEQ ID NO 143
<211> LENGTH: 19
<212> TYPE: RNA
<213> ORGANISM: Homo sapiens

<400> SEQUENCE: 143
ccacggcugu cgucaccaa                                            19

<210> SEQ ID NO 144
<211> LENGTH: 19
<212> TYPE: RNA
<213> ORGANISM: Homo sapiens

<400> SEQUENCE: 144
uuggugacga cagccgugg                                            19

<210> SEQ ID NO 145
<211> LENGTH: 19
<212> TYPE: RNA
<213> ORGANISM: Homo sapiens

<400> SEQUENCE: 145
acggcugucg ucaccaauc                                            19

<210> SEQ ID NO 146
<211> LENGTH: 19
<212> TYPE: RNA
<213> ORGANISM: Homo sapiens

<400> SEQUENCE: 146
gauuggugac gacagccgu                                            19

<210> SEQ ID NO 147
<211> LENGTH: 19
<212> TYPE: RNA
<213> ORGANISM: Homo sapiens

<400> SEQUENCE: 147
cggcugucgu caccaaucc                                            19

<210> SEQ ID NO 148
<211> LENGTH: 19
<212> TYPE: RNA
<213> ORGANISM: Homo sapiens

<400> SEQUENCE: 148
ggauugguga cgacagccg                                            19

<210> SEQ ID NO 149
<211> LENGTH: 19
<212> TYPE: RNA
<213> ORGANISM: Homo sapiens

<400> SEQUENCE: 149
cgucaccaau cccaaggaa                                            19

<210> SEQ ID NO 150
<211> LENGTH: 19
<212> TYPE: RNA
<213> ORGANISM: Homo sapiens

```
<400> SEQUENCE: 150
uuccuuggga uuggugacg                                           19

<210> SEQ ID NO 151
<211> LENGTH: 19
<212> TYPE: RNA
<213> ORGANISM: Homo sapiens

<400> SEQUENCE: 151
caaucccaag gaaugaggg                                           19

<210> SEQ ID NO 152
<211> LENGTH: 19
<212> TYPE: RNA
<213> ORGANISM: Homo sapiens

<400> SEQUENCE: 152
cccucauucc uugggauug                                           19

<210> SEQ ID NO 153
<211> LENGTH: 19
<212> TYPE: RNA
<213> ORGANISM: Homo sapiens

<400> SEQUENCE: 153
ccugaaggac gagggaugg                                           19

<210> SEQ ID NO 154
<211> LENGTH: 19
<212> TYPE: RNA
<213> ORGANISM: Homo sapiens

<400> SEQUENCE: 154
ccaucccucg uccuucagg                                           19

<210> SEQ ID NO 155
<211> LENGTH: 19
<212> TYPE: RNA
<213> ORGANISM: Homo sapiens

<400> SEQUENCE: 155
ggacgaggga ugggauuuc                                           19

<210> SEQ ID NO 156
<211> LENGTH: 19
<212> TYPE: RNA
<213> ORGANISM: Homo sapiens

<400> SEQUENCE: 156
gaaaucccau cccucgucc                                           19

<210> SEQ ID NO 157
<211> LENGTH: 19
<212> TYPE: RNA
<213> ORGANISM: Homo sapiens

<400> SEQUENCE: 157
aaguccacuc auucuuggc                                           19

<210> SEQ ID NO 158
<211> LENGTH: 19
<212> TYPE: RNA
<213> ORGANISM: Homo sapiens
```

-continued

```
<400> SEQUENCE: 158
gccaagaaug aguggacuu                                                    19

<210> SEQ ID NO 159
<211> LENGTH: 19
<212> TYPE: RNA
<213> ORGANISM: Homo sapiens

<400> SEQUENCE: 159
gggauuucau guaaccaag                                                    19

<210> SEQ ID NO 160
<211> LENGTH: 19
<212> TYPE: RNA
<213> ORGANISM: Homo sapiens

<400> SEQUENCE: 160
cuugguuaca ugaaauccc                                                    19

<210> SEQ ID NO 161
<211> LENGTH: 19
<212> TYPE: RNA
<213> ORGANISM: Homo sapiens

<400> SEQUENCE: 161
ggauuucaug uaaccaaga                                                    19

<210> SEQ ID NO 162
<211> LENGTH: 19
<212> TYPE: RNA
<213> ORGANISM: Homo sapiens

<400> SEQUENCE: 162
ucuugguuac augaaaucc                                                    19

<210> SEQ ID NO 163
<211> LENGTH: 19
<212> TYPE: RNA
<213> ORGANISM: Homo sapiens

<400> SEQUENCE: 163
ucauguaacc aagaguauu                                                    19

<210> SEQ ID NO 164
<211> LENGTH: 19
<212> TYPE: RNA
<213> ORGANISM: Homo sapiens

<400> SEQUENCE: 164
aauacucuug guuacauga                                                    19

<210> SEQ ID NO 165
<211> LENGTH: 19
<212> TYPE: RNA
<213> ORGANISM: Homo sapiens

<400> SEQUENCE: 165
auguaaccaa gaguauucc                                                    19

<210> SEQ ID NO 166
<211> LENGTH: 19
<212> TYPE: RNA
```

```
<213> ORGANISM: Homo sapiens

<400> SEQUENCE: 166
ggaauacucu ugguuacau                                            19

<210> SEQ ID NO 167
<211> LENGTH: 19
<212> TYPE: RNA
<213> ORGANISM: Homo sapiens

<400> SEQUENCE: 167
uguaaccaag aguauucca                                            19

<210> SEQ ID NO 168
<211> LENGTH: 19
<212> TYPE: RNA
<213> ORGANISM: Homo sapiens

<400> SEQUENCE: 168
uggaauacuc uugguuaca                                            19

<210> SEQ ID NO 169
<211> LENGTH: 19
<212> TYPE: RNA
<213> ORGANISM: Homo sapiens

<400> SEQUENCE: 169
guaaccaaga guauuccau                                            19

<210> SEQ ID NO 170
<211> LENGTH: 19
<212> TYPE: RNA
<213> ORGANISM: Homo sapiens

<400> SEQUENCE: 170
auggaauacu cuugguuac                                            19

<210> SEQ ID NO 171
<211> LENGTH: 19
<212> TYPE: RNA
<213> ORGANISM: Homo sapiens

<400> SEQUENCE: 171
ugccuugcug gacuggua u                                           19

<210> SEQ ID NO 172
<211> LENGTH: 19
<212> TYPE: RNA
<213> ORGANISM: Homo sapiens

<400> SEQUENCE: 172
auaccagucc agcaaggca                                            19

<210> SEQ ID NO 173
<211> LENGTH: 19
<212> TYPE: RNA
<213> ORGANISM: Homo sapiens

<400> SEQUENCE: 173
uaaagcagug uuuucaccu                                            19

<210> SEQ ID NO 174
<211> LENGTH: 19
```

```
<212> TYPE: RNA
<213> ORGANISM: Homo sapiens

<400> SEQUENCE: 174
aggugaaaac acugcuuua                                              19

<210> SEQ ID NO 175
<211> LENGTH: 19
<212> TYPE: RNA
<213> ORGANISM: Homo sapiens

<400> SEQUENCE: 175
gccuugcugg acugguauu                                              19

<210> SEQ ID NO 176
<211> LENGTH: 19
<212> TYPE: RNA
<213> ORGANISM: Homo sapiens

<400> SEQUENCE: 176
aauaccaguc cagcaaggc                                              19

<210> SEQ ID NO 177
<211> LENGTH: 19
<212> TYPE: RNA
<213> ORGANISM: Homo sapiens

<400> SEQUENCE: 177
uguuuucacc ucauaugcu                                              19

<210> SEQ ID NO 178
<211> LENGTH: 19
<212> TYPE: RNA
<213> ORGANISM: Homo sapiens

<400> SEQUENCE: 178
agcauaugag gugaaaaca                                              19

<210> SEQ ID NO 179
<211> LENGTH: 19
<212> TYPE: RNA
<213> ORGANISM: Homo sapiens

<400> SEQUENCE: 179
guuuucaccu cauaugcua                                              19

<210> SEQ ID NO 180
<211> LENGTH: 19
<212> TYPE: RNA
<213> ORGANISM: Homo sapiens

<400> SEQUENCE: 180
uagcauauga ggugaaaac                                              19

<210> SEQ ID NO 181
<211> LENGTH: 19
<212> TYPE: RNA
<213> ORGANISM: Homo sapiens

<400> SEQUENCE: 181
uuuucaccuc auaugcuau                                              19

<210> SEQ ID NO 182
```

```
<211> LENGTH: 19
<212> TYPE: RNA
<213> ORGANISM: Homo sapiens

<400> SEQUENCE: 182
auagcauaug aggugaaaa                                                        19

<210> SEQ ID NO 183
<211> LENGTH: 19
<212> TYPE: RNA
<213> ORGANISM: Homo sapiens

<400> SEQUENCE: 183
uucaccucau augcuaugu                                                        19

<210> SEQ ID NO 184
<211> LENGTH: 19
<212> TYPE: RNA
<213> ORGANISM: Homo sapiens

<400> SEQUENCE: 184
acauagcaua ugaggugaa                                                        19

<210> SEQ ID NO 185
<211> LENGTH: 19
<212> TYPE: RNA
<213> ORGANISM: Homo sapiens

<400> SEQUENCE: 185
caccucauau gcuauguua                                                        19

<210> SEQ ID NO 186
<211> LENGTH: 19
<212> TYPE: RNA
<213> ORGANISM: Homo sapiens

<400> SEQUENCE: 186
uaacauagca uaugaggug                                                        19

<210> SEQ ID NO 187
<211> LENGTH: 19
<212> TYPE: RNA
<213> ORGANISM: Homo sapiens

<400> SEQUENCE: 187
ccuugcugga cugguauuu                                                        19

<210> SEQ ID NO 188
<211> LENGTH: 19
<212> TYPE: RNA
<213> ORGANISM: Homo sapiens

<400> SEQUENCE: 188
aaauaccagu ccagcaagg                                                        19

<210> SEQ ID NO 189
<211> LENGTH: 19
<212> TYPE: RNA
<213> ORGANISM: Homo sapiens

<400> SEQUENCE: 189
auaugcuaug uuagaaguc                                                        19
```

```
<210> SEQ ID NO 190
<211> LENGTH: 19
<212> TYPE: RNA
<213> ORGANISM: Homo sapiens

<400> SEQUENCE: 190
gacuucuaac auagcauau                                                  19

<210> SEQ ID NO 191
<211> LENGTH: 19
<212> TYPE: RNA
<213> ORGANISM: Homo sapiens

<400> SEQUENCE: 191
uaugcuaugu uagaagucc                                                  19

<210> SEQ ID NO 192
<211> LENGTH: 19
<212> TYPE: RNA
<213> ORGANISM: Homo sapiens

<400> SEQUENCE: 192
ggacuucuaa cauagcaua                                                  19

<210> SEQ ID NO 193
<211> LENGTH: 19
<212> TYPE: RNA
<213> ORGANISM: Homo sapiens

<400> SEQUENCE: 193
ugcuauguua gaaguccag                                                  19

<210> SEQ ID NO 194
<211> LENGTH: 19
<212> TYPE: RNA
<213> ORGANISM: Homo sapiens

<400> SEQUENCE: 194
cuggacuucu aacauagca                                                  19

<210> SEQ ID NO 195
<211> LENGTH: 19
<212> TYPE: RNA
<213> ORGANISM: Homo sapiens

<400> SEQUENCE: 195
cuugcuggac ugguauuug                                                  19

<210> SEQ ID NO 196
<211> LENGTH: 19
<212> TYPE: RNA
<213> ORGANISM: Homo sapiens

<400> SEQUENCE: 196
caaauaccag uccagcaag                                                  19

<210> SEQ ID NO 197
<211> LENGTH: 19
<212> TYPE: RNA
<213> ORGANISM: Homo sapiens

<400> SEQUENCE: 197
aguccaggca gagacaaua                                                  19
```

```
<210> SEQ ID NO 198
<211> LENGTH: 20
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 198
auugucucug ccuggacutt                                               20

<210> SEQ ID NO 199
<211> LENGTH: 19
<212> TYPE: RNA
<213> ORGANISM: Homo sapiens

<400> SEQUENCE: 199
uccaggcaga gacaauaaa                                                19

<210> SEQ ID NO 200
<211> LENGTH: 19
<212> TYPE: RNA
<213> ORGANISM: Homo sapiens

<400> SEQUENCE: 200
uuuauugucu cugccugga                                                19

<210> SEQ ID NO 201
<211> LENGTH: 19
<212> TYPE: RNA
<213> ORGANISM: Homo sapiens

<400> SEQUENCE: 201
gugaaaggca cuuuucauu                                                19

<210> SEQ ID NO 202
<211> LENGTH: 19
<212> TYPE: RNA
<213> ORGANISM: Homo sapiens

<400> SEQUENCE: 202
aaugaaaagu gccuuucac                                                19

<210> SEQ ID NO 203
<211> LENGTH: 19
<212> TYPE: RNA
<213> ORGANISM: Homo sapiens

<400> SEQUENCE: 203
uggacuggua uuugugucu                                                19

<210> SEQ ID NO 204
<211> LENGTH: 19
<212> TYPE: RNA
<213> ORGANISM: Homo sapiens

<400> SEQUENCE: 204
agacacaaau accagucca                                                19

<210> SEQ ID NO 205
<211> LENGTH: 19
<212> TYPE: RNA
<213> ORGANISM: Homo sapiens
```

```
<400> SEQUENCE: 205
gucugaggcu ggcccuacg                                              19

<210> SEQ ID NO 206
<211> LENGTH: 19
<212> TYPE: RNA
<213> ORGANISM: Homo sapiens

<400> SEQUENCE: 206
cguagggcca gccucagac                                              19

<210> SEQ ID NO 207
<211> LENGTH: 19
<212> TYPE: RNA
<213> ORGANISM: Homo sapiens

<400> SEQUENCE: 207
cugaggcugg cccuacggg                                              19

<210> SEQ ID NO 208
<211> LENGTH: 19
<212> TYPE: RNA
<213> ORGANISM: Homo sapiens

<400> SEQUENCE: 208
cccguagggc cagccucag                                              19

<210> SEQ ID NO 209
<211> LENGTH: 19
<212> TYPE: RNA
<213> ORGANISM: Homo sapiens

<400> SEQUENCE: 209
gaggcuggcc cuacgggca                                              19

<210> SEQ ID NO 210
<211> LENGTH: 19
<212> TYPE: RNA
<213> ORGANISM: Homo sapiens

<400> SEQUENCE: 210
ugcccguagg gccagccuc                                              19

<210> SEQ ID NO 211
<211> LENGTH: 19
<212> TYPE: RNA
<213> ORGANISM: Homo sapiens

<400> SEQUENCE: 211
aggcuggccc uacgggcac                                              19

<210> SEQ ID NO 212
<211> LENGTH: 19
<212> TYPE: RNA
<213> ORGANISM: Homo sapiens

<400> SEQUENCE: 212
gugcccguag ggccagccu                                              19

<210> SEQ ID NO 213
<211> LENGTH: 19
<212> TYPE: RNA
<213> ORGANISM: Homo sapiens
```

```
<400> SEQUENCE: 213
gcuggcccua cgggcaccg                                           19

<210> SEQ ID NO 214
<211> LENGTH: 19
<212> TYPE: RNA
<213> ORGANISM: Homo sapiens

<400> SEQUENCE: 214
cggugcccgu agggccagc                                           19

<210> SEQ ID NO 215
<211> LENGTH: 19
<212> TYPE: RNA
<213> ORGANISM: Homo sapiens

<400> SEQUENCE: 215
cuggcccuac gggcaccgg                                           19

<210> SEQ ID NO 216
<211> LENGTH: 19
<212> TYPE: RNA
<213> ORGANISM: Homo sapiens

<400> SEQUENCE: 216
ccggugcccg uagggccag                                           19

<210> SEQ ID NO 217
<211> LENGTH: 19
<212> TYPE: RNA
<213> ORGANISM: Homo sapiens

<400> SEQUENCE: 217
ggcccuacgg gcaccggug                                           19

<210> SEQ ID NO 218
<211> LENGTH: 19
<212> TYPE: RNA
<213> ORGANISM: Homo sapiens

<400> SEQUENCE: 218
caccggugcc cguagggcc                                           19

<210> SEQ ID NO 219
<211> LENGTH: 19
<212> TYPE: RNA
<213> ORGANISM: Homo sapiens

<400> SEQUENCE: 219
ccacucauuc uuggcagga                                           19

<210> SEQ ID NO 220
<211> LENGTH: 19
<212> TYPE: RNA
<213> ORGANISM: Homo sapiens

<400> SEQUENCE: 220
uccugccaag aaugagugg                                           19

<210> SEQ ID NO 221
<211> LENGTH: 19
<212> TYPE: RNA
```

```
<213> ORGANISM: Homo sapiens

<400> SEQUENCE: 221
ccuacgggca ccgugaauu                                               19

<210> SEQ ID NO 222
<211> LENGTH: 19
<212> TYPE: RNA
<213> ORGANISM: Homo sapiens

<400> SEQUENCE: 222
auucaccggu gcccguagg                                               19

<210> SEQ ID NO 223
<211> LENGTH: 19
<212> TYPE: RNA
<213> ORGANISM: Homo sapiens

<400> SEQUENCE: 223
cuacgggcac cggugaauc                                               19

<210> SEQ ID NO 224
<211> LENGTH: 19
<212> TYPE: RNA
<213> ORGANISM: Homo sapiens

<400> SEQUENCE: 224
gauucaccgg ugcccguag                                               19

<210> SEQ ID NO 225
<211> LENGTH: 19
<212> TYPE: RNA
<213> ORGANISM: Homo sapiens

<400> SEQUENCE: 225
uacgggcacc ggugaaucc                                               19

<210> SEQ ID NO 226
<211> LENGTH: 19
<212> TYPE: RNA
<213> ORGANISM: Homo sapiens

<400> SEQUENCE: 226
ggauucaccg gugcccgua                                               19

<210> SEQ ID NO 227
<211> LENGTH: 19
<212> TYPE: RNA
<213> ORGANISM: Homo sapiens

<400> SEQUENCE: 227
acgggcaccg gugaaucca                                               19

<210> SEQ ID NO 228
<211> LENGTH: 19
<212> TYPE: RNA
<213> ORGANISM: Homo sapiens

<400> SEQUENCE: 228
uggauucacc ggugcccgu                                               19

<210> SEQ ID NO 229
<211> LENGTH: 19
```

```
<212> TYPE: RNA
<213> ORGANISM: Homo sapiens

<400> SEQUENCE: 229
gcaccgguga auccaagug                                               19

<210> SEQ ID NO 230
<211> LENGTH: 19
<212> TYPE: RNA
<213> ORGANISM: Homo sapiens

<400> SEQUENCE: 230
cacuuggauu caccggugc                                               19

<210> SEQ ID NO 231
<211> LENGTH: 19
<212> TYPE: RNA
<213> ORGANISM: Homo sapiens

<400> SEQUENCE: 231
caccggugaa uccaagugu                                               19

<210> SEQ ID NO 232
<211> LENGTH: 19
<212> TYPE: RNA
<213> ORGANISM: Homo sapiens

<400> SEQUENCE: 232
acacuuggau ucaccggug                                               19

<210> SEQ ID NO 233
<211> LENGTH: 19
<212> TYPE: RNA
<213> ORGANISM: Homo sapiens

<400> SEQUENCE: 233
uguggccaug cauguguuc                                               19

<210> SEQ ID NO 234
<211> LENGTH: 19
<212> TYPE: RNA
<213> ORGANISM: Homo sapiens

<400> SEQUENCE: 234
gaacacaugc auggccaca                                               19

<210> SEQ ID NO 235
<211> LENGTH: 19
<212> TYPE: RNA
<213> ORGANISM: Homo sapiens

<400> SEQUENCE: 235
guggccaugc auguuuca                                                19

<210> SEQ ID NO 236
<211> LENGTH: 19
<212> TYPE: RNA
<213> ORGANISM: Homo sapiens

<400> SEQUENCE: 236
ugaacacaug cauggccac                                               19

<210> SEQ ID NO 237
```

```
<211> LENGTH: 19
<212> TYPE: RNA
<213> ORGANISM: Homo sapiens

<400> SEQUENCE: 237
gccaugcaug uguucagaa                                                 19

<210> SEQ ID NO 238
<211> LENGTH: 19
<212> TYPE: RNA
<213> ORGANISM: Homo sapiens

<400> SEQUENCE: 238
uucugaacac augcauggc                                                 19

<210> SEQ ID NO 239
<211> LENGTH: 19
<212> TYPE: RNA
<213> ORGANISM: Homo sapiens

<400> SEQUENCE: 239
uauuccacca cggcuguca                                                 19

<210> SEQ ID NO 240
<211> LENGTH: 19
<212> TYPE: RNA
<213> ORGANISM: Homo sapiens

<400> SEQUENCE: 240
ugacagccgu gguggaaua                                                 19

<210> SEQ ID NO 241
<211> LENGTH: 19
<212> TYPE: RNA
<213> ORGANISM: Homo sapiens

<400> SEQUENCE: 241
gucaucacca aucccaagg                                                 19

<210> SEQ ID NO 242
<211> LENGTH: 19
<212> TYPE: RNA
<213> ORGANISM: Homo sapiens

<400> SEQUENCE: 242
ccuugggauu ggugaugac                                                 19

<210> SEQ ID NO 243
<211> LENGTH: 19
<212> TYPE: RNA
<213> ORGANISM: Homo sapiens

<400> SEQUENCE: 243
guccucugau ggucaaagu                                                 19

<210> SEQ ID NO 244
<211> LENGTH: 19
<212> TYPE: RNA
<213> ORGANISM: Homo sapiens

<400> SEQUENCE: 244
acuuugacca ucagaggac                                                 19
```

```
<210> SEQ ID NO 245
<211> LENGTH: 19
<212> TYPE: RNA
<213> ORGANISM: Homo sapiens

<400> SEQUENCE: 245
gauggucaaa guucuagau                                                       19

<210> SEQ ID NO 246
<211> LENGTH: 19
<212> TYPE: RNA
<213> ORGANISM: Homo sapiens

<400> SEQUENCE: 246
aucuagaacu uugaccauc                                                       19

<210> SEQ ID NO 247
<211> LENGTH: 19
<212> TYPE: RNA
<213> ORGANISM: Homo sapiens

<400> SEQUENCE: 247
augcuguccg aggcagucc                                                       19

<210> SEQ ID NO 248
<211> LENGTH: 19
<212> TYPE: RNA
<213> ORGANISM: Homo sapiens

<400> SEQUENCE: 248
ggacugccuc ggacagcau                                                       19

<210> SEQ ID NO 249
<211> LENGTH: 19
<212> TYPE: RNA
<213> ORGANISM: Homo sapiens

<400> SEQUENCE: 249
ccgugcaugu guucagaaa                                                       19

<210> SEQ ID NO 250
<211> LENGTH: 19
<212> TYPE: RNA
<213> ORGANISM: Homo sapiens

<400> SEQUENCE: 250
uuucugaaca caugcacgg                                                       19

<210> SEQ ID NO 251
<211> LENGTH: 19
<212> TYPE: RNA
<213> ORGANISM: Homo sapiens

<400> SEQUENCE: 251
agucuggaga gcugcaugg                                                       19

<210> SEQ ID NO 252
<211> LENGTH: 19
<212> TYPE: RNA
<213> ORGANISM: Homo sapiens

<400> SEQUENCE: 252
ccaugcagcu cuccagacu                                                       19
```

```
<210> SEQ ID NO 253
<211> LENGTH: 19
<212> TYPE: RNA
<213> ORGANISM: Homo sapiens

<400> SEQUENCE: 253
caugggcuca caacugagg                                                  19

<210> SEQ ID NO 254
<211> LENGTH: 19
<212> TYPE: RNA
<213> ORGANISM: Homo sapiens

<400> SEQUENCE: 254
ccucaguugu gagcccaug                                                  19

<210> SEQ ID NO 255
<211> LENGTH: 19
<212> TYPE: RNA
<213> ORGANISM: Homo sapiens

<400> SEQUENCE: 255
ucucaucguc ugcuccucc                                                  19

<210> SEQ ID NO 256
<211> LENGTH: 19
<212> TYPE: RNA
<213> ORGANISM: Homo sapiens

<400> SEQUENCE: 256
ggaggagcag acgaugaga                                                  19

<210> SEQ ID NO 257
<211> LENGTH: 19
<212> TYPE: RNA
<213> ORGANISM: Homo sapiens

<400> SEQUENCE: 257
ccccauucca ugagcaugc                                                  19

<210> SEQ ID NO 258
<211> LENGTH: 19
<212> TYPE: RNA
<213> ORGANISM: Homo sapiens

<400> SEQUENCE: 258
gcaugcucau ggaaugggg                                                  19

<210> SEQ ID NO 259
<211> LENGTH: 19
<212> TYPE: RNA
<213> ORGANISM: Homo sapiens

<400> SEQUENCE: 259
gccccuacuc cuauuccac                                                  19

<210> SEQ ID NO 260
<211> LENGTH: 19
<212> TYPE: RNA
<213> ORGANISM: Homo sapiens

<400> SEQUENCE: 260
guggaauagg aguagggc                                                   19
```

<210> SEQ ID NO 261
<211> LENGTH: 19
<212> TYPE: RNA
<213> ORGANISM: Homo sapiens

<400> SEQUENCE: 261
cuauuccacc acggcuguc					19

<210> SEQ ID NO 262
<211> LENGTH: 19
<212> TYPE: RNA
<213> ORGANISM: Homo sapiens

<400> SEQUENCE: 262
gacagccgug guggaauag					19

<210> SEQ ID NO 263
<211> LENGTH: 19
<212> TYPE: RNA
<213> ORGANISM: Homo sapiens

<400> SEQUENCE: 263
cacggcuguc gucaccaau					19

<210> SEQ ID NO 264
<211> LENGTH: 19
<212> TYPE: RNA
<213> ORGANISM: Homo sapiens

<400> SEQUENCE: 264
auuggugacg acagccgug					19

<210> SEQ ID NO 265
<211> LENGTH: 19
<212> TYPE: RNA
<213> ORGANISM: Homo sapiens

<400> SEQUENCE: 265
aggacgaggg augggauuu					19

<210> SEQ ID NO 266
<211> LENGTH: 19
<212> TYPE: RNA
<213> ORGANISM: Homo sapiens

<400> SEQUENCE: 266
aaaucccauc ccucguccu					19

<210> SEQ ID NO 267
<211> LENGTH: 19
<212> TYPE: RNA
<213> ORGANISM: Homo sapiens

<400> SEQUENCE: 267
ucaccucaua ugcuauguu					19

<210> SEQ ID NO 268
<211> LENGTH: 19
<212> TYPE: RNA
<213> ORGANISM: Homo sapiens

<400> SEQUENCE: 268
aacauagcau augagguga                                      19

<210> SEQ ID NO 269
<211> LENGTH: 19
<212> TYPE: RNA
<213> ORGANISM: Homo sapiens

<400> SEQUENCE: 269
ccucauaugc uauguuaga                                      19

<210> SEQ ID NO 270
<211> LENGTH: 19
<212> TYPE: RNA
<213> ORGANISM: Homo sapiens

<400> SEQUENCE: 270
ucuaacauag cauaugagg                                      19

<210> SEQ ID NO 271
<211> LENGTH: 19
<212> TYPE: RNA
<213> ORGANISM: Homo sapiens

<400> SEQUENCE: 271
auguuagaag uccaggcag                                      19

<210> SEQ ID NO 272
<211> LENGTH: 19
<212> TYPE: RNA
<213> ORGANISM: Homo sapiens

<400> SEQUENCE: 272
cugccuggac uucuaacau                                      19

<210> SEQ ID NO 273
<211> LENGTH: 19
<212> TYPE: RNA
<213> ORGANISM: Homo sapiens

<400> SEQUENCE: 273
ucugaggcug gcccuacgg                                      19

<210> SEQ ID NO 274
<211> LENGTH: 19
<212> TYPE: RNA
<213> ORGANISM: Homo sapiens

<400> SEQUENCE: 274
ccguagggcc agccucaga                                      19

<210> SEQ ID NO 275
<211> LENGTH: 19
<212> TYPE: RNA
<213> ORGANISM: Homo sapiens

<400> SEQUENCE: 275
ggcccuacgg gcaccggug                                      19

<210> SEQ ID NO 276
<211> LENGTH: 19
<212> TYPE: RNA
<213> ORGANISM: Homo sapiens

<400> SEQUENCE: 276

```
caccggugcc cguagggcc                                              19

<210> SEQ ID NO 277
<211> LENGTH: 19
<212> TYPE: RNA
<213> ORGANISM: Homo sapiens

<400> SEQUENCE: 277
gggcaccggu gaauccaag                                              19

<210> SEQ ID NO 278
<211> LENGTH: 19
<212> TYPE: RNA
<213> ORGANISM: Homo sapiens

<400> SEQUENCE: 278
cuuggauuca ccggugccc                                              19

<210> SEQ ID NO 279
<211> LENGTH: 19
<212> TYPE: RNA
<213> ORGANISM: Homo sapiens

<400> SEQUENCE: 279
ccaugcaugu guucagaaa                                              19

<210> SEQ ID NO 280
<211> LENGTH: 19
<212> TYPE: RNA
<213> ORGANISM: Homo sapiens

<400> SEQUENCE: 280
uuucugaaca caugcaugg                                              19

<210> SEQ ID NO 281
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 281
ccggugaauc caaguguccn n                                           21

<210> SEQ ID NO 282
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 282
ggacacuugg auucaccggn n                                           21

<210> SEQ ID NO 283
```

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 283
acucauucuu ggcaggaugn n                                               21

<210> SEQ ID NO 284
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 284
cauccugcca agaaugagun n                                               21

<210> SEQ ID NO 285
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 285
aaguguccuc ugauggucan n                                               21

<210> SEQ ID NO 286
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 286
ugaccaucag aggacacuun n                                               21

<210> SEQ ID NO 287
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

```
<400> SEQUENCE: 287
ucauucuugg caggauggcn n                                              21

<210> SEQ ID NO 288
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 288
gccauccugc caagaaugan n                                              21

<210> SEQ ID NO 289
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 289
aaguucuaga ugcuguccgn n                                              21

<210> SEQ ID NO 290
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 290
cggacagcau cuagaacuun n                                              21

<210> SEQ ID NO 291
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 291
guucuagaug cuguccgagn n                                              21

<210> SEQ ID NO 292
<211> LENGTH: 21
<212> TYPE: DNA
<213> ORGANISM: Homo sapiens
<220> FEATURE:
<223> OTHER INFORMATION: Description of Combined DNA/RNA Molecule:
```

```
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 292
cucggacagc aucuagaacn n                                              21

<210> SEQ ID NO 293
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 293
cuagaugcug uccgaggcan n                                              21

<210> SEQ ID NO 294
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 294
ugccucggac agcaucuagn n                                              21

<210> SEQ ID NO 295
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 295
gaugcugucc gaggcagucn n                                              21

<210> SEQ ID NO 296
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 296
gacugccucg gacagcaucn n                                              21
```

-continued

```
<210> SEQ ID NO 297
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 297
cauucuuggc aggauggcun n                                               21

<210> SEQ ID NO 298
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 298
agccauccug ccaagaaugn n                                               21

<210> SEQ ID NO 299
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 299
ugcuguccga ggcaguccun n                                               21

<210> SEQ ID NO 300
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 300
aggacugccu cggacagcan n                                               21

<210> SEQ ID NO 301
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

<400> SEQUENCE: 301
ccgaggcagu ccugccaucn n                                              21

<210> SEQ ID NO 302
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 302
gauggcagga cugccucggn n                                              21

<210> SEQ ID NO 303
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 303
caguccugcc aucaaugugn n                                              21

<210> SEQ ID NO 304
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 304
cacauugaug gcaggacugn n                                              21

<210> SEQ ID NO 305
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 305
caauguggcc gugcaugugn n                                              21

<210> SEQ ID NO 306
<211> LENGTH: 21
<212> TYPE: DNA
<213> ORGANISM: Homo sapiens
<220> FEATURE:

```
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 306
cacaugcacg gccacauugn n                                              21

<210> SEQ ID NO 307
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 307
auguguucag aaaggcugcn n                                              21

<210> SEQ ID NO 308
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 308
gcagccuuuc ugaacacaun n                                              21

<210> SEQ ID NO 309
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 309
cagaagucca cucauucuun n                                              21

<210> SEQ ID NO 310
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 310
aagaaugagu ggacuucugn n                                              21
```

```
<210> SEQ ID NO 311
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 311
ggcaggaugg cuucucaucn n                                              21

<210> SEQ ID NO 312
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 312
gaugagaagc cauccugccn n                                              21

<210> SEQ ID NO 313
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 313
gagccauuug ccucugggan n                                              21

<210> SEQ ID NO 314
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 314
ucccagaggc aaauggcucn n                                              21

<210> SEQ ID NO 315
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
```

<223> OTHER INFORMATION: a, c, t, g, unknown or other

<400> SEQUENCE: 315
caggauggcu ucucaucgun n    21

<210> SEQ ID NO 316
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 316
acgaugagaa gccauccugn n    21

<210> SEQ ID NO 317
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 317
aggauggcuu cucaucgucn n    21

<210> SEQ ID NO 318
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 318
gacgaugaga agccauccun n    21

<210> SEQ ID NO 319
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 319
agagcugcau gggcucacan n    21

<210> SEQ ID NO 320
<211> LENGTH: 21
<212> TYPE: DNA
<213> ORGANISM: Homo sapiens

```
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 320
ugugagccca ugcagcucun n                                              21

<210> SEQ ID NO 321
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 321
gcugcauggg cucacaacun n                                              21

<210> SEQ ID NO 322
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 322
aguugugagc ccaugcagcn n                                              21

<210> SEQ ID NO 323
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 323
ggauggcuuc ucaucgucun n                                              21

<210> SEQ ID NO 324
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 324
agacgaugag aagccauccn n                                              21
```

```
<210> SEQ ID NO 325
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 325
gcaugggcuc acaacugagn n                                              21

<210> SEQ ID NO 326
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 326
cucaguugug agcccaugcn n                                              21

<210> SEQ ID NO 327
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 327
augggcucac aacugaggan n                                              21

<210> SEQ ID NO 328
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 328
uccucaguug ugagcccaun n                                              21

<210> SEQ ID NO 329
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
```

```
<222> LOCATION: (20)..(21)
<223> OTHER INFORMATION: a, c, t, g, unknown or other

<400> SEQUENCE: 329
ugggcucaca acugaggagn n                                          21

<210> SEQ ID NO 330
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 330
cuccucaguu gugagcccan n                                          21

<210> SEQ ID NO 331
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 331
gaggaauuug uagaagggan n                                          21

<210> SEQ ID NO 332
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 332
ucccuucuac aaauuccucn n                                          21

<210> SEQ ID NO 333
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 333
uuuguagaag ggauauacan n                                          21

<210> SEQ ID NO 334
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 334
uguauauccc uucuacaaan n                                        21

<210> SEQ ID NO 335
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 335
uuguagaagg gauauacaan n                                        21

<210> SEQ ID NO 336
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 336
uuguauaucc cuucuacaan n                                        21

<210> SEQ ID NO 337
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 337
uguagaaggg auauacaaan n                                        21

<210> SEQ ID NO 338
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 338
```
uuuguauauc ccuucuacan n          21

<210> SEQ ID NO 339
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 339
agaagggaua uacaaagugn n          21

<210> SEQ ID NO 340
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 340
cacuuuguau aucccuucun n          21

<210> SEQ ID NO 341
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 341
aaguggaaau agacaccaan n          21

<210> SEQ ID NO 342
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 342
uuggugucua uuuccacuun n          21

<210> SEQ ID NO 343
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:

```
<221> NAME/KEY: modified_base
<222> LOCATION: (20)..(21)
<223> OTHER INFORMATION: a, c, t, g, unknown or other

<400> SEQUENCE: 343
ggaaauagac accaaaucun n                                              21

<210> SEQ ID NO 344
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 344
agauuuggug ucuauuuccn n                                              21

<210> SEQ ID NO 345
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 345
gaaauagaca ccaaaucuun n                                              21

<210> SEQ ID NO 346
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 346
aagauuuggu gucuauuucn n                                              21

<210> SEQ ID NO 347
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 347
auagacacca aaucuuacun n                                              21

<210> SEQ ID NO 348
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 348
aguaagauuu ggugucuaun n                                              21

<210> SEQ ID NO 349
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 349
uagacaccaa aucuuacugn n                                              21

<210> SEQ ID NO 350
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 350
caguaagauu uggugucuan n                                              21

<210> SEQ ID NO 351
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 351
agacaccaaa ucuuacuggn n                                              21

<210> SEQ ID NO 352
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 352
```
ccaguaagau uuggugucun n                                          21

<210> SEQ ID NO 353
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 353
uuacuggaag gcacuuggcn n                                          21

<210> SEQ ID NO 354
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 354
gccaagugcc uuccaguaan n                                          21

<210> SEQ ID NO 355
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 355
uucucaucgu cugcuccucn n                                          21

<210> SEQ ID NO 356
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 356
gaggagcaga cgaugagaan n                                          21

<210> SEQ ID NO 357
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens <220> FEATURE:
<221> NAME/KEY: modified_base
<222> LOCATION: (20)..(21)
<223> OTHER INFORMATION: a, c, t, g, unknown or other

<400> SEQUENCE: 357
ggaaggcacu uggcaucucn n            21

<210> SEQ ID NO 358
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 358
gagaugccaa gugccuuccn n            21

<210> SEQ ID NO 359
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 359
ggcacuuggc aucuccccan n            21

<210> SEQ ID NO 360
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 360
uggggagaug ccaagugccn n            21

<210> SEQ ID NO 361
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 361
ggcaucuccc cauuccaugn n            21

<210> SEQ ID NO 362

```
<211> LENGTH: 22
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 362
auggaauggg gagaugcctt nn                                              22

<210> SEQ ID NO 363
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 363 gcaucuccccc auuccaugan n                                              21

<210> SEQ ID NO 364
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 364
ucauggaaug gggagaugcn n                                               21

<210> SEQ ID NO 365
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 365
caucucccca uuccaugagn n                                               21

<210> SEQ ID NO 366
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

-continued

```
<400> SEQUENCE: 366
cucauggaau ggggagaugn n                                              21

<210> SEQ ID NO 367
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 367
aucuccccau uccaugagcn n                                              21

<210> SEQ ID NO 368
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 368
gcucauggaa ugggagaun n                                               21

<210> SEQ ID NO 369
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 369
cuccccauuc caugagcaun n                                              21

<210> SEQ ID NO 370
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 370
augcucaugg aaugggagn n                                               21

<210> SEQ ID NO 371
<211> LENGTH: 21
<212> TYPE: DNA
<213> ORGANISM: Homo sapiens
<220> FEATURE:
<223> OTHER INFORMATION: Description of Combined DNA/RNA Molecule:
```

```
            Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 371
cccauuccau gagcaugcan n                                                    21

<210> SEQ ID NO 372
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 372
ugcaugcuca uggaaugggn n                                                    21

<210> SEQ ID NO 373
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 373
ccaugagcau gcagaggugn n                                                    21

<210> SEQ ID NO 374
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 374
caccucugca ugcucauggn n                                                    21

<210> SEQ ID NO 375
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 375
agcaugcaga ggugguauun n                                                    21
```

-continued

```
<210> SEQ ID NO 376
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 376
aauaccaccu cugcaugcun n                                               21

<210> SEQ ID NO 377
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 377
caugcagagg ugguauucan n                                               21

<210> SEQ ID NO 378
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 378
ugaauaccac cucugcaugn n                                               21

<210> SEQ ID NO 379
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 379
augcagaggu gguauucacn n                                               21

<210> SEQ ID NO 380
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

```
<400> SEQUENCE: 380
gugaauacca ccucugcaun n                                              21

<210> SEQ ID NO 381
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 381
ggugguauuc acagccaacn n                                              21

<210> SEQ ID NO 382
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 382
guuggcugug aauaccaccn n                                              21

<210> SEQ ID NO 383
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 383
gugguauuca cagccaacgn n                                              21

<210> SEQ ID NO 384
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 384
cguuggcugu gaauaccacn n                                              21

<210> SEQ ID NO 385
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 385
ugguauucac agccaacgan n                                                    21

<210> SEQ ID NO 386
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 386
ucguuggcug ugaauaccan n                                                    21

<210> SEQ ID NO 387
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 387
gguauucaca gccaacgacn n                                                    21

<210> SEQ ID NO 388
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 388
gucguuggcu gugaauaccn n                                                    21

<210> SEQ ID NO 389
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 389
guauucacag ccaacgacun n                                                    21
```

```
<210> SEQ ID NO 390
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 390
agucguuggc ugugaauacn n                                             21

<210> SEQ ID NO 391
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 391
uauucacagc caacgacucn n                                             21

<210> SEQ ID NO 392
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 392
gagucguugg cugugaauan n                                             21

<210> SEQ ID NO 393
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 393
ucacagccaa cgacuccggn n                                             21

<210> SEQ ID NO 394
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
```

<223> OTHER INFORMATION: a, c, t, g, unknown or other

<400> SEQUENCE: 394
ccggagucgu uggcugugan n                                              21

<210> SEQ ID NO 395
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 395
ccccgccgcu acaccauugn n                                              21

<210> SEQ ID NO 396
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 396
caauggugua gcggcggggn n                                              21

<210> SEQ ID NO 397
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 397
gaaguccacu cauucuuggn n                                              21

<210> SEQ ID NO 398
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 398
ccaagaauga guggacuucn n                                              21

<210> SEQ ID NO 399
<211> LENGTH: 21
<212> TYPE: DNA
<213> ORGANISM: Homo sapiens

```
-continued

<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 399
cccugcugag ccccuacucn n                                              21

<210> SEQ ID NO 400
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 400
gaguaggggc ucagcagggn n                                              21

<210> SEQ ID NO 401
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 401
cugagccccu acuccuauun n                                              21

<210> SEQ ID NO 402
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 402
aauaggagua ggggcucagn n                                              21

<210> SEQ ID NO 403
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 403
ugagccccua cuccuauucn n                                              21
```

<210> SEQ ID NO 404
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 404
gaauaggagu aggggcucan n                                      21

<210> SEQ ID NO 405
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 405
ccccuacucc uauuccaccn n                                      21

<210> SEQ ID NO 406
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 406
gguggaauag gaguaggggn n                                      21

<210> SEQ ID NO 407
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 407
cuacuccuau uccaccacgn n                                      21

<210> SEQ ID NO 408
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base

```
<222> LOCATION: (20)..(21)
<223> OTHER INFORMATION: a, c, t, g, unknown or other

<400> SEQUENCE: 408
cgugguggaa uaggaguagn n                                              21

<210> SEQ ID NO 409
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 409
uacuccuauu ccaccacggn n                                              21

<210> SEQ ID NO 410
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 410
ccguggugga auaggaguan n                                              21

<210> SEQ ID NO 411
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 411
acuccuauuc caccacggcn n                                              21

<210> SEQ ID NO 412
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 412
gccguggugg aauaggagun n                                              21

<210> SEQ ID NO 413
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 413
uccuauucca ccacggcugn n                                           21

<210> SEQ ID NO 414
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 414
cagccguggu ggaauaggan n                                           21

<210> SEQ ID NO 415
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 415
uauuccacca cggcugucgn n                                           21

<210> SEQ ID NO 416
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 416
cgacagccgu gguggaauan n                                           21

<210> SEQ ID NO 417
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 417
```
auuccaccac ggcugucgun n                                             21

<210> SEQ ID NO 418
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 418
acgacagccg ugguggaaun n                                             21

<210> SEQ ID NO 419
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 419
caccacggcu gucgucaccn n                                             21

<210> SEQ ID NO 420
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 420
ggugacgaca gccguggugn n                                             21

<210> SEQ ID NO 421
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 421
accacggcug ucgucaccan n                                             21

<210> SEQ ID NO 422
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:

<221> NAME/KEY: modified_base
<222> LOCATION: (20)..(21)
<223> OTHER INFORMATION: a, c, t, g, unknown or other

<400> SEQUENCE: 422
uggugacgac agccguggun n                                              21

<210> SEQ ID NO 423
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 423
ccacggcugu cgucaccaan n                                              21

<210> SEQ ID NO 424
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 424
uuggugacga cagccguggn n                                              21

<210> SEQ ID NO 425
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 425
acggcugucg ucaccaaucn n                                              21

<210> SEQ ID NO 426
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 426
gauuggugac gacagccgun n                                              21

<210> SEQ ID NO 427
<211> LENGTH: 21

```
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 427
cggcugucgu caccaauccn n                                            21

<210> SEQ ID NO 428
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 428
ggauugguga cgacagccgn n                                            21

<210> SEQ ID NO 429
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 429
cgucaccaau cccaaggaan n                                            21

<210> SEQ ID NO 430
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 430
uuccuuggga uuggugacgn n                                            21

<210> SEQ ID NO 431
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 431
```
caaucccaag gaaugagggn n 21

<210> SEQ ID NO 432
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 432
cccucauucc uugggauugn n 21

<210> SEQ ID NO 433
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 433
ccugaaggac gagggauggn n 21

<210> SEQ ID NO 434
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 434
ccaucccucg uccuucaggn n 21

<210> SEQ ID NO 435
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 435
ggacgaggga ugggauuucn n 21

<210> SEQ ID NO 436
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens -continued

```
<220> FEATURE:
<221> NAME/KEY: modified_base
<222> LOCATION: (20)..(21)
<223> OTHER INFORMATION: a, c, t, g, unknown or other

<400> SEQUENCE: 436
gaaaucccau cccucguccn n                                              21

<210> SEQ ID NO 437
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 437
aaguccacuc auucuuggcn n                                              21

<210> SEQ ID NO 438
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 438
gccaagaaug aguggacuun n                                              21

<210> SEQ ID NO 439
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 439
gggauuucau guaaccaagn n                                              21

<210> SEQ ID NO 440
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 440
cuugguuaca ugaaucccn n                                               21

<210> SEQ ID NO 441
```

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 441
ggauuucaug uaaccaagan n                                        21

<210> SEQ ID NO 442
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 442
ucuugguuac augaaauccn n                                        21

<210> SEQ ID NO 443
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 443
ucauguaacc aagaguauun n                                        21

<210> SEQ ID NO 444
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 444
aauacucuug guuacaugan n                                        21

<210> SEQ ID NO 445
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

<400> SEQUENCE: 445
auguaaccaa gaguauuccn n                                              21

<210> SEQ ID NO 446
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 446
ggaauacucu ugguuacaun n                                              21

<210> SEQ ID NO 447
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 447
uguaaccaag aguauuccan n                                              21

<210> SEQ ID NO 448
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 448
uggaauacuc uugguuacan n                                              21

<210> SEQ ID NO 449
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 449
guaaccaaga guauuccaun n                                              21

<210> SEQ ID NO 450
<211> LENGTH: 21
<212> TYPE: DNA
<213> ORGANISM: Homo sapiens
<220> FEATURE:
<223> OTHER INFORMATION: Description of Combined DNA/RNA Molecule:

Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 450
auggaauacu cuugguuacn n                                              21

<210> SEQ ID NO 451
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 451
ugccuugcug gacugguaun n                                              21

<210> SEQ ID NO 452
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 452
auaccagucc agcaaggcan n                                              21

<210> SEQ ID NO 453
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 453
uaaagcagug uuuucaccun n                                              21

<210> SEQ ID NO 454
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 454
aggugaaaac acugcuuuan n                                              21

-continued

```
<210> SEQ ID NO 455
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 455
gccuugcugg acugguauun n                                              21

<210> SEQ ID NO 456
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 456
aauaccaguc cagcaaggcn n                                              21

<210> SEQ ID NO 457
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 457
uguuuucacc ucauaugcun n                                              21

<210> SEQ ID NO 458
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 458
agcauaugag gugaaaacan n                                              21

<210> SEQ ID NO 459
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

```
<400> SEQUENCE: 459
guuuucaccu cauaugcuan n                                          21

<210> SEQ ID NO 460
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 460
uagcauauga ggugaaaacn n                                          21

<210> SEQ ID NO 461
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 461
uuuucaccuc auaugcuaun n                                          21

<210> SEQ ID NO 462
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 462
auagcauaug aggugaaaan n                                          21

<210> SEQ ID NO 463
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 463
uucaccucau augcuaugun n                                          21

<210> SEQ ID NO 464
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 464
acauagcaua ugaggugaan n                                           21

<210> SEQ ID NO 465
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 465
caccucauau gcuauguuan n                                           21

<210> SEQ ID NO 466
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 466
uaacauagca uaugaggugn n                                           21

<210> SEQ ID NO 467
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 467
ccuugcugga cugguauuun n                                           21

<210> SEQ ID NO 468
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 468
aaauaccagu ccagcaaggn n                                           21
```

```
<210> SEQ ID NO 469
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 469
auaugcuaug uuagaagucn n                                              21

<210> SEQ ID NO 470
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 470
gacuucuaac auagcauaun n                                              21

<210> SEQ ID NO 471
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 471
uaugcuaugu uagaaguccn n                                              21

<210> SEQ ID NO 472
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 472
ggacuucuaa cauagcauan n                                              21

<210> SEQ ID NO 473
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
```

-continued

<223> OTHER INFORMATION: a, c, t, g, unknown or other

<400> SEQUENCE: 473
ugcuauguua gaaguccagn n                              21

<210> SEQ ID NO 474
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 474
cuggacuucu aacauagcan n                              21

<210> SEQ ID NO 475
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 475
cuugcuggac ugguauuugn n                              21

<210> SEQ ID NO 476
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 476
caaauaccag uccagcaagn n                              21

<210> SEQ ID NO 477
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 477
aguccaggca gagacaauan n                              21

<210> SEQ ID NO 478
<211> LENGTH: 22
<212> TYPE: DNA
<213> ORGANISM: Homo sapiens

```
<220> FEATURE:
<223> OTHER INFORMATION: Description of Combined DNA/RNA Molecule:
      Homo sapiens
<220> FEATURE:
<221> NAME/KEY: modified_base
<222> LOCATION: (21)..(22)
<223> OTHER INFORMATION: a, c, t, g, unknown or other

<400> SEQUENCE: 478
auugucucug ccuggacutt nn                                                  22

<210> SEQ ID NO 479
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 479
uccaggcaga gacaauaaan n                                                   21

<210> SEQ ID NO 480
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 480
uuuauugucu cugccuggan n                                                   21

<210> SEQ ID NO 481
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 481
gugaaaggca cuuuucauun n                                                   21

<210> SEQ ID NO 482
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 482
aaugaaaagu gccuuucacn n                                                   21
```

```
<210> SEQ ID NO 483
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 483
uggacuggua uuugugucun n                                               21

<210> SEQ ID NO 484
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 484
agacacaaau accaguccan n                                               21

<210> SEQ ID NO 485
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 485
gucugaggcu ggcccuacgn n                                               21

<210> SEQ ID NO 486
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 486
cguagggcca gccucagacn n                                               21

<210> SEQ ID NO 487
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
```

-continued

<222> LOCATION: (20)..(21)
<223> OTHER INFORMATION: a, c, t, g, unknown or other

<400> SEQUENCE: 487
cugaggcugg cccuacgggn n                                              21

<210> SEQ ID NO 488
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 488 cccguaggc cagccucagn n                                               21

<210> SEQ ID NO 489
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 489
gaggcuggcc cuacgggcan n                                              21

<210> SEQ ID NO 490
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 490
ugcccguagg gccagccucn n                                              21

<210> SEQ ID NO 491
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 491
aggcuggccc uacgggcacn n                                              21

<210> SEQ ID NO 492
<211> LENGTH: 21
<212> TYPE: DNA

-continued

<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 492
gugcccguag ggccagccun n                                              21

<210> SEQ ID NO 493
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 493
gcuggcccua cgggcaccgn n                                              21

<210> SEQ ID NO 494
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 494
cggugcccgu agggccagcn n                                              21

<210> SEQ ID NO 495
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 495
cuggcccuac gggcaccggn n                                              21

<210> SEQ ID NO 496
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 496
ccggugcccg uagggccagn n                                       21

<210> SEQ ID NO 497
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 497
ggcccuacgg gcaccggugn n                                       21

<210> SEQ ID NO 498
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 498
caccggugcc cguagggccn n                                       21

<210> SEQ ID NO 499
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 499
ccacucauuc uuggcaggan n                                       21

<210> SEQ ID NO 500
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 500
uccugccaag aaugaguggn n                                       21

<210> SEQ ID NO 501
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:

```
<221> NAME/KEY: modified_base
<222> LOCATION: (20)..(21)
<223> OTHER INFORMATION: a, c, t, g, unknown or other

<400> SEQUENCE: 501
ccuacgggca ccggugaaun n                                              21

<210> SEQ ID NO 502
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 502
auucaccggu gcccguaggn n                                              21

<210> SEQ ID NO 503
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 503
cuacgggcac cggugaaucn n                                              21

<210> SEQ ID NO 504
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 504
gauucaccgg ugcccguagn n                                              21

<210> SEQ ID NO 505
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 505
uacgggcacc ggugaauccn n                                              21

<210> SEQ ID NO 506
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 506
ggauucaccg gugcccguan n                                            21

<210> SEQ ID NO 507
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 507
acgggcaccg gugaauccan n                                            21

<210> SEQ ID NO 508
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 508
uggauucacc ggugcccgun n                                            21

<210> SEQ ID NO 509
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 509
gcaccgguga auccaagugn n                                            21

<210> SEQ ID NO 510
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 510
```
cacuuggauu caccggugcn n                                              21

<210> SEQ ID NO 511
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 511
caccggugaa uccaagugun n                                              21

<210> SEQ ID NO 512
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 512
acacuuggau ucaccggugn n                                              21

<210> SEQ ID NO 513
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 513
uguggccaug cauguguucn n                                              21

<210> SEQ ID NO 514
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 514
gaacacaugc auggccacan n                                              21

<210> SEQ ID NO 515
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens -continued

```
<220> FEATURE:
<221> NAME/KEY: modified_base
<222> LOCATION: (20)..(21)
<223> OTHER INFORMATION: a, c, t, g, unknown or other

<400> SEQUENCE: 515
guggccaugc auguguucan n                                              21

<210> SEQ ID NO 516
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 516
ugaacacaug cauggccacn n                                              21

<210> SEQ ID NO 517
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 517
gccaugcaug uguucagaan n                                              21

<210> SEQ ID NO 518
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 518
uucugaacac augcauggcn n                                              21

<210> SEQ ID NO 519
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 519
uauuccacca cggcugucan n                                              21

<210> SEQ ID NO 520
```

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 520
ugacagccgu gguggaauan n                                              21

<210> SEQ ID NO 521
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 521
gucaucacca aucccaaggn n                                              21

<210> SEQ ID NO 522
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 522
ccuugggauu ggugaugacn n                                              21

<210> SEQ ID NO 523
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 523
guccucugau ggucaaagun n                                              21

<210> SEQ ID NO 524
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

```
<400> SEQUENCE: 524
acuuugacca ucagaggacn n                                              21

<210> SEQ ID NO 525
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 525
gauggucaaa guucuagaun n                                              21

<210> SEQ ID NO 526
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 526
aucuagaacu uugaccaucn n                                              21

<210> SEQ ID NO 527
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 527
augcuguccg aggcaguccn n                                              21

<210> SEQ ID NO 528
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 528
ggacugccuc ggacagcaun n                                              21

<210> SEQ ID NO 529
<211> LENGTH: 21
<212> TYPE: DNA
<213> ORGANISM: Homo sapiens
<220> FEATURE:
<223> OTHER INFORMATION: Description of Combined DNA/RNA Molecule:
```

-continued

Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 529
ccgugcaugu guucagaaan n                                              21

<210> SEQ ID NO 530
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 530
uuucugaaca caugcacggn n                                              21

<210> SEQ ID NO 531
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 531
agucuggaga gcugcauggn n                                              21

<210> SEQ ID NO 532
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 532
ccaugcagcu cuccagacun n                                              21

<210> SEQ ID NO 533
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 533
caugggcuca caacugaggn n                                              21

-continued

```
<210> SEQ ID NO 534
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 534
ccucaguugu gagcccaugn n                                              21

<210> SEQ ID NO 535
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 535
ucucaucguc ugcuccuccn n                                              21

<210> SEQ ID NO 536
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 536
ggaggagcag acgaugagan n                                              21

<210> SEQ ID NO 537
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 537
ccccauucca ugagcaugcn n                                              21

<210> SEQ ID NO 538
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other
```

```
<400> SEQUENCE: 538
gcaugcucau ggaauggggn n                                              21

<210> SEQ ID NO 539
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 539
gccccuacuc cuauuccacn n                                              21

<210> SEQ ID NO 540
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 540
guggaauagg aguagggcn n                                               21

<210> SEQ ID NO 541
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 541
cuauuccacc acggcugucn n                                              21

<210> SEQ ID NO 542
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 542
gacagccgug guggaauagn n                                              21

<210> SEQ ID NO 543
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 543
cacggcuguc gucaccaaun n                                                  21

<210> SEQ ID NO 544
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 544
auuggugacg acagccgugn n                                                  21

<210> SEQ ID NO 545
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 545
aggacgaggg augggauuun n                                                  21

<210> SEQ ID NO 546
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 546
aaaucccauc ccucguccun n                                                  21

<210> SEQ ID NO 547
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 547
ucaccucaua ugcuauguun n                                                  21
```

<210> SEQ ID NO 548
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 548
aacauagcau augaggugan n                                              21

<210> SEQ ID NO 549
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 549
ccucauaugc uauguuagan n                                              21

<210> SEQ ID NO 550
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 550
ucuaacauag cauaugaggn n                                              21

<210> SEQ ID NO 551
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 551
auguuagaag uccaggcagn n                                              21

<210> SEQ ID NO 552
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)

<223> OTHER INFORMATION: a, c, t, g, unknown or other

<400> SEQUENCE: 552
cugccuggac uucuaacaun n                                              21

<210> SEQ ID NO 553
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 553
ucugaggcug gcccuacggn n                                              21

<210> SEQ ID NO 554
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 554
ccguagggcc agccucagan n                                              21

<210> SEQ ID NO 555
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 555
ggcccuacgg gcaccggugn n                                              21

<210> SEQ ID NO 556
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 556
caccggugcc cguagggccn n                                              21

<210> SEQ ID NO 557
<211> LENGTH: 21
<212> TYPE: DNA
<213> ORGANISM: Homo sapiens

```
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 557
gggcaccggu gaauccaagn n                                              21

<210> SEQ ID NO 558
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 558
cuuggauuca ccggugcccn n                                              21

<210> SEQ ID NO 559
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 559
ccaugcaugu guucagaaan n                                              21

<210> SEQ ID NO 560
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
<220> FEATURE:
<221> NAME/KEY: modified_base
<222> LOCATION: (20)..(21)
<223> OTHER INFORMATION: a, c, t, g, unknown or other

<400> SEQUENCE: 560
uuucugaaca caugcauggn n                                              21

<210> SEQ ID NO 561
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 561
ccggugaauc caagugucct t                                              21

<210> SEQ ID NO 562
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 562
ggacacuugg auucaccggt t                                              21

<210> SEQ ID NO 563
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 563
acucauucuu ggcaggaugt t                                              21

<210> SEQ ID NO 564
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 564
cauccugcca agaaugagut t                                              21

<210> SEQ ID NO 565
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 565
aaguguccuc ugauggucat t                                              21

<210> SEQ ID NO 566
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 566
ugaccaucag aggacacuut t                                              21

<210> SEQ ID NO 567
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 567
ucauucuugg caggauggct t                                              21

<210> SEQ ID NO 568
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens

<400> SEQUENCE: 568
gccauccugc caagaaugat t                                              21

<210> SEQ ID NO 569
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 569
aaguucuaga ugcuguccgt t                                              21

<210> SEQ ID NO 570
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 570
cggacagcau cuagaacuut t                                              21

<210> SEQ ID NO 571
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 571
guucuagaug cuguccgagt t                                              21

<210> SEQ ID NO 572
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 572
cucggacagc aucuagaact t                                              21

<210> SEQ ID NO 573
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 573
cuagaugcug uccgaggcat t                                              21

<210> SEQ ID NO 574
<211> LENGTH: 21
<212> TYPE: DNA
<213> ORGANISM: Homo sapiens
```

```
<220> FEATURE:
<223> OTHER INFORMATION: Description of Combined DNA/RNA Molecule:
      Homo sapiens

<400> SEQUENCE: 574
ugccucggac agcaucuagt t                                              21

<210> SEQ ID NO 575
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 575
gaugcugucc gaggcaguct t                                              21

<210> SEQ ID NO 576
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 576
gacugccucg gacagcauct t                                              21

<210> SEQ ID NO 577
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 577
cauucuuggc aggauggcut t                                              21

<210> SEQ ID NO 578
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 578
agccauccug ccaagaaugt t                                              21

<210> SEQ ID NO 579
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 579
ugcuguccga ggcaguccut t                                              21

<210> SEQ ID NO 580
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens

<400> SEQUENCE: 580
aggacugccu cggacagcat t                                              21

<210> SEQ ID NO 581
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 581
ccgaggcagu ccugccauct t                                              21

<210> SEQ ID NO 582
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 582
gauggcagga cugccucggt t                                              21

<210> SEQ ID NO 583
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 583
caguccugcc aucaaugugt t                                              21

<210> SEQ ID NO 584
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 584
cacauugaug gcaggacugt t                                              21

<210> SEQ ID NO 585
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 585
caauguggcc gugcaugugt t                                              21

<210> SEQ ID NO 586
<211> LENGTH: 21
<212> TYPE: DNA
<213> ORGANISM: Homo sapiens
<220> FEATURE:
<223> OTHER INFORMATION: Description of Combined DNA/RNA Molecule:
```

Homo sapiens

<400> SEQUENCE: 586
cacaugcacg gccacauugt t                                              21

<210> SEQ ID NO 587
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 587
auguguucag aaaggcugct t                                              21

<210> SEQ ID NO 588
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 588
gcagccuuuc ugaacacaut t                                              21

<210> SEQ ID NO 589
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 589
cagaagucca cucauucuut t                                              21

<210> SEQ ID NO 590
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 590
aagaaugagu ggacuucugt t                                              21

<210> SEQ ID NO 591
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 591
ggcaggaugg cuucucauct t                                              21

<210> SEQ ID NO 592
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 592
gaugagaagc cauccugcct t                                              21

<210> SEQ ID NO 593
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 593
gagccauuug ccucugggat t                                              21

<210> SEQ ID NO 594
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 594
ucccagaggc aaauggcuct t                                              21

<210> SEQ ID NO 595
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 595
caggauggcu ucucaucgut t                                              21

<210> SEQ ID NO 596
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 596
acgaugagaa gccauccugt t                                              21

<210> SEQ ID NO 597
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 597
aggauggcuu cucaucguct t                                              21

<210> SEQ ID NO 598
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 598
gacgaugaga agccauccut t                                              21

<210> SEQ ID NO 599
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 599
agagcugcau gggcucacat t                                              21

<210> SEQ ID NO 600
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 600
ugugagccca ugcagcucut t                                              21

<210> SEQ ID NO 601
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 601
gcugcauggg cucacaacut t                                              21

<210> SEQ ID NO 602
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 602
aguugugagc ccaugcagct t                                              21

<210> SEQ ID NO 603
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 603
ggauggcuuc ucaucgucut t                                              21

<210> SEQ ID NO 604
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 604
```
agacgaugag aagccaucct t                                            21

<210> SEQ ID NO 605
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 605
gcaugggcuc acaacugagt t                                            21

<210> SEQ ID NO 606
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 606
cucaguugug agcccaugct t                                            21

<210> SEQ ID NO 607
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 607
augggcucac aacugaggat t                                            21

<210> SEQ ID NO 608
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 608
uccucaguug ugagcccaut t                                            21

<210> SEQ ID NO 609
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 609
ugggcucaca acugaggagt t                                            21

<210> SEQ ID NO 610
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 610

```
cuccucaguu gugagcccat t                                              21

<210> SEQ ID NO 611
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 611
gaggaauuug uagaagggat t                                              21

<210> SEQ ID NO 612
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 612
ucccuucuac aaauuccuct t                                              21

<210> SEQ ID NO 613
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 613
uuuguagaag ggauauacat t                                              21

<210> SEQ ID NO 614
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 614
uguauauccc uucuacaaat t                                              21

<210> SEQ ID NO 615
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 615
uuguagaagg gauauacaat t                                              21

<210> SEQ ID NO 616
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 616
uuguauaucc cuucuacaat t                                              21
```

-continued

<210> SEQ ID NO 617
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 617
uguagaaggg auauacaaat t                                                 21

<210> SEQ ID NO 618
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 618
uuuguauauc ccuucuacat t                                                 21

<210> SEQ ID NO 619
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 619
agaagggaua uacaaagugt t                                                 21

<210> SEQ ID NO 620
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 620
cacuuuguau aucccuucut t                                                 21

<210> SEQ ID NO 621
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 621
aaguggaaau agacaccaat t                                                 21

<210> SEQ ID NO 622
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 622
uuggugucua uuuccacuut t                                                 21

<210> SEQ ID NO 623
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 623
ggaaauagac accaaaucut t                                              21

<210> SEQ ID NO 624
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 624
agauuuggug ucuauuucct t                                              21

<210> SEQ ID NO 625
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 625
gaaauagaca ccaaaucuut t                                              21

<210> SEQ ID NO 626
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 626
aagauuuggu gucuauuuct t                                              21

<210> SEQ ID NO 627
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 627
auagacacca aaucuuacut t                                              21

<210> SEQ ID NO 628
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 628
aguaagauuu ggugucuaut t                                              21

-continued

<210> SEQ ID NO 629
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 629
uagacaccaa aucuuacugt t                                              21

<210> SEQ ID NO 630
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 630
caguaagauu uggugucuat t                                              21

<210> SEQ ID NO 631
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 631
agacaccaaa ucuuacuggt t                                              21

<210> SEQ ID NO 632
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 632
ccaguaagau uggugucut t                                               21

<210> SEQ ID NO 633
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 633
uuacuggaag gcacuuggct t                                              21

<210> SEQ ID NO 634
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 634
gccaagugcc uuccaguaat t                                              21

<210> SEQ ID NO 635

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 635
uucucaucgu cugcuccuct t                                              21

<210> SEQ ID NO 636
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 636
gaggagcaga cgaugagaat t                                              21

<210> SEQ ID NO 637
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 637
ggaaggcacu uggcaucuct t                                              21

<210> SEQ ID NO 638
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 638
gagaugccaa gugccuucct t                                              21

<210> SEQ ID NO 639
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 639
ggcacuuggc aucccccat t                                               21

<210> SEQ ID NO 640
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 640 ugggggagaug ccaagugcct t                                             21

<210> SEQ ID NO 641
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 641
ggcaucuccc cauuccaugt t                                              21

<210> SEQ ID NO 642
<211> LENGTH: 22
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 642
auggaauggg gagaugcctt tt                                             22

<210> SEQ ID NO 643
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 643 gcaucuccccc auuccaugat t                                             21

<210> SEQ ID NO 644
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 644
ucauggaaug gggagaugct t                                              21

<210> SEQ ID NO 645
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 645
caucucccca uuccaugagt t                                              21

<210> SEQ ID NO 646
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 646
cucauggaau ggggagaugt t                                              21

<210> SEQ ID NO 647
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens

<400> SEQUENCE: 647 aucucccau uccaugagct t                                              21

<210> SEQ ID NO 648
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 648
gcucauggaa ugggagaut t                                              21

<210> SEQ ID NO 649
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 649
cuccccauuc caugagcaut t                                             21

<210> SEQ ID NO 650
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 650
augcucaugg aaugggagt t                                              21

<210> SEQ ID NO 651
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 651
cccauuccau gagcaugcat t                                             21

<210> SEQ ID NO 652
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 652
ugcaugcuca uggaaugggt t                                             21

<210> SEQ ID NO 653
<211> LENGTH: 21
<212> TYPE: DNA
<213> ORGANISM: Homo sapiens
```

```
<220> FEATURE:
<223> OTHER INFORMATION: Description of Combined DNA/RNA Molecule:
      Homo sapiens

<400> SEQUENCE: 653
ccaugagcau gcagaggugt t                                              21

<210> SEQ ID NO 654
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 654
caccucugca ugcucauggt t                                              21

<210> SEQ ID NO 655
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 655
agcaugcaga ggugguauut t                                              21

<210> SEQ ID NO 656
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 656
aauaccaccu cugcaugcut t                                              21

<210> SEQ ID NO 657
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 657
caugcagagg ugguauucat t                                              21

<210> SEQ ID NO 658
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 658
ugaauaccac cucugcaugt t                                              21

<210> SEQ ID NO 659
<211> LENGTH: 21
<212> TYPE: DNA
<213> ORGANISM: Homo sapiens
<220> FEATURE:
```

<223> OTHER INFORMATION: Description of Combined DNA/RNA Molecule:
     Homo sapiens

<400> SEQUENCE: 659
augcagaggu gguauucact t                                              21

<210> SEQ ID NO 660
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 660
gugaauacca ccucugcaut t                                              21

<210> SEQ ID NO 661
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 661
ggugguauuc acagccaact t                                              21

<210> SEQ ID NO 662
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 662
guuggcugug aauaccacct t                                              21

<210> SEQ ID NO 663
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 663
gugguauuca cagccaacgt t                                              21

<210> SEQ ID NO 664
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 664
cguuggcugu gaauaccact t                                              21

<210> SEQ ID NO 665
<211> LENGTH: 21
<212> TYPE: DNA
<213> ORGANISM: Homo sapiens
<220> FEATURE:
<223> OTHER INFORMATION: Description of Combined DNA/RNA Molecule:

Homo sapiens

<400> SEQUENCE: 665
ugguauucac agccaacgat t                                         21

<210> SEQ ID NO 666
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 666
ucguuggcug ugaauaccat t                                         21

<210> SEQ ID NO 667
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 667
gguauucaca gccaacgact t                                         21

<210> SEQ ID NO 668
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 668
gucguuggcu gugaauacct t                                         21

<210> SEQ ID NO 669
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 669
guauucacag ccaacgacut t                                         21

<210> SEQ ID NO 670
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 670
agucguuggc ugugaauact t                                         21

<210> SEQ ID NO 671
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 671
uauucacagc caacgacucu t                                           21

<210> SEQ ID NO 672
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 672
gagucguugg cugugaauau t                                           21

<210> SEQ ID NO 673
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 673
ucacagccaa cgacuccggt t                                           21

<210> SEQ ID NO 674
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 674
ccggagucgu uggcugugat t                                           21

<210> SEQ ID NO 675
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 675
ccccgccgcu acaccauugt t                                           21

<210> SEQ ID NO 676
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 676
caauggugua gcggcggggt t                                           21

<210> SEQ ID NO 677
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
```

<400> SEQUENCE: 677
gaaguccacu cauucuuggt t                                              21

<210> SEQ ID NO 678
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 678
ccaagaauga guggacuuct t                                              21

<210> SEQ ID NO 679
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 679
cccugcugag ccccuacuct t                                              21

<210> SEQ ID NO 680
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 680
gaguaggggc ucagcagggt t                                              21

<210> SEQ ID NO 681
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 681
cugagccccu acuccuauut t                                              21

<210> SEQ ID NO 682
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 682
aauaggagua ggggcucagt t                                              21

<210> SEQ ID NO 683
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 683 ugagcccua cuccuauuct t                                              21

<210> SEQ ID NO 684
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 684
gaauaggagu aggggcucat t                                             21

<210> SEQ ID NO 685
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 685
ccccuacucc uauuccacct t                                             21

<210> SEQ ID NO 686
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 686
gguggaauag gaguaggggt t                                             21

<210> SEQ ID NO 687
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 687
cuacuccuau uccaccacgt t                                             21

<210> SEQ ID NO 688
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 688
cgugguggaa uaggaguagt t                                             21

<210> SEQ ID NO 689
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 689
uacuccuauu ccaccacggt t                                              21

<210> SEQ ID NO 690
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 690
ccguggugga auaggaguat t                                              21

<210> SEQ ID NO 691
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 691
acuccuauuc caccacggct t                                              21

<210> SEQ ID NO 692
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 692
gccguggugg aauaggagut t                                              21

<210> SEQ ID NO 693
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 693
uccuauucca ccacggcugt t                                              21

<210> SEQ ID NO 694
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 694
cagccguggu ggaauaggat t                                              21

<210> SEQ ID NO 695
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 695
uauuccacca cggcugucgt t                                              21

```
<210> SEQ ID NO 696
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 696
cgacagccgu gguggaauat t                                               21

<210> SEQ ID NO 697
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 697
auuccaccac ggcugucgut t                                               21

<210> SEQ ID NO 698
<211> LENGTH: 21
<212> TYPE: DNA
<213> ORGANISM: Homo sapiens
<220> FEATURE:
<221> NAME/KEY: source
<223> OTHER INFORMATION: Description of Combined DNA/RNA Molecule:
      Homo sapiens

<400> SEQUENCE: 698
acgacagccg ugguggaaut t                                               21

<210> SEQ ID NO 699
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 699
caccacggcu gucgucacct t                                               21

<210> SEQ ID NO 700
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 700
ggugacgaca gccguggugt t                                               21

<210> SEQ ID NO 701
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 701
accacggcug ucgucaccat t                                               21
```

```
<210> SEQ ID NO 702
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 702
uggugacgac agccguggut t                                             21

<210> SEQ ID NO 703
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 703
ccacggcugu cgucaccaat t                                             21

<210> SEQ ID NO 704
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 704
uuggugacga cagccguggt t                                             21

<210> SEQ ID NO 705
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 705
acggcugucg ucaccaauct t                                             21

<210> SEQ ID NO 706
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 706
gauuggugac gacagccgut t                                             21

<210> SEQ ID NO 707
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 707
cggcugucgu caccaaucct t                                             21
```

```
<210> SEQ ID NO 708
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 708
ggauugguga cgacagccgt t                                             21

<210> SEQ ID NO 709
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 709
cgucaccaau cccaaggaat t                                             21

<210> SEQ ID NO 710
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 710
uuccuuggga uuggugacgt t                                             21

<210> SEQ ID NO 711
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 711
caaucccaag gaaugagggt t                                             21

<210> SEQ ID NO 712
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 712
cccucauucc uugggauugt t                                             21

<210> SEQ ID NO 713
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 713
ccugaaggac gagggauggt t                                             21
```

```
<210> SEQ ID NO 714
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 714
ccaucccucg uccuucaggt t                                              21

<210> SEQ ID NO 715
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 715
ggacgaggga ugggauuuct t                                              21

<210> SEQ ID NO 716
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 716
gaaaucccau cccucguccct t                                             21

<210> SEQ ID NO 717
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 717
aaguccacuc auucuuggct t                                              21

<210> SEQ ID NO 718
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 718
gccaagaaug aguggacuut t                                              21

<210> SEQ ID NO 719
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 719
gggauuucau guaaccaagt t                                              21

<210> SEQ ID NO 720
```

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 720
cuugguuaca ugaaauccct t                                             21

<210> SEQ ID NO 721
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 721
ggauuucaug uaaccaagat t                                             21

<210> SEQ ID NO 722
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 722
ucuugguuac augaaaucct t                                             21

<210> SEQ ID NO 723
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 723
ucauguaacc aagaguauut t                                             21

<210> SEQ ID NO 724
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 724
aauacucuug guuacaugat t                                             21

<210> SEQ ID NO 725
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 725
auguaaccaa gaguauucct t                                             21

<210> SEQ ID NO 726
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 726
ggaauacucu ugguuacaut t                                              21

<210> SEQ ID NO 727
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 727
uguaaccaag aguauuccat t                                              21

<210> SEQ ID NO 728
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 728
uggaauacuc uugguuacat t                                              21

<210> SEQ ID NO 729
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 729
guaaccaaga guauuccaut t                                              21

<210> SEQ ID NO 730
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 730
auggaauacu cuugguuact t                                              21

<210> SEQ ID NO 731
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 731
ugccuugcug gacuggauut t                                              21

<210> SEQ ID NO 732
<211> LENGTH: 21
<212> TYPE: DNA
```

<213> ORGANISM: Homo sapiens
<220> FEATURE:
<223> OTHER INFORMATION: Description of Combined DNA/RNA Molecule:
      Homo sapiens

<400> SEQUENCE: 732
auaccagucc agcaaggcat t                                              21

<210> SEQ ID NO 733
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 733
uaaagcagug uuuucaccut t                                              21

<210> SEQ ID NO 734
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 734
aggugaaaac acugcuuuat t                                              21

<210> SEQ ID NO 735
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 735
gccuugcugg acugguauut t                                              21

<210> SEQ ID NO 736
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 736
aauaccaguc cagcaaggct t                                              21

<210> SEQ ID NO 737
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 737
uguuuucacc ucauaugcut t                                              21

<210> SEQ ID NO 738
<211> LENGTH: 21
<212> TYPE: DNA
<213> ORGANISM: Homo sapiens

```
<220> FEATURE:
<223> OTHER INFORMATION: Description of Combined DNA/RNA Molecule:
      Homo sapiens

<400> SEQUENCE: 738
agcauaugag gugaaaacat t                                              21

<210> SEQ ID NO 739
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 739 guuucaccu cauaugcuat t                                               21

<210> SEQ ID NO 740
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 740
uagcauauga ggugaaaact t                                              21

<210> SEQ ID NO 741
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 741
uuuucaccuc auaugcuaut t                                              21

<210> SEQ ID NO 742
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 742
auagcauaug aggugaaaat t                                              21

<210> SEQ ID NO 743
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 743
uucaccucau augcuaugut t                                              21

<210> SEQ ID NO 744
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens

<400> SEQUENCE: 744
acauagcaua ugaggugaat t                                              21

<210> SEQ ID NO 745
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 745
caccucauau gcuauguuat t                                              21

<210> SEQ ID NO 746
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 746
uaacauagca uaugaggugt t                                              21

<210> SEQ ID NO 747
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 747
ccuugcugga cugguauuut t                                              21

<210> SEQ ID NO 748
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 748
aaauaccagu ccagcaaggt t                                              21

<210> SEQ ID NO 749
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 749
auaugcuaug uuagaaguct t                                              21

<210> SEQ ID NO 750
<211> LENGTH: 21
<212> TYPE: DNA
<213> ORGANISM: Homo sapiens
<220> FEATURE:
<223> OTHER INFORMATION: Description of Combined DNA/RNA Molecule:
```

Homo sapiens

<400> SEQUENCE: 750
gacuucuaac auagcauaut t                                              21

<210> SEQ ID NO 751
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 751
uaugcuaugu uagaagucct t                                              21

<210> SEQ ID NO 752
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 752
ggacuucuaa cauagcauat t                                              21

<210> SEQ ID NO 753
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 753
ugcuauguua gaaguccagt t                                              21

<210> SEQ ID NO 754
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 754
cuggacuucu aacauagcat t                                              21

<210> SEQ ID NO 755
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 755
cuugcuggac ugguauuugt t                                              21

<210> SEQ ID NO 756
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 756
caaauaccag uccagcaagt t                                              21

<210> SEQ ID NO 757
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 757
aguccaggca gagacaauau t                                              21

<210> SEQ ID NO 758
<211> LENGTH: 22
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 758
auugucucug ccuggacutt tt                                             22

<210> SEQ ID NO 759
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 759
uccaggcaga gacaauaaat t                                              21

<210> SEQ ID NO 760
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 760
uuuauugucu cugccuggat t                                              21

<210> SEQ ID NO 761
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 761
gugaaaggca cuuuucauut t                                              21

<210> SEQ ID NO 762
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
```

-continued

```
<400> SEQUENCE: 762
aaugaaaagu gccuuucact t                                              21

<210> SEQ ID NO 763
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 763
uggacuggua uuugugucut t                                              21

<210> SEQ ID NO 764
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 764
agacacaaau accaguccat t                                              21

<210> SEQ ID NO 765
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 765
gucugaggcu ggcccuacgt t                                              21

<210> SEQ ID NO 766
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 766
cguagggcca gccucagact t                                              21

<210> SEQ ID NO 767
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 767
cugaggcugg cccuacgggt t                                              21

<210> SEQ ID NO 768
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 768
```
cccguagggc cagccucagt t                                                    21

<210> SEQ ID NO 769
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 769
gaggcuggcc cuacgggcat t                                                    21

<210> SEQ ID NO 770
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 770
ugcccguagg gccagccuct t                                                    21

<210> SEQ ID NO 771
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 771
aggcuggccc uacgggcact t                                                    21

<210> SEQ ID NO 772
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 772
gugcccguag ggccagccut t                                                    21

<210> SEQ ID NO 773
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 773
gcuggcccua cgggcaccgt t                                                    21

<210> SEQ ID NO 774
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 774
cggugcccgu agggccagct t         21

<210> SEQ ID NO 775
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 775
cuggcccuac gggcaccggt t         21

<210> SEQ ID NO 776
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 776
ccggugcccg uagggccagt t         21

<210> SEQ ID NO 777
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 777
ggcccuacgg gcaccggugt t         21

<210> SEQ ID NO 778
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 778
caccggugcc cguagggcct t         21

<210> SEQ ID NO 779
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 779
ccacucauuc uuggcaggat t         21

<210> SEQ ID NO 780
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 780
uccugccaag aaugaguggt t         21

```
<210> SEQ ID NO 781
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 781
ccuacgggca ccggugaaut t                                             21

<210> SEQ ID NO 782
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 782
auucaccggu gcccguaggt t                                             21

<210> SEQ ID NO 783
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 783
cuacgggcac cggugaauct t                                             21

<210> SEQ ID NO 784
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 784
gauucaccgg ugcccguagt t                                             21

<210> SEQ ID NO 785
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 785
uacgggcacc ggugaaucct t                                             21

<210> SEQ ID NO 786
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 786
ggauucaccg gugcccguat t                                             21
```

```
<210> SEQ ID NO 787
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 787
acgggcaccg gugaauccat t                                              21

<210> SEQ ID NO 788
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 788
uggauucacc ggugcccgut t                                              21

<210> SEQ ID NO 789
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 789
gcaccgguga auccaagugt t                                              21

<210> SEQ ID NO 790
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 790
cacuuggauu caccggugct t                                              21

<210> SEQ ID NO 791
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 791
caccggugaa uccaagugut t                                              21

<210> SEQ ID NO 792
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 792
acacuuggau ucaccggugt t                                              21
```

```
<210> SEQ ID NO 793
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 793
uguggccaug cauguguuct t                                               21

<210> SEQ ID NO 794
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 794
gaacacaugc auggccacat t                                               21

<210> SEQ ID NO 795
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 795
guggccaugc auguuucat t                                                21

<210> SEQ ID NO 796
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 796
ugaacacaug cauggccact t                                               21

<210> SEQ ID NO 797
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 797
gccaugcaug uguucagaat t                                               21

<210> SEQ ID NO 798
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 798
uucugaacac augcauggct t                                               21

<210> SEQ ID NO 799
```

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 799
uauuccacca cggcugucat t                                            21

<210> SEQ ID NO 800
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 800
ugacagccgu gguggaauat t                                            21

<210> SEQ ID NO 801
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 801
gucaucacca aucccaaggt t                                            21

<210> SEQ ID NO 802
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 802
ccuugggauu ggugaugact t                                            21

<210> SEQ ID NO 803
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 803
guccucugau ggucaaagut t                                            21

<210> SEQ ID NO 804
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 804
acuuugacca ucagaggact t                                            21

<210> SEQ ID NO 805
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 805
gauggucaaa guucuagaut t                                              21

<210> SEQ ID NO 806
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 806
aucuagaacu uugaccauct t                                              21

<210> SEQ ID NO 807
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 807
augcuguccg aggcagucct t                                              21

<210> SEQ ID NO 808
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 808
ggacugccuc ggacagcaut t                                              21

<210> SEQ ID NO 809
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 809
ccgugcaugu guucagaaat t                                              21

<210> SEQ ID NO 810
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 810
uuucugaaca caugcacggt t                                              21

<210> SEQ ID NO 811
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens

<400> SEQUENCE: 811
agucuggaga gcugcauggt t                                              21

<210> SEQ ID NO 812
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 812
ccaugcagcu cuccagacut t                                              21

<210> SEQ ID NO 813
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 813
caugggcuca caacugaggt t                                              21

<210> SEQ ID NO 814
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 814
ccucaguugu gagcccaugt t                                              21

<210> SEQ ID NO 815
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 815
ucucaucguc ugcuccucct t                                              21

<210> SEQ ID NO 816
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 816
ggaggagcag acgaugagat t                                              21

<210> SEQ ID NO 817
<211> LENGTH: 21
<212> TYPE: DNA
<213> ORGANISM: Homo sapiens
```

```
<220> FEATURE:
<223> OTHER INFORMATION: Description of Combined DNA/RNA Molecule:
      Homo sapiens

<400> SEQUENCE: 817
ccccauucca ugagcaugct t                                              21

<210> SEQ ID NO 818
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 818
gcaugcucau ggaauggggt t                                              21

<210> SEQ ID NO 819
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 819
gccccuacuc cuauuccact t                                              21

<210> SEQ ID NO 820
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 820
guggaauagg aguaggggct t                                              21

<210> SEQ ID NO 821
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 821
cuauuccacc acggcuguct t                                              21

<210> SEQ ID NO 822
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 822
gacagccgug guggaauagt t                                              21

<210> SEQ ID NO 823
<211> LENGTH: 21
<212> TYPE: DNA
<213> ORGANISM: Homo sapiens
<220> FEATURE:
```

<223> OTHER INFORMATION: Description of Combined DNA/RNA Molecule:
    Homo sapiens

<400> SEQUENCE: 823
cacggcuguc gucaccaaut t                                              21

<210> SEQ ID NO 824
<211> LENGTH: 21
<212> TYPE: DNA
<213> ORGANISM: Homo sapiens
<220> FEATURE:
<223> OTHER INFORMATION: Description of Combined DNA/RNA Molecule:
    Homo sapiens

<400> SEQUENCE: 824
auuggugacg acagccgugt t                                              21

<210> SEQ ID NO 825
<211> LENGTH: 21
<212> TYPE: DNA
<213> ORGANISM: Homo sapiens
<220> FEATURE:
<223> OTHER INFORMATION: Description of Combined DNA/RNA Molecule:
    Homo sapiens

<400> SEQUENCE: 825
aggacgaggg augggauuut t                                              21

<210> SEQ ID NO 826
<211> LENGTH: 21
<212> TYPE: DNA
<213> ORGANISM: Homo sapiens
<220> FEATURE:
<223> OTHER INFORMATION: Description of Combined DNA/RNA Molecule:
    Homo sapiens

<400> SEQUENCE: 826
aaaucccauc ccucguccut t                                              21

<210> SEQ ID NO 827
<211> LENGTH: 21
<212> TYPE: DNA
<213> ORGANISM: Homo sapiens
<220> FEATURE:
<223> OTHER INFORMATION: Description of Combined DNA/RNA Molecule:
    Homo sapiens

<400> SEQUENCE: 827
ucaccucaua ugcuauguut t                                              21

<210> SEQ ID NO 828
<211> LENGTH: 21
<212> TYPE: DNA
<213> ORGANISM: Homo sapiens
<220> FEATURE:
<223> OTHER INFORMATION: Description of Combined DNA/RNA Molecule:
    Homo sapiens

<400> SEQUENCE: 828
aacauagcau augaggugat t                                              21

<210> SEQ ID NO 829
<211> LENGTH: 21
<212> TYPE: DNA
<213> ORGANISM: Homo sapiens
<220> FEATURE:
<223> OTHER INFORMATION: Description of Combined DNA/RNA Molecule:

Homo sapiens

<400> SEQUENCE: 829
ccucauaugc uauguuagat t                     21

<210> SEQ ID NO 830
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 830
ucuaacauag cauaugaggt t                     21

<210> SEQ ID NO 831
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 831
auguuagaag uccaggcagt t                     21

<210> SEQ ID NO 832
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 832
cugccuggac uucuaacaut t                     21

<210> SEQ ID NO 833
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 833
ucugaggcug gcccuacggt t                     21

<210> SEQ ID NO 834
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 834
ccguagggcc agccucagat t                     21

<210> SEQ ID NO 835
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 835
ggcccuacgg gcaccggugt t                                              21

<210> SEQ ID NO 836
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 836
caccggugcc cguagggcct t                                              21

<210> SEQ ID NO 837
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 837
gggcaccggu gaauccaagt t                                              21

<210> SEQ ID NO 838
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 838
cuuggauuca ccggugccct t                                              21

<210> SEQ ID NO 839
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 839
ccaugcaugu guucagaaat t                                              21

<210> SEQ ID NO 840
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 840
uuucugaaca caugcauggt t                                              21

<210> SEQ ID NO 841
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
```

```
<400> SEQUENCE: 841 ccgugaauc caagugucct t                                              21

<210> SEQ ID NO 842
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 842
ggacacuugg auucaccggt t                                             21

<210> SEQ ID NO 843
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 843
acucauucuu ggcaggaugt t                                             21

<210> SEQ ID NO 844
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 844
cauccugcca agaaugagut t                                             21

<210> SEQ ID NO 845
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 845
aaguguccuc ugauggucat t                                             21

<210> SEQ ID NO 846
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 846
ugaccaucag aggacacuut t                                             21

<210> SEQ ID NO 847
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 847
```
ucauucuugg caggauggct t                                              21

<210> SEQ ID NO 848
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 848
gccauccugc caagaaugat t                                              21

<210> SEQ ID NO 849
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 849
aaguucuaga ugcuguccgt t                                              21

<210> SEQ ID NO 850
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 850
cggacagcau cuagaacuut t                                              21

<210> SEQ ID NO 851
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 851
guucuagaug cuguccgagt t                                              21

<210> SEQ ID NO 852
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 852
cucggacagc aucuagaact t                                              21

<210> SEQ ID NO 853
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 853

-continued cuagaugcug uccgaggcat t                                    21

<210> SEQ ID NO 854
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 854
ugccucggac agcaucuagt t                                    21

<210> SEQ ID NO 855
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 855
gaugcugucc gaggcaguct t                                    21

<210> SEQ ID NO 856
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 856
gacugccucg gacagcauct t                                    21

<210> SEQ ID NO 857
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 857
cauucuuggc aggauggcut t                                    21

<210> SEQ ID NO 858
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 858
agccauccug ccaagaaugt t                                    21

<210> SEQ ID NO 859
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 859
ugcuguccga ggcaguccut t                                    21

```
<210> SEQ ID NO 860
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 860
aggacugccu cggacagcat t                                          21

<210> SEQ ID NO 861
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 861
ccgaggcagu ccugccauct t                                          21

<210> SEQ ID NO 862
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 862
gauggcagga cugccucggt t                                          21

<210> SEQ ID NO 863
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 863
caguccugcc aucaaugugt t                                          21

<210> SEQ ID NO 864
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 864
cacauugaug gcaggacugt t                                          21

<210> SEQ ID NO 865
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 865
caauguggcc gugcaugugt t                                          21
```

```
<210> SEQ ID NO 866
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 866
cacaugcacg gccacauugt t                                              21

<210> SEQ ID NO 867
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 867
auguguucag aaaggcugct t                                              21

<210> SEQ ID NO 868
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 868
gcagccuuuc ugaacacaut t                                              21

<210> SEQ ID NO 869
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 869
cagaagucca cucauucuut t                                              21

<210> SEQ ID NO 870
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 870
aagaaugagu ggacuucugt t                                              21

<210> SEQ ID NO 871
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 871
ggcaggaugg cuucucauct t                                              21
```

```
<210> SEQ ID NO 872
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 872
gaugagaagc cauccugcct t                                              21

<210> SEQ ID NO 873
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 873
gagccauuug ccucugggat t                                              21

<210> SEQ ID NO 874
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 874
ucccagaggc aaauggcuct t                                              21

<210> SEQ ID NO 875
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 875
caggauggcu ucucaucgut t                                              21

<210> SEQ ID NO 876
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 876
acgaugagaa gccauccugt t                                              21

<210> SEQ ID NO 877
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 877
aggauggcuu cucaucguct t                                              21

<210> SEQ ID NO 878
```

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 878
gacgaugaga agccauccut t                                                    21

<210> SEQ ID NO 879
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 879
agagcugcau gggcucacat t                                                    21

<210> SEQ ID NO 880
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 880
ugugagccca ugcagcucut t                                                    21

<210> SEQ ID NO 881
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 881
gcugcauggg cucacaacut t                                                    21

<210> SEQ ID NO 882
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 882
aguugugagc ccaugcagct t                                                    21

<210> SEQ ID NO 883
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 883
ggauggcuuc ucaucgucut t                                                    21

<210> SEQ ID NO 884
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 884
agacgaugag aagccaucct t                                              21

<210> SEQ ID NO 885
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 885
gcaugggcuc acaacugagt t                                              21

<210> SEQ ID NO 886
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 886
cucaguugug agcccaugct t                                              21

<210> SEQ ID NO 887
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 887
augggcucac aacugaggat t                                              21

<210> SEQ ID NO 888
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 888
uccucaguug ugagcccaut t                                              21

<210> SEQ ID NO 889
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 889
ugggcucaca acugaggagt t                                              21

<210> SEQ ID NO 890
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens

<400> SEQUENCE: 890
cuccucaguu gugagcccat t                                             21

<210> SEQ ID NO 891
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 891
gaggaauuug uagaagggat t                                             21

<210> SEQ ID NO 892
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 892
ucccuucuac aaauuccuct t                                             21

<210> SEQ ID NO 893
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 893
uuuguagaag ggauauacat t                                             21

<210> SEQ ID NO 894
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 894
uguauauccc uucuacaaat t                                             21

<210> SEQ ID NO 895
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 895
uuguagaagg gauauacaat t                                             21

<210> SEQ ID NO 896
<211> LENGTH: 21
<212> TYPE: DNA
<213> ORGANISM: Homo sapiens
```

-continued

```
<220> FEATURE:
<223> OTHER INFORMATION: Description of Combined DNA/RNA Molecule:
      Homo sapiens

<400> SEQUENCE: 896
uuguauaucc cuucuacaat t                                          21

<210> SEQ ID NO 897
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 897
uguagaaggg auauacaaat t                                          21

<210> SEQ ID NO 898
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 898
uuuguauauc ccuucuacat t                                          21

<210> SEQ ID NO 899
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 899
agaagggaua uacaaagugt t                                          21

<210> SEQ ID NO 900
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 900
cacuuuguau aucccuucut t                                          21

<210> SEQ ID NO 901
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 901
aaguggaaau agacaccaat t                                          21

<210> SEQ ID NO 902
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens

<400> SEQUENCE: 902
uuggugucua uuuccacuut t                                              21

<210> SEQ ID NO 903
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 903
ggaaauagac accaaaucut t                                              21

<210> SEQ ID NO 904
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 904
agauuuggug ucuauuucct t                                              21

<210> SEQ ID NO 905
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 905
gaaauagaca ccaaaucuut t                                              21

<210> SEQ ID NO 906
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 906
aagauuuggu gucuauuuct t                                              21

<210> SEQ ID NO 907
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 907
auagacacca aaucuuacut t                                              21

<210> SEQ ID NO 908
<211> LENGTH: 21
<212> TYPE: DNA
<213> ORGANISM: Homo sapiens
<220> FEATURE:
<223> OTHER INFORMATION: Description of Combined DNA/RNA Molecule:
```

-continued

Homo sapiens

<400> SEQUENCE: 908
aguaagauuu ggugucuaut t                                          21

<210> SEQ ID NO 909
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 909
uagacaccaa aucuuacugt t                                          21

<210> SEQ ID NO 910
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 910
caguaagauu uggugucuat t                                          21

<210> SEQ ID NO 911
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 911
agacaccaaa ucuuacuggt t                                          21

<210> SEQ ID NO 912
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 912
ccaguaagau uggugucut t                                           21

<210> SEQ ID NO 913
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 913
uuacuggaag gcacuuggct t                                          21

<210> SEQ ID NO 914
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 914
gccaagugcc uuccaguaat t                                              21

<210> SEQ ID NO 915
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 915
uucucaucgu cugcucccuct t                                             21

<210> SEQ ID NO 916
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 916
gaggagcaga cgaugagaat t                                              21

<210> SEQ ID NO 917
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 917
ggaaggcacu uggcaucuct t                                              21

<210> SEQ ID NO 918
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 918
gagaugccaa gugccuucct t                                              21

<210> SEQ ID NO 919
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 919
ggcacuuggc aucucccat t                                               21

<210> SEQ ID NO 920
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
```

<400> SEQUENCE: 920 ugggagaug ccaagugcct t                                                    21

<210> SEQ ID NO 921
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 921
ggcaucuccc cauuccaugt t                                                   21

<210> SEQ ID NO 922
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 922
cauggaaugg ggagaugcct t                                                   21

<210> SEQ ID NO 923
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 923 gcaucuccccc auuccaugat t                                                  21

<210> SEQ ID NO 924
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 924
ucauggaaug gggagaugct t                                                   21

<210> SEQ ID NO 925
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 925
caucucccca uuccaugagt t                                                   21

<210> SEQ ID NO 926
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 926

```
cucauggaau ggggagaugt t                                              21

<210> SEQ ID NO 927
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 927
aucuccccau uccaugagct t                                              21

<210> SEQ ID NO 928
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 928
gcucauggaa ugggagaut t                                               21

<210> SEQ ID NO 929
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 929
cuccccauuc caugagcaut t                                              21

<210> SEQ ID NO 930
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 930
augcucaugg aauggggagt t                                              21

<210> SEQ ID NO 931
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 931
cccauuccau gagcaugcat t                                              21

<210> SEQ ID NO 932
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 932
```

-continued ugcaugcuca uggaaugggt t                                              21

<210> SEQ ID NO 933
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 933
ccaugagcau gcagaggugt t                                              21

<210> SEQ ID NO 934
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 934
caccucugca ugcucauggt t                                              21

<210> SEQ ID NO 935
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 935
agcaugcaga ggugguauut t                                              21

<210> SEQ ID NO 936
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 936
aauaccaccu cugcaugcut t                                              21

<210> SEQ ID NO 937
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 937
caugcagagg ugguauucat t                                              21

<210> SEQ ID NO 938
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 938
ugaauaccac cucugcaugt t                                              21

```
<210> SEQ ID NO 939
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 939
augcagaggu gguauucact t                                              21

<210> SEQ ID NO 940
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 940
gugaauacca ccucugcaut t                                              21

<210> SEQ ID NO 941
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 941
ggugguauuc acagccaact t                                              21

<210> SEQ ID NO 942
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 942
guuggcugug aauaccacct t                                              21

<210> SEQ ID NO 943
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 943
gugguauuca cagccaacgt t                                              21

<210> SEQ ID NO 944
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 944
cguuggcugu gaauaccact t                                              21
```

```
<210> SEQ ID NO 945
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 945
ugguauucac agccaacgat t                                                   21

<210> SEQ ID NO 946
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 946
ucguuggcug ugaauaccat t                                                   21

<210> SEQ ID NO 947
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 947
gguauucaca gccaacgact t                                                   21

<210> SEQ ID NO 948
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 948
gucguuggcu gugaauacct t                                                   21

<210> SEQ ID NO 949
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 949
guauucacag ccaacgacut t                                                   21

<210> SEQ ID NO 950
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 950
agucguuggc ugugaauact t                                                   21
```

<210> SEQ ID NO 951
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 951
uauucacagc caacgacuct t                                              21

<210> SEQ ID NO 952
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 952
gagucguugg cugugaauat t                                              21

<210> SEQ ID NO 953
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 953
ucacagccaa cgacuccggt t                                              21

<210> SEQ ID NO 954
<211> LENGTH: 21
<212> TYPE: DNA
<213> ORGANISM: Homo sapiens
<220> FEATURE:
<221> NAME/KEY: source
<223> OTHER INFORMATION: Description of Combined DNA/RNA Molecule:
      Homo sapiens

<400> SEQUENCE: 954
ccggagucgu uggcugugat t                                              21

<210> SEQ ID NO 955
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 955
ccccgccgcu acaccauugt t                                              21

<210> SEQ ID NO 956
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 956 cauggugua gcggcggggt t                                               21

-continued

```
<210> SEQ ID NO 957
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 957
gaaguccacu cauucuuggt t                                              21

<210> SEQ ID NO 958
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 958
ccaagaauga guggacuuct t                                              21

<210> SEQ ID NO 959
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 959
cccugcugag ccccuacuct t                                              21

<210> SEQ ID NO 960
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 960
gaguaggggc ucagcagggt t                                              21

<210> SEQ ID NO 961
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 961
cugagccccu acuccuauut t                                              21

<210> SEQ ID NO 962
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 962
aauaggagua ggggcucagt t                                              21

<210> SEQ ID NO 963
```

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 963 ugagcccua cuccuauuct t                                              21

<210> SEQ ID NO 964
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 964
gaauaggagu agggcucat t                                              21

<210> SEQ ID NO 965
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 965
ccccuacucc uauuccacct t                                             21

<210> SEQ ID NO 966
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 966
gguggaauag gaguaggggt t                                             21

<210> SEQ ID NO 967
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 967
cuacuccuau uccaccacgt t                                             21

<210> SEQ ID NO 968
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 968
cgugguggaa uaggaguagt t                                             21

<210> SEQ ID NO 969
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 969
uacuccuauu ccaccacggt t                                             21

<210> SEQ ID NO 970
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 970
ccguggugga auaggaguat t                                             21

<210> SEQ ID NO 971
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 971
acuccuauuc caccacggct t                                             21

<210> SEQ ID NO 972
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 972
gccguggugg aauaggagut t                                             21

<210> SEQ ID NO 973
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 973
uccuauucca ccacggcugt t                                             21

<210> SEQ ID NO 974
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 974
cagccguggu ggaauaggat t                                             21

<210> SEQ ID NO 975
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens

<400> SEQUENCE: 975
uauuccacca cggcugucgt t                                              21

<210> SEQ ID NO 976
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 976
cgacagccgu gguggaauat t                                              21

<210> SEQ ID NO 977
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 977
auuccaccac ggcugucgut t                                              21

<210> SEQ ID NO 978
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 978
acgacagccg ugguggaaut t                                              21

<210> SEQ ID NO 979
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 979
caccacggcu gucgucacct t                                              21

<210> SEQ ID NO 980
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 980
ggugacgaca gccguggugt t                                              21

<210> SEQ ID NO 981
<211> LENGTH: 21
<212> TYPE: DNA
<213> ORGANISM: Homo sapiens
```

```
<220> FEATURE:
<223> OTHER INFORMATION: Description of Combined DNA/RNA Molecule:
      Homo sapiens

<400> SEQUENCE: 981
accacggcug ucgucaccat t                                              21

<210> SEQ ID NO 982
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 982
uggugacgac agccguggut t                                              21

<210> SEQ ID NO 983
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 983
ccacggcugu cgucaccaat t                                              21

<210> SEQ ID NO 984
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 984
uuggugacga cagccguggt t                                              21

<210> SEQ ID NO 985
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 985
acggcugucg ucaccaauct t                                              21

<210> SEQ ID NO 986
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 986
gauuggugac gacagccgut t                                              21

<210> SEQ ID NO 987
<211> LENGTH: 21
<212> TYPE: DNA
<213> ORGANISM: Homo sapiens
<220> FEATURE:
```

<223> OTHER INFORMATION: Description of Combined DNA/RNA Molecule:
     Homo sapiens

<400> SEQUENCE: 987
cggcugucgu caccaaucct t                                              21

<210> SEQ ID NO 988
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 988
ggauugguga cgacagccgt t                                              21

<210> SEQ ID NO 989
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 989
cgucaccaau cccaaggaat t                                              21

<210> SEQ ID NO 990
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 990
uuccuuggga uuggugacgt t                                              21

<210> SEQ ID NO 991
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 991
caaucccaag gaaugagggt t                                              21

<210> SEQ ID NO 992
<211> LENGTH: 21
<212> TYPE: DNA
<213> ORGANISM: Homo sapiens
<220> FEATURE:
<223> OTHER INFORMATION: Description of Combined DNA/RNA Molecule:
     Homo sapiens

<400> SEQUENCE: 992 ccccucauucc uugggauugt t                                             21

<210> SEQ ID NO 993
<211> LENGTH: 21
<212> TYPE: DNA
<213> ORGANISM: Homo sapiens
<220> FEATURE:
<223> OTHER INFORMATION: Description of Combined DNA/RNA Molecule:

Homo sapiens

<400> SEQUENCE: 993
ccugaaggac gagggauggt t					21

<210> SEQ ID NO 994
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 994
ccaucccucg uccuucaggt t					21

<210> SEQ ID NO 995
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 995
ggacgaggga ugggauuuct t					21

<210> SEQ ID NO 996
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 996
gaaaucccau cccucguect t					21

<210> SEQ ID NO 997
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 997
aaguccacuc auucuuggct t					21

<210> SEQ ID NO 998
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 998
gccaagaaug aguggacuut t					21

<210> SEQ ID NO 999
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens -continued

```
<400> SEQUENCE: 999
gggauuucau guaaccaagt t                                              21

<210> SEQ ID NO 1000
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1000
cuugguuaca ugaaauccct t                                              21

<210> SEQ ID NO 1001
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1001
ggauuucaug uaaccaagat t                                              21

<210> SEQ ID NO 1002
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1002
ucuugguuac augaaaucct t                                              21

<210> SEQ ID NO 1003
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1003
ucauguaacc aagaguauut t                                              21

<210> SEQ ID NO 1004
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1004
aauacucuug guuacaugat t                                              21

<210> SEQ ID NO 1005
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
```

```
<400> SEQUENCE: 1005
auguaaccaa gaguauucct t                                              21

<210> SEQ ID NO 1006
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1006
ggaauacucu ugguuacaut t                                              21

<210> SEQ ID NO 1007
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1007
uguaaccaag aguauuccat t                                              21

<210> SEQ ID NO 1008
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1008
uggaauacuc uugguuacat t                                              21

<210> SEQ ID NO 1009
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1009
guaaccaaga guauuccaut t                                              21

<210> SEQ ID NO 1010
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1010
auggaauacu cuugguuact t                                              21

<210> SEQ ID NO 1011
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1011
```
ugccuugcug gacuggguaut t                                        21

<210> SEQ ID NO 1012
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1012
auaccagucc agcaaggcat t                                         21

<210> SEQ ID NO 1013
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1013
uaaagcagug uuuucaccut t                                         21

<210> SEQ ID NO 1014
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1014
aggugaaaac acugcuuuat t                                         21

<210> SEQ ID NO 1015
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1015
gccuugcugg acugguauut t                                         21

<210> SEQ ID NO 1016
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1016
aauaccaguc cagcaaggct t                                         21

<210> SEQ ID NO 1017
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1017
uguuuucacc ucauaugcut t       21

<210> SEQ ID NO 1018
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1018
agcauaugag gugaaaacat t       21

<210> SEQ ID NO 1019
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1019
guuuucaccu cauaugcuat t       21

<210> SEQ ID NO 1020
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1020
uagcauauga ggugaaaact t       21

<210> SEQ ID NO 1021
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1021
uuuucaccuc auaugcuaut t       21

<210> SEQ ID NO 1022
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1022
auagcauaug aggugaaaat t       21

<210> SEQ ID NO 1023
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1023
uucaccucau augcuaugut t       21

<210> SEQ ID NO 1024
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1024
acauagcaua ugaggugaat t                                              21

<210> SEQ ID NO 1025
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1025
caccucauau gcuauguuat t                                              21

<210> SEQ ID NO 1026
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1026
uaacauagca uaugaggugt t                                              21

<210> SEQ ID NO 1027
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1027
ccuugcugga cugguauuut t                                              21

<210> SEQ ID NO 1028
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1028
aaauaccagu ccagcaaggt t                                              21

<210> SEQ ID NO 1029
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1029
auaugcuaug uuagaaguct t                                              21

<210> SEQ ID NO 1030
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1030
gacuucuaac auagcauaut t                                              21

<210> SEQ ID NO 1031
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1031
uaugcuaugu uagaagucct t                                              21

<210> SEQ ID NO 1032
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1032
ggacuucuaa cauagcauat t                                              21

<210> SEQ ID NO 1033
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1033
ugcuauguua gaaguccagt t                                              21

<210> SEQ ID NO 1034
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1034
cuggacuucu aacauagcat t                                              21

<210> SEQ ID NO 1035
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1035
cuugcuggac ugguauuugt t                                              21

-continued

```
<210> SEQ ID NO 1036
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1036
caaauaccag uccagcaagt t                                              21

<210> SEQ ID NO 1037
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1037
aguccaggca gagacaauat t                                              21

<210> SEQ ID NO 1038
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1038
uauugucucu gccuggacut t                                              21

<210> SEQ ID NO 1039
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1039
uccaggcaga gacaauaaat t                                              21

<210> SEQ ID NO 1040
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1040
uuuauugucu cugccuggat t                                              21

<210> SEQ ID NO 1041
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1041
gugaaaggca cuuuucauut t                                              21

<210> SEQ ID NO 1042
```

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1042
aaugaaaagu gccuuucact t                                              21

<210> SEQ ID NO 1043
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1043
uggacuggua uuugugucut t                                              21

<210> SEQ ID NO 1044
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1044
agacacaaau accaguccat t                                              21

<210> SEQ ID NO 1045
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1045
gucugaggcu ggcccuacgt t                                              21

<210> SEQ ID NO 1046
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1046
cguagggcca gccucagact t                                              21

<210> SEQ ID NO 1047
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1047
cugaggcugg cccuacgggt t                                              21

<210> SEQ ID NO 1048
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1048
cccguagggc cagccucagt t                                              21

<210> SEQ ID NO 1049
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1049
gaggcuggcc cuacgggcat t                                              21

<210> SEQ ID NO 1050
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1050
ugcccguagg gccagccuct t                                              21

<210> SEQ ID NO 1051
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1051
aggcuggccc uacgggcact t                                              21

<210> SEQ ID NO 1052
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1052
gugcccguag ggccagccut t                                              21

<210> SEQ ID NO 1053
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1053
gcuggcccua cgggcaccgt t                                              21

<210> SEQ ID NO 1054
<211> LENGTH: 21
<212> TYPE: DNA
```

```
<213> ORGANISM: Homo sapiens
<220> FEATURE:
<223> OTHER INFORMATION: Description of Combined DNA/RNA Molecule:
      Homo sapiens

<400> SEQUENCE: 1054
cggugcccgu agggccagct t                                              21

<210> SEQ ID NO 1055
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1055
cuggcccuac gggcaccggt t                                              21

<210> SEQ ID NO 1056
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1056
ccggugcccg uagggccagt t                                              21

<210> SEQ ID NO 1057
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1057
ggcccuacgg gcaccggugt t                                              21

<210> SEQ ID NO 1058
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1058
caccggugcc cguagggcct t                                              21

<210> SEQ ID NO 1059
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1059
ccacucauuc uuggcaggat t                                              21

<210> SEQ ID NO 1060
<211> LENGTH: 21
<212> TYPE: DNA
<213> ORGANISM: Homo sapiens
```

```
<220> FEATURE:
<223> OTHER INFORMATION: Description of Combined DNA/RNA Molecule:
      Homo sapiens

<400> SEQUENCE: 1060
uccugccaag aaugaguggt t                                              21

<210> SEQ ID NO 1061
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1061
ccuacgggca ccggugaaut t                                              21

<210> SEQ ID NO 1062
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1062
auucaccggu gcccguaggt t                                              21

<210> SEQ ID NO 1063
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1063
cuacgggcac cggugaauct t                                              21

<210> SEQ ID NO 1064
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1064
gauucaccgg ugcccguagt t                                              21

<210> SEQ ID NO 1065
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1065
uacgggcacc ggugaaucct t                                              21

<210> SEQ ID NO 1066
<211> LENGTH: 21
<212> TYPE: DNA
<213> ORGANISM: Homo sapiens
<220> FEATURE:
```

```
<223> OTHER INFORMATION: Description of Combined DNA/RNA Molecule:
      Homo sapiens

<400> SEQUENCE: 1066
ggauucaccg gugcccguat t                                              21

<210> SEQ ID NO 1067
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1067
acgggcaccg gugaauccat t                                              21

<210> SEQ ID NO 1068
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1068
uggauucacc ggugcccgut t                                              21

<210> SEQ ID NO 1069
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1069
gcaccgguga auccaagugt t                                              21

<210> SEQ ID NO 1070
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1070
cacuuggauu caccggugct t                                              21

<210> SEQ ID NO 1071
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1071
caccggugaa uccaagugut t                                              21

<210> SEQ ID NO 1072
<211> LENGTH: 21
<212> TYPE: DNA
<213> ORGANISM: Homo sapiens
<220> FEATURE:
<223> OTHER INFORMATION: Description of Combined DNA/RNA Molecule:
```

-continued

Homo sapiens

<400> SEQUENCE: 1072
acacuuggau ucaccggugt t					21

<210> SEQ ID NO 1073
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1073
uguggccaug cauguguuct t					21

<210> SEQ ID NO 1074
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1074
gaacacaugc auggccacat t					21

<210> SEQ ID NO 1075
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1075
guggccaugc auguuucat t					21

<210> SEQ ID NO 1076
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1076
ugaacacaug cauggccact t					21

<210> SEQ ID NO 1077
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1077
gccaugcaug uguucagaat t					21

<210> SEQ ID NO 1078
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1078
uucugaacac augcauggct t                                              21

<210> SEQ ID NO 1079
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1079
uauuccacca cggcugucat t                                              21

<210> SEQ ID NO 1080
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1080
ugacagccgu gguggaauat t                                              21

<210> SEQ ID NO 1081
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1081
gucaucacca aucccaaggt t                                              21

<210> SEQ ID NO 1082
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1082
ccuugggauu ggugaugact t                                              21

<210> SEQ ID NO 1083
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1083
guccucugau ggucaaagut t                                              21

<210> SEQ ID NO 1084
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 1084
acuuugacca ucagaggact t                                              21

<210> SEQ ID NO 1085
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1085
gauggucaaa guucuagaut t                                              21

<210> SEQ ID NO 1086
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1086
aucuagaacu uugaccauct t                                              21

<210> SEQ ID NO 1087
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1087
augcuguccg aggcagucct t                                              21

<210> SEQ ID NO 1088
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1088
ggacugccuc ggacagcaut t                                              21

<210> SEQ ID NO 1089
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1089
ccgugcaugu guucagaaat t                                              21

<210> SEQ ID NO 1090
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1090
```
uuucugaaca caugcacggt t                                            21

<210> SEQ ID NO 1091
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1091
agucuggaga gcugcauggt t                                            21

<210> SEQ ID NO 1092
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1092
ccaugcagcu cuccagacut t                                            21

<210> SEQ ID NO 1093
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1093
caugggcuca caacugaggt t                                            21

<210> SEQ ID NO 1094
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1094
ccucaguugu gagcccaugt t                                            21

<210> SEQ ID NO 1095
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1095
ucucaucguc ugcuccucct t                                            21

<210> SEQ ID NO 1096
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1096
ggaggagcag acgaugagat t                                              21

<210> SEQ ID NO 1097
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1097
ccccauucca ugagcaugct t                                              21

<210> SEQ ID NO 1098
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1098
gcaugcucau ggaauggggt t                                              21

<210> SEQ ID NO 1099
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1099
gccccuacuc cuauuccact t                                              21

<210> SEQ ID NO 1100
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1100
guggaauagg aguaggggct t                                              21

<210> SEQ ID NO 1101
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1101
cuauuccacc acggcuguct t                                              21

<210> SEQ ID NO 1102
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1102
gacagccgug guggaauagt t                                              21

-continued

```
<210> SEQ ID NO 1103
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1103
cacggcuguc gucaccaaut t                                              21

<210> SEQ ID NO 1104
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1104
auuggugacg acagccgugt t                                              21

<210> SEQ ID NO 1105
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1105
aggacgaggg augggauuut t                                              21

<210> SEQ ID NO 1106
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1106
aaaucccauc ccucguccut t                                              21

<210> SEQ ID NO 1107
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1107
ucaccucaua ugcuauguut t                                              21

<210> SEQ ID NO 1108
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1108
aacauagcau augaggugat t                                              21
```

```
<210> SEQ ID NO 1109
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1109
ccucauaugc uauguuagat t                                              21

<210> SEQ ID NO 1110
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1110
ucuaacauag cauaugaggt t                                              21

<210> SEQ ID NO 1111
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1111
auguuagaag uccaggcagt t                                              21

<210> SEQ ID NO 1112
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1112
cugccuggac uucuaacaut t                                              21

<210> SEQ ID NO 1113
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1113
ucugaggcug gcccuacggt t                                              21

<210> SEQ ID NO 1114
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1114
ccguagggcc agccucagat t                                              21
```

```
<210> SEQ ID NO 1115
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1115
ggcccuacgg gcaccggugt t                                               21

<210> SEQ ID NO 1116
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1116
caccggugcc cguagggcct t                                               21

<210> SEQ ID NO 1117
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1117
gggcaccggu gaauccaagt t                                               21

<210> SEQ ID NO 1118
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1118
cuuggauuca ccggugccct t                                               21

<210> SEQ ID NO 1119
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1119
ccaugcaugu guucagaaat t                                               21

<210> SEQ ID NO 1120
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1120
uuucugaaca caugcauggt t                                               21

<210> SEQ ID NO 1121
```

```
<211> LENGTH: 19
<212> TYPE: RNA
<213> ORGANISM: Rattus norvegicus

<400> SEQUENCE: 1121
guccucugau ggucaaagu                                                    19

<210> SEQ ID NO 1122
<211> LENGTH: 19
<212> TYPE: RNA
<213> ORGANISM: Rattus norvegicus

<400> SEQUENCE: 1122
acuuugacca ucagaggac                                                    19

<210> SEQ ID NO 1123
<211> LENGTH: 19
<212> TYPE: RNA
<213> ORGANISM: Rattus norvegicus

<400> SEQUENCE: 1123
uucuugcucu auaaaccgu                                                    19

<210> SEQ ID NO 1124
<211> LENGTH: 19
<212> TYPE: RNA
<213> ORGANISM: Rattus norvegicus

<400> SEQUENCE: 1124
acgguuuaua gagcaagaa                                                    19

<210> SEQ ID NO 1125
<211> LENGTH: 19
<212> TYPE: RNA
<213> ORGANISM: Rattus norvegicus

<400> SEQUENCE: 1125
cucuauaaac cguguuagc                                                    19

<210> SEQ ID NO 1126
<211> LENGTH: 19
<212> TYPE: RNA
<213> ORGANISM: Rattus norvegicus

<400> SEQUENCE: 1126
gcuaacacgg uuuauagag                                                    19

<210> SEQ ID NO 1127
<211> LENGTH: 19
<212> TYPE: RNA
<213> ORGANISM: Rattus norvegicus

<400> SEQUENCE: 1127
ucgccacuac accaucgca                                                    19

<210> SEQ ID NO 1128
<211> LENGTH: 19
<212> TYPE: RNA
<213> ORGANISM: Rattus norvegicus

<400> SEQUENCE: 1128
ugcgauggug uaguggcga                                                    19
```

```
<210> SEQ ID NO 1129
<211> LENGTH: 19
<212> TYPE: RNA
<213> ORGANISM: Rattus norvegicus

<400> SEQUENCE: 1129
ucuugcucua uaaaccgug                                                   19

<210> SEQ ID NO 1130
<211> LENGTH: 19
<212> TYPE: RNA
<213> ORGANISM: Rattus norvegicus

<400> SEQUENCE: 1130
cacgguuuau agagcaaga                                                   19

<210> SEQ ID NO 1131
<211> LENGTH: 19
<212> TYPE: RNA
<213> ORGANISM: Rattus norvegicus

<400> SEQUENCE: 1131
ugcucuauaa accguguua                                                   19

<210> SEQ ID NO 1132
<211> LENGTH: 19
<212> TYPE: RNA
<213> ORGANISM: Rattus norvegicus

<400> SEQUENCE: 1132
uaacacgguu uauagagca                                                   19

<210> SEQ ID NO 1133
<211> LENGTH: 19
<212> TYPE: RNA
<213> ORGANISM: Rattus norvegicus

<400> SEQUENCE: 1133
caguguucuu gcucuauaa                                                   19

<210> SEQ ID NO 1134
<211> LENGTH: 19
<212> TYPE: RNA
<213> ORGANISM: Rattus norvegicus

<400> SEQUENCE: 1134
uuauagagca agaacacug                                                   19

<210> SEQ ID NO 1135
<211> LENGTH: 19
<212> TYPE: RNA
<213> ORGANISM: Rattus norvegicus

<400> SEQUENCE: 1135
gcucuauaaa ccguguuag                                                   19

<210> SEQ ID NO 1136
<211> LENGTH: 19
<212> TYPE: RNA
<213> ORGANISM: Rattus norvegicus

<400> SEQUENCE: 1136
cuaacacggu uuauagagc                                                   19
```

```
<210> SEQ ID NO 1137
<211> LENGTH: 19
<212> TYPE: RNA
<213> ORGANISM: Rattus norvegicus

<400> SEQUENCE: 1137
ccuggaugcu guccgaggc                                                    19

<210> SEQ ID NO 1138
<211> LENGTH: 19
<212> TYPE: RNA
<213> ORGANISM: Rattus norvegicus

<400> SEQUENCE: 1138
gccucggaca gcauccagg                                                    19

<210> SEQ ID NO 1139
<211> LENGTH: 19
<212> TYPE: RNA
<213> ORGANISM: Rattus norvegicus

<400> SEQUENCE: 1139
ucugaugguc aaaguccug                                                    19

<210> SEQ ID NO 1140
<211> LENGTH: 19
<212> TYPE: RNA
<213> ORGANISM: Rattus norvegicus

<400> SEQUENCE: 1140
caggacuuug accaucaga                                                    19

<210> SEQ ID NO 1141
<211> LENGTH: 19
<212> TYPE: RNA
<213> ORGANISM: Rattus norvegicus

<400> SEQUENCE: 1141
cuggagagcu gcacgggcu                                                    19

<210> SEQ ID NO 1142
<211> LENGTH: 19
<212> TYPE: RNA
<213> ORGANISM: Rattus norvegicus

<400> SEQUENCE: 1142
agcccgugca gcucuccag                                                    19

<210> SEQ ID NO 1143
<211> LENGTH: 19
<212> TYPE: RNA
<213> ORGANISM: Rattus norvegicus

<400> SEQUENCE: 1143
ucuauaaacc guguuagca                                                    19

<210> SEQ ID NO 1144
<211> LENGTH: 19
<212> TYPE: RNA
<213> ORGANISM: Rattus norvegicus

<400> SEQUENCE: 1144
ugcuaacacg guuuauaga                                                    19
```

<210> SEQ ID NO 1145
<211> LENGTH: 19
<212> TYPE: RNA
<213> ORGANISM: Rattus norvegicus

<400> SEQUENCE: 1145
aacaguguuc uugcucuau                                                19

<210> SEQ ID NO 1146
<211> LENGTH: 19
<212> TYPE: RNA
<213> ORGANISM: Rattus norvegicus

<400> SEQUENCE: 1146
auagagcaag aacacuguu                                                19

<210> SEQ ID NO 1147
<211> LENGTH: 19
<212> TYPE: RNA
<213> ORGANISM: Rattus norvegicus

<400> SEQUENCE: 1147
cucugauggu caaaguccu                                                19

<210> SEQ ID NO 1148
<211> LENGTH: 19
<212> TYPE: RNA
<213> ORGANISM: Rattus norvegicus

<400> SEQUENCE: 1148
aggacuuuga ccaucagag                                                19

<210> SEQ ID NO 1149
<211> LENGTH: 19
<212> TYPE: RNA
<213> ORGANISM: Rattus norvegicus

<400> SEQUENCE: 1149
ugcuguccga ggcagcccu                                                19

<210> SEQ ID NO 1150
<211> LENGTH: 19
<212> TYPE: RNA
<213> ORGANISM: Rattus norvegicus

<400> SEQUENCE: 1150
agggcugccu cggacagca                                                19

<210> SEQ ID NO 1151
<211> LENGTH: 19
<212> TYPE: RNA
<213> ORGANISM: Rattus norvegicus

<400> SEQUENCE: 1151
gucuggagag cugcacggg                                                19

<210> SEQ ID NO 1152
<211> LENGTH: 19
<212> TYPE: RNA
<213> ORGANISM: Rattus norvegicus

<400> SEQUENCE: 1152
cccgugcagc ucuccagac                                                19

<210> SEQ ID NO 1153
<211> LENGTH: 19
<212> TYPE: RNA
<213> ORGANISM: Rattus norvegicus

<400> SEQUENCE: 1153
acaguguucu ugcucuaua                                                19

<210> SEQ ID NO 1154
<211> LENGTH: 19
<212> TYPE: RNA
<213> ORGANISM: Rattus norvegicus

<400> SEQUENCE: 1154
uauagagcaa gaacacugu                                                19

<210> SEQ ID NO 1155
<211> LENGTH: 19
<212> TYPE: RNA
<213> ORGANISM: Rattus norvegicus

<400> SEQUENCE: 1155
ccucugaugg ucaaagucc                                                19

<210> SEQ ID NO 1156
<211> LENGTH: 19
<212> TYPE: RNA
<213> ORGANISM: Rattus norvegicus

<400> SEQUENCE: 1156
ggacuuugac caucagagg                                                19

<210> SEQ ID NO 1157
<211> LENGTH: 19
<212> TYPE: RNA
<213> ORGANISM: Rattus norvegicus

<400> SEQUENCE: 1157
aguccuggau gcuguccga                                                19

<210> SEQ ID NO 1158
<211> LENGTH: 19
<212> TYPE: RNA
<213> ORGANISM: Rattus norvegicus

<400> SEQUENCE: 1158
ucggacagca uccaggacu                                                19

<210> SEQ ID NO 1159
<211> LENGTH: 19
<212> TYPE: RNA
<213> ORGANISM: Rattus norvegicus

<400> SEQUENCE: 1159
uugccucugg gaagaccgc                                                19

<210> SEQ ID NO 1160
<211> LENGTH: 19
<212> TYPE: RNA
<213> ORGANISM: Rattus norvegicus

<400> SEQUENCE: 1160
gcggucuucc cagaggcaa                                                19

<210> SEQ ID NO 1161
<211> LENGTH: 19
<212> TYPE: RNA
<213> ORGANISM: Rattus norvegicus

<400> SEQUENCE: 1161
uggagagcug cacgggcuc                                                19

<210> SEQ ID NO 1162
<211> LENGTH: 19
<212> TYPE: RNA
<213> ORGANISM: Rattus norvegicus

<400> SEQUENCE: 1162
gagcccgugc agcucucca                                                19

<210> SEQ ID NO 1163
<211> LENGTH: 19
<212> TYPE: RNA
<213> ORGANISM: Rattus norvegicus

<400> SEQUENCE: 1163
gagagcugca cgggcucac                                                19

<210> SEQ ID NO 1164
<211> LENGTH: 19
<212> TYPE: RNA
<213> ORGANISM: Rattus norvegicus

<400> SEQUENCE: 1164
gugagcccgu gcagcucuc                                                19

<210> SEQ ID NO 1165
<211> LENGTH: 19
<212> TYPE: RNA
<213> ORGANISM: Rattus norvegicus

<400> SEQUENCE: 1165
gagcugcacg ggcucacca                                                19

<210> SEQ ID NO 1166
<211> LENGTH: 19
<212> TYPE: RNA
<213> ORGANISM: Rattus norvegicus

<400> SEQUENCE: 1166
uggugagccc gugcagcuc                                                19

<210> SEQ ID NO 1167
<211> LENGTH: 19
<212> TYPE: RNA
<213> ORGANISM: Rattus norvegicus

<400> SEQUENCE: 1167
uacaccaucg cagcccugc                                                19

<210> SEQ ID NO 1168
<211> LENGTH: 19
<212> TYPE: RNA
<213> ORGANISM: Rattus norvegicus

```
<400> SEQUENCE: 1168
gcagggcugc gauggugua                                          19

<210> SEQ ID NO 1169
<211> LENGTH: 19
<212> TYPE: RNA
<213> ORGANISM: Rattus norvegicus

<400> SEQUENCE: 1169
guccuggaug cguccgag                                           19

<210> SEQ ID NO 1170
<211> LENGTH: 19
<212> TYPE: RNA
<213> ORGANISM: Rattus norvegicus

<400> SEQUENCE: 1170
cucggacagc auccaggac                                          19

<210> SEQ ID NO 1171
<211> LENGTH: 19
<212> TYPE: RNA
<213> ORGANISM: Rattus norvegicus

<400> SEQUENCE: 1171
agagcugcac gggcucacc                                          19

<210> SEQ ID NO 1172
<211> LENGTH: 19
<212> TYPE: RNA
<213> ORGANISM: Rattus norvegicus

<400> SEQUENCE: 1172
ggugagcccg ugcagcucu                                          19

<210> SEQ ID NO 1173
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1173
guccucugau ggucaaagun n                                       21

<210> SEQ ID NO 1174
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1174
acuuugacca ucagaggacn n                                       21
```

```
<210> SEQ ID NO 1175
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1175
uucuugcucu auaaaccgun n                                              21

<210> SEQ ID NO 1176
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1176
acgguuuaua gagcaagaan n                                              21

<210> SEQ ID NO 1177
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1177
cucuauaaac cguguuagcn n                                              21

<210> SEQ ID NO 1178
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1178
gcuaacacgg uuuauagagn n                                              21

<210> SEQ ID NO 1179
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other
```

```
<400> SEQUENCE: 1179
ucgccacuac accaucgcan n                                        21

<210> SEQ ID NO 1180
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1180
ugcgauggug uaguggcgan n                                        21

<210> SEQ ID NO 1181
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1181
ucuugcucua uaaaccgugn n                                        21

<210> SEQ ID NO 1182
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1182
cacgguuuau agagcaagan n                                        21

<210> SEQ ID NO 1183
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1183
ugcucuauaa accguguuan n                                        21

<210> SEQ ID NO 1184
<211> LENGTH: 21
<212> TYPE: DNA
<213> ORGANISM: Rattus norvegicus
<220> FEATURE:
```

```
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1184
uaacacgguu uauagagcan n                                              21

<210> SEQ ID NO 1185
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1185
caguguucuu gcucuauaan n                                              21

<210> SEQ ID NO 1186
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1186
uuauagagca agaacacugn n                                              21

<210> SEQ ID NO 1187
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1187
gcucuauaaa ccguguuagn n                                              21

<210> SEQ ID NO 1188
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1188
cuaacacggu uuauagagcn n                                              21
```

```
<210> SEQ ID NO 1189
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1189
ccuggaugcu guccgaggcn n                                              21

<210> SEQ ID NO 1190
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1190
gccucggaca gcauccaggn n                                              21

<210> SEQ ID NO 1191
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1191
ucugaugguc aaaguccugn n                                              21

<210> SEQ ID NO 1192
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1192
caggacuuug accaucagan n                                              21

<210> SEQ ID NO 1193
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
```

```
<223> OTHER INFORMATION: a, c, t, g, unknown or other

<400> SEQUENCE: 1193
cuggagagcu gcacgggcun n                                              21

<210> SEQ ID NO 1194
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1194
agcccgugca gcucuccagn n                                              21

<210> SEQ ID NO 1195
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1195
ucuauaaacc guguuagcan n                                              21

<210> SEQ ID NO 1196
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1196
ugcuaacacg guuuauagan n                                              21

<210> SEQ ID NO 1197
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1197
aacaguguuc uugcucuaun n                                              21

<210> SEQ ID NO 1198
<211> LENGTH: 21
<212> TYPE: DNA
<213> ORGANISM: Rattus norvegicus
```

```
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1198
auagagcaag aacacuguun n                                              21

<210> SEQ ID NO 1199
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1199
cucugauggu caaaguccun n                                              21

<210> SEQ ID NO 1200
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1200
aggacuuuga ccaucagagn n                                              21

<210> SEQ ID NO 1201
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1201
ugcuguccga ggcagcccun n                                              21

<210> SEQ ID NO 1202
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1202
agggcugccu cggacagcan n                                              21
```

<210> SEQ ID NO 1203
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1203
gucuggagag cugcacgggn n                                              21

<210> SEQ ID NO 1204
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1204
cccgugcagc ucuccagacn n                                              21

<210> SEQ ID NO 1205
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1205
acaguguucu ugcucuauan n                                              21

<210> SEQ ID NO 1206
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1206
uauagagcaa gaacacugun n                                              21

<210> SEQ ID NO 1207
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base

```
<222> LOCATION: (20)..(21)
<223> OTHER INFORMATION: a, c, t, g, unknown or other

<400> SEQUENCE: 1207
ccucugaugg ucaaaguccn n                                            21

<210> SEQ ID NO 1208
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1208
ggacuuugac caucagaggn n                                            21

<210> SEQ ID NO 1209
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1209
aguccuggau gcuguccgan n                                            21

<210> SEQ ID NO 1210
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1210
ucggacagca uccaggacun n                                            21

<210> SEQ ID NO 1211
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1211
uugccucugg gaagaccgcn n                                            21

<210> SEQ ID NO 1212
<211> LENGTH: 21
<212> TYPE: DNA
```

<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1212
gcggucuucc cagaggcaan n                                              21

<210> SEQ ID NO 1213
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1213
uggagagcug cacgggcucn n                                              21

<210> SEQ ID NO 1214
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1214
gagcccgugc agcucuccan n                                              21

<210> SEQ ID NO 1215
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1215
gagagcugca cgggcucacn n                                              21

<210> SEQ ID NO 1216
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1216
gugagcccgu gcagcucucn n    21

<210> SEQ ID NO 1217
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1217
gagcugcacg ggcucaccan n    21

<210> SEQ ID NO 1218
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1218
uggugagccc gugcagcucn n    21

<210> SEQ ID NO 1219
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1219
uacaccaucg cagcccugcn n    21

<210> SEQ ID NO 1220
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1220
gcagggcugc gaugguguan n    21

<210> SEQ ID NO 1221
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:

```
<221> NAME/KEY: modified_base
<222> LOCATION: (20)..(21)
<223> OTHER INFORMATION: a, c, t, g, unknown or other

<400> SEQUENCE: 1221
guccuggaug cguccgagn n                                        21

<210> SEQ ID NO 1222
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1222
cucggacagc auccaggacn n                                       21

<210> SEQ ID NO 1223
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1223
agagcugcac gggcucaccn n                                       21

<210> SEQ ID NO 1224
<211> LENGTH: 21
<212> TYPE: DNA
<213> ORGANISM: Rattus norvegicus
<220> FEATURE:
<221> NAME/KEY: source
<223> OTHER INFORMATION: Description of Combined DNA/RNA Molecule:
      Rattus norvegicus
<220> FEATURE:
<221> NAME/KEY: modified_base
<222> LOCATION: (20)..(21)
<223> OTHER INFORMATION: a, c, t, g, unknown or other

<400> SEQUENCE: 1224
ggugagcccg ugcagcucun n                                       21

<210> SEQ ID NO 1225
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1225
guccucugau ggucaaagut t                                       21

<210> SEQ ID NO 1226
<211> LENGTH: 21
<212> TYPE: DNA
<213> ORGANISM: Rattus norvegicus
<220> FEATURE:
```

```
<223> OTHER INFORMATION: Description of Combined DNA/RNA Molecule:
      Rattus norvegicus

<400> SEQUENCE: 1226
acuuugacca ucagaggact t                                              21

<210> SEQ ID NO 1227
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1227
uucuugcucu auaaaccgut t                                              21

<210> SEQ ID NO 1228
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1228
acgguuuaua gagcaagaat t                                              21

<210> SEQ ID NO 1229
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1229
cucuauaaac cguguuagct t                                              21

<210> SEQ ID NO 1230
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1230
gcuaacacgg uuuauagagt t                                              21

<210> SEQ ID NO 1231
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1231
ucgccacuac accaucgcat t                                              21

<210> SEQ ID NO 1232
<211> LENGTH: 21
<212> TYPE: DNA
<213> ORGANISM: Rattus norvegicus
<220> FEATURE:
<223> OTHER INFORMATION: Description of Combined DNA/RNA Molecule:
```

Rattus norvegicus

<400> SEQUENCE: 1232
ugcgauggug uaguggcgat t                                              21

<210> SEQ ID NO 1233
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1233
ucuugcucua uaaaccgugt t                                              21

<210> SEQ ID NO 1234
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1234
cacgguuuau agagcaagat t                                              21

<210> SEQ ID NO 1235
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1235
ugcucuauaa accguguuat t                                              21

<210> SEQ ID NO 1236
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1236
uaacacgguu uauagagcat t                                              21

<210> SEQ ID NO 1237
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1237
caguguucuu gcucuauaat t                                              21

<210> SEQ ID NO 1238
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1238
uuauagagca agaacacugt t                                              21

<210> SEQ ID NO 1239
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1239
gcucuauaaa ccguguuagt t                                              21

<210> SEQ ID NO 1240
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1240
cuaacacggu uuauagagct t                                              21

<210> SEQ ID NO 1241
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1241
ccuggaugcu guccgaggct t                                              21

<210> SEQ ID NO 1242
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1242
gccucggaca gcauccaggt t                                              21

<210> SEQ ID NO 1243
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1243
ucugaugguc aaaguccugt t                                              21

<210> SEQ ID NO 1244
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1244
caggacuuug accaucagat t                                              21

<210> SEQ ID NO 1245
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1245
cuggagagcu gcacgggcut t                                              21

<210> SEQ ID NO 1246
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1246
agcccgugca gcucuccagt t                                              21

<210> SEQ ID NO 1247
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1247
ucuauaaacc guguuagcat t                                              21

<210> SEQ ID NO 1248
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1248
ugcuaacacg guuuauagat t                                              21

<210> SEQ ID NO 1249
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1249
aacaguguuc uugcucuaut t                                              21

<210> SEQ ID NO 1250
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1250
auagagcaag aacacuguut t                                                  21

<210> SEQ ID NO 1251
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1251
cucugauggu caaaguccut t                                                  21

<210> SEQ ID NO 1252
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1252
aggacuuuga ccaucagagt t                                                  21

<210> SEQ ID NO 1253
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1253
ugcuguccga ggcagcccut t                                                  21

<210> SEQ ID NO 1254
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1254
agggcugccu cggacagcat t                                                  21

<210> SEQ ID NO 1255
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1255
gucuggagag cugcacgggt t                                                  21

<210> SEQ ID NO 1256
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1256
cccgugcagc ucuccagact t                                              21

<210> SEQ ID NO 1257
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1257
acaguguucu ugcucuauat t                                              21

<210> SEQ ID NO 1258
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1258
uauagagcaa gaacacugut t                                              21

<210> SEQ ID NO 1259
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1259
ccucugaugg ucaaaguccu t                                              21

<210> SEQ ID NO 1260
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1260
ggacuuugac caucagaggt t                                              21

<210> SEQ ID NO 1261
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1261
aguccuggau gcuguccgat t                                              21

<210> SEQ ID NO 1262
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1262
ucggacagca uccaggacut t                                              21

<210> SEQ ID NO 1263
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1263
uugccucugg gaagaccgct t                                              21

<210> SEQ ID NO 1264
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1264
gcggucuucc cagaggcaat t                                              21

<210> SEQ ID NO 1265
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1265
uggagagcug cacgggcuct t                                              21

<210> SEQ ID NO 1266
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1266
gagcccgugc agcucuccat t                                              21

<210> SEQ ID NO 1267
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1267
gagagcugca cgggcucact t                                              21

<210> SEQ ID NO 1268
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1268
gugagcccgu gcagcucuct t                                              21

<210> SEQ ID NO 1269
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1269
gagcugcacg ggcucaccat t                                             21

<210> SEQ ID NO 1270
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1270
uggugagccc gugcagcuct t                                             21

<210> SEQ ID NO 1271
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1271
uacaccaucg cagcccugct t                                             21

<210> SEQ ID NO 1272
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1272
gcagggcugc gaugguguat t                                             21

<210> SEQ ID NO 1273
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1273
guccuggaug cuguccgagt t                                             21

<210> SEQ ID NO 1274
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1274
cucggacagc auccaggact t                                             21

```
<210> SEQ ID NO 1275
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1275
agagcugcac gggcucacct t                                              21

<210> SEQ ID NO 1276
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1276
ggugagcccg ugcagcucut t                                              21

<210> SEQ ID NO 1277
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1277
guccucugau ggucaaagut t                                              21

<210> SEQ ID NO 1278
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1278
acuuugacca ucagaggact t                                              21

<210> SEQ ID NO 1279
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1279
uucuugcucu auaaaccgut t                                              21

<210> SEQ ID NO 1280
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1280
acgguuuaua gagcaagaat t                                              21

<210> SEQ ID NO 1281
```

```
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1281
cucuauaaac cguguuagct t                                             21

<210> SEQ ID NO 1282
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1282
gcuaacacgg uuuauagagt t                                             21

<210> SEQ ID NO 1283
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1283
ucgccacuac accaucgcat t                                             21

<210> SEQ ID NO 1284
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1284
ugcgauggug uaguggcgat t                                             21

<210> SEQ ID NO 1285
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1285
ucuugcucua uaaaccgugt t                                             21

<210> SEQ ID NO 1286
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1286
cacgguuuau agagcaagat t                                             21

<210> SEQ ID NO 1287
<211> LENGTH: 21
```

```
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1287
ugcucuauaa accguguuat t                                              21

<210> SEQ ID NO 1288
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1288
uaacacgguu uauagagcat t                                              21

<210> SEQ ID NO 1289
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1289
caguguucuu gcucuauaat t                                              21

<210> SEQ ID NO 1290
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1290
uuauagagca agaacacugt t                                              21

<210> SEQ ID NO 1291
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1291
gcucuauaaa ccguguuagt t                                              21

<210> SEQ ID NO 1292
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1292
cuaacacggu uuauagagct t                                              21

<210> SEQ ID NO 1293
<211> LENGTH: 21
<212> TYPE: DNA
```

```
<213> ORGANISM: Rattus norvegicus
<220> FEATURE:
<223> OTHER INFORMATION: Description of Combined DNA/RNA Molecule:
      Rattus norvegicus

<400> SEQUENCE: 1293
ccuggaugcu guccgaggct t                                              21

<210> SEQ ID NO 1294
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1294
gccucggaca gcauccaggt t                                              21

<210> SEQ ID NO 1295
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1295
ucugaugguc aaaguccugt t                                              21

<210> SEQ ID NO 1296
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1296
caggacuuug accaucagat t                                              21

<210> SEQ ID NO 1297
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1297
cuggagagcu gcacgggcut t                                              21

<210> SEQ ID NO 1298
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1298
agcccgugca gcucuccagt t                                              21

<210> SEQ ID NO 1299
<211> LENGTH: 21
<212> TYPE: DNA
<213> ORGANISM: Rattus norvegicus
```

```
<220> FEATURE:
<223> OTHER INFORMATION: Description of Combined DNA/RNA Molecule:
      Rattus norvegicus

<400> SEQUENCE: 1299
ucuauaaacc guguuagcat t                                              21

<210> SEQ ID NO 1300
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1300
ugcuaacacg guuuauagat t                                              21

<210> SEQ ID NO 1301
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1301
aacaguguuc uugcucuaut t                                              21

<210> SEQ ID NO 1302
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1302
auagagcaag aacacuguut t                                              21

<210> SEQ ID NO 1303
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1303
cucugauggu caaaguccut t                                              21

<210> SEQ ID NO 1304
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1304
aggacuuuga ccaucagagt t                                              21

<210> SEQ ID NO 1305
<211> LENGTH: 21
<212> TYPE: DNA
<213> ORGANISM: Rattus norvegicus
<220> FEATURE:
```

<223> OTHER INFORMATION: Description of Combined DNA/RNA Molecule:
      Rattus norvegicus

<400> SEQUENCE: 1305
ugcuguccga ggcagcccut t                                              21

<210> SEQ ID NO 1306
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1306
agggcugccu cggacagcat t                                              21

<210> SEQ ID NO 1307
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1307
gucuggagag cugcacgggt t                                              21

<210> SEQ ID NO 1308
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1308
cccgugcagc ucuccagact t                                              21

<210> SEQ ID NO 1309
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1309
acaguguucu ugcucuauat t                                              21

<210> SEQ ID NO 1310
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1310
uauagagcaa gaacacugut t                                              21

<210> SEQ ID NO 1311
<211> LENGTH: 21
<212> TYPE: DNA
<213> ORGANISM: Rattus norvegicus
<220> FEATURE:
<223> OTHER INFORMATION: Description of Combined DNA/RNA Molecule:

Rattus norvegicus

<400> SEQUENCE: 1311
ccucugaugg ucaaagucct t                                              21

<210> SEQ ID NO 1312
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1312
ggacuuugac caucagaggt t                                              21

<210> SEQ ID NO 1313
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1313
aguccuggau gcuguccgat t                                              21

<210> SEQ ID NO 1314
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1314
ucggacagca uccaggacut t                                              21

<210> SEQ ID NO 1315
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1315
uugccucugg gaagaccgct t                                              21

<210> SEQ ID NO 1316
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1316
gcggucuucc cagaggcaat t                                              21

<210> SEQ ID NO 1317
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1317
uggagagcug cacgggcuct t                                           21

<210> SEQ ID NO 1318
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1318
gagcccgugc agcucuccat t                                           21

<210> SEQ ID NO 1319
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1319
gagagcugca cgggcucact t                                           21

<210> SEQ ID NO 1320
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1320
gugagcccgu gcagcucuct t                                           21

<210> SEQ ID NO 1321
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1321
gagcugcacg ggcucaccat t                                           21

<210> SEQ ID NO 1322
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1322
uggugagccc gugcagcuct t                                           21

<210> SEQ ID NO 1323
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

```
<400> SEQUENCE: 1323
uacaccaucg cagcccugct t                                              21

<210> SEQ ID NO 1324
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1324
gcagggcugc gaugguguat t                                              21

<210> SEQ ID NO 1325
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1325
guccuggaug cguccgagt t                                               21

<210> SEQ ID NO 1326
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1326
cucggacagc auccaggact t                                              21

<210> SEQ ID NO 1327
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1327
agagcugcac gggcucacct t                                              21

<210> SEQ ID NO 1328
<211> LENGTH: 21
<212> TYPE: DNA
<213> ORGANISM: Rattus norvegicus
<220> FEATURE:
<223> OTHER INFORMATION: Description of Combined DNA/RNA Molecule:
      Rattus norvegicus

<400> SEQUENCE: 1328
ggugagcccg ugcagcucut t                                              21

<210> SEQ ID NO 1329
<211> LENGTH: 650
<212> TYPE: DNA
<213> ORGANISM: Homo sapiens

<400> SEQUENCE: 1329
acagaagtcc actcattctt ggcaggatgg cttctcatcg tctgctcctc ctctgccttg    60
```

```
ctggactggt atttgtgtct gaggctggcc ctacgggcac cggtgaatcc aagtgtcctc      120
tgatggtcaa agttctagat gctgtccgag gcagtcctgc catcaatgtg gccgtgcatg      180
tgttcagaaa ggctgctgat gacacctggg agccatttgc ctctgggaaa accagtgagt      240
ctggagagct gcatgggctc acaactgagg aggaatttgt agaagggata tacaaagtgg      300
aaatagacac caaatcttac tggaaggcac ttggcatctc cccattccat gagcatgcag      360
aggtggtatt cacagccaac gactccggcc ccgccgcta caccattgcc gccctgctga      420
gcccctactc ctattccacc acggctgtcg tcaccaatcc caaggaatga gggacttctc      480
ctccagtgga cctgaaggac gagggatggg atttcatgta accaagagta ttccatttt      540 actaaagcag tgttttcacc tcatatgcta tgttagaagt ccaggcagag acaataaaac      600
attcctgtga aaggcacttt tcattccaaa aaaaaaaaaa aaaaaaaaa                  650
```

<210> SEQ ID NO 1330
<211> LENGTH: 595
<212> TYPE: DNA
<213> ORGANISM: Rattus norvegicus

<400> SEQUENCE: 1330

```
cctgacagga tggcttccct tcgcctgttc ctcctctgcc tcgctggact gatatttgcg       60
tctgaagctg gccctggggg tgctggagaa tccaagtgtc ctctgatggt caaagtcctg      120
gatgctgtcc gaggcagccc tgctgtcgat gtggccgtga agtgttcaa aaggactgca      180 gacggaagct gggagccgtt tgcctctggg aagaccgccg agtctggaga gctgcacggg      240
ctcaccacag atgagaagtt cacggaaggg gtgtacaggg tagaactgga caccaaatca      300
tactggaagg ctcttggcat ttccccattc catgaatacg cagaggtggt tttcacagcc      360
aatgactctg gtcatcgcca ctacaccatc gcagccctgc tcagcccgta ctcctacagc      420
accactgctg tcgtcagtaa ccccccagaac tgagggaccc agcccacgag gaccaagatc      480
ttgccaaagc agtagctccc atttgtactg aaacagtgtt cttgctctat aaaccgtgtt      540
agcaactcgg gaagatgccg tgaaacgttc ttattaaacc acctttattt cattc           595
```

<210> SEQ ID NO 1331
<211> LENGTH: 938
<212> TYPE: DNA
<213> ORGANISM: Homo sapiens

<400> SEQUENCE: 1331

```
gttgactaag tcaataatca gaatcagcag gtttgcagtc agattggcag ggataagcag       60
cctagctcag gagaagtgag tataaaagcc ccaggctggg agcagccatc acagaagtcc      120
actcattctt ggcaggatgg cttctcatcg tctgctcctc ctctgccttg ctggactggt      180
atttgtgtct gaggctggcc ctacgggcac cggtgaatcc aagtgtcctc tgatggtcaa      240
agttctagat gctgtccgag gcagtcctgc catcaatgtg gccgtgcatg tgttcagaaa      300
ggctgctgat gacacctggg agccatttgc ctctgggaaa accagtgagt ctggagagct      360
gcatgggctc acaactgagg aggaatttgt agaagggata tacaaagtgg aaatagacac      420
caaatcttac tggaaggcac ttggcatctc cccattccat gagcatgcag aggtggtatt      480
cacagccaac gactccggcc ccgccgcta caccattgcc gccctgctga gcccctactc      540
ctattccacc acggctgtcg tcaccaatcc caaggaatga gggacttctc ctccagtgga      600
cctgaaggac gagggatggg atttcatgta accaagagta ttccatttt actaaagcag      660 tgttttcacc tcatatgcta tgttagaagt ccaggcagag acaataaaac attcctgtga      720
```

```
aaggcactt  tcattccact  ttaacttgat  tttttaaatt  cccttattgt  cccttccaaa      780
aaaaagagaa  tcaaaatttt  acaaagaatc  aaaggaattc  tagaaagtat  ctgggcagaa      840
cgctaggaga  gatccaaatt  tccattgtct  tgcaagcaaa  gcacgtatta  aatatgatct      900
gcagccatta  aaaagacaca  ttctgtaaaa  aaaaaaaa                                 938
```

<210> SEQ ID NO 1332
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1332
gggauuucau guaaccaagt t                                                      21

<210> SEQ ID NO 1333
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1333
cuugguuaca ugaaauccct t                                                      21

<210> SEQ ID NO 1334
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1334
ggauuucaug uaaccaagat t                                                      21

<210> SEQ ID NO 1335
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1335
ucuugguuac augaaaucct t                                                      21

<210> SEQ ID NO 1336
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1336
gauuucaugu aaccaagagt t                                                      21

<210> SEQ ID NO 1337
<211> LENGTH: 21
<212> TYPE: DNA
<213> ORGANISM: Homo sapiens

```
<220> FEATURE:
<223> OTHER INFORMATION: Description of Combined DNA/RNA Molecule:
      Homo sapiens

<400> SEQUENCE: 1337
cucuugguua caugaaauct t                                              21

<210> SEQ ID NO 1338
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1338
auuucaugua accaagagut t                                              21

<210> SEQ ID NO 1339
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1339
acucuugguu acaugaaaut t                                              21

<210> SEQ ID NO 1340
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1340
uuucauguaa ccaagaguat t                                              21

<210> SEQ ID NO 1341
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1341
uacucuuggu uacaugaaat t                                              21

<210> SEQ ID NO 1342
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1342
uucauguaac caagaguaut t                                              21

<210> SEQ ID NO 1343
<211> LENGTH: 21
<212> TYPE: DNA
<213> ORGANISM: Homo sapiens
<220> FEATURE:
```

<223> OTHER INFORMATION: Description of Combined DNA/RNA Molecule:
      Homo sapiens

<400> SEQUENCE: 1343
auacucuugg uuacaugaat t                                              21

<210> SEQ ID NO 1344
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1344
ucauguaacc aagaguauut t                                              21

<210> SEQ ID NO 1345
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1345
aauacucuug guuacaugat t                                              21

<210> SEQ ID NO 1346
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1346
cauguaacca agaguauuct t                                              21

<210> SEQ ID NO 1347
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1347
gaauacucuu gguuacaugt t                                              21

<210> SEQ ID NO 1348
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1348
auguaaccaa gaguauucct t                                              21

<210> SEQ ID NO 1349
<211> LENGTH: 21
<212> TYPE: DNA
<213> ORGANISM: Homo sapiens
<220> FEATURE:
<223> OTHER INFORMATION: Description of Combined DNA/RNA Molecule:

-continued

Homo sapiens

<400> SEQUENCE: 1349
ggaauacucu ugguuacaut t                                              21

<210> SEQ ID NO 1350
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1350
uguaaccaag aguauuccat t                                              21

<210> SEQ ID NO 1351
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1351
uggaauacuc uugguuacat t                                              21

<210> SEQ ID NO 1352
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1352
uaaccaagag uauuccauut t                                              21

<210> SEQ ID NO 1353
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1353
aauggaauac ucuugguuat t                                              21

<210> SEQ ID NO 1354
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1354
aaccaagagu auuccauuut t                                              21

<210> SEQ ID NO 1355
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

```
<400> SEQUENCE: 1355
aaauggaaua cucuugguut t                                          21

<210> SEQ ID NO 1356
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1356
accaagagua uuccauuuut t                                          21

<210> SEQ ID NO 1357
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1357
aaaauggaau acucuuggut t                                          21

<210> SEQ ID NO 1358
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1358
ccaagaguau uccauuuuut t                                          21

<210> SEQ ID NO 1359
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1359
aaaaauggaa uacucuuggt t                                          21

<210> SEQ ID NO 1360
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1360
caagaguauu ccauuuuuat t                                          21

<210> SEQ ID NO 1361
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens
```

<400> SEQUENCE: 1361
uaaaaaugga auacucuugt t					21

<210> SEQ ID NO 1362
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1362
aagaguauuc cauuuuuact t					21

<210> SEQ ID NO 1363
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1363 guaaaaugg aauacucuut t					21

<210> SEQ ID NO 1364
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1364
agaguauucc auuuuuacut t					21

<210> SEQ ID NO 1365
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1365
aguaaaaaug gaauacucut t					21

<210> SEQ ID NO 1366
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1366
gaguauucca uuuuuacuat t					21

<210> SEQ ID NO 1367
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1367
uaguaaaaau ggaauacuct t                                              21

<210> SEQ ID NO 1368
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1368
aguauuccau uuuuacuaat t                                              21

<210> SEQ ID NO 1369
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1369
uuaguaaaaa uggaauacut t                                              21

<210> SEQ ID NO 1370
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1370
guauuccauu uuuacuaaat t                                              21

<210> SEQ ID NO 1371
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1371
uuuaguaaaa auggaauact t                                              21

<210> SEQ ID NO 1372
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1372
uauuccauuu uuacuaaagt t                                              21

<210> SEQ ID NO 1373
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1373

```
cuuuaguaaa aauggaauau t                                           21

<210> SEQ ID NO 1374
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1374
auuccauuuu uacuaaagct t                                           21

<210> SEQ ID NO 1375
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1375
gcuuuaguaa aaauggaaut t                                           21

<210> SEQ ID NO 1376
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1376
uuccauuuuu acuaaagcat t                                           21

<210> SEQ ID NO 1377
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1377
ugcuuuagua aaauggaat t                                            21

<210> SEQ ID NO 1378
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1378
uccauuuuua cuaaagcagt t                                           21

<210> SEQ ID NO 1379
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1379
cugcuuuagu aaaauggat t                                            21
```

```
<210> SEQ ID NO 1380
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1380
ccauuuuuac uaaagcagut t                                              21

<210> SEQ ID NO 1381
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1381
acugcuuuag uaaaaauggt t                                              21

<210> SEQ ID NO 1382
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1382
cauuuuuacu aaagcagugt t                                              21

<210> SEQ ID NO 1383
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1383
cacugcuuua guaaaaaugt t                                              21

<210> SEQ ID NO 1384
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1384
auuuuuacua aagcagugut t                                              21

<210> SEQ ID NO 1385
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1385
acacugcuuu aguaaaaaut t                                              21
```

```
<210> SEQ ID NO 1386
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1386
uuuuuacuaa agcaguguut t                                              21

<210> SEQ ID NO 1387
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1387
aacacugcuu uaguaaaaat t                                              21

<210> SEQ ID NO 1388
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1388
uuuuacuaaa gcaguguuut t                                              21

<210> SEQ ID NO 1389
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1389
aaacacugcu uuaguaaaat t                                              21

<210> SEQ ID NO 1390
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1390
uuuacuaaag caguguuuut t                                              21

<210> SEQ ID NO 1391
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1391
aaaacacugc uuuaguaaat t                                              21
```

<210> SEQ ID NO 1392
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1392
uuacuaaagc aguguuuuct t                                             21

<210> SEQ ID NO 1393
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1393
gaaaacacug cuuuaguaat t                                             21

<210> SEQ ID NO 1394
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1394
uacuaaagca guguuuucat t                                             21

<210> SEQ ID NO 1395
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1395
ugaaaacacu gcuuuaguat t                                             21

<210> SEQ ID NO 1396
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1396
acuaaagcag uguuuucact t                                             21

<210> SEQ ID NO 1397
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1397
gugaaaacac ugcuuuagut t                                             21

<210> SEQ ID NO 1398

-continued

```
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1398
cuaaagcagu guuucacct t                                                    21

<210> SEQ ID NO 1399
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1399
ggugaaaaca cugcuuuagt t                                                   21

<210> SEQ ID NO 1400
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1400
uaaagcagug uuucaccut t                                                    21

<210> SEQ ID NO 1401
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1401
aggugaaaac acugcuuuat t                                                   21

<210> SEQ ID NO 1402
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1402
aaagcagugu uuucaccuct t                                                   21

<210> SEQ ID NO 1403
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1403
gaggugaaaa cacugcuuut t                                                   21

<210> SEQ ID NO 1404
<211> LENGTH: 21
```

```
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1404
aagcaguguu uucaccucat t                                              21

<210> SEQ ID NO 1405
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1405
ugaggugaaa acacugcuut t                                              21

<210> SEQ ID NO 1406
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1406
agcaguguuu ucaccucaut t                                              21

<210> SEQ ID NO 1407
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1407
augaggugaa aacacugcut t                                              21

<210> SEQ ID NO 1408
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1408
guaaccaaga guauuccaut t                                              21

<210> SEQ ID NO 1409
<211> LENGTH: 21
<212> TYPE: DNA
<213> ORGANISM: Homo sapiens
<220> FEATURE:
<223> OTHER INFORMATION: Description of Combined DNA/RNA Molecule:
      Homo sapiens

<400> SEQUENCE: 1409
auggaauacu cuugguuact t                                              21

<210> SEQ ID NO 1410
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1410 gtaaccaa gagtattccat                                                      19
```

COMPOSITIONS AND METHODS FOR INHIBITING EXPRESSION OF TRANSTHYRETIN

CROSS REFERENCE TO RELATED APPLICATIONS

This application is a continuation of U.S. patent application Ser. No. 14/965,825, filed Dec. 10, 2015, (pending), which is a continuation of U.S. patent application Ser. No. 14/220,829, filed Mar. 20, 2014, now U.S. Pat. No. 9,234,196, issued Jan. 12, 2016, which is a continuation of U.S. patent application Ser. No. 13/410,262, filed Mar. 1, 2012, now U.S. Pat. No. 8,741,866, issued Jun. 3, 2014, which is a continuation of U.S. patent application Ser. No. 12/582,669, filed Oct. 20, 2009, now U.S. Pat. No. 8,168,775, issued May 1, 2012, which claims the benefit of U.S. Provisional Application No. 61/106,956, filed Oct. 20, 2008; U.S. Provisional Application No. 61/115,738, filed Nov. 18, 2008; U.S. Provisional Application No. 61/156,670, filed Mar. 2, 2009; U.S. Provisional Application No. 61/185,545, filed Jun. 9, 2009; U.S. Provisional Application No. 61/242,783, filed Sep. 15, 2009; and U.S. Provisional Application No. 61/244,794, filed Sep. 22, 2009, all of which are incorporated herein by reference, in their entirety, for all purposes.

FIELD OF THE INVENTION

The invention relates to a double-stranded ribonucleic acid (dsRNA) targeting a transthyretin (TTR) gene, and methods of using the dsRNA to inhibit expression of TTR.

REFERENCE TO SEQUENCE LISTING

The instant application contains a Sequence Listing which has been submitted via EFS-Web and is hereby incorporated by reference in its entirety. Said ASCII copy, created on Dec. 5, 2016, is named 35642_US_sequencelisting.txt, which contains 1410 sequences and is 323,584 bytes in size.

BACKGROUND OF THE INVENTION

Transthyretin (TTR) is a secreted thyroid hormone-binding protein. TTR binds and transports retinol binding protein (RBP)/Vitamin A, and serum thyroxine (T4) in plasma and cerebrospinal fluid.

Both normal-sequence TTR and variant-sequence TTR cause amyloidosis. Normal-sequence TTR causes cardiac amyloidosis in people who are elderly and is termed senile systemic amyloidosis (SSA) (also called senile cardiac amyloidosis (SCA)). SSA often is accompanied by microscopic deposits in many other organs. TTR mutations accelerate the process of TTR amyloid formation and are the most important risk factor for the development of clinically significant TTR amyloidosis (also called ATTR (amyloidosis-transthyretin type)). More than 85 amyloidogenic TTR variants are known to cause systemic familial amyloidosis. The liver is the major site of TTR expression. Other significant sites of expression include the choroid plexus, retina and pancreas.

TTR amyloidosis manifests in various forms. When the peripheral nervous system is affected more prominently, the disease is termed familial amyloidotic polyneuropathy (FAP). When the heart is primarily involved but the nervous system is not, the disease is called familial amyloidotic cardiomyopathy (FAC). A third major type of TTR amyloidosis is called leptomeningeal/CNS (Central Nervous System) amyloidosis.

Double-stranded RNA molecules (dsRNA) have been shown to block gene expression in a highly conserved regulatory mechanism known as RNA interference (RNAi). WO 99/32619 (Fire et al.) disclosed the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al.; and WO 99/61631, Heifetz et al.), *Drosophila* (see, e.g., Yang, D., et al., *Curr. Biol.* (2000) 10:1191-1200), and mammals (see WO 00/44895, Limmer; and DE 101 00 586.5, Kreutzer et al.).

U.S. 20070207974 discloses functional and hyperfunctional siRNAs. U.S. 20090082300 discloses antisense molecules directed against TTR. U.S. Pat. No. 7,250,496 discloses microRNAs directed against TTR.

SUMMARY OF THE INVENTION

In one embodiment, the invention provides a double-stranded ribonucleic acid (dsRNA) for inhibiting expression of transthyretin (TTR), wherein said dsRNA comprises a sense strand and an antisense strand, the antisense strand comprising a region complementary to a part of a mRNA encoding transthyretin (TTR), wherein said region of complementarity is less than 30 nucleotides in length and the antisense strand comprises 15 or more contiguous nucleotides of SEQ ID NO:170, SEQ ID NO:450, SEQ ID NO:730, or SEQ ID NO:1010. In a related embodiment, the sense strand comprises 15 or more contiguous nucleotides of SEQ ID NO: 169, SEQ ID NO:449, SEQ ID NO:729, or SEQ ID NO: 1009. In yet another related embodiment, the sense strand consists of SEQ ID NO:449 and the antisense strand consists of SEQ ID NO:450. In yet another related embodiment, the sense strand consists of SEQ ID NO:729 and the antisense strand consists of SEQ ID NO:730. In still another related embodiment, the sense strand consists of SEQ ID NO:1009 and the antisense strand consists of SEQ ID NO:1010. In yet another related embodiment, the dsRNA comprises a sense strand selected from Tables 3A, 3B, 4, 6A, 6B, 7, and 16, and an antisense strand selected from Tables 3A, 3B, 4, 6A, 6B, 7, and 16.

In certain embodiments, the region of complementarity between the antisense strand of the dsRNA and the mRNA encoding transthyretin is 19 nucleotides in length. In another embodiment, the region of complementary consists of SEQ ID NO: 169. In other embodiments, each strand of the dsRNA is 19, 20, 21, 22, 23, or 24 nucleotides in length. In still another embodiment, each strand is 21 nucleotides in length.

In certain embodiments, the dsRNA for inhibiting expression of transthyretin does not cleave a TTR mRNA between the adenine nucleotide at position 637 of SEQ ID NO: 1331 and the guanine nucleotide at position 638 of SEQ ID NO:1331. In other embodiments, the dsRNA cleaves a TTR mRNA between the guanine nucleotide at position 636 of SEQ ID NO: 1331 and the adenine nucleotide at position 637 of SEQ ID NO:1331. In certain embodiments, the dsRNA anneals to a TTR mRNA between the guanine nucleotide at position 628 of SEQ ID NO: 1331 and the uracil nucleotide at position 646 of SEQ ID NO: 1331.

In still other related embodiments, the invention provides dsRNA as described above for inhibiting expression of transthyretin wherein the dsRNA comprises one or more modified nucleotides. In related embodiments, at least one modified nucleotide (or nucleotides) is chosen from the group consisting of: a 2'-O-methyl modified nucleotide, a nucleotide comprising a 5'-phosphorothioate group, and a terminal nucleotide linked to a cholesteryl derivative or dodecanoic acid bisdecylamide group. In another related embodiment, the modified nucleotide is chosen from the group of: a 2'-deoxy-2'-fluoro modified nucleotide, a 2'-deoxy-modified nucleotide, a locked nucleotide, an a basic nucleotide, 2'-amino-modified nucleotide, 2'-alkyl-modified nucleotide, morpholino nucleotide, a phosphoramidate, and a non-natural base comprising nucleotide. In certain embodiments, the dsRNA comprises at least one 2'-O-methyl modified nucleotide.

In other embodiments, a dsRNA as described above for inhibiting expression of transthyretin is conjugated to a ligand, or formulated in a lipid formulation. In certain embodiments, the lipid formulation may be a LNP formulation, a LNP01 formulation, a XTC-SNALP formulation, or a SNALP formulation. In related embodiments, the XTC-SNALP formulation is as follows: using 2,2-Dilinoleyl-4-dimethylaminoethyl-[1,3]-dioxolane (XTC) with XTC/DPPC/Cholesterol/PEG-cDMA in a ratio of 57.1/7.1/34.4/1.4 and a lipid:siRNA ratio of about 7. In still other related embodiments, the sense strand of the dsRNA consists of SEQ ID NO:1009 and the antisense strand consists of SEQ ID NO:1010, and the dsRNA is formulated in a XTC-SNALP formulation as follows: using 2,2-Dilinoleyl-4-dimethylaminoethyl-[1,3]-dioxolane (XTC) with a XTC/DPPC/Cholesterol/PEG-cDMA in a ratio of 57.1/7.1/34.4/1.4 and a lipid:siRNA ratio of about 7. Alternatively, a dsRNA such as those described above can be formulated in a LNP09 formulation as follows: using XTC/DSPC/Chol/PEG$_{2000}$-C14 in a ratio of 50/10/38.5/1.5 mol % and a lipid:siRNA ratio of about 11:1. In another variation, the dsRNA is formulated in a LNP11 formulation as follows: using MC3/DSPC/Chol/PEG$_{2000}$-C14 in a ratio of 50/10/38.5/1.5 mol % and a lipid:siRNA ratio of about 11:1. In still another embodiment, the dsRNA is formulated in a LNP09 formulation or a LNP11 formulation and reduces TTR mRNA levels by about 85 to 90% at a dose of 0.3 mg/kg, relative to a PBS control group. In yet another embodiment, the dsRNA is formulated in a LNP09 formulation or a LNP11 formulation and reduces TTR mRNA levels by about 50% at a dose of 0.1 mg/kg, relative to a PBS control group. In yet another embodiment, the dsRNA is formulated in a LNP09 formulation or a LNP11 formulation and reduces TTR protein levels in a dose-dependent manner relative to a PBS control group as measured by a western blot. In yet another embodiment, the dsRNA is formulated in a SNALP formulation as follows: using DlinDMA with a DLinDMA/DPPC/Cholesterol/PEG2000-cDMA in a ratio of 57.1/7.1/34.4/1.4 and a lipid:siRNA ratio of about 7.

In certain embodiments, the invention provides a dsRNA such as those described above for inhibiting expression of transthyretin, wherein administration of the dsRNA to a cell results in about 95% inhibition of TTR mRNA expression as measured by a real time PCR assay, wherein the cell is a HepG2 cell or a Hep3B cell, and wherein the concentration of the dsRNA is 10 nM. In related embodiments, administration of the dsRNA to a cell results in about 74% inhibition of TTR mRNA expression as measured by a branched DNA assay, wherein the cell is a HepG2 cell or a Hep3B cell, and wherein the concentration of the dsRNA is 10 nM. In other related embodiments, the dsRNA has an IC50 of less than 10 pM in a HepG2 cell, wherein the concentration of the dsRNA is 10 nM. In still other related embodiments, the dsRNA has an ED50 of about 1 mg/kg. In still other related embodiments, administration of the dsRNA reduces TTR mRNA by about 80% in cynomolgus monkey liver, wherein the concentration of the dsRNA is 3 mg/kg. In still other related embodiments, administration of the dsRNA does not result in immunostimulatory activity in human peripheral blood mononuclear cells (PBMCs) as measured by IFN-alpha and TNF-alpha ELISA assays. In still other related embodiments, administration of the dsRNA reduces liver TTR mRNA levels by about 97% or serum TTR protein levels by about 90%, wherein the concentration of the dsRNA is 6 mg/kg. In still other related embodiments, administration of the dsRNA reduces liver TTR mRNA levels and/or serum TTR protein levels up to 22 days, wherein the concentration of the dsRNA is 6 mg/kg or 3 mg/kg. In still other related embodiments, the dsRNA suppresses serum TTR protein levels up to day 14 post-treatment when administered to a subject in need thereof at 1 mg/kg or 3 mg/kg. In still other related embodiments, the dsRNA reduces TTR expression by 98.9% in a Hep3B cell at a concentration of 0.1 nM as measured by real-time PCR. In still other related embodiments, the dsRNA reduces TTR expression by 99.4% in a Hep3B cell at a concentration of 10 nM as measured by real-time PCR.

In other embodiments, the invention provides a double-stranded ribonucleic acid (dsRNA) for inhibiting expression of transthyretin (TTR), wherein said dsRNA comprises a sense strand and an antisense strand, the antisense strand comprising a region complementary to a part of a mRNA encoding transthyretin (TTR), wherein said region of complementarity is less than 30 nucleotides in length and wherein the dsRNA comprises a sense strand selected from Tables 3A, 3B, 4, 6A, 6B, 7, and 16, and an antisense strand selected from Tables 3A, 3B, 4, 6A, 6B, 7, and 16.

In another embodiment, the invention provides a double-stranded ribonucleic acid (dsRNA) for inhibiting expression of transthyretin (TTR), wherein said dsRNA comprises an antisense strand comprising a region complementary to 15-30 nucleotides of nucleotides 618-648 of SEQ ID NO: 1331 and wherein said antisense strand base pairs with the guanine at position 628 of SEQ ID NO:1331.

In certain embodiments, the invention provides a cell containing any of the dsRNAs described in the Summary, above. In certain other embodiments, the invention provides a vector comprising a nucleotide sequence that encodes at least one strand of any of the dsRNAs described in the Summary, above. In certain embodiments, the vector is in a cell.

In other embodiments, the invention provides a pharmaceutical composition for inhibiting expression of a TTR gene comprising any of the dsRNAs described in the Summary, above, and a pharmaceutically acceptable carrier. In related embodiments, the invention provides a pharmaceutical composition for inhibiting expression of a TTR gene comprising a dsRNA and a SNALP formulation, wherein the dsRNA comprises an antisense strand which is less than 30 nucleotides in length and comprises 15 or more contiguous nucleotides of SEQ ID NO: 170, SEQ ID NO:450, SEQ ID NO:730, or SEQ ID NO: 1010, and wherein the SNALP formulation comprises DlinDMA, DPPC, Cholesterol and PEG2000-cDMA in a ratio of 57.1/7.1/34.4/1.4 respectively.

In yet another embodiment, the invention provides a method of inhibiting TTR expression in a cell, the method comprising: (a) contacting the cell with any of dsRNAs described in the Summary, above; and (b) maintaining the cell produced in step (a) for a time sufficient to obtain degradation of the mRNA transcript of a TTR gene, thereby inhibiting expression of the TTR gene in the cell.

In yet another embodiment, the invention provides a method of treating a disorder mediated by TTR expression comprising administering to a human in need of such treatment a therapeutically effective amount of any of the dsRNAs describe in the Summary, above. In related embodiments, the dsRNA is administered to the human at about 0.01, 0.1, 0.5, 1.0, 2.5, or 5.0 mg/kg. In yet another related embodiment, the dsRNA is administered to the human at about 1.0 mg/kg. In yet another related embodiment, the human being treated has transthyretin amyloidosis, and/or a liver disorder. In a related embodiment, the human is further provided a liver transplant. In yet another embodiment, administration of the dsRNA reduces TTR mRNA by about 80% in human liver, wherein the concentration of the dsRNA is 3 mg/kg. In yet another related embodiment, administration of the dsRNA does not result in immunostimulatory activity in the human as measured by IFN-alpha and TNF-alpha ELISA assays. In yet another related embodiment, administration of the dsRNA reduces liver TTR mRNA levels by about 97% or serum TTR protein levels by about 90%, wherein the concentration of the dsRNA is 6 mg/kg. In yet another related embodiment, administration of the dsRNA reduces liver TTR mRNA levels and/or serum TTR protein levels up to 22 days, wherein the concentration of the dsRNA is 6 mg/kg or 3 mg/kg. In yet another related embodiment, the dsRNA is formulated in a LNP09 formulation as follows: using XTC/DSPC/Chol/PEG$_{2000}$-C14 in a ratio of 50/10/38.5/1.5 mol % and a lipid:siRNA ratio of about 11:1. In yet another related embodiment, the dsRNA is formulated in a LNP11 formulation as follows: using MC3/DSPC/Chol/PEG$_{2000}$-C14 in a ratio of 50/10/38.5/1.5 mol % and a lipid:siRNA ratio of about 11:1. In yet another related embodiment, the dsRNA is formulated in a LNP09 formulation or a LNP11 formulation and reduces TTR mRNA levels by about 85 to 90% at a dose of 0.3 mg/kg, relative to a PBC control group. In yet another related embodiment, the dsRNA is formulated in a LNP09 formulation or a LNP11 formulation and reduces TTR mRNA levels by about 50% at a dose of 0.1 mg/kg, relative to a PBC control group. In still another related embodiment, the dsRNA is formulated in a LNP09 formulation or a LNP11 formulation and reduces TTR protein levels in a dose-dependent manner relative to a PBC control group as measured by a western blot. In still another related embodiment, administration of the dsRNA suppresses serum TTR protein levels up to day 14 post-treatment when administered to human at 1 mg/kg or 3 mg/kg. In still another related embodiment, the dsRNA is formulated in a SNALP formulation as follows: using DlinDMA with a DLinDMA/DPPC/Cholesterol/PEG2000-cDMA in a ratio of 57.1/7.1/34.4/1.4 and a lipid:siRNA ratio of about 7.

In another embodiment, the invention provides the use of a dsRNA for treating a disorder mediated by TTR expression comprising administering to a human in need of such treatment a therapeutically effective amount of any of the dsRNAs described in the Summary, above. In related embodiments, the dsRNA is administered to the human at about 0.01, 0.1, 0.5, 1.0, 2.5, or 5.0 mg/kg. In a particular related embodiment, the dsRNA is administered to the human at about 1.0 mg/kg. In another related embodiment, the human has transthyretin amyloidosis, and/or a liver disorder. In yet another embodiment of the use provided by the invention, the treated human is further provided a liver transplant.

In yet another embodiment, the invention provides the use of a dsRNA in a method for inhibiting TTR expression in a cell, wherein the method comprises (a) contacting the cell with a dsRNA described in the Summary, above; and (b) maintaining the cell produced in step (a) for a time sufficient to obtain degradation of the mRNA transcript of a TTR gene, thereby inhibiting expression of the TTR gene in the cell.

The details of one or more embodiments of the invention are set forth in the description below. Other features, objects, and advantages of the invention will be apparent from the description and the drawings, and from the claims.

DESCRIPTION OF THE DRAWINGS

FIG. 6A and FIG. 6B show inhibition of human V30M TTR liver mRNA and serum protein levels, respectively, in transgenic mice by an intravenous bolus administration of SNALP-18328. Group means were determined, normalized to the PBS control group, and then plotted. Error bars represent standard deviations. The percentage reduction of the group mean, relative to PBS, is indicated for the SNALP-1955 and SNALP-18328 groups. (***$p<0.001$, One-way ANOVA, with Dunn's post-hoc test).

FIG. 7A and FIG. 7B show the durability of reduction of human V30M TTR liver mRNA and serum protein levels, respectively, in transgenic mice over 22 days following a single intravenous bolus administration of SNALP-18328. Group means were determined. TTR/GAPDH mRNA levels were normalized to day 0 levels and plotted. The percent reduction of normalized TTR mRNA levels relative to SNALP-1955 for each time point were calculated and are indicated for the SNALP-18328 groups. (***$p<0.001$, One-way ANOVA, with Dunn's post-hoc test).

FIGS. 11A and 11B show the measurements of TTR mRNA and serum protein levels, respectively, in livers of non-human primates following 15-minute intravenous infusion of LNP09-18328 or LNP11-18328.

FIG. 12 shows the sequence of human TTR mRNA (Ref. Seq. NM_000371.3, SEQ ID NO:1331).

FIGS. 13A and 13B are the sequences of human and rat TTR mRNA, respectively. FIG. 13A is the sequence of human TTR mRNA (Ref Seq. NM_000371.2, SEQ ID NO:

1329). FIG. 13B is the sequence of rat TTR mRNA (Ref. Seq. NM_012681.1, SEQ ID NO: 1330).

FIG. 14 shows the nucleotide alignment of NM_000371.3 (SEQ ID NO: 1331), NM_000371.2 (SEQ ID NO: 1329), and AD-18328 (SEQ ID NO: 1410).

FIG. 15 illustrates symptoms and mutations in TTR associated with familial amyloidotic neuropathy, familial amyloidotic cardiomyopathy and CNS amyloidosis.

DETAILED DESCRIPTION OF THE INVENTION

Figure 1:
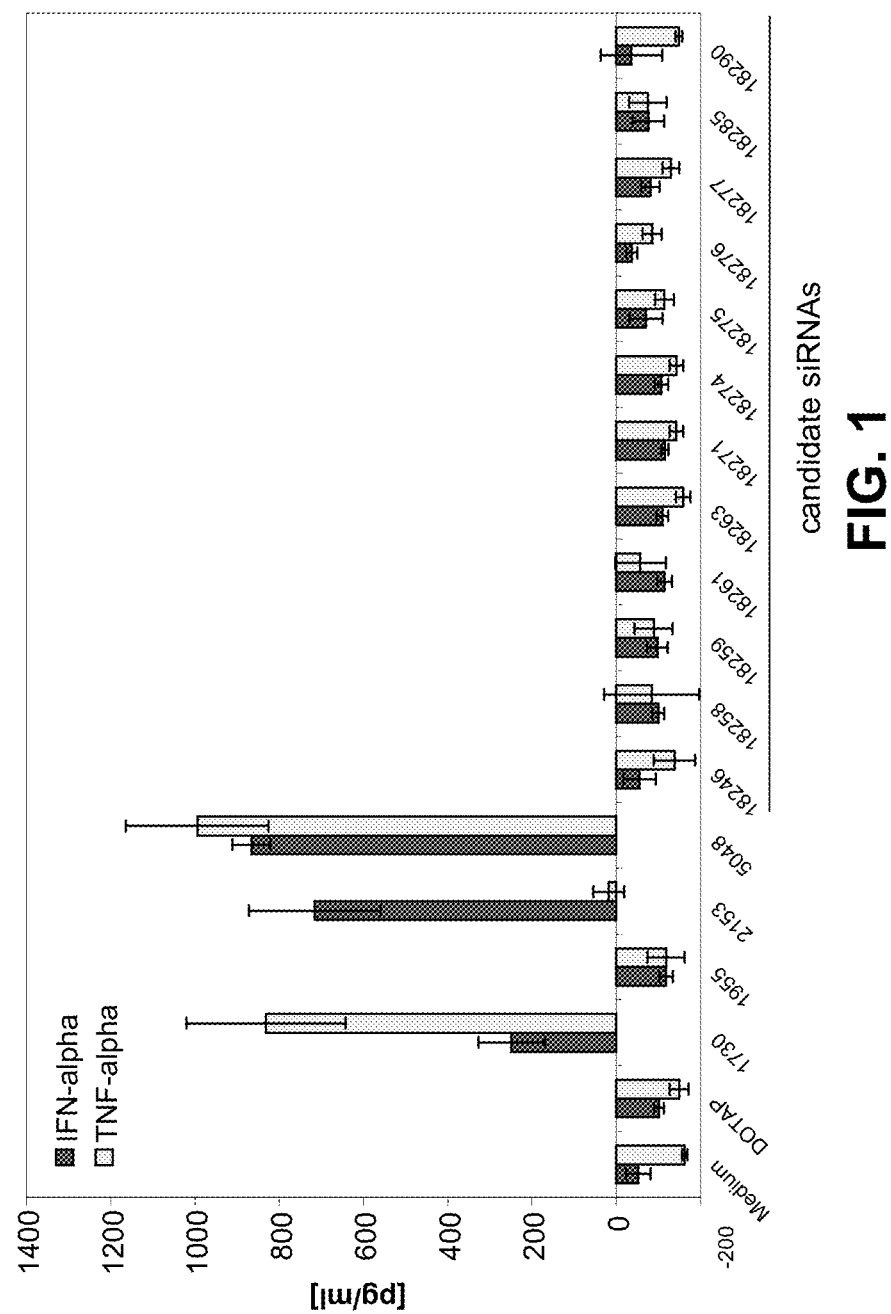
FIG. 1 is a graph of TNFalpha and IFNalpha levels in cultured human PBMCs following transfection with TTR siRNAs.

The invention provides dsRNAs and methods of using the dsRNAs for inhibiting the expression of a TTR gene in a cell or a mammal where the dsRNA targets a TTR gene. The invention also provides compositions and methods for treating pathological conditions and diseases, such as a TTR amyloidosis, in a mammal caused by the expression of a TTR gene. dsRNA directs the sequence-specific degradation of mRNA through a process known as RNA interference (RNAi).

The dsRNAs of the compositions featured herein include an RNA strand (the antisense strand) having a region which is less than 30 nucleotides in length, generally 19-24 nucleotides in length, and is substantially complementary to at least part of an mRNA transcript of a TTR gene. The use of these dsRNAs enables the targeted degradation of mRNAs of genes that are implicated in pathologies associated with TTR expression in mammals. Very low dosages of TTR dsRNAs in particular can specifically and efficiently mediate RNAi, resulting in significant inhibition of expression of a TTR gene. Using cell-based assays, the present inventors have demonstrated that dsRNAs targeting TTR can specifically and efficiently mediate RNAi, resulting in significant inhibition of expression of a TTR gene. Thus, methods and compositions including these dsRNAs are useful for treating pathological processes that can be mediated by down regulating TTR, such as in the treatment of a liver disorder or a TTR amyloidosis, e.g., FAP.

The methods and compositions containing a TTR dsRNA are useful for treating pathological processes mediated by TTR expression, such as a TTR amyloidosis. In an embodiment, a method of treating a disorder mediated by TTR expression includes administering to a human in need of such treatment a therapeutically effective amount of a dsRNA targeted to TTR. In an embodiment, a dsRNA is administered to the human at about 0.01, 0.1, 0.5, 1.0, 2, 2.5, 3, 4, 5, 6, 7, 8, 9, 10, 11, 12, 13, 14, 15, 16, 17, 18, 19, 20, 21, 22, 23, 24, or 25 mg/kg.

The following detailed description discloses how to make and use the compositions containing dsRNAs to inhibit the expression of a TTR gene, as well as compositions and methods for treating diseases and disorders caused by the expression of this gene. The pharmaceutical compositions featured in the invention include a dsRNA having an antisense strand comprising a region of complementarity which is less than 30 nucleotides in length, generally 19-24 nucleotides in length, and is substantially complementary to at least part of an RNA transcript of a TTR gene, together with a pharmaceutically acceptable carrier. The compositions featured in the invention also include a dsRNA having an antisense strand having a region of complementarity which is less than 30 nucleotides in length, generally 19-24 nucleotides in length, and is substantially complementary to at least part of an RNA transcript of a TTR gene.

The sense strand of a dsRNA can include 15, 16, 17, 18, 19, 20, 21, or more contiguous nucleotides of SEQ ID NO:169, SEQ ID NO:449, SEQ ID NO:729, or SEQ ID NO:1009. The antisense strand of a dsRNA can include 15, 16, 17, 18, 19, 20, 21, or more contiguous nucleotides of SEQ ID NO:170, SEQ ID NO:450, SEQ ID NO:730, or SEQ ID NO:1010. In an embodiment, the sense strand of a dsRNA can consist of SEQ ID NO:449 or fragments thereof and the antisense strand can consist of SEQ ID NO:450 or fragments thereof. In an embodiment, the sense strand of a dsRNA can consist of SEQ ID NO:729 or fragments thereof and the antisense strand can consist of SEQ ID NO:730 or fragments thereof. In an embodiment, the sense strand of a dsRNA can consist of SEQ ID NO: 1009 or fragments thereof and the antisense strand can consist of SEQ ID NO: 1010 or fragments thereof.

In an embodiment, a dsRNA can include at least 1, 2, 3, 4, 5, 6, 7, 8, 9, 10, or more modified nucleotides. In an embodiment, a modified nucleotide can include a 2'-O-methyl modified nucleotide, a nucleotide comprising a 5'-phosphorothioate group, and/or a terminal nucleotide linked to a cholesteryl derivative or dodecanoic acid bisdecylamide group. In an embodiment, a modified nucleotide can include a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and/or a non-natural base comprising nucleotide.

In an embodiment, the region of complementary of a dsRNA is at least 10, 11, 12, 13, 14, 15, 16, 17, 18, 19, 20, 21, or more nucleotides in length. In an embodiment, the region of complementary includes 10, 11, 12, 13, 14, 15, 16, 17, 18, 19, 20, 21, or more contiguous nucleotides of SEQ ID NO:169.

In an embodiment, each strand of a dsRNA is 15, 16, 17, 18, 19, 20, 21, 22, 23, 24, 25, 26, 27, 28, 29, 30 or more nucleotides in length. In an embodiment, the dsRNA includes a sense strand, or 10, 11, 12, 13, 14, 15, 16, 17, 18, 19, 20, or 21 nucleotide fragment thereof, selected from Tables 3A, 3B, 4, 6A, 6B, 7, and 16, and an antisense strand, or 10, 11, 12, 13, 14, 15, 16, 17, 18, 19, 20, or 21 nucleotide fragment thereof, selected from Tables 3A, 3B, 4, 6A, 6B, 7, and 16.

In an embodiment, administration of a dsRNA to a cell results in about 40%, 45%, 50%, 55%, 60%, 65%, 70%, 75%, 80%, 90%, 95% or more inhibition of TTR mRNA expression as measured by a real time PCR assay. In an embodiment, administration of a dsRNA to a cell results in about 40% to 45%, 45% to 50%, 50% to 55%, 55% to 60%, 60% to 65%, 65% to 70%, 70% to 75%, 75% to 80%, 80% to 85%, 85% to 90%, 90% to 95% or more inhibition of TTR mRNA expression as measured by a real time PCR assay. In an embodiment, administration of a dsRNA to a cell results in about 40%, 45%, 50%, 55%, 60%, 65%, 70%, 75%, 80%, 90%, 95% or more inhibition of TTR mRNA expression as measured by a branched DNA assay. In an embodiment, administration of a dsRNA to a cell results in about 40% to 45%, 45% to 50%, 50% to 55%, 55% to 60%, 60% to 65%, 65% to 70%, 70% to 75%, 75% to 80%, 80% to 85%, 85% to 90%, 90% to 95% or more inhibition of TTR mRNA expression as measured by a branched DNA assay.

In an embodiment, a dsRNA has an IC50 of less than 0.01 pM, 0.1 pM, 1 pM, 5 pM, 10 pM, 100 pM, or 1000 pM. In an embodiment, a dsRNA has an ED50 of about 0.01, 0.1, 1, 5, or 10 mg/kg.

In an embodiment, administration of a dsRNA can reduce TTR mRNA by about 40%, 45%, 50%, 55%, 60%, 65%, 70%, 75%, 80%, 90%, 95% or more in cynomolgus monkeys. In an embodiment, administration of a dsRNA reduces liver TTR mRNA levels by about 40%, 45%, 50%, 55%, 60%, 65%, 70%, 75%, 80%, 90%, 95% or more or serum TTR protein levels by about 40%, 45%, 50%, 55%, 60%, 65%, 70%, 75%, 80%, 90%, 95% or more. In an embodiment, administration of a dsRNA reduces liver TTR mRNA levels and/or serum TTR protein levels up to 1, 2, 3, 4, 5, 6, 7, 8, 9, 10, 11, 12, 13, 14, 15, 16, 17, 18, 19, 20, 21, 22, 23, 24, 25, or more days.

In an embodiment, a dsRNA is formulated in a LNP formulation and reduces TTR mRNA levels by about 40%, 45%, 50%, 55%, 60%, 65%, 70%, 75%, 80%, 90%, 95% or more at a dose of 0.1, 0.2, 0.3, 0.4, 0.5, 0.6, 0.7, 0.8, 0.9, or 1 mg/kg, relative to a PBC control group. In an embodiment, a dsRNA is formulated in a LNP formulation and reduces TTR protein levels about 40%, 45%, 50%, 55%, 60%, 65%, 70%, 75%, 80%, 90%, 95% or more relative to a PBC control group as measured by a western blot. In an embodiment, a dsRNA suppresses serum TTR protein levels up to day 1, 2, 3, 4, 5, 6, 7, 8, 9, 10, 11, 12, 13, 14, 15, 16, 17, 18, 19, 20, 21, 22, 23, 24, or 25 post-treatment when administered to a subject in need thereof at 1, 2, 3, 4, 5, 6, 7, 8, 9, 10, 11, 12, 13, 14, 15, 16, 17, 18, 19, 20, 21, 22, 23, 24, or 25 mg/kg.

Accordingly, in some aspects, pharmaceutical compositions containing a TTR dsRNA and a pharmaceutically acceptable carrier, methods of using the compositions to inhibit expression of a TTR gene, and methods of using the pharmaceutical compositions to treat diseases caused by expression of a TTR gene are featured in the invention.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "transthyretin" ("TTR") refers to a gene in a cell. TTR is also known as ATTR, HsT2651, PALB, prealbumin, TBPA, and transthyretin (prealbumin, amyloidosis type I). The sequence of a human TTR mRNA transcript can be found at NM_000371. The sequence of mouse TTR mRNA can be found at NM_013697.2, and the sequence of rat TTR mRNA can be found at NM_012681.1.

As used herein, "target sequence" refers to a contiguous portion of the nucleotide sequence of an mRNA molecule formed during the transcription of a TTR gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding TTR) including a 5' UTR, an open reading frame (ORF), or a 3' UTR. For example, a polynucleotide is complementary to at least a part of a TTR mRNA if the sequence is substantially complementary to a non-interrupted portion of an mRNA encoding TTR.

The term "double-stranded RNA" or "dsRNA," as used herein, refers to a complex of ribonucleic acid molecules, having a duplex structure comprising two anti-parallel and substantially complementary, as defined above, nucleic acid strands. In general, the majority of nucleotides of each strand are ribonucleotides, but as described in detail herein, each or both strands can also include at least one non-ribonucleotide, e.g., a deoxyribonucleotide and/or a modified nucleotide. In addition, as used in this specification, "dsRNA" may include chemical modifications to ribonucleotides, including substantial modifications at multiple nucleotides and including all types of modifications disclosed herein or known in the art. Any such modifications, as used in an siRNA type molecule, are encompassed by "dsRNA" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs. The term "siRNA" is also used herein to refer to a dsRNA as described above.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

As used herein, the term "SNALP" refers to a stable nucleic acid-lipid particle. A SNALP represents a vesicle of lipids coating a reduced aqueous interior comprising a nucleic acid such as a dsRNA or a plasmid from which a dsRNA is transcribed. SNALP are described, e.g., in U.S. Patent Application Publication Nos. 20060240093, 20070135372, and U.S. Ser. No. 61/045,228 filed on Apr. 15, 2008. These applications are hereby incorporated by reference.

"Introducing into a cell," when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell," wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection. Further approaches are described herein or known in the art.

The terms "silence," "inhibit the expression of," "down-regulate the expression of," "suppress the expression of" and the like in as far as they refer to a TTR gene, herein refer to the at least partial suppression of the expression of a TTR gene, as manifested by a reduction of the amount of mRNA which may be isolated from a first cell or group of cells in which a TTR gene is transcribed and which has or have been treated such that the expression of a TTR gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to TTR gene expression, e.g., the amount of protein encoded by a TTR gene which is secreted by a cell, or the number of cells displaying a certain phenotype, e.g., apoptosis. In principle, TTR gene silencing may be determined in any cell expressing the target, either constitutively or by genomic engineering, and by any appropriate assay. However, when a reference is needed in order to determine whether a given dsRNA inhibits the expression of a TTR gene by a certain degree and therefore is encompassed by the instant invention, the assays provided in the Examples below shall serve as such reference.

For example, in certain instances, expression of a TTR gene is suppressed by at least about 5%, 10%, 15%, 20%, 25%, 30%, 35%, 40%, 45%, or 50% by administration of the double-stranded oligonucleotide featured in the invention. In some embodiments, a TTR gene is suppressed by at least about 60%, 70%, or 80% by administration of the double-stranded oligonucleotide featured in the invention. In some embodiments, a TTR gene is suppressed by at least about 85%, 90%, or 95% by administration of the double-stranded oligonucleotide featured in the invention.

As used herein in the context of TTR expression, the terms "treat," "treatment," and the like, refer to relief from or alleviation of pathological processes mediated by TTR expression. In the context of the present invention insofar as it relates to any of the other conditions recited herein below (other than pathological processes mediated by TTR expression), the terms "treat," "treatment," and the like mean to relieve or alleviate at least one symptom associated with such condition, or to slow or reverse the progression of such condition, such as the slowing the progression of a TTR amyloidosis, such as FAP. Symptoms of TTR amyloidosis include sensory neuropathy (e.g. paresthesia, hypesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and corneal lattice dystrophy.

As used herein, the phrases "therapeutically effective amount" and "prophylactically effective amount" refer to an amount that provides a therapeutic benefit in the treatment, prevention, or management of pathological processes mediated by TTR expression or an overt symptom of pathological processes mediated by TTR expression. The specific amount that is therapeutically effective can be readily determined by an ordinary medical practitioner, and may vary depending on factors known in the art, such as, for example, the type of pathological processes mediated by TTR expression, the patient's history and age, the stage of pathological processes mediated by TTR expression, and the administration of other anti-pathological processes mediated by TTR expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter. For example, a therapeutically effective amount of a dsRNA targeting TTR can reduce TTR serum levels by at least 25%. In another example, a therapeutically effective amount of a dsRNA targeting TTR can improve liver function or renal function by at least 25%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-Stranded Ribonucleic Acid (dsRNA)

As described in more detail herein, the invention provides double-stranded ribonucleic acid (dsRNA) molecules for inhibiting the expression of a TTR gene in a cell or mammal, e.g., in a human having a TTR amyloidosis, where the dsRNA includes an antisense strand having a region of complementarity which is complementary to at least a part of an mRNA formed in the expression of a TTR gene, and where the region of complementarity is less than 30 nucleotides in length, generally 19-24 nucleotides in length, and where said dsRNA, upon contact with a cell expressing said TTR gene, inhibits the expression of said TTR gene by at least 30% as assayed by, for example, a PCR or branched DNA (bDNA)-based method, or by a protein-based method, such as by Western blot. Expression of a TTR gene can be reduced by at least 30% when measured by an assay as described in the Examples below. For example, expression of a TTR gene in cell culture, such as in Hep3B cells, can be assayed by measuring TTR mRNA levels, such as by bDNA or TaqMan assay, or by measuring protein levels, such as by ELISA assay. The dsRNA of the invention can further include one or more single-stranded nucleotide overhangs.

The dsRNA can be synthesized by standard methods known in the art as further discussed below, e.g., by use of an automated DNA synthesizer, such as are commercially available from, for example, Biosearch, Applied Biosystems, Inc. The dsRNA includes two RNA strands that are sufficiently complementary to hybridize to form a duplex structure. One strand of the dsRNA (the antisense strand) includes a region of complementarity that is substantially complementary, and generally fully complementary, to a target sequence, derived from the sequence of an mRNA formed during the expression of a TTR gene, the other strand (the sense strand) includes a region that is complementary to the antisense strand, such that the two strands hybridize and form a duplex structure when combined under suitable conditions. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

Each strand of the dsRNA of invention is generally between 15 and 30, or between 18 and 25, or 18, 19, 20, 21, 22, 23, 24, or 25 nucleotides in length. In other embodiments, each is strand is 25-30 nucleotides in length. Each strand of the duplex can be the same length or of different lengths. When two different siRNAs are used in combination, the lengths of each strand of each siRNA can be identical or can differ.

The dsRNA of the invention can include one or more single-stranded overhang(s) of one or more nucleotides. In one embodiment, at least one end of the dsRNA has a single-stranded nucleotide overhang of 1 to 4, generally 1 or 2 nucleotides. In another embodiment, the antisense strand of the dsRNA has 1-10 nucleotides overhangs each at the 3' end and the 5' end over the sense strand. In further embodiments, the sense strand of the dsRNA has 1-10 nucleotides overhangs each at the 3' end and the 5' end over the antisense strand.

A dsRNAs having at least one nucleotide overhang can have unexpectedly superior inhibitory properties than the blunt-ended counterpart. In some embodiments the presence of only one nucleotide overhang strengthens the interference activity of the dsRNA, without affecting its overall stability. A dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA can also have a blunt end, generally located at the 5'-end of the antisense strand. Such dsRNAs can have improved stability and inhibitory activity, thus allowing administration at low dosages, i.e., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In one embodiment, a TTR gene is a human TTR gene. In specific embodiments, the sense strand of the dsRNA is one of the sense sequences from Tables 3A, 3B, 4, 6A, 6B, or 7, and the antisense strand is one of the antisense sequences of Tables 3A, 3B, 4, 6A, 6B, or 7. Alternative antisense agents that target elsewhere in the target sequence provided in Tables 3A, 3B, 4, 6A, 6B, or 7 can readily be determined using the target sequence and the flanking TTR sequence.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 3A, 3B, 4, 6A, 6B, and 7, the dsRNAs featured in the invention can include at least one strand of a length described herein. It can be reasonably expected that shorter dsRNAs having one of the sequences of Tables 3A, 3B, 4, 6A, 6B, or 7 minus only a few nucleotides on one or both ends may be similarly effective as compared to the dsRNAs described above. Hence, dsRNAs having a partial sequence of at least 15, 16, 17, 18, 19, 20, or more contiguous nucleotides from one of the sequences of Tables 3, 4, 6 or 7, and differing in their ability to inhibit the expression of a TTR gene in an assay as described herein below by not more than 5, 10, 15, 20, 25, or 30% inhibition from a dsRNA comprising the full sequence, are contemplated by the invention. Further, dsRNAs that cleave within a desired TTR target sequence can readily be made using the corresponding TTR antisense sequence and a complementary sense sequence.

In addition, the dsRNAs provided in Tables 3A, 3B, 4, 6A, 6B, or 7 identify a site in a TTR that is susceptible to RNAi based cleavage. As such, the present invention further features dsRNAs that target within the sequence targeted by one of the agents of the present invention. As used herein, a second dsRNA is said to target within the sequence of a first dsRNA if the second dsRNA cleaves the message anywhere within the mRNA that is complementary to the antisense strand of the first dsRNA. Such a second dsRNA will generally consist of at least 15 contiguous nucleotides from one of the sequences provided in Tables 3A, 3B, 4, 6A, 6B, or 7 coupled to additional nucleotide sequences taken from the region contiguous to the selected sequence in a TTR gene.

The dsRNA featured in the invention can contain one or more mismatches to the target sequence. In one embodiment, the dsRNA featured in the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of a TTR gene, the dsRNA generally does not contain any mismatch within the central 13 nucleotides. The methods described within the invention can be used to determine whether a dsRNA containing a mismatch to a target sequence is effective in inhibiting the expression of a TTR gene. Consideration of the efficacy of dsRNAs with mismatches in inhibiting expression of a TTR gene is important, especially if the particular region of complementarity in a TTR gene is known to have polymorphic sequence variation within the population.

Modifications

In yet another embodiment, the dsRNA is chemically modified to enhance stability. The nucleic acids featured in the invention may be synthesized and/or modified by methods well established in the art, such as those described in "Current protocols in nucleic acid chemistry," Beaucage, S. L. et al. (Eds.), John Wiley & Sons, Inc., New York, N.Y., USA, which is hereby incorporated herein by reference. Specific examples of dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which is herein incorporated by reference Modified dsRNA backbones that do not include a phosphorus atom therein have backbones that are formed by short chain alkyl or cycloalkyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other suitable dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, a dsRNA mimetic that has been shown to have excellent hybridization properties, is referred to as a peptide nucleic acid (PNA). In PNA compounds, the sugar backbone of a dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Other embodiments of the invention are dsRNAs with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. Also preferred are dsRNAs having morpholino backbone structures of the above-referenced U.S. Pat. No. 5,034,506.

Modified dsRNAs may also contain one or more substituted sugar moieties. Preferred dsRNAs comprise one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$, also described in examples herein below.

Other preferred modifications include 2'-methoxy (2'-$OCH_3$), 2'-aminopropoxy (2'-$OCH_2CH_2CH_2NH_2$) and 2'-fluoro (2'-F). Similar modifications may also be made at other positions on the dsRNA, particularly the 3' position of the sugar on the 3' terminal nucleotide or in 2'-5' linked dsRNAs and the 5' position of 5' terminal nucleotide. DsRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

dsRNAs may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., DsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, each of which is herein incorporated by reference, and U.S. Pat. No. 5,750,692, also herein incorporated by reference.

Conjugates

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-Hphosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylaminocarbonyloxycholesterol moiety (Crooke et al., J. Pharmacol. Exp. Ther., 1996, 277:923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within a dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of a dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region.

Cleavage of the RNA target can be routinely detected by gel electrophoresis and, if necessary, associated nucleic acid hybridization techniques known in the art. The cleavage site on the target mRNA of a dsRNA can be determined using methods generally known to one of ordinary skill in the art, e.g., the 5'-RACE method described in Soutschek et al., Nature; 2004, Vol. 432, pp. 173-178 (which is herein incorporated by reference for all purposes). In an embodiment, using the 5'-RACE method described by Soutschek et al., ALN-18328 was determined to cleave a TTR mRNA between the guanine nucleotide at position 636 of SEQ ID NO:1331 (NM_000371.3) and the adenine nucleotide at position 637 of SEQ ID NO:1331. In an embodiment, it was determined that ALN-18328 does not cleave a TTR mRNA between the adenine nucleotide at position 637 of SEQ ID NO: 1331 and the guanine nucleotide at position 638 of SEQ ID NO:1331.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded dsRNAs

In another aspect, TTR dsRNA molecules are expressed from transcription units inserted into DNA or RNA vectors (see, e.g., Couture, A, et al., *TIG*. (1996), 12:5-10; Skillern, A., et al., International PCT Publication No. WO 00/22113, Conrad, International PCT Publication No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In one embodiment, a dsRNA is expressed as an inverted repeat joined by a linker polynucleotide sequence such that the dsRNA has a stem and loop structure.

The recombinant dsRNA expression vectors are generally DNA plasmids or viral vectors. dsRNA expressing viral vectors can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Domburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. In one embodiment, the dsRNA featured in the invention is expressed as two separate, complementary single-stranded RNA molecules from a recombinant AAV vector having, for example, either the U6 or H1 RNA promoters, or the cytomegalovirus (CMV) promoter.

A suitable AV vector for expressing the dsRNA featured in the invention, a method for constructing the recombinant AV vector, and a method for delivering the vector into target cells, are described in Xia H et al. (2002), *Nat. Biotech.* 20: 1006-1010.

Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

The promoter driving dsRNA expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single TTR gene or multiple TTR genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

TTR specific dsRNA molecules can also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions Containing dsRNA

In one embodiment, the invention provides pharmaceutical compositions containing a dsRNA, as described herein, and a pharmaceutically acceptable carrier. The pharmaceutical composition containing the dsRNA is useful for treating a disease or disorder associated with the expression or activity of a TTR gene, such as pathological processes mediated by TTR expression. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions featured herein are administered in dosages sufficient to inhibit expression of TTR genes.

In general, a suitable dose of dsRNA will be in the range of 0.01 to 200.0 milligrams per kilogram body weight of the recipient per day, generally in the range of 1 to 50 mg per kilogram body weight per day. For example, the dsRNA can be administered at 0.0059 mg/kg, 0.01 mg/kg, 0.0295 mg/kg, 0.05 mg/kg, 0.0590 mg/kg, 0.163 mg/kg, 0.2 mg/kg, 0.3 mg/kg, 0.4 mg/kg, 0.5 mg/kg, 0.543 mg/kg, 0.5900 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.628 mg/kg, 2 mg/kg, 3 mg/kg, 5.0 mg/kg, 10 mg/kg, 20 mg/kg, 30 mg/kg, 40 mg/kg, or 50 mg/kg per single dose.

In one embodiment, the dosage is between 0.01 and 0.2 mg/kg. For example, the dsRNA can be administered at a dose of 0.01 mg/kg, 0.02 mg/kg, 0.3 mg/kg, 0.04 mg/kg, 0.05 mg/kg, 0.06 mg/kg, 0.07 mg/kg 0.08 mg/kg 0.09 mg/kg, 0.10 mg/kg, 0.11 mg/kg, 0.12 mg/kg, 0.13 mg/kg, 0.14 mg/kg, 0.15 mg/kg, 0.16 mg/kg, 0.17 mg/kg, 0.18 mg/kg, 0.19 mg/kg, or 0.20 mg/kg.

In one embodiment, the dosage is between 0.005 mg/kg and 1.628 mg/kg. For example, the dsRNA can be administered at a dose of 0.0059 mg/kg, 0.0295 mg/kg, 0.0590 mg/kg, 0.163 mg/kg, 0.543 mg/kg, 0.5900 mg/kg, or 1.628 mg/kg.

In one embodiment, the dosage is between 0.2 mg/kg and 1.5 mg/kg. For example, the dsRNA can be administered at a dose of 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, or 1.5 mg/kg.

The pharmaceutical composition may be administered once daily, or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on TTR levels is long lasting, such that subsequent doses are administered at not more than 3, 4, or 5 day intervals, or at not more than 1, 2, 3, or 4 week intervals, or at not more than 5, 6, 7, 8, 9, or 10 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by TTR expression. Such models are used for in vivo testing of dsRNA, as well as for determining a therapeutically effective dose. A suitable mouse model is, for example, a mouse containing a plasmid expressing human TTR. Another suitable mouse model is a transgenic mouse carrying a transgene that expresses human TTR.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The dsRNAs featured in the invention can be administered in combination with other known agents effective in treatment of pathological processes mediated by target gene expression. In any event, the administering physician can adjust the amount and timing of dsRNA administration on the basis of results observed using standard measures of efficacy known in the art or described herein.

Administration

The present invention also includes pharmaceutical compositions and formulations which include the dsRNA compounds featured in the invention. The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g., intraparenchymal, intrathecal or intraventricular, administration.

The dsRNA can be delivered in a manner to target a particular tissue, such as the liver (e.g., the hepatocytes of the liver).

The present invention includes pharmaceutical compositions that can be delivered by injection directly into the brain. The injection can be by stereotactic injection into a particular region of the brain (e.g., the substantia nigra, cortex, hippocampus, striatum, or globus pallidus), or the dsRNA can be delivered into multiple regions of the central nervous system (e.g., into multiple regions of the brain, and/or into the spinal cord). The dsRNA can also be delivered into diffuse regions of the brain (e.g., diffuse delivery to the cortex of the brain).

In one embodiment, a dsRNA targeting TTR can be delivered by way of a cannula or other delivery device having one end implanted in a tissue, e.g., the brain, e.g., the substantia nigra, cortex, hippocampus, striatum, corpus callosum or globus pallidus of the brain. The cannula can be connected to a reservoir of the dsRNA composition. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Infusion of the dsRNA composition into the brain can be over several hours or for several days, e.g., for 1, 2, 3, 5, or 7 days or more. Devices for delivery to the brain are described, for example, in U.S. Pat. Nos. 6,093,180, and 5,814,014.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the dsRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearoylphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). DsRNAs featured in the invention may be encapsulated within liposomes or may form complexes thereto, in particular to cationic liposomes. Alternatively, dsRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE).

Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S. T. P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a TTR dsRNA featured in the invention is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLin-DAP), 1,2-Dilinoleylthio-3-dimethylaminopropane (DLin-S-DMA), 1-Linoleoyl-2-linoleyloxy-3-dimethylamin opropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLin-AP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d] [1,3]dioxol-5-amine (ALN 100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

LNP01

In one embodiment, the lipidoid ND98.4 HCl (MW 1487) (Formula 1), Cholesterol (Sigma-Aldrich), and PEG-Ceramide C16 (Avanti Polar Lipids) can be used to prepare lipid-siRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous siRNA (e.g., in sodium acetate pH 5) such that the final ethanol concentration is about 35-45% and the final sodium acetate concentration is about 100-300 mM. Lipid-siRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

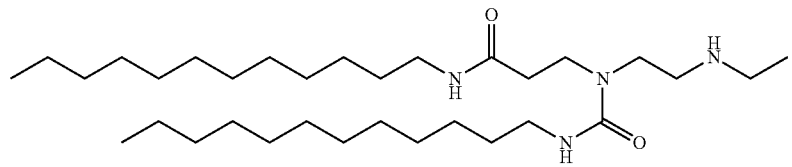

-continued

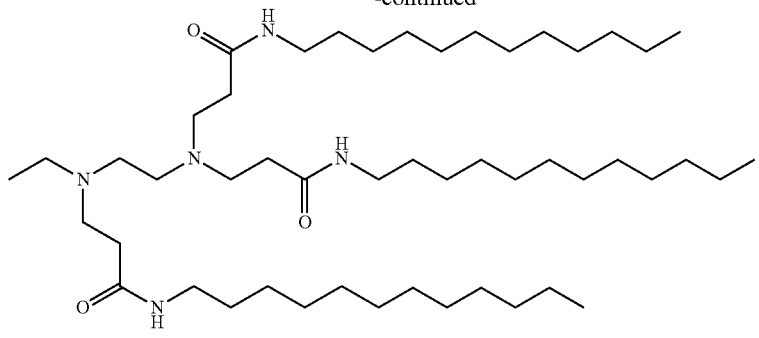

ND98 Isomer I

LNP01 formulations are described, e.g., in International Application Publication No. WO 2008/042973, which is hereby incorporated by reference.

Additional exemplary lipid-siRNA formulations are as follows:

|  | Cationic Lipid | cationic lipid/non-cationic lipid/cholesterol/PEG-lipid conjugate Lipid:siRNA ratio | Process |
|---|---|---|---|
| SNALP | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA~7:1 |  |
| SNALP-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA~7:1 |  |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~6:1 | Extrusion |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~11:1 | Extrusion |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~6:1 | In-line mixing |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~11:1 | In-line mixing |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 | In-line mixing |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 | In-line mixing |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 | In-line mixing |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 | In-line mixing |

LNP09 formulations and XTC comprising formulations are described, e.g., in U.S. Provisional Ser. No. 61/239,686, filed Sep. 3, 2009, which is hereby incorporated by reference. LNP11 formulations and MC3 comprising formulations are described, e.g., in U.S. Provisional Ser. No. 61/244,834, filed Sep. 22, 2009, which is hereby incorporated by reference.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total siRNA concentration in the formulation, as well as the entrapped fraction, is estimated using a dye exclusion assay. A sample of the formulated siRNA can be incubated with an RNA-binding dye, such as Ribogreen (Molecular Probes) in the presence or absence of a formulation disrupting surfactant, e.g., 0.5% Triton-X100. The total siRNA in the formulation can be determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcamitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; poly-alkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyomithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

The compositions of the present invention may be prepared and formulated as emulsions. Emulsions are typically heterogeneous systems of one liquid dispersed in another in the form of droplets usually exceeding 0.1 m in diameter (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly dsRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcamitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucosa (Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

In some embodiments, pharmaceutical compositions featured in the invention include (a) one or more dsRNA compounds and (b) one or more anti-cytokine biologic agents which function by a non-RNAi mechanism. Examples of such biologics include, biologics that target IL1β (e.g., anakinra), IL6 (tocilizumab), or TNF (etanercept, infliximab, adlimumab, or certolizumab).

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration, as discussed above, the dsRNAs featured in the invention can be administered in combination with other known agents effective in treatment of pathological processes mediated by TTR expression. In any event, the administering physician can adjust the amount and timing of dsRNA administration on the basis of results observed using standard measures of efficacy known in the art or described herein.

Methods for Treating Diseases Caused by Expression of a TTR Gene

The invention relates in particular to the use of a dsRNA targeting TTR and compositions containing at least one such dsRNA for the treatment of a TTR-mediated disorder or disease. For example, a dsRNA targeting a TTR gene can be useful for the treatment of a TTR amyloidosis, such as familial amyloidotic polyneuropathy (FAP), familial amyloidotic cardiomyopathy (FAC), leptomeningeal/CNS amyloidosis, amyloidosis VII form (also known as leptomeningeal or meningocerebrovascular amyloidosis), hyperthyroxinemia, and cardiac amyloidosis (also called senile systemic amyloidosis (SSA) and senile cardiac amyloidosis (SCA)).

FIG. 15 illustrates symptoms and mutations in TTR associated with familial amyloidotic neuropathy, familial amyloidotic cardiomyopathy and CNS amyloidosis. The invention includes compositions and methods for treatment of these diseases and symptoms, and directed to these mutant versions of TTR.

A dsRNA targeting a TTR gene is also used for treatment of symptoms and disorders, such as TTR amyloidosis. Symptoms associated with such amyloidosis include, e.g., seizures, dementia, myelopathy, polyneuropathy, carpal tunnel syndrome, autonomic insufficiency, cardiomyopathy, gastrointestinal dysfunction (e.g., gastric ulcers, diarrhea, constipation, malabsorption), weight loss, hepatomegaly, lymphadenopathy, goiter, vitreous opacities, renal insufficiency (including proteinuria and kidney failure), nephropathy, cranial nerve dysfunction, corneal lattice dystrophy, and congestive heart failure with generalized weakness and difficulties breathing from fluid retention.

Owing to the inhibitory effects on TTR expression, a composition according to the invention or a pharmaceutical composition prepared therefrom can enhance the quality of life.

The invention further relates to the use of a dsRNA or a pharmaceutical composition thereof, e.g., for treating a TTR amyloidosis, in combination with other pharmaceuticals and/or other therapeutic methods, e.g., with known pharmaceuticals and/or known therapeutic methods, such as, for example, those which are currently employed for treating these disorders. In one example, a dsRNA targeting TTR can be administered in combination with a liver transplant. In other examples, a dsRNA targeting TTR can be administered in combination with a pharmaceutical or therapeutic method for treating a symptom of a TTR disease, such as diuretics, ACE (angiotensin converting enzyme) inhibitors, angiotensin receptor blockers (ARBs), or dialysis, e.g., for management of renal function.

The dsRNA and an additional therapeutic agent can be administered in the same combination, e.g., parenterally, or the additional therapeutic agent can be administered as part of a separate composition or by another method described herein.

The invention features a method of administering a dsRNA targeting TTR to a patient having a disease or disorder mediated by TTR expression, such as a TTR amyloidosis, e.g., FAP. Administration of the dsRNA can stabilize and improve peripheral neurological function, for example, in a patient with FAP. Patients can be administered a therapeutic amount of dsRNA, such as 0.1 mg/kg, 0.2 mg/kg, 0.5 mg/kg, 1.0 mg/kg, 1.5 mg/kg, 2.0 mg/kg, or 2.5 mg/kg dsRNA. The dsRNA can be administered by intravenous infusion over a period of time, such as over a 5 minute, 10 minute, 15 minute, 20 minute, 25 minute, 60 minute, 120 minute or 180 minute period. The administration is repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the dsRNA can reduce TTR levels in the blood or urine of the patient by at least 20%, 25%, 30%, 40%, 50%, 60%, 70%, 80% or 90% or more.

Before administration of a full dose of the dsRNA, patients can be administered a smaller dose, such as a dose that is 5% of the full dose, and monitored for adverse effects, such as an allergic reaction or a change in liver function. For example, in patients monitored for changes in liver function, a low incidence of LFT (Liver Function Test) change (e.g., a 10-20% incidence of LFT) is acceptable (e.g., a reversible, 3-fold increase in ALT (alanine aminotransferase) and/or AST (aspartate aminotransferase) levels).

Many TTR-associated diseases and disorders are hereditary. Therefore, a patient in need of a TTR dsRNA can be identified by taking a family history. A healthcare provider, such as a doctor, nurse, or family member, can take a family history before prescribing or administering a TTR dsRNA. A DNA test may also be performed on the patient to identify a mutation in the TTR gene, before a TTR dsRNA is administered to the patient.

The patient may have a biopsy performed before receiving a TTR dsRNA. The biopsy can be, for example, on a tissue, such as the gastric mucosa, peripheral nerve, skin, abdominal fat, liver, or kidney, and the biopsy may reveal amyloid plaques, which are indicative of a TTR-mediated disorder. Upon the identification of amyloid plaques, the patient is administered a TTR dsRNA.

Methods for Inhibiting Expression of a TTR Gene

In yet another aspect, the invention provides a method for inhibiting the expression of a TTR gene in a mammal. The method includes administering a composition featured in the invention to the mammal such that expression of the target TTR gene is silenced.

When the organism to be treated is a mammal such as a human, the composition may be administered by any means known in the art including, but not limited to oral or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the dsRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 dsRNA Synthesis

Source of Reagents

Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemie GmbH, Hamburg, Germany). These building blocks were incorporated at selected sites within the sequence of the oligoribonucleotide chain using standard nucleoside phosphoramidite chemistry such as described in Current protocols in nucleic acid chemistry, Beaucage, S. L. et al. (Edrs.), John Wiley & Sons, Inc., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), heated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

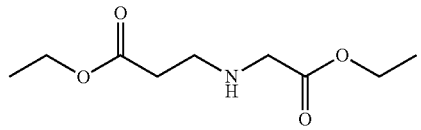

A 4.7 M aqueous solution of sodium hydroxide (50 mL) was added into a stirred, ice-cooled solution of ethyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

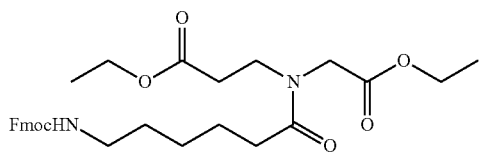

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl urea. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

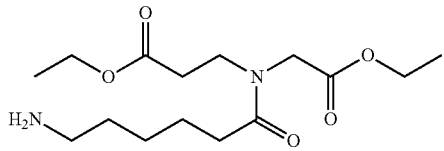

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-(1,5-Dimethyl-hexyl)-10,13-dimethyl-2,3,4,7,8,9,10,11,12,13,14,15,16,17-tetradecahydro-1H-cyclopenta[a]phenanthren-3-yloxycarbonylamino]-hexanoyl}ethoxycarbonylmethyl-amino)-propionic acid ethyl ester AD

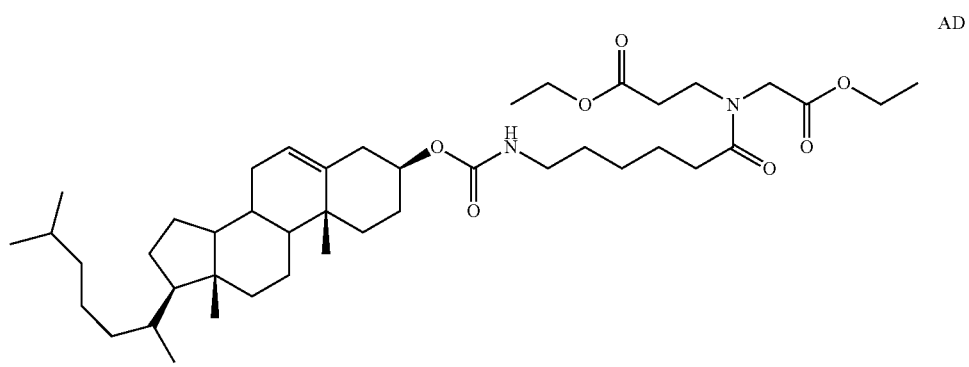 [SMILES: CCOC(=O)CCN(CC(=O)OCC)C(=O)CCCCCNC(=O)O[C@H]1CC[C@@]2(C)C(=CCC3C2CC[C@@]2(C)C3CC[C@@H]2C(C)CCCC(C)C)C1]

The hydrochloride salt of 3-[(6-Amino-hexanoyl)-ethoxycarbonylmethyl-amino]-propionic acid ethyl ester AC (4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,4,7,8,9,10,11,12,13,14,15,16,17-tetradecahydro-1H-cyclopenta[a] phenanthren-3-yloxycarbonylamino]-hexanoyl}-4-oxo-pyrrolidine-3-carboxylic acid ethyl ester AE

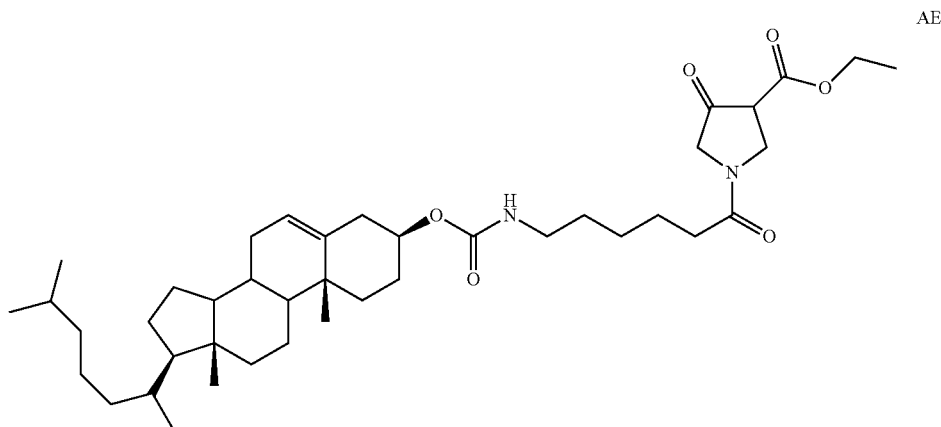 [SMILES: CCOC(=O)C1CN(C(=O)CCCCCNC(=O)O[C@H]2CC[C@@]3(C)C(=CCC4C3CC[C@@]3(C)C4CC[C@@H]3C(C)CCCC(C)C)C2)CC1=O]

Potassium t-butoxide (1.1 g, 9.8 mmol) was slurried in 30 mL of dry toluene. The mixture was cooled to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of NaH$_2$PO$_4$.H$_2$O in 40 mL of water The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-ketoester (39%).

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF

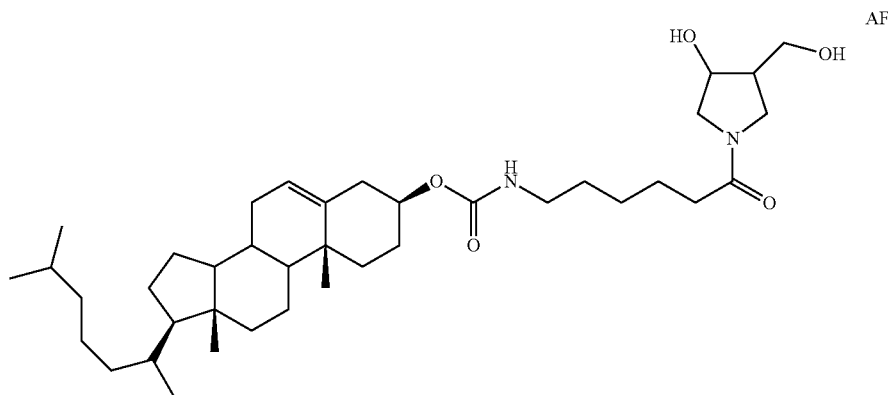 [SMILES: CC(C)CCCC(C)[C@H]1CCC2C3CC=C4C[C@@H](OC(=O)NCCCCCC(=O)N5CC(O)C(CO)C5)CC[C@]4(C)C3CC[C@@]21C]

Methanol (2 mL) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N HCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl$_3$) (89%).

(6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

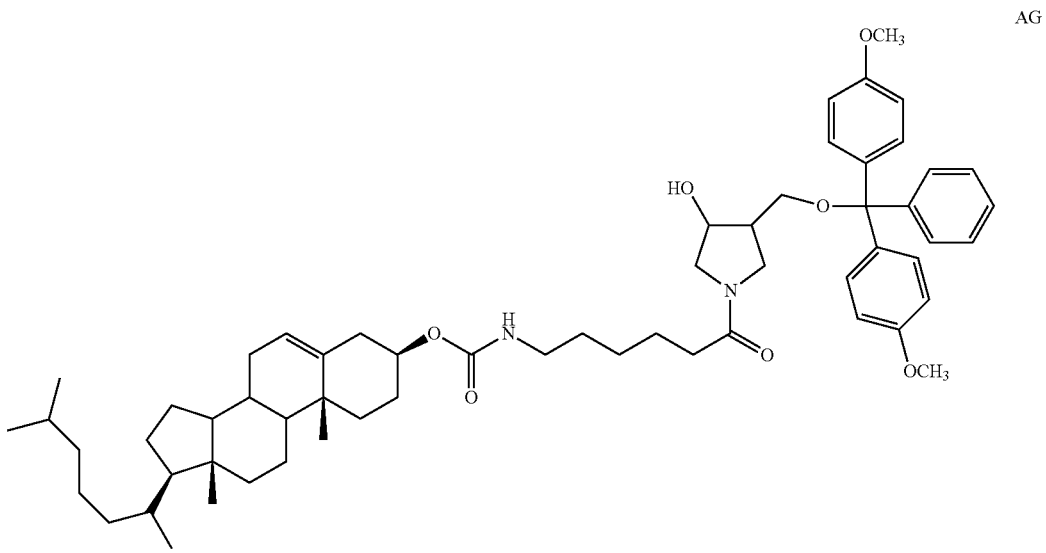 [SMILES: COc1ccc(C(OCC2CN(C(=O)CCCCCNC(=O)O[C@H]3CC[C@@]4(C)C(=CCC5C4CC[C@@]4(C)C5CC[C@@H]4C(C)CCCC(C)C)C3)CC2O)(c2ccccc2)c2ccc(OC)cc2)cc1]

Diol AF (1.25 gm 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl3) (1.75 g, 95%).

Succinic Acid mono-(4-[bis-(4-methoxy-phenyl)-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

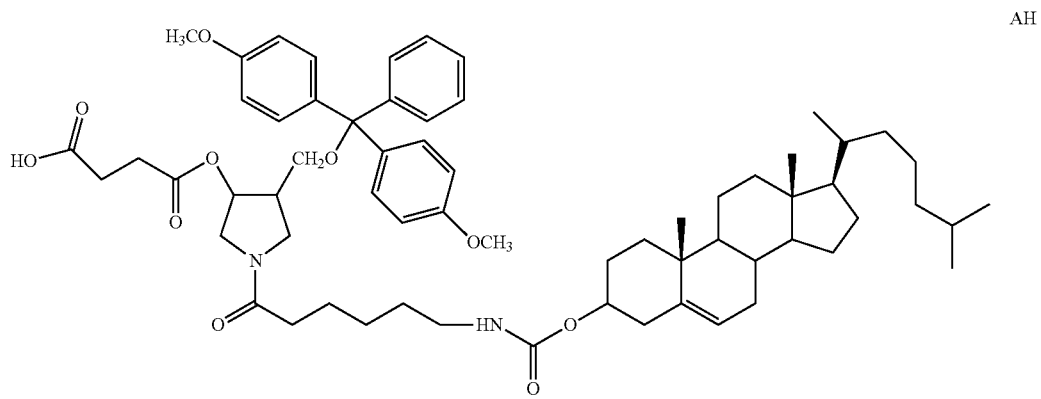

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

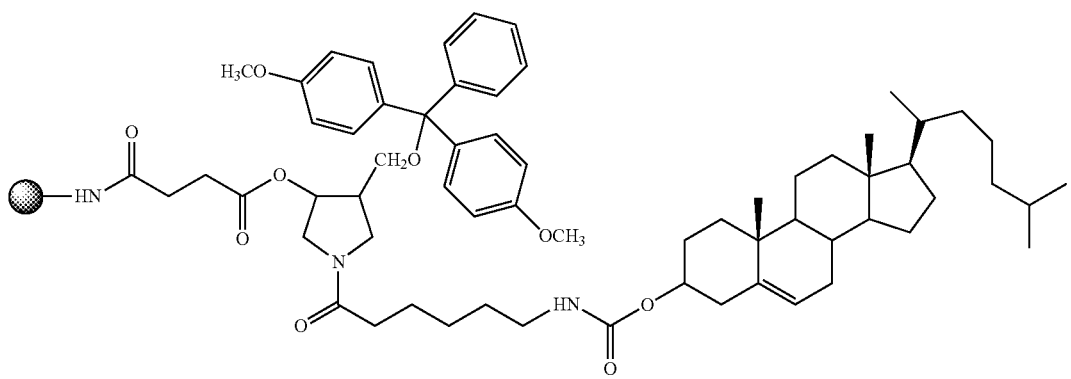

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/pyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented below using standard nomenclature, and specifically the abbreviations of Table 1.

TABLE 1

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
| --- | --- |
| A | adenosine-3'-phosphate |
| C | cytidine-3'-phosphate |
| G | guanosine-3'-phosphate |
| T | 5-methyluridine-3'-phosphate |
| U | uridine-3'-phosphate |
| N | any nucleotide (G, A, C, or T) |
| a | 2'-O-methyladenosine-3'-phosphate |
| c | 2'-O-methylcytidine-3'-phosphate |
| g | 2'-O-methylguanosine-3'-phosphate |
| u | 2'-O-methyluridine-3'-phosphate |
| dT | 2'-deoxythymidine-3'-phosphate |
| sT; sdT | 2'-deoxy-thymidine-5'phosphate-phosphorothioate |

Example 2A

TTR siRNA Design

Transcripts siRNA design was carried out to identify siRNAs targeting the gene transthyretin from human (symbol TTR) and rat (symbol Ttr). The design used the TTR transcripts NM_000371.2 (SEQ ID NO: 1329) (human) and NM_012681.1 (SEQ ID NO: 1330) (rat) from the NCBI Refseq collection. The siRNA duplexes were designed with 100% identity to their respective TTR genes.

siRNA Design and Specificity Prediction

The predicted specificity of all possible 19mers was determined for each sequence. The TTR siRNAs were used in a comprehensive search against the human and rat transcriptomes (defined as the set of NM_and XM_records within the NCBI Refseq set) using the FASTA algorithm. The Python script 'offtargetFasta.py' was then used to parse the alignments and generate a score based on the position and number of mismatches between the siRNA and any potential 'off-target' transcript. The off-target score is weighted to emphasize differences in the 'seed' region of siRNAs, in positions 2-9 from the 5' end of the molecule. The off-target score is calculated as follows: mismatches between the oligo and the transcript are given penalties. A mismatch in the seed region in positions 2-9 of the oligo is given a penalty of 2.8; mismatches in the putative cleavage sites 10 and 11 are given a penalty of 1.2, and mismatches in positions 12-19 a penalty of 1. Mismatches in position 1 are not considered. The off-target score for each oligo-transcript pair is then calculated by summing the mismatch penalties. The lowest off-target score from all the oligo-transcript pairs is then determined and used in subsequent sorting of oligos. Both siRNA strands were assigned to a category of specificity according to the calculated scores: a score above 3 qualifies as highly specific, equal to 3 as specific, and between 2.2 and 2.8 as moderately specific. In picking which oligos to synthesize, off-target scores of the antisense strand were sorted from high to low, and the 144 best (lowest off-target score) oligo pairs from human, and the best 26 pairs from rat were selected.

siRNA Sequence Selection

A total of 140 sense and 140 antisense human TTR derived siRNA oligos were synthesized and formed into duplexes. A total of 26 sense and 26 antisense rat TTR derived siRNA oligos were synthesized and formed into duplexes. Duplexes included The oligos are presented in Tables 2-4 (human TTR) and Tables 5-7 (rat TTR).

TABLE 2

Identification numbers for human TTR dsRNAs
See Table 4 for sequences and modifications of oligos.

| Duplex # | Sense Oligo # | Antisense Oligo # |
| --- | --- | --- |
| AD-18243 | A-32153 | A-32154 |
| AD-18244 | A-32155 | A-32156 |
| AD-18245 | A-32157 | A-32158 |
| AD-18246 | A-32159 | A-32160 |
| AD-18247 | A-32163 | A-32164 |
| AD-18248 | A-32165 | A-32166 |
| AD-18249 | A-32167 | A-32168 |
| AD-18250 | A-32169 | A-32170 |
| AD-18251 | A-32171 | A-32172 |
| AD-18252 | A-32175 | A-32176 |
| AD-18253 | A-32177 | A-32178 |
| AD-18254 | A-32179 | A-32180 |
| AD-18255 | A-32181 | A-32182 |
| AD-18256 | A-32183 | A-32184 |
| AD-18257 | A-32187 | A-32188 |
| AD-18258 | A-32189 | A-32190 |
| AD-18259 | A-32191 | A-32192 |
| AD-18260 | A-32193 | A-32194 |
| AD-18261 | A-32195 | A-32196 |
| AD-18262 | A-32199 | A-32200 |
| AD-18263 | A-32201 | A-32202 |
| AD-18264 | A-32203 | A-32204 |
| AD-18265 | A-32205 | A-32206 |
| AD-18266 | A-32207 | A-32208 |
| AD-18267 | A-32211 | A-32212 |
| AD-18268 | A-32213 | A-32214 |
| AD-18269 | A-32215 | A-32216 |
| AD-18270 | A-32217 | A-32218 |
| AD-18271 | A-32219 | A-32220 |
| AD-18272 | A-32221 | A-32222 |
| AD-18273 | A-32223 | A-32224 |
| AD-18274 | A-32225 | A-32226 |
| AD-18275 | A-32227 | A-32228 |
| AD-18276 | A-32229 | A-32230 |
| AD-18277 | A-32231 | A-32232 |
| AD-18278 | A-32233 | A-32234 |

TABLE 2-continued

Identification numbers for human TTR dsRNAs
See Table 4 for sequences and modifications of oligos.

| Duplex # | Sense Oligo # | Antisense Oligo # |
|---|---|---|
| AD-18279 | A-32235 | A-32236 |
| AD-18280 | A-32237 | A-32238 |
| AD-18281 | A-32239 | A-32240 |
| AD-18282 | A-32241 | A-32242 |
| AD-18283 | A-32243 | A-32244 |
| AD-18284 | A-32247 | A-32248 |
| AD-18285 | A-32249 | A-32250 |
| AD-18286 | A-32251 | A-32252 |
| AD-18287 | A-32253 | A-32254 |
| AD-18288 | A-32255 | A-32256 |
| AD-18289 | A-32259 | A-32260 |
| AD-18290 | A-32261 | A-32262 |
| AD-18291 | A-32263 | A-32264 |
| AD-18292 | A-32265 | A-32266 |
| AD-18293 | A-32267 | A-32268 |
| AD-18294 | A-32269 | A-32270 |
| AD-18295 | A-32271 | A-32272 |
| AD-18296 | A-32273 | A-32274 |
| AD-18297 | A-32275 | A-32276 |
| AD-18298 | A-32277 | A-32278 |
| AD-18299 | A-32279 | A-32280 |
| AD-18300 | A-32281 | A-32282 |
| AD-18301 | A-32283 | A-32284 |
| AD-18302 | A-32285 | A-32286 |
| AD-18303 | A-32287 | A-32288 |
| AD-18304 | A-32289 | A-32290 |
| AD-18305 | A-32291 | A-32292 |
| AD-18306 | A-32295 | A-32296 |
| AD-18307 | A-32297 | A-32298 |
| AD-18308 | A-32299 | A-32300 |
| AD-18309 | A-32301 | A-32302 |
| AD-18310 | A-32303 | A-32304 |
| AD-18311 | A-32307 | A-32308 |
| AD-18312 | A-32309 | A-32310 |
| AD-18313 | A-32311 | A-32312 |
| AD-18314 | A-32313 | A-32314 |
| AD-18315 | A-32315 | A-32316 |
| AD-18316 | A-32319 | A-32320 |
| AD-18317 | A-32321 | A-32322 |
| AD-18318 | A-32323 | A-32324 |
| AD-18319 | A-32325 | A-32326 |
| AD-18320 | A-32327 | A-32328 |
| AD-18321 | A-32331 | A-32332 |
| AD-18322 | A-32333 | A-32334 |
| AD-18323 | A-32335 | A-32336 |
| AD-18324 | A-32337 | A-32338 |
| AD-18325 | A-32339 | A-32340 |
| AD-18326 | A-32341 | A-32342 |
| AD-18327 | A-32343 | A-32344 |
| AD-18328 | A-32345 | A-32346 |
| AD-18329 | A-32347 | A-32348 |
| AD-18330 | A-32349 | A-32350 |
| AD-18331 | A-32351 | A-32352 |
| AD-18332 | A-32353 | A-32354 |
| AD-18333 | A-32355 | A-32356 |
| AD-18334 | A-32357 | A-32358 |
| AD-18335 | A-32359 | A-32360 |
| AD-18336 | A-32363 | A-32364 |
| AD-18337 | A-32367 | A-32368 |
| AD-18338 | A-32369 | A-32370 |
| AD-18339 | A-32371 | A-32372 |
| AD-18340 | A-32373 | A-32374 |
| AD-18341 | A-32375 | A-32376 |
| AD-18342 | A-32379 | A-32380 |
| AD-18343 | A-32381 | A-32382 |
| AD-18344 | A-32383 | A-32384 |
| AD-18345 | A-32385 | A-32386 |
| AD-18346 | A-32387 | A-32388 |
| AD-18347 | A-32391 | A-32392 |
| AD-18348 | A-32393 | A-32394 |
| AD-18349 | A-32395 | A-32396 |
| AD-18350 | A-32397 | A-32398 |
| AD-18351 | A-32399 | A-32400 |
| AD-18352 | A-32401 | A-32402 |
| AD-18353 | A-32403 | A-32404 |
| AD-18354 | A-32405 | A-32406 |
| AD-18355 | A-32407 | A-32408 |
| AD-18356 | A-32409 | A-32410 |
| AD-18357 | A-32411 | A-32412 |
| AD-18358 | A-32415 | A-32416 |
| AD-18359 | A-32417 | A-32418 |
| AD-18360 | A-32419 | A-32420 |
| AD-18361 | A-32421 | A-32422 |
| AD-18362 | A-32423 | A-32424 |
| AD-18363 | A-32427 | A-32428 |
| AD-18364 | A-32429 | A-32430 |
| AD-18446 | A-32161 | A-32162 |
| AD-18447 | A-32173 | A-32174 |
| AD-18448 | A-32185 | A-32186 |
| AD-18449 | A-32197 | A-32198 |
| AD-18450 | A-32209 | A-32210 |
| AD-18451 | A-32245 | A-32246 |
| AD-18452 | A-32257 | A-32258 |
| AD-18453 | A-32293 | A-32294 |
| AD-18454 | A-32305 | A-32306 |
| AD-18455 | A-32317 | A-32318 |
| AD-18456 | A-32329 | A-32330 |
| AD-18457 | A-32361 | A-32362 |
| AD-18458 | A-32365 | A-32366 |
| AD-18459 | A-32377 | A-32378 |
| AD-18460 | A-32389 | A-32390 |
| AD-18461 | A-32401 | A-32402 |
| AD-18462 | A-32413 | A-32414 |
| AD-18463 | A-32425 | A-32426 |

TABLE 3

Sense and antisense strand sequences of human TTR dsRNAs
(NM_000371.2, SEQ ID NO: 1329)

A.

| Strand | Position | Sequence (5' to 3') | SEQ ID NO: | Sequence with 3' dinucleotide overhang (5' to 3') | SEQ ID NO: |
|---|---|---|---|---|---|
| s | 100 | CCGGUGAAUCCAAGUGUCC | 1 | CCGGUGAAUCCAAGUGUCCNN | 281 |
| as | 118 | GGACACUUGGAUUCACCGG | 2 | GGACACUUGGAUUCACCGGNN | 282 |
| s | 11 | ACUCAUUCUUGGCAGGAUG | 3 | ACUCAUUCUUGGCAGGAUGNN | 283 |
| as | 29 | CAUCCUGCCAAGAAUGAGU | 4 | CAUCCUGCCAAGAAUGAGUNN | 284 |

TABLE 3-continued

Sense and antisense strand sequences of human TTR dsRNAs
(NM_000371.2, SEQ ID NO: 1329)

| | | | | | |
|---|---|---|---|---|---|
| s | 111 | AAGUGUCCUCUGAUGGUCA | 5 | AAGUGUCCUCUGAUGGUCANN | 285 |
| as | 129 | UGACCAUCAGAGGACACUU | 6 | UGACCAUCAGAGGACACUUNN | 286 |
| s | 13 | UCAUUCUUGGCAGGAUGGC | 7 | UCAUUCUUGGCAGGAUGGCNN | 287 |
| as | 31 | GCCAUCCUGCCAAGAAUGA | 8 | GCCAUCCUGCCAAGAAUGANN | 288 |
| s | 130 | AAGUUCUAGAUGCUGUCCG | 9 | AAGUUCUAGAUGCUGUCCGNN | 289 |
| as | 148 | CGGACAGCAUCUAGAACUU | 10 | CGGACAGCAUCUAGAACUUNN | 290 |
| s | 132 | GUUCUAGAUGCUGUCCGAG | 11 | GUUCUAGAUGCUGUCCGAGNN | 291 |
| as | 150 | CUCGGACAGCAUCUAGAAC | 12 | CUCGGACAGCAUCUAGAACNN | 292 |
| s | 135 | CUAGAUGCUGUCCGAGGCA | 13 | CUAGAUGCUGUCCGAGGCANN | 293 |
| as | 153 | UGCCUCGGACAGCAUCUAG | 14 | UGCCUCGGACAGCAUCUAGNN | 294 |
| s | 138 | GAUGCUGUCCGAGGCAGUC | 15 | GAUGCUGUCCGAGGCAGUCNN | 295 |
| as | 156 | GACUGCCUCGGACAGCAUC | 16 | GACUGCCUCGGACAGCAUCNN | 296 |
| s | 14 | CAUUCUUGGCAGGAUGGCU | 17 | CAUUCUUGGCAGGAUGGCUNN | 297 |
| as | 32 | AGCCAUCCUGCCAAGAAUG | 18 | AGCCAUCCUGCCAAGAAUGNN | 298 |
| s | 140 | UGCUGUCCGAGGCAGUCCU | 19 | UGCUGUCCGAGGCAGUCCUNN | 299 |
| as | 158 | AGGACUGCCUCGGACAGCA | 20 | AGGACUGCCUCGGACAGCANN | 300 |
| s | 146 | CCGAGGCAGUCCUGCCAUC | 21 | CCGAGGCAGUCCUGCCAUCNN | 301 |
| as | 164 | GAUGGCAGGACUGCCUCGG | 22 | GAUGGCAGGACUGCCUCGGNN | 302 |
| s | 152 | CAGUCCUGCCAUCAAUGUG | 23 | CAGUCCUGCCAUCAAUGUGNN | 303 |
| as | 170 | CACAUUGAUGGCAGGACUG | 24 | CACAUUGAUGGCAGGACUGNN | 304 |
| s | 164 | CAAUGUGGCCGUGCAUGUG | 25 | CAAUGUGGCCGUGCAUGUGNN | 305 |
| as | 182 | CACAUGCACGGCCACAUUG | 26 | CACAUGCACGGCCACAUUGNN | 306 |
| s | 178 | AUGUGUUCAGAAAGGCUGC | 27 | AUGUGUUCAGAAAGGCUGCNN | 307 |
| as | 196 | GCAGCCUUUCUGAACACAU | 28 | GCAGCCUUUCUGAACACAUNN | 308 |
| s | 2 | CAGAAGUCCACUCAUUCUU | 29 | CAGAAGUCCACUCAUUCUUNN | 309 |
| as | 20 | AAGAAUGAGUGGACUUCUG | 30 | AAGAAUGAGUGGACUUCUGNN | 310 |
| s | 21 | GGCAGGAUGGCUUCUCAUC | 31 | GGCAGGAUGGCUUCUCAUCNN | 311 |
| as | 39 | GAUGAGAAGCCAUCCUGCC | 32 | GAUGAGAAGCCAUCCUGCCNN | 312 |
| s | 210 | GAGCCAUUUGCCUCUGGGA | 33 | GAGCCAUUUGCCUCUGGGANN | 313 |
| as | 228 | UCCCAGAGGCAAAUGGCUC | 34 | UCCCAGAGGCAAAUGGCUCNN | 314 |
| s | 23 | CAGGAUGGCUUCUCAUCGU | 35 | CAGGAUGGCUUCUCAUCGUNN | 315 |
| as | 41 | ACGAUGAGAAGCCAUCCUG | 36 | ACGAUGAGAAGCCAUCCUGNN | 316 |
| s | 24 | AGGAUGGCUUCUCAUCGUC | 37 | AGGAUGGCUUCUCAUCGUCNN | 317 |
| as | 42 | GACGAUGAGAAGCCAUCCU | 38 | GACGAUGAGAAGCCAUCCUNN | 318 |
| s | 245 | AGAGCUGCAUGGGCUCACA | 39 | AGAGCUGCAUGGGCUCACANN | 319 |
| as | 263 | UGUGAGCCCAUGGAGCUCU | 40 | UGUGAGCCCAUGGAGCUCUNN | 320 |
| s | 248 | GCUGCAUGGGCUCACAACU | 41 | GCUGCAUGGGCUCACAACUNN | 321 |
| as | 266 | AGUUGUGAGCCCAUGGAGC | 42 | AGUUGUGAGCCCAUGGAGCNN | 322 |
| s | 25 | GGAUGGCUUCUCAUCGUCU | 43 | GGAUGGCUUCUCAUCGUCUNN | 323 |

TABLE 3-continued

Sense and antisense strand sequences of human TTR dsRNAs
(NM_000371.2, SEQ ID NO: 1329)

| | | | | | |
|---|---|---|---|---|---|
| as | 43 | AGACGAUGAGAAGCCAUCC | 44 | AGACGAUGAGAAGCCAUCCNN | 324 |
| s | 251 | GCAUGGGCUCACAACUGAG | 45 | GCAUGGGCUCACAACUGAGNN | 325 |
| as | 269 | CUCAGUUGUGAGCCCAUGC | 46 | CUCAGUUGUGAGCCCAUGCNN | 326 |
| s | 253 | AUGGGCUCACAACUGAGGA | 47 | AUGGGCUCACAACUGAGGANN | 327 |
| as | 271 | UCCUCAGUUGUGAGCCCAU | 48 | UCCUCAGUUGUGAGCCCAUNN | 328 |
| s | 254 | UGGGCUCACAACUGAGGAG | 49 | UGGGCUCACAACUGAGGAGNN | 329 |
| as | 272 | CUCCUCAGUUGUGAGCCCA | 50 | CUCCUCAGUUGUGAGCCCANN | 330 |
| s | 270 | GAGGAAUUUGUAGAAGGGA | 51 | GAGGAAUUUGUAGAAGGGANN | 331 |
| as | 288 | UCCCUUCUACAAAUUCCUC | 52 | UCCCUUCUACAAAUUCCUCNN | 332 |
| s | 276 | UUUGUAGAAGGGAUAUACA | 53 | UUUGUAGAAGGGAUAUACANN | 333 |
| as | 294 | UGUAUAUCCCUUCUACAAA | 54 | UGUAUAUCCCUUCUACAAANN | 334 |
| s | 277 | UUGUAGAAGGGAUAUACAA | 55 | UUGUAGAAGGGAUAUACAANN | 335 |
| as | 295 | UUGUAUAUCCCUUCUACAA | 56 | UUGUAUAUCCCUUCUACAANN | 336 |
| s | 278 | UGUAGAAGGGAUAUACAAA | 57 | UGUAGAAGGGAUAUACAAANN | 337 |
| as | 296 | UUUGUAUAUCCCUUCUACA | 58 | UUUGUAUAUCCCUUCUACANN | 338 |
| s | 281 | AGAAGGGAUAUACAAAGUG | 59 | AGAAGGGAUAUACAAAGUGNN | 339 |
| as | 299 | CACUUUGUAUAUCCCUUCU | 60 | CACUUUGUAUAUCCCUUCUNN | 340 |
| s | 295 | AAGUGGAAAUAGACACCAA | 61 | AAGUGGAAAUAGACACCAANN | 341 |
| as | 313 | UUGGUGUCUAUUUCCACUU | 62 | UUGGUGUCUAUUUCCACUUNN | 342 |
| s | 299 | GGAAAUAGACACCAAAUCU | 63 | GGAAAUAGACACCAAAUCUNN | 343 |
| as | 317 | AGAUUUGGUGUCUAUUUCC | 64 | AGAUUUGGUGUCUAUUUCCNN | 344 |
| s | 300 | GAAAUAGACACCAAAUCUU | 65 | GAAAUAGACACCAAAUCUUNN | 345 |
| as | 318 | AAGAUUUGGUGUCUAUUUC | 66 | AAGAUUUGGUGUCUAUUUCNN | 346 |
| s | 303 | AUAGACACCAAAUCUUACU | 67 | AUAGACACCAAAUCUUACUNN | 347 |
| as | 321 | AGUAAGAUUUGGUGUCUAU | 68 | AGUAAGAUUUGGUGUCUAUNN | 348 |
| s | 304 | UAGACACCAAAUCUUACUG | 69 | UAGACACCAAAUCUUACUGNN | 349 |
| as | 322 | CAGUAAGAUUUGGUGUCUA | 70 | CAGUAAGAUUUGGUGUCUANN | 350 |
| s | 305 | AGACACCAAAUCUUACUGG | 71 | AGACACCAAAUCUUACUGGNN | 351 |
| as | 323 | CCAGUAAGAUUUGGUGUCU | 72 | CCAGUAAGAUUUGGUGUCUNN | 352 |
| s | 317 | UUACUGGAAGGCACUUGGC | 73 | UUACUGGAAGGCACUUGGCNN | 353 |
| as | 335 | GCCAAGUGCCUUCCAGUAA | 74 | GCCAAGUGCCUUCCAGUAANN | 354 |
| s | 32 | UUCUCAUCGUCUGCUCCUC | 75 | UUCUCAUCGUCUGCUCCUCNN | 355 |
| as | 50 | GAGGAGCAGACGAUGAGAA | 76 | GAGGAGCAGACGAUGAGAANN | 356 |
| s | 322 | GGAAGGCACUUGGCAUCUC | 77 | GGAAGGCACUUGGCAUCUCNN | 357 |
| as | 340 | GAGAUGCCAAGUGCCUUCC | 78 | GAGAUGCCAAGUGCCUUCCNN | 358 |
| s | 326 | GGCACUUGGCAUCUCCCCA | 79 | GGCACUUGGCAUCUCCCCANN | 359 |
| as | 344 | UGGGGAGAUGCCAAGUGCC | 80 | UGGGGAGAUGCCAAGUGCCNN | 360 |
| s | 333 | GGCAUCUCCCCAUUCCAUG | 81 | GGCAUCUCCCCAUUCCAUGNN | 361 |

TABLE 3-continued

Sense and antisense strand sequences of human TTR dsRNAs
(NM_000371.2, SEQ ID NO: 1329)

| | | | | | |
|---|---|---|---|---|---|
| as | 351 | AUGGAAUGGGGAGAUGCCUU | 82 | AUGGAAUGGGGAGAUGCCUUNN | 362 |
| s | 334 | GCAUCUCCCCAUUCCAUGA | 83 | GCAUCUCCCCAUUCCAUGANN | 363 |
| as | 352 | UCAUGGAAUGGGGAGAUGC | 84 | UCAUGGAAUGGGGAGAUGCNN | 364 |
| s | 335 | CAUCUCCCCAUUCCAUGAG | 85 | CAUCUCCCCAUUCCAUGAGNN | 365 |
| as | 353 | CUCAUGGAAUGGGGAGAUG | 86 | CUCAUGGAAUGGGGAGAUGNN | 366 |
| s | 336 | AUCUCCCCAUUCCAUGAGC | 87 | AUCUCCCCAUUCCAUGAGCNN | 367 |
| as | 354 | GCUCAUGGAAUGGGGAGAU | 88 | GCUCAUGGAAUGGGGAGAUNN | 368 |
| s | 338 | CUCCCCAUUCCAUGAGCAU | 89 | CUCCCCAUUCCAUGAGCAUNN | 369 |
| as | 356 | AUGCUCAUGGAAUGGGGAG | 90 | AUGCUCAUGGAAUGGGGAGNN | 370 |
| s | 341 | CCCAUUCCAUGAGCAUGCA | 91 | CCCAUUCCAUGAGCAUGCANN | 371 |
| as | 359 | UGCAUGCUCAUGGAAUGGG | 92 | UGCAUGCUCAUGGAAUGGGNN | 372 |
| s | 347 | CCAUGAGCAUGCAGAGGUG | 93 | CCAUGAGCAUGCAGAGGUGNN | 373 |
| as | 365 | CACCUCUGCAUGCUCAUGG | 94 | CACCUCUGCAUGCUCAUGGNN | 374 |
| s | 352 | AGCAUGCAGAGGUGGUAUU | 95 | AGCAUGCAGAGGUGGUAUUNN | 375 |
| as | 370 | AAUACCACCUCUGCAUGCU | 96 | AAUACCACCUCUGCAUGCUNN | 376 |
| s | 354 | CAUGCAGAGGUGGUAUUCA | 97 | CAUGCAGAGGUGGUAUUCANN | 377 |
| as | 372 | UGAAUACCACCUCUGCAUG | 98 | UGAAUACCACCUCUGCAUGNN | 378 |
| s | 355 | AUGCAGAGGUGGUAUUCAC | 99 | AUGCAGAGGUGGUAUUCACNN | 379 |
| as | 373 | GUGAAUACCACCUCUGCAU | 100 | GUGAAUACCACCUCUGCAUNN | 380 |
| s | 362 | GGUGGUAUUCACAGCCAAC | 101 | GGUGGUAUUCACAGCCAACNN | 381 |
| as | 380 | GUUGGCUGUGAAUACCACC | 102 | GUUGGCUGUGAAUACCACCNN | 382 |
| s | 363 | GUGGUAUUCACAGCCAACG | 103 | GUGGUAUUCACAGCCAACGNN | 383 |
| as | 381 | CGUUGGCUGUGAAUACCAC | 104 | CGUUGGCUGUGAAUACCACNN | 384 |
| s | 364 | UGGUAUUCACAGCCAACGA | 105 | UGGUAUUCACAGCCAACGANN | 385 |
| as | 382 | UCGUUGGCUGUGAAUACCA | 106 | UCGUUGGCUGUGAAUACCANN | 386 |
| s | 365 | GGUAUUCACAGCCAACGAC | 107 | GGUAUUCACAGCCAACGACNN | 387 |
| as | 383 | GUCGUUGGCUGUGAAUACC | 108 | GUCGUUGGCUGUGAAUACCNN | 388 |
| s | 366 | GUAUUCACAGCCAACGACU | 109 | GUAUUCACAGCCAACGACUNN | 389 |
| as | 384 | AGUCGUUGGCUGUGAAUAC | 110 | AGUCGUUGGCUGUGAAUACNN | 390 |
| s | 367 | UAUUCACAGCCAACGACUC | 111 | UAUUCACAGCCAACGACUCNN | 391 |
| as | 385 | GAGUCGUUGGCUGUGAAUA | 112 | GAGUCGUUGGCUGUGAAUANN | 392 |
| s | 370 | UCACAGCCAACGACUCCGG | 113 | UCACAGCCAACGACUCCGGNN | 393 |
| as | 388 | CCGGAGUCGUUGGCUGUGA | 114 | CCGGAGUCGUUGGCUGUGANN | 394 |
| s | 390 | CCCCGCCGCUACACCAUUG | 115 | CCCCGCCGCUACACCAUUGNN | 395 |
| as | 408 | CAAUGGUGUAGCGGCGGGG | 116 | CAAUGGUGUAGCGGCGGGGNN | 396 |
| s | 4 | GAAGUCCACUCAUUCUUGG | 117 | GAAGUCCACUCAUUCUUGGNN | 397 |
| as | 22 | CCAAGAAUGAGUGGACUUC | 118 | CCAAGAAUGAGUGGACUUCNN | 398 |
| s | 412 | CCCUGCUGAGCCCCUACUC | 119 | CCCUGCUGAGCCCCUACUCNN | 399 |
| as | 430 | GAGUAGGGGCUCAGCAGGG | 120 | GAGUAGGGGCUCAGCAGGGNN | 400 |

TABLE 3-continued

Sense and antisense strand sequences of human TTR dsRNAs
(NM_000371.2, SEQ ID NO: 1329)

| | | | | | |
|---|---|---|---|---|---|
| s | 417 | CUGAGCCCUACUCCUAUU | 121 | CUGAGCCCCUACUCCUAUUNN | 401 |
| as | 435 | AAUAGGAGUAGGGGCUCAG | 122 | AAUAGGAGUAGGGGCUCAGNN | 402 |
| s | 418 | UGAGCCCUACUCCUAUUC | 123 | UGAGCCCCUACUCCUAUUCNN | 403 |
| as | 436 | GAAUAGGAGUAGGGGCUCA | 124 | GAAUAGGAGUAGGGGCUCANN | 404 |
| s | 422 | CCCCUACUCCUAUUCCACC | 125 | CCCCUACUCCUAUUCCACCNN | 405 |
| as | 440 | GGUGGAAUAGGAGUAGGGG | 126 | GGUGGAAUAGGAGUAGGGGNN | 406 |
| s | 425 | CUACUCCUAUUCCACCACG | 127 | CUACUCCUAUUCCACCACGNN | 407 |
| as | 443 | CGUGGUGGAAUAGGAGUAG | 128 | CGUGGUGGAAUAGGAGUAGNN | 408 |
| s | 426 | UACUCCUAUUCCACCACGG | 129 | UACUCCUAUUCCACCACGGNN | 409 |
| as | 444 | CCGUGGUGGAAUAGGAGUA | 130 | CCGUGGUGGAAUAGGAGUANN | 410 |
| s | 427 | ACUCCUAUUCCACCACGGC | 131 | ACUCCUAUUCCACCACGGCNN | 411 |
| as | 445 | GCCGUGGUGGAAUAGGAGU | 132 | GCCGUGGUGGAAUAGGAGUNN | 412 |
| s | 429 | UCCUAUUCCACCACGGCUG | 133 | UCCUAUUCCACCACGGCUGNN | 413 |
| as | 447 | CAGCCGUGGUGGAAUAGGA | 134 | CAGCCGUGGUGGAAUAGGANN | 414 |
| s | 432 | UAUUCCACCACGGCUGUCG | 135 | UAUUCCACCACGGCUGUCGNN | 415 |
| as | 450 | CGACAGCCGUGGUGGAAUA | 136 | CGACAGCCGUGGUGGAAUANN | 416 |
| s | 433 | AUUCCACCACGGCUGUCGU | 137 | AUUCCACCACGGCUGUCGUNN | 417 |
| as | 451 | ACGACAGCCGUGGUGGAAU | 138 | ACGACAGCCGUGGUGGAAUNN | 418 |
| s | 437 | CACCACGGCUGUCGUCACC | 139 | CACCACGGCUGUCGUCACCNN | 419 |
| as | 455 | GGUGACGACAGCCGUGGUG | 140 | GGUGACGACAGCCGUGGUGNN | 420 |
| s | 438 | ACCACGGCUGUCGUCACCA | 141 | ACCACGGCUGUCGUCACCANN | 421 |
| as | 456 | UGGUGACGACAGCCGUGGU | 142 | UGGUGACGACAGCCGUGGUNN | 422 |
| s | 439 | CCACGGCUGUCGUCACCAA | 143 | CCACGGCUGUCGUCACCAANN | 423 |
| as | 457 | UUGGUGACGACAGCCGUGG | 144 | UUGGUGACGACAGCCGUGGNN | 424 |
| s | 441 | ACGGCUGUCGUCACCAAUC | 145 | ACGGCUGUCGUCACCAAUCNN | 425 |
| as | 459 | GAUUGGUGACGACAGCCGU | 146 | GAUUGGUGACGACAGCCGUNN | 426 |
| s | 442 | CGGCUGUCGUCACCAAUCC | 147 | CGGCUGUCGUCACCAAUCCNN | 427 |
| as | 460 | GGAUUGGUGACGACAGCCG | 148 | GGAUUGGUGACGACAGCCGNN | 428 |
| s | 449 | CGUCACCAAUCCCAAGGAA | 149 | CGUCACCAAUCCCAAGGAANN | 429 |
| as | 467 | UUCCUUGGGAUUGGUGACG | 150 | UUCCUUGGGAUUGGUGACGNN | 430 |
| s | 455 | CAAUCCCAAGGAAUGAGGG | 151 | CAAUCCCAAGGAAUGAGGGNN | 431 |
| as | 473 | CCCUCAUUCCUUGGGAUUG | 152 | CCCUCAUUCCUUGGGAUUGNN | 432 |
| s | 491 | CCUGAAGGACGAGGGAUGG | 153 | CCUGAAGGACGAGGGAUGGNN | 433 |
| as | 509 | CCAUCCCUCGUCCUUCAGG | 154 | CCAUCCCUCGUCCUUCAGGNN | 434 |
| s | 497 | GGACGAGGGAUGGGAUUUC | 155 | GGACGAGGGAUGGGAUUUCNN | 435 |
| as | 515 | GAAAUCCCAUCCCUCGUCC | 156 | GAAAUCCCAUCCCUCGUCCNN | 436 |
| s | 5 | AAGUCCACUCAUUCUUGGC | 157 | AAGUCCACUCAUUCUUGGCNN | 437 |
| as | 23 | GCCAAGAAUGAGUGGACUU | 158 | GCCAAGAAUGAGUGGACUUNN | 438 |

TABLE 3-continued

Sense and antisense strand sequences of human TTR dsRNAs
(NM_000371.2, SEQ ID NO: 1329)

| | | | | | |
|---|---|---|---|---|---|
| s | 508 | GGGAUUUCAUGUAACCAAG | 159 | GGGAUUUCAUGUAACCAAGNN | 439 |
| as | 526 | CUUGGUUACAUGAAAUCCC | 160 | CUUGGUUACAUGAAAUCCCNN | 440 |
| s | 509 | GGAUUUCAUGUAACCAAGA | 161 | GGAUUUCAUGUAACCAAGANN | 441 |
| as | 527 | UCUUGGUUACAUGAAAUCC | 162 | UCUUGGUUACAUGAAAUCCNN | 442 |
| s | 514 | UCAUGUAACCAAGAGUAUU | 163 | UCAUGUAACCAAGAGUAUUNN | 443 |
| as | 532 | AAUACUCUUGGUUACAUGA | 164 | AAUACUCUUGGUUACAUGANN | 444 |
| s | 516 | AUGUAACCAAGAGUAUUCC | 165 | AUGUAACCAAGAGUAUUCCNN | 445 |
| as | 534 | GGAAUACUCUUGGUUACAU | 166 | GGAAUACUCUUGGUUACAUNN | 446 |
| s | 517 | UGUAACCAAGAGUAUUCCA | 167 | UGUAACCAAGAGUAUUCCANN | 447 |
| as | 535 | UGGAAUACUCUUGGUUACA | 168 | UGGAAUACUCUUGGUUACANN | 448 |
| s | 518 | GUAACCAAGAGUAUUCCAU | 169 | GUAACCAAGAGUAUUCCAUNN | 449 |
| as | 536 | AUGGAAUACUCUUGGUUAC | 170 | AUGGAAUACUCUUGGUUACNN | 450 |
| s | 54 | UGCCUUGCUGGACUGGUAU | 171 | UGCCUUGCUGGACUGGUAUNN | 451 |
| as | 72 | AUACCAGUCCAGCAAGGCA | 172 | AUACCAGUCCAGCAAGGCANN | 452 |
| s | 543 | UAAAGCAGUGUUUUCACCU | 173 | UAAAGCAGUGUUUUCACCUNN | 453 |
| as | 561 | AGGUGAAAACACUGCUUUA | 174 | AGGUGAAAACACUGCUUUANN | 454 |
| s | 55 | GCCUUGCUGGACUGGUAUU | 175 | GCCUUGCUGGACUGGUAUUNN | 455 |
| as | 73 | AAUACCAGUCCAGCAAGGC | 176 | AAUACCAGUCCAGCAAGGCNN | 456 |
| s | 551 | UGUUUUCACCUCAUAUGCU | 177 | UGUUUUCACCUCAUAUGCUNN | 457 |
| as | 569 | AGCAUAUGAGGUGAAAACA | 178 | AGCAUAUGAGGUGAAAACANN | 458 |
| s | 552 | GUUUUCACCUCAUAUGCUA | 179 | GUUUUCACCUCAUAUGCUANN | 459 |
| as | 570 | UAGCAUAUGAGGUGAAAAC | 180 | UAGCAUAUGAGGUGAAAACNN | 460 |
| s | 553 | UUUUCACCUCAUAUGCUAU | 181 | UUUUCACCUCAUAUGCUAUNN | 461 |
| as | 571 | AUAGCAUAUGAGGUGAAAA | 182 | AUAGCAUAUGAGGUGAAAANN | 462 |
| s | 555 | UUCACCUCAUAUGCUAUGU | 183 | UUCACCUCAUAUGCUAUGUNN | 463 |
| as | 573 | ACAUAGCAUAUGAGGUGAA | 184 | ACAUAGCAUAUGAGGUGAANN | 464 |
| s | 557 | CACCUCAUAUGCUAUGUUA | 185 | CACCUCAUAUGCUAUGUUANN | 465 |
| as | 575 | UAACAUAGCAUAUGAGGUG | 186 | UAACAUAGCAUAUGAGGUGNN | 466 |
| s | 56 | CCUUGCUGGACUGGUAUUU | 187 | CCUUGCUGGACUGGUAUUUNN | 467 |
| as | 74 | AAAUACCAGUCCAGCAAGG | 188 | AAAUACCAGUCCAGCAAGGNN | 468 |
| s | 563 | AUAUGCUAUGUUAGAAGUC | 189 | AUAUGCUAUGUUAGAAGUCNN | 469 |
| as | 581 | GACUUCUAACAUAGCAUAU | 190 | GACUUCUAACAUAGCAUAUNN | 470 |
| s | 564 | UAUGCUAUGUUAGAAGUCC | 191 | UAUGCUAUGUUAGAAGUCCNN | 471 |
| as | 582 | GGACUUCUAACAUAGCAUA | 192 | GGACUUCUAACAUAGCAUANN | 472 |
| s | 566 | UGCUAUGUUAGAAGUCCAG | 193 | UGCUAUGUUAGAAGUCCAGNN | 473 |
| as | 584 | CUGGACUUCUAACAUAGCA | 194 | CUGGACUUCUAACAUAGCANN | 474 |
| s | 57 | CUUGCUGGACUGGUAUUUG | 195 | CUUGCUGGACUGGUAUUUGNN | 475 |
| as | 75 | CAAAUACCAGUCCAGCAAG | 196 | CAAAUACCAGUCCAGCAAGNN | 476 |
| s | 578 | AGUCCAGGCAGAGACAAUA | 197 | AGUCCAGGCAGAGACAAUANN | 477 |

TABLE 3-continued

Sense and antisense strand sequences of human TTR dsRNAs
(NM_000371.2, SEQ ID NO: 1329)

| | | | | | |
|---|---|---|---|---|---|
| as | 596 | AUUGUCUCUGCCUGGACUTT | 198 | AUUGUCUCUGCCUGGACUTTNN | 478 |
| s | 580 | UCCAGGCAGAGACAAUAAA | 199 | UCCAGGCAGAGACAAUAAANN | 479 |
| as | 598 | UUUAUUGUCUCUGCCUGGA | 200 | UUUAUUGUCUCUGCCUGGANN | 480 |
| s | 607 | GUGAAAGGCACUUUUCAUU | 201 | GUGAAAGGCACUUUUCAUUNN | 481 |
| as | 625 | AAUGAAAGUGCCUUUCAC | 202 | AAUGAAAGUGCCUUUCACNN | 482 |
| s | 62 | UGGACUGGUAUUUGUGUCU | 203 | UGGACUGGUAUUUGUGUCUNN | 483 |
| as | 80 | AGACACAAAUACCAGUCCA | 204 | AGACACAAAUACCAGUCCANN | 484 |
| s | 77 | GUCUGAGGCUGGCCCUACG | 205 | GUCUGAGGCUGGCCCUACGNN | 485 |
| as | 95 | CGUAGGGCCAGCCUCAGAC | 206 | CGUAGGGCCAGCCUCAGACNN | 486 |
| s | 79 | CUGAGGCUGGCCCUACGGG | 207 | CUGAGGCUGGCCCUACGGGNN | 487 |
| as | 97 | CCCGUAGGGCCAGCCUCAG | 208 | CCCGUAGGGCCAGCCUCAGNN | 488 |
| s | 81 | GAGGCUGGCCCUACGGGCA | 209 | GAGGCUGGCCCUACGGGCANN | 489 |
| as | 99 | UGCCCGUAGGGCCAGCCUC | 210 | UGCCCGUAGGGCCAGCCUCNN | 490 |
| s | 82 | AGGCUGGCCCUACGGGCAC | 211 | AGGCUGGCCCUACGGGCACNN | 491 |
| as | 100 | GUGCCCGUAGGGCCAGCCU | 212 | GUGCCCGUAGGGCCAGCCUNN | 492 |
| s | 84 | GCUGGCCCUACGGGCACCG | 213 | GCUGGCCCUACGGGCACCGNN | 493 |
| as | 102 | CGGUGCCCGUAGGGCCAGC | 214 | CGGUGCCCGUAGGGCCAGCNN | 494 |
| s | 85 | CUGGCCCUACGGGCACCGG | 215 | CUGGCCCUACGGGCACCGGNN | 495 |
| as | 103 | CCGGUGCCCGUAGGGCCAG | 216 | CCGGUGCCCGUAGGGCCAGNN | 496 |
| s | 87 | GGCCCUACGGGCACCGGUG | 217 | GGCCCUACGGGCACCGGUGNN | 497 |
| as | 105 | CACCGGUGCCCGUAGGGCC | 218 | CACCGGUGCCCGUAGGGCCNN | 498 |
| s | 9 | CCACUCAUUCUUGGCAGGA | 219 | CCACUCAUUCUUGGCAGGANN | 499 |
| as | 27 | UCCUGCCAAGAAUGAGUGG | 220 | UCCUGCCAAGAAUGAGUGGNN | 500 |
| s | 90 | CCUACGGGCACCGGUGAAU | 221 | CCUACGGGCACCGGUGAAUNN | 501 |
| as | 108 | AUUCACCGGUGCCCGUAGG | 222 | AUUCACCGGUGCCCGUAGGNN | 502 |
| s | 91 | CUACGGGCACCGGUGAAUC | 223 | CUACGGGCACCGGUGAAUCNN | 503 |
| as | 109 | GAUUCACCGGUGCCCGUAG | 224 | GAUUCACCGGUGCCCGUAGNN | 504 |
| s | 92 | UACGGGCACCGGUGAAUCC | 225 | UACGGGCACCGGUGAAUCCNN | 505 |
| as | 110 | GGAUUCACCGGUGCCCGUA | 226 | GGAUUCACCGGUGCCCGUANN | 506 |
| s | 93 | ACGGGCACCGGUGAAUCCA | 227 | ACGGGCACCGGUGAAUCCANN | 507 |
| as | 111 | UGGAUUCACCGGUGCCCGU | 228 | UGGAUUCACCGGUGCCCGUNN | 508 |
| s | 97 | GCACCGGUGAAUCCAAGUG | 229 | GCACCGGUGAAUCCAAGUGNN | 509 |
| as | 115 | CACUUGGAUUCACCGGUGC | 230 | CACUUGGAUUCACCGGUGCNN | 510 |
| s | 98 | CACCGGUGAAUCCAAGUGU | 231 | CACCGGUGAAUCCAAGUGUNN | 511 |
| as | 116 | ACACUUGGAUUCACCGGUG | 232 | ACACUUGGAUUCACCGGUGNN | 512 |
| s | 167 | UGUGGCCAUGCAUGUGUUC | 233 | UGUGGCCAUGCAUGUGUUCNN | 513 |
| as | 185 | GAACACAUGCAUGGCCACA | 234 | GAACACAUGCAUGGCCACANN | 514 |
| s | 168 | GUGGCCAUGCAUGUGUUCA | 235 | GUGGCCAUGCAUGUGUUCANN | 515 |

TABLE 3-continued

Sense and antisense strand sequences of human TTR dsRNAs
(NM_000371.2, SEQ ID NO: 1329)

| | | | | | |
|---|---|---|---|---|---|
| as | 186 | UGAACACAUGCAUGGCCAC | 236 | UGAACACAUGCAUGGCCACNN | 516 |
| s | 171 | GCCAUGCAUGUGUUCAGAA | 237 | GCCAUGCAUGUGUUCAGAANN | 517 |
| as | 189 | UUCUGAACACAUGCAUGGC | 238 | UUCUGAACACAUGCAUGGCNN | 518 |
| s | 432 | UAUUCCACCACGGCUGUCA | 239 | UAUUCCACCACGGCUGUCANN | 519 |
| as | 449 | UGACAGCCGUGGUGGAAUA | 240 | UGACAGCCGUGGUGGAAUANN | 520 |
| s | 447 | GUCAUCACCAAUCCCAAGG | 241 | GUCAUCACCAAUCCCAAGGNN | 521 |
| as | 465 | CCUUGGGAUUGGUGAUGAC | 242 | CCUUGGGAUUGGUGAUGACNN | 522 |
| s | 115 | GUCCUCUGAUGGUCAAAGU | 243 | GUCCUCUGAUGGUCAAAGUNN | 523 |
| as | 133 | ACUUUGACCAUCAGAGGAC | 244 | ACUUUGACCAUCAGAGGACNN | 524 |
| s | 122 | GAUGGUCAAAGUUCUAGAU | 245 | GAUGGUCAAAGUUCUAGAUNN | 525 |
| as | 140 | AUCUAGAACUUUGACCAUC | 246 | AUCUAGAACUUUGACCAUCNN | 526 |
| s | 139 | AUGCUGUCCGAGGCAGUCC | 247 | AUGCUGUCCGAGGCAGUCCNN | 527 |
| as | 157 | GGACUGCCUCGGACAGCAU | 248 | GGACUGCCUCGGACAGCAUNN | 528 |
| s | 172 | CCGUGCAUGUGUUCAGAAA | 249 | CCGUGCAUGUGUUCAGAAANN | 529 |
| as | 190 | UUUCUGAACACAUGCACGG | 250 | UUUCUGAACACAUGCACGGNN | 530 |
| s | 238 | AGUCUGGAGAGCUGCAUGG | 251 | AGUCUGGAGAGCUGCAUGGNN | 531 |
| as | 256 | CCAUGCAGCUCUCCAGACU | 252 | CCAUGCAGCUCUCCAGACUNN | 532 |
| s | 252 | CAUGGGCUCACAACUGAGG | 253 | CAUGGGCUCACAACUGAGGNN | 533 |
| as | 270 | CCUCAGUUGUGAGCCCAUG | 254 | CCUCAGUUGUGAGCCCAUGNN | 534 |
| s | 33 | UCUCAUCGUCUGCUCCUCC | 255 | UCUCAUCGUCUGCUCCUCCNN | 535 |
| as | 51 | GGAGGAGCAGACGAUGAGA | 256 | GGAGGAGCAGACGAUGAGANN | 536 |
| s | 340 | CCCCAUUCCAUGAGCAUGC | 257 | CCCCAUUCCAUGAGCAUGCNN | 537 |
| as | 358 | GCAUGCUCAUGGAAUGGGG | 258 | GCAUGCUCAUGGAAUGGGGNN | 538 |
| s | 421 | GCCCCUACUCCUAUUCCAC | 259 | GCCCCUACUCCUAUUCCACNN | 539 |
| as | 439 | GUGGAAUAGGAGUAGGGGC | 260 | GUGGAAUAGGAGUAGGGGCNN | 540 |
| s | 431 | CUAUUCCACCACGGCUGUC | 261 | CUAUUCCACCACGGCUGUCNN | 541 |
| as | 449 | GACAGCCGUGGUGGAAUAG | 262 | GACAGCCGUGGUGGAAUAGNN | 542 |
| s | 440 | CACGGCUGUCGUCACCAAU | 263 | CACGGCUGUCGUCACCAAUNN | 543 |
| as | 458 | AUUGGUGACGACAGCCGUG | 264 | AUUGGUGACGACAGCCGUGNN | 544 |
| s | 496 | AGGACGAGGGAUGGGAUUU | 265 | AGGACGAGGGAUGGGAUUUNN | 545 |
| as | 514 | AAAUCCCAUCCCUCGUCCU | 266 | AAAUCCCAUCCCUCGUCCUNN | 546 |
| s | 556 | UCACCUCAUAUGCUAUGUU | 267 | UCACCUCAUAUGCUAUGUUNN | 547 |
| as | 574 | AACAUAGCAUAUGAGGUGA | 268 | AACAUAGCAUAUGAGGUGANN | 548 |
| s | 559 | CCUCAUAUGCUAUGUUAGA | 269 | CCUCAUAUGCUAUGUUAGANN | 549 |
| as | 577 | UCUAACAUAGCAUAUGAGG | 270 | UCUAACAUAGCAUAUGAGGNN | 550 |
| s | 570 | AUGUUAGAAGUCCAGGCAG | 271 | AUGUUAGAAGUCCAGGCAGNN | 551 |
| as | 588 | CUGCCUGGACUUCUAACAU | 272 | CUGCCUGGACUUCUAACAUNN | 552 |
| s | 78 | UCUGAGGCUGGCCCUACGG | 273 | UCUGAGGCUGGCCCUACGGNN | 553 |
| as | 96 | CCGUAGGGCCAGCCUCAGA | 274 | CCGUAGGGCCAGCCUCAGANN | 554 |

TABLE 3-continued

Sense and antisense strand sequences of human TTR dsRNAs
(NM_000371.2, SEQ ID NO: 1329)

| Strand | Position | | | | |
|---|---|---|---|---|---|
| s | 87 | GGCCCUACGGGCACCGGUG | 275 | GGCCCUACGGGCACCGGUGNN | 555 |
| as | 105 | CACCGGUGCCCGUAGGGCC | 276 | CACCGGUGCCCGUAGGGCCNN | 556 |
| s | 95 | GGGCACCGGUGAAUCCAAG | 277 | GGGCACCGGUGAAUCCAAGNN | 557 |
| as | 113 | CUUGGAUUCACCGGUGCCC | 278 | CUUGGAUUCACCGGUGCCCNN | 558 |
| s | 167 | CCAUGCAUGUGUUCAGAAA | 279 | CCAUGCAUGUGUUCAGAAANN | 559 |
| as | 185 | UUUCUGAACACAUGCAUGG | 280 | UUUCUGAACACAUGCAUGGNN | 560 |

B.

| Strand | Position | Sequence with 3' deoxythimidine overhang (5' to 3') | SEQ ID NO: |
|---|---|---|---|
| s | 100 | CCGGUGAAUCCAAGUGUCCdTdT | 561 |
| as | 118 | GGACACUUGGAUUCACCGGdTdT | 562 |
| s | 11 | ACUCAUUCUUGGCAGGAUGdTdT | 563 |
| as | 29 | CAUCCUGCCAAGAAUGAGUdTdT | 564 |
| s | 111 | AAGUGUCCUCUGAUGGUCAdTdT | 565 |
| as | 129 | UGACCAUCAGAGGACACUUdTdT | 566 |
| s | 13 | UCAUUCUUGGCAGGAUGGCdTdT | 567 |
| as | 31 | GCCAUCCUGCCAAGAAUGAdTdT | 568 |
| s | 130 | AAGUUCUAGAUGCUGUCCGdTdT | 569 |
| as | 148 | CGGACAGCAUCUAGAACUUdTdT | 570 |
| s | 132 | GUUCUAGAUGCUGUCCGAGdTdT | 571 |
| as | 150 | CUCGGACAGCAUCUAGAACdTdT | 572 |
| s | 135 | CUAGAUGCUGUCCGAGGCAdTdT | 573 |
| as | 153 | UGCCUCGGACAGCAUCUAGdTdT | 574 |
| s | 138 | GAUGCUGUCCGAGGCAGUCdTdT | 575 |
| as | 156 | GACUGCCUCGGACAGCAUCdTdT | 576 |
| s | 14 | CAUUCUUGGCAGGAUGGCUdTdT | 577 |
| as | 32 | AGCCAUCCUGCCAAGAAUGdTdT | 578 |
| s | 140 | UGCUGUCCGAGGCAGUCCUdTdT | 579 |
| as | 158 | AGGACUGCCUCGGACAGCAdTdT | 580 |
| s | 146 | CCGAGGCAGUCCUGCCAUCdTdT | 581 |
| as | 164 | GAUGGCAGGACUGCCUCGGdTdT | 582 |
| s | 152 | CAGUCCUGCCAUCAAUGUGdTdT | 583 |
| as | 170 | CACAUUGAUGGCAGGACUGdTdT | 584 |
| s | 164 | CAAUGUGGCCGUGCAUGUGdTdT | 585 |
| as | 182 | CACAUGCACGGCCACAUUGdTdT | 586 |
| s | 178 | AUGUGUUCAGAAAGGCUGCdTdT | 587 |
| as | 196 | GCAGCCUUUCUGAACACAUdTdT | 588 |
| s | 2 | CAGAAGUCCACUCAUUCUUdTdT | 589 |
| as | 20 | AAGAAUGAGUGGACUUCUGdTdT | 590 |

TABLE 3-continued

Sense and antisense strand sequences of human TTR dsRNAs
(NM_000371.2, SEQ ID NO: 1329)

| | | | |
|---|---|---|---|
| s | 21 | GGCAGGAUGGCUUCUCAUCdTdT | 591 |
| as | 39 | GAUGAGAAGCCAUCCUGCCdTdT | 592 |
| s | 210 | GAGCCAUUUGCCUCUGGGAdTdT | 593 |
| as | 228 | UCCCAGAGGCAAAUGGCUCdTdT | 594 |
| s | 23 | CAGGAUGGCUUCUCAUCGUdTdT | 595 |
| as | 41 | ACGAUGAGAAGCCAUCCUGdTdT | 596 |
| s | 24 | AGGAUGGCUUCUCAUCGUCdTdT | 597 |
| as | 42 | GACGAUGAGAAGCCAUCCUdTdT | 598 |
| s | 245 | AGAGCUGCAUGGGCUCACAdTdT | 599 |
| as | 263 | UGUGAGCCCAUGCAGCUCUdTdT | 600 |
| s | 248 | GCUGCAUGGGCUCACAACUdTdT | 601 |
| as | 266 | AGUUGUGAGCCCAUGCAGCdTdT | 602 |
| s | 25 | GGAUGGCUUCUCAUCGUCUdTdT | 603 |
| as | 43 | AGACGAUGAGAAGCCAUCCdTdT | 604 |
| s | 251 | GCAUGGGCUCACAACUGAGdTdT | 605 |
| as | 269 | CUCAGUUGUGAGCCCAUGCdTdT | 606 |
| s | 253 | AUGGGCUCACAACUGAGGAdTdT | 607 |
| as | 271 | UCCUCAGUUGUGAGCCCAUdTdT | 608 |
| s | 254 | UGGGCUCACAACUGAGGAGdTdT | 609 |
| as | 272 | CUCCUCAGUUGUGAGCCCAdTdT | 610 |
| s | 270 | GAGGAAUUUGUAGAAGGGAdTdT | 611 |
| as | 288 | UCCCUUCUACAAAUUCCUCdTdT | 612 |
| s | 276 | UUUGUAGAAGGGAUAUACAdTdT | 613 |
| as | 294 | UGUAUAUCCCUUCUACAAAdTdT | 614 |
| s | 277 | UUGUAGAAGGGAUAUACAAdTdT | 615 |
| as | 295 | UUGUAUAUCCCUUCUACAAdTdT | 616 |
| s | 278 | UGUAGAAGGGAUAUACAAAdTdT | 617 |
| as | 296 | UUUGUAUAUCCCUUCUACAdTdT | 618 |
| s | 281 | AGAAGGGAUAUACAAAGUGdTdT | 619 |
| as | 299 | CACUUUGUAUAUCCCUUCUdTdT | 620 |
| s | 295 | AAGUGGAAAUAGACACCAAdTdT | 621 |
| as | 313 | UUGGUGUCUAUUUCCACUUdTdT | 622 |
| s | 299 | GGAAAUAGACACCAAAUCUdTdT | 623 |
| as | 317 | AGAUUUGGUGUCUAUUUCCdTdT | 624 |
| s | 300 | GAAAUAGACACCAAAUCUUdTdT | 625 |
| as | 318 | AAGAUUUGGUGUCUAUUUCdTdT | 626 |
| s | 303 | AUAGACACCAAAUCUUACdTdT | 627 |
| as | 321 | AGUAAGAUUUGGUGUCUAUdTdT | 628 |

TABLE 3-continued

Sense and antisense strand sequences of human TTR dsRNAs
(NM_000371.2, SEQ ID NO: 1329)

| | | | |
|---|---|---|---|
| s | 304 | UAGACACCAAAUCUUACUGdTdT | 629 |
| as | 322 | CAGUAAGAUUUGGUGUCUAdTdT | 630 |
| s | 305 | AGACACCAAAUCUUACUGGdTdT | 631 |
| as | 323 | CCAGUAAGAUUUGGUGUCUdTdT | 632 |
| s | 317 | UUACUGGAAGGCACUUGGCdTdT | 633 |
| as | 335 | GCCAAGUGCCUUCCAGUAAdTdT | 634 |
| s | 32 | UUCUCAUCGUCUGCUCCUCdTdT | 635 |
| as | 50 | GAGGAGCAGACGAUGAGAAdTdT | 636 |
| s | 322 | GGAAGGCACUUGGCAUCUCdTdT | 637 |
| as | 340 | GAGAUGCCAAGUGCCUUCCdTdT | 638 |
| s | 326 | GGCACUUGGCAUCUCCCCAdTdT | 639 |
| as | 344 | UGGGGAGAUGCCAAGUGCCdTdT | 640 |
| s | 333 | GGCAUCUCCCCAUUCCAUGdTdT | 641 |
| as | 351 | AUGGAAUGGGGAGAUGCCTTdTdT | 642 |
| s | 334 | GCAUCUCCCCAUUCCAUGAdTdT | 643 |
| as | 352 | UCAUGGAAUGGGGAGAUGCdTdT | 644 |
| s | 335 | CAUCUCCCCAUUCCAUGAGdTdT | 645 |
| as | 353 | CUCAUGGAAUGGGGAGAUGdTdT | 646 |
| s | 336 | AUCUCCCCAUUCCAUGAGCdTdT | 647 |
| as | 354 | GCUCAUGGAAUGGGGAGAUdTdT | 648 |
| s | 338 | CUCCCCAUUCCAUGAGCAUdTdT | 649 |
| as | 356 | AUGCUCAUGGAAUGGGGAGdTdT | 650 |
| s | 341 | CCCAUUCCAUGAGCAUGCAdTdT | 651 |
| as | 359 | UGCAUGCUCAUGGAAUGGGdTdT | 652 |
| s | 347 | CCAUGAGCAUGCAGAGGUGdTdT | 653 |
| as | 365 | CACCUCUGCAUGCUCAUGGdTdT | 654 |
| s | 352 | AGCAUGCAGAGGUGGUAUUdTdT | 655 |
| as | 370 | AAUACCACCUCUGCAUGCUdTdT | 656 |
| s | 354 | CAUGGAGAGGUGGUAUUCAdTdT | 657 |
| as | 372 | UGAAUACCACCUCUGCAUGdTdT | 658 |
| s | 355 | AUGCAGAGGUGGUAUUCACdTdT | 659 |
| as | 373 | GUGAAUACCACCUCUGCAUdTdT | 660 |
| s | 362 | GGUGGUAUUCACAGCCAACdTdT | 661 |
| as | 380 | GUUGGCUGUGAAUACCACCdTdT | 662 |
| s | 363 | GUGGUAUUCACAGCCAACGdTdT | 663 |
| as | 381 | CGUUGGCUGUGAAUACCACdTdT | 664 |
| s | 364 | UGGUAUUCACAGCCAACGAdTdT | 665 |
| as | 382 | UCGUUGGCUGUGAAUACCAdTdT | 666 |
| s | 365 | GGUAUUCACAGCCAACGACdTdT | 667 |

TABLE 3-continued

Sense and antisense strand sequences of human TTR dsRNAs (NM_000371.2, SEQ ID NO: 1329)

| | | | |
|---|---|---|---|
| as | 383 | GUCGUUGGCUGUGAAUACCdTdT | 668 |
| s | 366 | GUAUUCACAGCCAACGACUdTdT | 669 |
| as | 384 | AGUCGUUGGCUGUGAAUACdTdT | 670 |
| s | 367 | UAUUCACAGCCAACGACUCdTdT | 671 |
| as | 385 | GAGUCGUUGGCUGUGAAUAdTdT | 672 |
| s | 370 | UCACAGCCAACGACUCCGGdTdT | 673 |
| as | 388 | CCGGAGUCGUUGGCUGUGAdTdT | 674 |
| s | 390 | CCCCGCCGCUACACCAUUGdTdT | 675 |
| as | 408 | CAAUGGUGUAGCGGCGGGGdTdT | 676 |
| s | 4 | GAAGUCCACUCAUUCUUGGdTdT | 677 |
| as | 22 | CCAAGAAUGAGUGGACUUCdTdT | 678 |
| s | 412 | CCCUGCUGAGCCCCUACUCdTdT | 679 |
| as | 430 | GAGUAGGGGCUCAGCAGGGdTdT | 680 |
| s | 417 | CUGAGCCCCUACUCCUAUUdTdT | 681 |
| as | 435 | AAUAGGAGUAGGGGCUCAGdTdT | 682 |
| s | 418 | UGAGCCCCUACUCCUAUUCdTdT | 683 |
| as | 436 | GAAUAGGAGUAGGGGCUCAdTdT | 684 |
| s | 422 | CCCCUACUCCUAUUCCACCdTdT | 685 |
| as | 440 | GGUGGAAUAGGAGUAGGGGdTdT | 686 |
| s | 425 | CUACUCCUAUUCCACCACGdTdT | 687 |
| as | 443 | CGUGGUGGAAUAGGAGUAGdTdT | 688 |
| s | 426 | UACUCCUAUUCCACCACGGdTdT | 689 |
| as | 444 | CCGUGGUGGAAUAGGAGUAdTdT | 690 |
| s | 427 | ACUCCUAUUCCACCACGGCdTdT | 691 |
| as | 445 | GCCGUGGUGGAAUAGGAGUdTdT | 692 |
| s | 429 | UCCUAUUCCACCACGGCUGdTdT | 693 |
| as | 447 | CAGCCGUGGUGGAAUAGGAdTdT | 694 |
| s | 432 | UAUUCCACCACGGCUGUCGdTdT | 695 |
| as | 450 | CGACAGCCGUGGUGGAAUAdTdT | 696 |
| s | 433 | AUUCCACCACGGCUGUCGUdTdT | 697 |
| as | 451 | ACGACAGCCGUGGUGGAAUdTdT | 698 |
| s | 437 | CACCACGGCUGUCGUCACCdTdT | 699 |
| as | 455 | GGUGACGACAGCCGUGGUGdTdT | 700 |
| s | 438 | ACCACGGCUGUCGUCACCAdTdT | 701 |
| as | 456 | UGGUGACGACAGCCGUGGUdTdT | 702 |
| s | 439 | CCACGGCUGUCGUCACCAAdTdT | 703 |
| as | 457 | UUGGUGACGACAGCCGUGGdTdT | 704 |
| s | 441 | ACGGCUGUCGUCACCAAUCdTdT | 705 |

TABLE 3-continued

Sense and antisense strand sequences of human TTR dsRNAs
(NM_000371.2, SEQ ID NO: 1329)

| | | | |
|---|---|---|---|
| as | 459 | GAUUGGUGACGACAGCCGUdTdT | 706 |
| s | 442 | CGGCUGUCGUCACCAAUCCdTdT | 707 |
| as | 460 | GGAUUGGUGACGACAGCCGdTdT | 708 |
| s | 449 | CGUCACCAAUCCCAAGGAAdTdT | 709 |
| as | 467 | UUCCUUGGGAUUGGUGACGdTdT | 710 |
| s | 455 | CAAUCCCAAGGAAUGAGGGdTdT | 711 |
| as | 473 | CCCUCAUUCCUUGGGAUUGdTdT | 712 |
| s | 491 | CCUGAAGGACGAGGGAUGGdTdT | 713 |
| as | 509 | CCAUCCCUCGUCCUUCAGGdTdT | 714 |
| s | 497 | GGACGAGGGAUGGGAUUUCdTdT | 715 |
| as | 515 | GAAAUCCCAUCCCUCGUCCdTdT | 716 |
| s | 5 | AAGUCCACUCAUUCUUGGCdTdT | 717 |
| as | 23 | GCCAAGAAUGAGUGGACUUdTdT | 718 |
| s | 508 | GGGAUUUCAUGUAACCAAGdTdT | 719 |
| as | 526 | CUUGGUUACAUGAAAUCCCdTdT | 720 |
| s | 509 | GGAUUUCAUGUAACCAAGAdTdT | 721 |
| as | 527 | UCUUGGUUACAUGAAAUCCdTdT | 722 |
| s | 514 | UCAUGUAACCAAGAGUAUUdTdT | 723 |
| as | 532 | AAUACUCUUGGUUACAUGAdTdT | 724 |
| s | 516 | AUGUAACCAAGAGUAUUCCdTdT | 725 |
| as | 534 | GGAAUACUCUUGGUUACAUdTdT | 726 |
| s | 517 | UGUAACCAAGAGUAUUCCAdTdT | 727 |
| as | 535 | UGGAAUACUCUUGGUUACAdTdT | 728 |
| s | 518 | GUAACCAAGAGUAUUCCAUdTdT | 729 |
| as | 536 | AUGGAAUACUCUUGGUUACdTdT | 730 |
| s | 54 | UGCCUUGCUGGACUGGUAUdTdT | 731 |
| as | 72 | AUACCAGUCCAGCAAGGCAdTdT | 732 |
| s | 543 | UAAAGCAGUGUUUUCACCUdTdT | 733 |
| as | 561 | AGGUGAAAACACUGCUUUAdTdT | 734 |
| s | 55 | GCCUUGCUGGACUGGUAUUdTdT | 735 |
| as | 73 | AAUACCAGUCCAGCAAGGCdTdT | 736 |
| s | 551 | UGUUUUCACCUCAUAUGCUdTdT | 737 |
| as | 569 | AGCAUAUGAGGUGAAAACAdTdT | 738 |
| s | 552 | GUUUUCACCUCAUAUGCUAdTdT | 739 |
| as | 570 | UAGCAUAUGAGGUGAAAACdTdT | 740 |
| s | 553 | UUUUCACCUCAUAUGCUAUdTdT | 741 |
| as | 571 | AUAGCAUAUGAGGUGAAAAdTdT | 742 |
| s | 555 | UUCACCUCAUAUGCUAUGUdTdT | 743 |
| as | 573 | ACAUAGCAUAUGAGGUGAAdTdT | 744 |

TABLE 3-continued

Sense and antisense strand sequences of human TTR dsRNAs
(NM_000371.2, SEQ ID NO: 1329)

| | | | |
|---|---|---|---|
| s | 557 | CACCUCAUAUGCUAUGUUAdTdT | 745 |
| as | 575 | UAACAUAGCAUAUGAGGUGdTdT | 746 |
| s | 56 | CCUUGCUGGACUGGUAUUUdTdT | 747 |
| as | 74 | AAAUACCAGUCCAGCAAGGdTdT | 748 |
| s | 563 | AUAUGCUAUGUUAGAAGUCdTdT | 749 |
| as | 581 | GACUUCUAACAUAGCAUAUdTdT | 750 |
| s | 564 | UAUGCUAUGUUAGAAGUCCdTdT | 751 |
| as | 582 | GGACUUCUAACAUAGCAUAdTdT | 752 |
| s | 566 | UGCUAUGUUAGAAGUCCAGdTdT | 753 |
| as | 584 | CUGGACUUCUAACAUAGCAdTdT | 754 |
| s | 57 | CUUGCUGGACUGGUAUUUGdTdT | 755 |
| as | 75 | CAAAUACCAGUCCAGCAAGdTdT | 756 |
| s | 578 | AGUCCAGGCAGAGACAAUAdTdT | 757 |
| as | 596 | AUUGUCUCUGCCUGGACUUdTdT | 758 |
| s | 580 | UCCAGGCAGAGACAAUAAAdTdT | 759 |
| as | 598 | UUUAUUGUCUCUGCCUGGAdTdT | 760 |
| s | 607 | GUGAAAGGCACUUUUCAUUdTdT | 761 |
| as | 625 | AAUGAAAAGUGCCUUUCACdTdT | 762 |
| s | 62 | UGGACUGGUAUUUGUGUCUdTdT | 763 |
| as | 80 | AGACACAAAUACCAGUCCAdTdT | 764 |
| s | 77 | GUCUGAGGCUGGCCCUACGdTdT | 765 |
| as | 95 | CGUAGGGCCAGCCUCAGACdTdT | 766 |
| s | 79 | CUGAGGCUGGCCCUACGGGdTdT | 767 |
| as | 97 | CCCGUAGGGCCAGCCUCAGdTdT | 768 |
| s | 81 | GAGGCUGGCCCUACGGGCAdTdT | 769 |
| as | 99 | UGCCCGUAGGGCCAGCCUCdTdT | 770 |
| s | 82 | AGGCUGGCCCUACGGGCACdTdT | 771 |
| as | 100 | GUGCCCGUAGGGCCAGCCUdTdT | 772 |
| s | 84 | GCUGGCCCUACGGGCACCGdTdT | 773 |
| as | 102 | CGGUGCCCGUAGGGCCAGCdTdT | 774 |
| s | 85 | CUGGCCCUACGGGCACCGGdTdT | 775 |
| as | 103 | CCGGUGCCCGUAGGGCCAGdTdT | 776 |
| s | 87 | GGCCCUACGGGCACCGGUGdTdT | 777 |
| as | 105 | CACCGGUGCCCGUAGGGCCdTdT | 778 |
| s | 9 | CCACUCAUUCUUGGCAGGAdTdT | 779 |
| as | 27 | UCCUGCCAAGAAUGAGUGGdTdT | 780 |
| s | 90 | CCUACGGGCACCGGUGAAUdTdT | 781 |
| as | 108 | AUUCACCGGUGCCCGUAGGdTdT | 782 |

TABLE 3-continued

Sense and antisense strand sequences of human TTR dsRNAs
(NM_000371.2, SEQ ID NO: 1329)

| | | | |
|---|---|---|---|
| s | 91 | CUACGGGCACCGGUGAAUCdTdT | 783 |
| as | 109 | GAUUCACCGGUGCCCGUAGdTdT | 784 |
| s | 92 | UACGGGCACCGGUGAAUCCdTdT | 785 |
| as | 110 | GGAUUCACCGGUGCCCGUAdTdT | 786 |
| s | 93 | ACGGGCACCGGUGAAUCCAdTdT | 787 |
| as | 111 | UGGAUUCACCGGUGCCCGUdTdT | 788 |
| s | 97 | GCACCGGUGAAUCCAAGUGdTdT | 789 |
| as | 115 | CACUUGGAUUCACCGGUGCdTdT | 790 |
| s | 98 | CACCGGUGAAUCCAAGUGUdTdT | 791 |
| as | 116 | ACACUUGGAUUCACCGGUGdTdT | 792 |
| s | 167 | UGUGGCCAUGCAUGUGUUCdTdT | 793 |
| as | 185 | GAACACAUGCAUGGCCACAdTdT | 794 |
| s | 168 | GUGGCCAUGCAUGUGUUCAdTdT | 795 |
| as | 186 | UGAACACAUGCAUGGCCACdTdT | 796 |
| s | 171 | GCCAUGCAUGUGUUCAGAAdTdT | 797 |
| as | 189 | UUCUGAACACAUGCAUGGCdTdT | 798 |
| s | 432 | UAUUCCACCACGGCUGUCAdTdT | 799 |
| as | 449 | UGACAGCCGUGGUGGAAUAdTdT | 800 |
| s | 447 | GUCAUCACCAAUCCCAAGGdTdT | 801 |
| as | 465 | CCUUGGGAUUGGUGAUGACdTdT | 802 |
| s | 115 | GUCCUCUGAUGGUCAAAGUdTdT | 803 |
| as | 133 | ACUUUGACCAUCAGAGGACdTdT | 804 |
| s | 122 | GAUGGUCAAAGUUCUAGAUdTdT | 805 |
| as | 140 | AUCUAGAACUUUGACCAUCdTdT | 806 |
| s | 139 | AUGCUGUCCGAGGCAGUCCdTdT | 807 |
| as | 157 | GGACUGCCUCGGACAGCAUdTdT | 808 |
| s | 172 | CCGUGCAUGUGUUCAGAAAdTdT | 809 |
| as | 190 | UUUCUGAACACAUGCACGGdTdT | 810 |
| s | 238 | AGUCUGGAGAGCUGCAUGGdTdT | 811 |
| as | 256 | CCAUGCAGCUCUCCAGACUdTdT | 812 |
| s | 252 | CAUGGGCUCACAACUGAGGdTdT | 813 |
| as | 270 | CCUCAGUUGUGAGCCCAUGdTdT | 814 |
| s | 33 | UCUCAUCGUCUGCUCCUCCdTdT | 815 |
| as | 51 | GGAGGAGCAGACGAUGAGAdTdT | 816 |
| s | 340 | CCCCAUUCCAUGAGCAUGCdTdT | 817 |
| as | 358 | GCAUGCUCAUGGAAUGGGGdTdT | 818 |
| s | 421 | GCCCCUACUCCUAUUCCACdTdT | 819 |
| as | 439 | GUGGAAUAGGAGUAGGGGCdTdT | 820 |
| s | 431 | CUAUUCCACCACGGCUGUCdTdT | 821 |

TABLE 3-continued

Sense and antisense strand sequences of human TTR dsRNAs
(NM_000371.2, SEQ ID NO: 1329)

| Strand | Position | Sequence | SEQ ID NO |
|---|---|---|---|
| as | 449 | GACAGCCGUGGUGGAAUAGdTdT | 822 |
| s | 440 | CACGGCUGUCGUCACCAAUdTdT | 823 |
| as | 458 | AUUGGUGACGACAGCCGUGdTdT | 824 |
| s | 496 | AGGACGAGGGAUGGGAUUUdTdT | 825 |
| as | 514 | AAAUCCCAUCCCUCGUCCUdTdT | 826 |
| s | 556 | UCACCUCAUAUGCUAUGUUdTdT | 827 |
| as | 574 | AACAUAGCAUAUGAGGUGAdTdT | 828 |
| s | 559 | CCUCAUAUGCUAUGUUAGAdTdT | 829 |
| as | 577 | UCUAACAUAGCAUAUGAGGdTdT | 830 |
| s | 570 | AUGUUAGAAGUCCAGGCAGdTdT | 831 |
| as | 588 | CUGCCUGGACUUCUAACAUdTdT | 832 |
| s | 78 | UCUGAGGCUGGCCCUACGGdTdT | 833 |
| as | 96 | CCGUAGGGCCAGCCUCAGAdTdT | 834 |
| s | 87 | GGCCCUACGGGCACCGGUGdTdT | 835 |
| as | 105 | CACCGGUGCCCGUAGGGCCdTdT | 836 |
| s | 95 | GGGCACCGGUGAAUCCAAGdTdT | 837 |
| as | 113 | CUUGGAUUCACCGGUGCCCdTdT | 838 |
| s | 167 | CCAUGCAUGUGUUCAGAAAdTdT | 839 |
| as | 185 | UUUCUGAACACAUGCAUGGdTdT | 840 |

Strand:
s = sense;
as = antisense;
Position: position of 5' base on transcript

TABLE 4

Chemically modified sense and antisense
strand sequences of human TTR dsRNAs

| Strand | Oligo # | Position | Sequence(5' to 3') | SEQ ID NO: |
|---|---|---|---|---|
| s | A-32153 | 100 | ccGGuGAAuccAAGuGuccdTdT | 841 |
| as | A-32154 | 118 | GGAcACUUGGAUUcACCGGdTdT | 842 |
| s | A-32155 | 11 | AcucAuucuuGGcAGGAuGdTdT | 843 |
| as | A-32156 | 29 | cAUCCUGCcAAGAAUGAGUdTdT | 844 |
| s | A-32157 | 111 | AAGuGuccucuGAuGGucAdTdT | 845 |
| as | A-32158 | 129 | UGACcAUcAGAGGAcACUUdTdT | 846 |
| s | A-32163 | 13 | ucAuucuuGGcAGGAuGGcdTdT | 847 |
| as | A-32164 | 31 | GCcAUCCUGCcAAGAAUGAdTdT | 848 |
| s | A-32165 | 130 | AAGuucuAGAuGcuGuccGdTdT | 849 |
| as | A-32166 | 148 | CGGAcAGcAUCuAGAACUUdTdT | 850 |
| s | A-32167 | 132 | GuucuAGAuGcuGuccGAGdTdT | 851 |
| as | A-32168 | 150 | CUCGGAcAGcAUCuAGAACdTdT | 852 |

TABLE 4-continued

Chemically modified sense and antisense strand sequences of human TTR dsRNAs

| Strand | Oligo # | Position | Sequence(5' to 3') | SEQ ID NO: |
|---|---|---|---|---|
| s | A-32169 | 135 | cuAGAuGcuGuccGAGGcAdTdT | 853 |
| as | A-32170 | 153 | UGCCUCGGAcAGcAUCuAGdTdT | 854 |
| s | A-32171 | 138 | GAuGcuGuccGAGGcAGucdTdT | 855 |
| as | A-32172 | 156 | GACUGCCUCGGAcAGcAUCdTdT | 856 |
| s | A-32175 | 14 | cAuucuuGGcAGGAuGGcudTdT | 857 |
| as | A-32176 | 32 | AGCcAUCCUGCcAAGAAUGdTdT | 858 |
| s | A-32177 | 140 | uGcuGuccGAGGcAGuccudTdT | 859 |
| as | A-32178 | 158 | AGGACUGCCUCGGAcAGcAdTdT | 860 |
| s | A-32179 | 146 | ccGAGGcAGuccuGccAucdTdT | 861 |
| as | A-32180 | 164 | GAUGGcAGGACUGCCUCGGdTdT | 862 |
| s | A-32181 | 152 | cAGuccuGccAucAAuGuGdTdT | 863 |
| as | A-32182 | 170 | cAcAUUGAUGGcAGGACUGdTdT | 864 |
| s | A-32183 | 164 | cAAuGuGGccGuGcAuGuGdTdT | 865 |
| as | A-32184 | 182 | cAcAUGcACGGCcAcAUUGdTdT | 866 |
| s | A-32187 | 178 | AuGuGuucAGAAAGGcuGcdTdT | 867 |
| as | A-32188 | 196 | GcAGCCUUUCUGAAcAcAUdTdT | 868 |
| s | A-32189 | 2 | cAGAAGuccAcucAuucuudTdT | 869 |
| as | A-32190 | 20 | AAGAAUGAGUGGACUUCUGdTdT | 870 |
| s | A-32191 | 21 | GGcAGGAuGGcuucucAucdTdT | 871 |
| as | A-32192 | 39 | GAUGAGAAGCcAUCCUGCCdTdT | 872 |
| s | A-32193 | 210 | GAGccAuuuGccucuGGGAdTdT | 873 |
| as | A-32194 | 228 | UCCcAGAGGcAAAUGGCUCdTdT | 874 |
| s | A-32195 | 23 | cAGGAuGGcuucucAucGudTdT | 875 |
| as | A-32196 | 41 | ACGAUGAGAAGCcAUCCUGdTdT | 876 |
| s | A-32199 | 24 | AGGAuGGcuucucAucGucdTdT | 877 |
| as | A-32200 | 42 | GACGAUGAGAAGCcAUCCUdTdT | 878 |
| s | A-32201 | 245 | AGAGcuGcAuGGGcucAcAdTdT | 879 |
| as | A-32202 | 263 | UGUGAGCCcAUGcAGCUCUdTdT | 880 |
| s | A-32203 | 248 | GcuGcAuGGGcucAcAAcudTdT | 881 |
| as | A-32204 | 266 | AGUUGUGAGCCcAUGcAGCdTdT | 882 |
| s | A-32205 | 25 | GGAuGGcuucucAucGucudTdT | 883 |
| as | A-32206 | 43 | AGACGAUGAGAAGCcAUCCdTdT | 884 |
| s | A-32207 | 251 | GcAuGGGcucAcAAcuGAGdTdT | 885 |
| as | A-32208 | 269 | CUcAGUUGUGAGCCcAUGCdTdT | 886 |
| s | A-32211 | 253 | AuGGGcucAcAAcuGAGGAdTdT | 887 |
| as | A-32212 | 271 | UCCUcAGUUGUGAGCCcAUdTdT | 888 |
| s | A-32213 | 254 | uGGGcucAcAAcuGAGGAGdTdT | 889 |
| as | A-32214 | 272 | CUCCUcAGUUGUGAGCCcAdTdT | 890 |

TABLE 4-continued

Chemically modified sense and antisense strand sequences of human TTR dsRNAs

| Strand | Oligo # | Position | Sequence(5' to 3') | SEQ ID NO: |
|---|---|---|---|---|
| s | A-32215 | 270 | GAGGAAuuuGuAGAAGGGAdTdT | 891 |
| as | A-32216 | 288 | UCCCUUCuAcAAAUUCCUCdTdT | 892 |
| s | A-32217 | 276 | uuuGuAGAAGGGAuAuAcAdTdT | 893 |
| as | A-32218 | 294 | UGuAuAUCCCUUCuAcAAAdTdT | 894 |
| s | A-32219 | 277 | uuGuAGAAGGGAuAuAcAAdTdT | 895 |
| as | A-32220 | 295 | UUGuAuAUCCCUUCuAcAAdTdT | 896 |
| s | A-32221 | 278 | uGuAGAAGGGAuAuAcAAAdTdT | 897 |
| as | A-32222 | 296 | UUUGuAuAUCCCUUCuAcAdTdT | 898 |
| s | A-32223 | 281 | AGAAGGGAuAuAcAAAGuGdTdT | 899 |
| as | A-32224 | 299 | cACUUUGuAuAUCCCUUCUdTdT | 900 |
| s | A-32225 | 295 | AAGuGGAAAuAGAcAccAAdTdT | 901 |
| as | A-32226 | 313 | UUGGUGUCuAUUUCcACUUdTdT | 902 |
| s | A-32227 | 299 | GGAAAuAGAcAccAAAucudTdT | 903 |
| as | A-32228 | 317 | AGAUUUGGUGUCuAUUUCCdTdT | 904 |
| s | A-32229 | 300 | GAAAuAGAcAccAAAucuudTdT | 905 |
| as | A-32230 | 318 | AAGAUUUGGUGUCuAUUUCdTdT | 906 |
| s | A-32231 | 303 | AuAGAcAccAAAucuuAcudTdT | 907 |
| as | A-32232 | 321 | AGuAAGAUUUGGUGUCuAUdTdT | 908 |
| s | A-32233 | 304 | uAGAcAccAAAucuuAcuGdTdT | 909 |
| as | A-32234 | 322 | cAGuAAGAUUUGGUGUCuAdTdT | 910 |
| s | A-32235 | 305 | AGAcAccAAAucuuAcuGGdTdT | 911 |
| as | A-32236 | 323 | CcAGuAAGAUUUGGUGUCUdTdT | 912 |
| s | A-32237 | 317 | uuAcuGGAAGGcAcuuGGcdTdT | 913 |
| as | A-32238 | 335 | GCcAAGUGCCUUCcAGuAAdTdT | 914 |
| s | A-32239 | 32 | uucucAucGucuGcuccucdTdT | 915 |
| as | A-32240 | 50 | GAGGAGcAGACGAUGAGAAdTdT | 916 |
| s | A-32241 | 322 | GGAAGGcAcuuGGcAucucdTdT | 917 |
| as | A-32242 | 340 | GAGAUGCcAAGUGCCUUCCdTdT | 918 |
| s | A-32243 | 326 | GGcAcuuGGcAucuccccAdTdT | 919 |
| as | A-32244 | 344 | UGGGGAGAUGCcAAGUGCCdTdT | 920 |
| s | A-32247 | 333 | GGcAucuccccAuuccAuGdTdT | 921 |
| as | A-32248 | 351 | cAUGGAAUGGGGAGAUGCCdTdT | 922 |
| s | A-32249 | 334 | GcAucuccccAuuccAuGAdTdT | 923 |
| as | A-32250 | 352 | UcAUGGAAUGGGGAGAUGCdTdT | 924 |
| s | A-32251 | 335 | cAucuccccAuuccAuGAGdTdT | 925 |
| as | A-32252 | 353 | CUcAUGGAAUGGGGAGAUGdTdT | 926 |
| s | A-32253 | 336 | AucuccccAuuccAuGAGcdTdT | 927 |

TABLE 4-continued

Chemically modified sense and antisense strand sequences of human TTR dsRNAs

| Strand | Oligo # | Position | Sequence(5' to 3') | SEQ ID NO: |
|---|---|---|---|---|
| as | A-32254 | 354 | GCUcAUGGAAUGGGGAGAUdTdT | 928 |
| s | A-32255 | 338 | cuccccAuuccAuGAGcAudTdT | 929 |
| as | A-32256 | 356 | AUGCUcAUGGAAUGGGGAGdTdT | 930 |
| s | A-32259 | 341 | cccAuuccAuGAGcAuGcAdTdT | 931 |
| as | A-32260 | 359 | UGcAUGCUcAUGGAAUGGGdTdT | 932 |
| s | A-32261 | 347 | ccAuGAGcAuGcAGAGGuGdTdT | 933 |
| as | A-32262 | 365 | cACCUCUGcAUGCUcAUGGdTdT | 934 |
| s | A-32263 | 352 | AGcAuGcAGAGGuGGuAuudTdT | 935 |
| as | A-32264 | 370 | AAuACcACCUCUGcAUGCUdTdT | 936 |
| s | A-32265 | 354 | cAuGcAGAGGuGGuAuucAdTdT | 937 |
| as | A-32266 | 372 | UGAAuACcACCUCUGcAUGdTdT | 938 |
| s | A-32267 | 355 | AuGcAGAGGuGGuAuucAcdTdT | 939 |
| as | A-32268 | 373 | GUGAAuACcACCUCUGcAUdTdT | 940 |
| s | A-32269 | 362 | GGuGGuAuucAcAGccAAcdTdT | 941 |
| as | A-32270 | 380 | GUUGGCUGUGAAuACcACCdTdT | 942 |
| s | A-32271 | 363 | GuGGuAuucAcAGccAAcGdTdT | 943 |
| as | A-32272 | 381 | CGUUGGCUGUGAAuACcACdTdT | 944 |
| s | A-32273 | 364 | uGGuAuucAcAGccAAcGAdTdT | 945 |
| as | A-32274 | 382 | UCGUUGGCUGUGAAuACcAdTdT | 946 |
| s | A-32275 | 365 | GGuAuucAcAGccAAcGAcdTdT | 947 |
| as | A-32276 | 383 | GUCGUUGGCUGUGAAuACCdTdT | 948 |
| s | A-32277 | 366 | GuAuucAcAGccAAcGAcudTdT | 949 |
| as | A-32278 | 384 | AGUCGUUGGCUGUGAAuACdTdT | 950 |
| s | A-32279 | 367 | uAuucAcAGccAAcGAcucdTdT | 951 |
| as | A-32280 | 385 | GAGUCGUUGGCUGUGAAuAdTdT | 952 |
| s | A-32281 | 370 | ucAcAGccAAcGAcuccGGdTdT | 953 |
| as | A-32282 | 388 | CCGGAGUCGUUGGCUGUGAdTdT | 954 |
| s | A-32283 | 390 | ccccGccGcuAcAccAuuGdTdT | 955 |
| as | A-32284 | 408 | cAAUGGUGuAGCGGCGGGGdTdT | 956 |
| s | A-32285 | 4 | GAAGuccAcucAuucuuGGdTdT | 957 |
| as | A-32286 | 22 | CcAAGAAUGAGUGGACUUCdTdT | 958 |
| s | A-32287 | 412 | cccuGcuGAGccccuAcucdTdT | 959 |
| as | A-32288 | 430 | GAGuAGGGGCUcAGcAGGGdTdT | 960 |
| s | A-32289 | 417 | cuGAGccccuAcuccuAuudTdT | 961 |
| as | A-32290 | 435 | AAuAGGAGuAGGGGCUcAGdTdT | 962 |
| s | A-32291 | 418 | uGAGccccuAcuccuAuucdTdT | 963 |
| as | A-32292 | 436 | GAAuAGGAGuAGGGGCUcAdTdT | 964 |
| s | A-32295 | 422 | ccccuAcuccuAuuccAccdTdT | 965 |

TABLE 4-continued

Chemically modified sense and antisense
strand sequences of human TTR dsRNAs

| Strand | Oligo # | Position | Sequence(5' to 3') | SEQ ID NO: |
|---|---|---|---|---|
| as | A-32296 | 440 | GGUGGAAuAGGAGuAGGGGdTdT | 966 |
| s | A-32297 | 425 | cuAcuccuAuuccAccAcGdTdT | 967 |
| as | A-32298 | 443 | CGUGGUGGAAuAGGAGuAGdTdT | 968 |
| s | A-32299 | 426 | uAcuccuAuuccAccAcGGdTdT | 969 |
| as | A-32300 | 444 | CCGUGGUGGAAuAGGAGuAdTdT | 970 |
| s | A-32301 | 427 | AcuccuAuuccAccAcGGcdTdT | 971 |
| as | A-32302 | 445 | GCCGUGGUGGAAuAGGAGUdTdT | 972 |
| s | A-32303 | 429 | uccuAuuccAccAcGGcuGdTdT | 973 |
| as | A-32304 | 447 | cAGCCGUGGUGGAAuAGGAdTdT | 974 |
| s | A-32307 | 432 | uAuuccAccAcGGcuGucGdTdT | 975 |
| as | A-32308 | 450 | CGAcAGCCGUGGUGGAAuAdTdT | 976 |
| s | A-32309 | 433 | AuuccAccAcGGcuGucGudTdT | 977 |
| as | A-32310 | 451 | ACGAcAGCCGUGGUGGAAUdTdT | 978 |
| s | A-32311 | 437 | cAccAcGGcuGucGucAccdTdT | 979 |
| as | A-32312 | 455 | GGUGACGAcAGCCGUGGUGdTdT | 980 |
| s | A-32313 | 438 | AccAcGGcuGucGucAccAdTdT | 981 |
| as | A-32314 | 456 | UGGUGACGAcAGCCGUGGUdTdT | 982 |
| s | A-32315 | 439 | ccAcGGcuGucGucAccAAdTdT | 983 |
| as | A-32316 | 457 | UUGGUGACGAcAGCCGUGGdTdT | 984 |
| s | A-32319 | 441 | AcGGcuGucGucAccAAucdTdT | 985 |
| as | A-32320 | 459 | GAUUGGUGACGAcAGCCGUdTdT | 986 |
| s | A-32321 | 442 | cGGcuGucGucAccAAuccdTdT | 987 |
| as | A-32322 | 460 | GGAUUGGUGACGAcAGCCGdTdT | 988 |
| s | A-32323 | 449 | cGucAccAAucccAAGGAAdTdT | 989 |
| as | A-32324 | 467 | UUCCUUGGGAUUGGUGACGdTdT | 990 |
| s | A-32325 | 455 | cAAucccAAGGAAuGAGGGdTdT | 991 |
| as | A-32326 | 473 | CCCUcAUUCCUUGGGAUUGdTdT | 992 |
| s | A-32327 | 491 | ccuGAAGGAcGAGGGAuGGdTdT | 993 |
| as | A-32328 | 509 | CcAUCCCUCGUCCUUcAGGdTdT | 994 |
| s | A-32331 | 497 | GGAcGAGGGAuGGGAuuucdTdT | 995 |
| as | A-32332 | 515 | GAAAUCCcAUCCCUCGUCCdTdT | 996 |
| s | A-32333 | 5 | AAGuccAcucAuucuuGGcdTdT | 997 |
| as | A-32334 | 23 | GCcAAGAAuGAGUGGACUUdTdT | 998 |
| s | A-32335 | 508 | GGGAuuucAuGuAAccAAGdTdT | 999 |
| as | A-32336 | 526 | CUUGGUuAcAUGAAAUCCCdTdT | 1000 |
| s | A-32337 | 509 | GGAuuucAuGuAAccAAGAdTdT | 1001 |
| as | A-32338 | 527 | UCUUGGUuAcAUGAAAUCCdTdT | 1002 |

TABLE 4-continued

Chemically modified sense and antisense
strand sequences of human TTR dsRNAs

| Strand | Oligo # | Position | Sequence(5' to 3') | SEQ ID NO: |
|---|---|---|---|---|
| s | A-32339 | 514 | ucAuGuAAccAAGAGuAuudTdT | 1003 |
| as | A-32340 | 532 | AAuACUCUUGGUuAcAUGAdTdT | 1004 |
| s | A-32341 | 516 | AuGuAAccAAGAGuAuuccdTdT | 1005 |
| as | A-32342 | 534 | GGAAuACUCUUGGUuAcAUdTdT | 1006 |
| s | A-32343 | 517 | uGuAAccAAGAGuAuuccAdTdT | 1007 |
| as | A-32344 | 535 | UGGAAuACUCUUGGUuAcAdTdT | 1008 |
| s | A-32345 | 518 | GuAAccAAGAGuAuuccAudTdT | 1009 |
| as | A-32346 | 536 | AUGGAAuACUCUUGGUuACdTdT | 1010 |
| s | A-32347 | 54 | uGccuuGcuGGAcuGGuAudTdT | 1011 |
| as | A-32348 | 72 | AuACcAGUCcAGcAAGGcAdTdT | 1012 |
| s | A-32349 | 543 | uAAAGcAGuGuuuucAccudTdT | 1013 |
| as | A-32350 | 561 | AGGUGAAAAcACUGCUUuAdTdT | 1014 |
| s | A-32351 | 55 | GccuuGcuGGAcuGGuAuudTdT | 1015 |
| as | A-32352 | 73 | AAuACcAGUCcAGcAAGGcdTdT | 1016 |
| s | A-32353 | 551 | uGuuuucAccucAuAuGcudTdT | 1017 |
| as | A-32354 | 569 | AGcAuAUGAGGUGAAAAcAdTdT | 1018 |
| s | A-32355 | 552 | GuuuucAccucAuAuGcuAdTdT | 1019 |
| as | A-32356 | 570 | uAGcAuAUGAGGUGAAAACdTdT | 1020 |
| s | A-32357 | 553 | uuuucAccucAuAuGcuAudTdT | 1021 |
| as | A-32358 | 571 | AuAGcAuAUGAGGUGAAAAdTdT | 1022 |
| s | A-32359 | 555 | uucAccucAuAuGcuAuGudTdT | 1023 |
| as | A-32360 | 573 | AcAuAGcAuAUGAGGUGAAdTdT | 1024 |
| s | A-32363 | 557 | cAccucAuAuGcuAuGuuAdTdT | 1025 |
| as | A-32364 | 575 | uAAcAuAGcAuAUGAGGUGdTdT | 1026 |
| s | A-32367 | 56 | ccuuGcuGGAcuGGuAuuudTdT | 1027 |
| as | A-32368 | 74 | AAAuACcAGUCcAGcAAGGdTdT | 1028 |
| s | A-32369 | 563 | AuAuGcuAuGuuAGAAGucdTdT | 1029 |
| as | A-32370 | 581 | GACUUCuAAcAuAGcAuAUdTdT | 1030 |
| s | A-32371 | 564 | uAuGcuAuGuuAGAAGuccdTdT | 1031 |
| as | A-32372 | 582 | GGACUUCuAAcAuAGcAuAdTdT | 1032 |
| s | A-32373 | 566 | uGcuAuGuuAGAAGuccAGdTdT | 1033 |
| as | A-32374 | 584 | CUGGACUUCuAAcAuAGcAdTdT | 1034 |
| s | A-32375 | 57 | cuuGcuGGAcuGGuAuuuGdTdT | 1035 |
| as | A-32376 | 75 | cAAAuACcAGUCcAGcAAGdTdT | 1036 |
| s | A-32379 | 578 | AGuccAGGcAGAGAcAAuAdTdT | 1037 |
| as | A-32380 | 596 | uAUUGUCUCUGCCUGGACUdTdT | 1038 |
| s | A-32381 | 580 | uccAGGcAGAGAcAAuAAAdTdT | 1039 |
| as | A-32382 | 598 | UUuAUUGUCUCUGCCUGGAdTdT | 1040 |

TABLE 4-continued

Chemically modified sense and antisense
strand sequences of human TTR dsRNAs

| Strand | Oligo # | Position | Sequence(5' to 3') | SEQ ID NO: |
|---|---|---|---|---|
| s | A-32383 | 607 | GuGAAAGGcAcuuuucAuudTdT | 1041 |
| as | A-32384 | 625 | AAUGAAAAGUGCCUUUcACdTdT | 1042 |
| s | A-32385 | 62 | uGGAcuGGuAuuuGuGucudTdT | 1043 |
| as | A-32386 | 80 | AGAcAcAAAuACcAGUCcAdTdT | 1044 |
| s | A-32387 | 77 | GucuGAGGcuGGcccuAcGdTdT | 1045 |
| as | A-32388 | 95 | CGuAGGGCcAGCCUcAGACdTdT | 1046 |
| s | A-32391 | 79 | cuGAGGcuGGcccuAcGGGdTdT | 1047 |
| as | A-32392 | 97 | CCCGuAGGGCcAGCCUcAGdTdT | 1048 |
| s | A-32393 | 81 | GAGGcuGGcccuAcGGGcAdTdT | 1049 |
| as | A-32394 | 99 | UGCCCGuAGGGCcAGCCUCdTdT | 1050 |
| s | A-32395 | 82 | AGGcuGGcccuAcGGGcAcdTdT | 1051 |
| as | A-32396 | 100 | GUGCCCGuAGGGCcAGCCUdTdT | 1052 |
| s | A-32397 | 84 | GcuGGcccuAcGGGcAccGdTdT | 1053 |
| as | A-32398 | 102 | CGGUGCCCGuAGGGCcAGCdTdT | 1054 |
| s | A-32399 | 85 | cuGGcccuAcGGGcAccGGdTdT | 1055 |
| as | A-32400 | 103 | CCGGUGCCCGuAGGGCcAGdTdT | 1056 |
| s | A-32401 | 87 | GGcccuAcGGGcAccGGuGdTdT | 1057 |
| as | A-32402 | 105 | cACCGGUGCCCGuAGGGCCdTdT | 1058 |
| s | A-32403 | 9 | ccAcucAuucuuGGcAGGAdTdT | 1059 |
| as | A-32404 | 27 | UCCUGCcAAGAAUGAGUGGdTdT | 1060 |
| s | A-32405 | 90 | ccuAcGGGcAccGGuGAAudTdT | 1061 |
| as | A-32406 | 108 | AUUcACCGGUGCCCGuAGGdTdT | 1062 |
| s | A-32407 | 91 | cuAcGGGcAccGGuGAAucdTdT | 1063 |
| as | A-32408 | 109 | GAUUcACCGGUGCCCGuAGdTdT | 1064 |
| s | A-32409 | 92 | uAcGGGcAccGGuGAAuccdTdT | 1065 |
| as | A-32410 | 110 | GGAUUcACCGGUGCCCGuAdTdT | 1066 |
| s | A-32411 | 93 | AcGGGcAccGGuGAAuccAdTdT | 1067 |
| as | A-32412 | 111 | UGGAUUcACCGGUGCCCGUdTdT | 1068 |
| s | A-32415 | 97 | GcAccGGuGAAuccAAGuGdTdT | 1069 |
| as | A-32416 | 115 | cACUUGGAUUcACCGGUGCdTdT | 1070 |
| s | A-32417 | 98 | cAccGGuGAAuccAAGuGudTdT | 1071 |
| as | A-32418 | 116 | AcACUUGGAUUcACCGGUGdTdT | 1072 |
| s | A-32419 | 167 | uGuGGccAuGcAuGuGuucdTdT | 1073 |
| as | A-32420 | 185 | GAAcAcAUGcAUGGCcAcAdTdT | 1074 |
| s | A-32421 | 168 | GuGGccAuGcAuGuGuucAdTdT | 1075 |
| as | A-32422 | 186 | UGAAcAcAUGcAUGGCcACdTdT | 1076 |
| s | A-32423 | 171 | GccAuGcAuGuGuucAGAAdTdT | 1077 |

TABLE 4-continued

Chemically modified sense and antisense strand sequences of human TTR dsRNAs

| Strand | Oligo # | Position | Sequence(5' to 3') | SEQ ID NO: |
|---|---|---|---|---|
| as | A-32424 | 189 | UUCUGAAcAcAUGcAUGGCdTdT | 1078 |
| s | A-32427 | 432 | uAuuccAccAcGGcuGucAdTdT | 1079 |
| as | A-32428 | 449 | UGAcAGCCGUGGUGGAAuAdTdT | 1080 |
| s | A-32429 | 447 | GucAucAccAAucccAAGGdTdT | 1081 |
| as | A-32430 | 465 | CCUUGGGAUUGGUGAUGACdTdT | 1082 |
| s | A-32159 | 115 | GuccucuGAuGGucAAAGudTdT | 1083 |
| as | A-32160 | 133 | ACUUUGACcAUcAGAGGACdTdT | 1084 |
| s | A-32161 | 122 | GAuGGucAAAGuucuAGAudTdT | 1085 |
| as | A-32162 | 140 | AUCuAGAACUUUGACcAUCdTdT | 1086 |
| s | A-32173 | 139 | AuGcuGuccGAGGcAGuccdTdT | 1087 |
| as | A-32174 | 157 | GGACUGCCUCGGAcAGcAUdTdT | 1088 |
| s | A-32185 | 172 | ccGuGcAuGuGuucAGAAAdTdT | 1089 |
| as | A-32186 | 190 | UUUCUGAAcAcAUGcACGGdTdT | 1090 |
| s | A-32197 | 238 | AGucuGGAGAGcuGcAuGGdTdT | 1091 |
| as | A-32198 | 256 | CcAUGcAGCUCUCcAGACUdTdT | 1092 |
| s | A-32209 | 252 | cAuGGGcucAcAAcuGAGGdTdT | 1093 |
| as | A-32210 | 270 | CCUcAGUUGUGAGCCcAUGdTdT | 1094 |
| s | A-32245 | 33 | ucucAucGucuGcuccuccdTdT | 1095 |
| as | A-32246 | 51 | GGAGGAGcAGACGAUGAGAdTdT | 1096 |
| s | A-32257 | 340 | ccccAuuccAuGAGcAuGcdTdT | 1097 |
| as | A-32258 | 358 | GcAUGCUcAUGGAAUGGGGdTdT | 1098 |
| s | A-32293 | 421 | GccccuAcuccuAuuccAcdTdT | 1099 |
| as | A-32294 | 439 | GUGGAAuAGGAGuAGGGGCdTdT | 1100 |
| s | A-32305 | 431 | cuAuuccAccAcGGcuGucdTdT | 1101 |
| as | A-32306 | 449 | GAcAGCCGUGGUGGAAuAGdTdT | 1102 |
| s | A-32317 | 440 | cAcGGcuGucGucAccAAudTdT | 1103 |
| as | A-32318 | 458 | AUUGGUGACGAcAGCCGUGdTdT | 1104 |
| s | A-32329 | 496 | AGGAcGAGGGAuGGGAuuudTdT | 1105 |
| as | A-32330 | 514 | AAAUCCcAUCCCUCGUCCUdTdT | 1106 |
| s | A-32361 | 556 | ucAccucAuAuGcuAuGuudTdT | 1107 |
| as | A-32362 | 574 | AAcAuAGcAuAUGAGGUGAdTdT | 1108 |
| s | A-32365 | 559 | ccucAuAuGcuAuGuuAGAdTdT | 1109 |
| as | A-32366 | 577 | UCuAAcAuAGcAuAUGAGGdTdT | 1110 |
| s | A-32377 | 570 | AuGuuAGAAGuccAGGcAGdTdT | 1111 |
| as | A-32378 | 588 | CUGCCUGGACUUCuAAcAUdTdT | 1112 |
| s | A-32389 | 78 | ucuGAGGcuGGcccuAcGcdTdT | 1113 |
| as | A-32390 | 96 | CCGuAGGGCcAGCCUcAGAdTdT | 1114 |
| s | A-32401 | 87 | GGcccuAcGGGcAccGGuGdTdT | 1115 |

TABLE 4-continued

Chemically modified sense and antisense strand sequences of human TTR dsRNAs

| Strand | Oligo # | Position | Sequence (5' to 3') | SEQ ID NO: |
|---|---|---|---|---|
| as | A-32402 | 105 | cACCGGUGCCCGuAGGGCCdTdT | 1116 |
| s | A-32413 | 95 | GGGcAccGGuGAAuccAAGdTdT | 1117 |
| as | A-32414 | 113 | CUUGGAUUcACCGGUGCCCdTdT | 1118 |
| s | A-32425 | 167 | ccAuGcAuGuGuucAGAAAdTdT | 1119 |
| as | A-32426 | 185 | UUUCUGAAcAcAUGcAUGGdTdT | 1120 |

See Table 2 for duplex #.
Strand:
s = sense;
as = antisense;
Position: position of 5' base on transcript (NM_000371.2, SEQ ID NO: 1329)

TABLE 5

Identification numbers for rat TTR dsRNAs
See Table 7 for sequences.

| Duplex # | Sense Oligo # | Antisense Oligo # |
|---|---|---|
| AD-18529 | A-32745 | A-32746 |
| AD-18530 | A-32747 | A-32748 |
| AD-18531 | A-32749 | A-32750 |
| AD-18532 | A-32751 | A-32752 |
| AD-18533 | A-32753 | A-32754 |
| AD-18534 | A-32755 | A-32756 |
| AD-18535 | A-32757 | A-32758 |
| AD-18536 | A-32759 | A-32760 |
| AD-18537 | A-32761 | A-32762 |
| AD-18538 | A-32763 | A-32764 |
| AD-18539 | A-32159 | A-32160 |
| AD-18540 | A-32765 | A-32766 |
| AD-18541 | A-32767 | A-32768 |
| AD-18542 | A-32769 | A-32770 |
| AD-18543 | A-32771 | A-32772 |
| AD-18544 | A-32773 | A-32774 |
| AD-18545 | A-32775 | A-32776 |
| AD-18546 | A-32777 | A-32778 |
| AD-18547 | A-32779 | A-32780 |
| AD-18548 | A-32781 | A-32782 |
| AD-18549 | A-32783 | A-32784 |
| AD-18550 | A-32785 | A-32786 |
| AD-18551 | A-32787 | A-32788 |
| AD-18552 | A-32791 | A-32792 |
| AD-18553 | A-32793 | A-32794 |
| AD-18554 | A-32795 | A-32796 |

TABLE 6

Sense and antisense strand sequences for rat TTR dsRNAs

A.

| Strand | Position | Sequence (5' to 3') | SEQ ID NO: | Sequence with 3' dinucleotide overhang (5' to 3') | SEQ ID NO: |
|---|---|---|---|---|---|
| s | 115 | GUCCUCUGAUGGUCAAAGU | 1121 | GUCCUCUGAUGGUCAAAGUNN | 1173 |
| as | 133 | ACUUUGACCAUCAGAGGAC | 1122 | ACUUUGACCAUCAGAGGACNN | 1174 |
| s | 537 | UUCUUGCUCUAUAAACCGU | 1123 | UUCUUGCUCUAUAAACCGUNN | 1175 |
| as | 555 | ACGGUUUAUAGAGCAAGAA | 1124 | ACGGUUUAUAGAGCAAGAANN | 1176 |
| s | 543 | CUCUAUAAACCGUGUUAGC | 1125 | CUCUAUAAACCGUGUUAGCNN | 1177 |
| as | 561 | GCUAACACGGUUUAUAGAG | 1126 | GCUAACACGGUUUAUAGAGNN | 1178 |
| s | 392 | UCGCCACUACACCAUCGCA | 1127 | UCGCCACUACACCAUCGCANN | 1179 |
| as | 410 | UGCGAUGGUGUAGUGGCGA | 1128 | UGCGAUGGUGUAGUGGCGANN | 1180 |
| s | 538 | UCUUGCUCUAUAAACCGUG | 1129 | UCUUGCUCUAUAAACCGUGNN | 1181 |
| as | 556 | CACGGUUUAUAGAGCAAGA | 1130 | CACGGUUUAUAGAGCAAGANN | 1182 |
| s | 541 | UGCUCUAUAAACCGUGUUA | 1131 | UGCUCUAUAAACCGUGUUANN | 1183 |

TABLE 6-continued

Sense and antisense strand sequences for rat TTR dsRNAs

| | | | | | |
|---|---|---|---|---|---|
| as | 559 | UAACACGGUUUAUAGAGCA | 1132 | UAACACGGUUUAUAGAGCANN | 1184 |
| s | 532 | CAGUGUUCUUGCUCUAUAA | 1133 | CAGUGUUCUUGCUCUAUAANN | 1185 |
| as | 550 | UUAUAGAGCAAGAACACUG | 1134 | UUAUAGAGCAAGAACACUGNN | 1186 |
| s | 542 | GCUCUAUAAACCGUGUUAG | 1135 | GCUCUAUAAACCGUGUUAGNN | 1187 |
| as | 560 | CUAACACGGUUUAUAGAGC | 1136 | CUAACACGGUUUAUAGAGCNN | 1188 |
| s | 134 | CCUGGAUGCUGUCCGAGGC | 1137 | CCUGGAUGCUGUCCGAGGCNN | 1189 |
| as | 152 | GCCUCGGACAGCAUCCAGG | 1138 | GCCUCGGACAGCAUCCAGGNN | 1190 |
| s | 119 | UCUGAUGGUCAAAGUCCUG | 1139 | UCUGAUGGUCAAAGUCCUGNN | 1191 |
| as | 137 | CAGGACUUUGACCAUCAGA | 1140 | CAGGACUUUGACCAUCAGANN | 1192 |
| s | 241 | CUGGAGAGCUGCACGGGCU | 1141 | CUGGAGAGCUGCACGGGCUNN | 1193 |
| as | 259 | AGCCCGUGCAGCUCUCCAG | 1142 | AGCCCGUGCAGCUCUCCAGNN | 1194 |
| s | 544 | UCUAUAAACCGUGUUAGCA | 1143 | UCUAUAAACCGUGUUAGCANN | 1195 |
| as | 562 | UGCUAACACGGUUUAUAGA | 1144 | UGCUAACACGGUUUAUAGANN | 1196 |
| s | 530 | AACAGUGUUCUUGCUCUAU | 1145 | AACAGUGUUCUUGCUCUAUNN | 1197 |
| as | 548 | AUAGAGCAAGAACACUGUU | 1146 | AUAGAGCAAGAACACUGUUNN | 1198 |
| s | 118 | CUCUGAUGGUCAAAGUCCU | 1147 | CUCUGAUGGUCAAAGUCCUNN | 1199 |
| as | 136 | AGGACUUUGACCAUCAGAG | 1148 | AGGACUUUGACCAUCAGAGNN | 1200 |
| s | 140 | UGCUGUCCGAGGCAGCCCU | 1149 | UGCUGUCCGAGGCAGCCCUNN | 1201 |
| as | 158 | AGGGCUGCCUCGGACAGCA | 1150 | AGGGCUGCCUCGGACAGCANN | 1202 |
| s | 239 | GUCUGGAGAGCUGCACGGG | 1151 | GUCUGGAGAGCUGCACGGGNN | 1203 |
| as | 257 | CCCGUGCAGCUCUCCAGAC | 1152 | CCCGUGCAGCUCUCCAGACNN | 1204 |
| s | 531 | ACAGUGUUCUUGCUCUAUA | 1153 | ACAGUGUUCUUGCUCUAUANN | 1205 |
| as | 549 | UAUAGAGCAAGAACACUGU | 1154 | UAUAGAGCAAGAACACUGUNN | 1206 |
| s | 117 | CCUCUGAUGGUCAAAGUCC | 1155 | CCUCUGAUGGUCAAAGUCCNN | 1207 |
| as | 135 | GGACUUUGACCAUCAGAGG | 1156 | GGACUUUGACCAUCAGAGGNN | 1208 |
| s | 131 | AGUCCUGGAUGCUGUCCGA | 1157 | AGUCCUGGAUGCUGUCCGANN | 1209 |
| as | 149 | UCGGACAGCAUCCAGGACU | 1158 | UCGGACAGCAUCCAGGACUNN | 1210 |
| s | 217 | UUGCCUCUGGGAAGACCGC | 1159 | UUGCCUCUGGGAAGACCGCNN | 1211 |
| as | 235 | GCGGUCUUCCCAGAGGCAA | 1160 | GCGGUCUUCCCAGAGGCAANN | 1212 |
| s | 242 | UGGAGAGCUGCACGGGCUC | 1161 | UGGAGAGCUGCACGGGCUCNN | 1213 |
| as | 260 | GAGCCCGUGCAGCUCUCCA | 1162 | GAGCCCGUGCAGCUCUCCANN | 1214 |
| s | 244 | GAGAGCUGCACGGGCUCAC | 1163 | GAGAGCUGCACGGGCUCACNN | 1215 |
| as | 262 | GUGAGCCCGUGCAGCUCUC | 1164 | GUGAGCCCGUGCAGCUCUCNN | 1216 |
| s | 246 | GAGCUGCACGGGCUCACCA | 1165 | GAGCUGCACGGGCUCACCANN | 1217 |
| as | 264 | UGGUGAGCCCGUGCAGCUC | 1166 | UGGUGAGCCCGUGCAGCUCNN | 1218 |
| s | 399 | UACACCAUCGCAGCCCUGC | 1167 | UACACCAUCGCAGCCCUGCNN | 1219 |
| as | 417 | GCAGGGCUGCGAUGGUGUA | 1168 | GCAGGGCUGCGAUGGUGUANN | 1220 |
| s | 132 | GUCCUGGAUGCUGUCCGAG | 1169 | GUCCUGGAUGCUGUCCGAGNN | 1221 |
| as | 150 | CUCGGACAGCAUCCAGGAC | 1170 | CUCGGACAGCAUCCAGGACNN | 1222 |

TABLE 6-continued

Sense and antisense strand sequences for rat TTR dsRNAs

| | | | | | |
|---|---|---|---|---|---|
| s | 245 | AGAGCUGCACGGGCUCACC | 1171 | AGAGCUGCACGGGCUCACCNN | 1223 |
| as | 263 | GGUGAGCCCGUGCAGCUCU | 1172 | GGUGAGCCCGUGCAGCUCUNN | 1224 |

B.

| Strand | Position | Sequence with 3'deoxythimidine overhang (5' to 3') | SEQ ID NO: |
|---|---|---|---|
| s | 115 | GUCCUCUGAUGGUCAAAGUdTdT | 1225 |
| as | 133 | ACUUUGACCAUCAGAGGACdTdT | 1226 |
| s | 537 | UUCUUGCUCUAUAAACCGUdTdT | 1227 |
| as | 555 | ACGGUUUAUAGAGCAAGAAdTdT | 1228 |
| s | 543 | CUCUAUAAACCGUGUUAGCdTdT | 1229 |
| as | 561 | GCUAACACGGUUUAUAGAGdTdT | 1230 |
| s | 392 | UCGCCACUACACCAUCGCAdTdT | 1231 |
| as | 410 | UGCGAUGGUGUAGUGGCGAdTdT | 1232 |
| s | 538 | UCUUGCUCUAUAAACCGUGdTdT | 1233 |
| as | 556 | CACGGUUUAUAGAGCAAGAdTdT | 1234 |
| s | 541 | UGCUCUAUAAACCGUGUUAdTdT | 1235 |
| as | 559 | UAACACGGUUUAUAGAGCAdTdT | 1236 |
| s | 532 | CAGUGUUCUUGCUCUAUAAdTdT | 1237 |
| as | 550 | UUAUAGAGCAAGAACACUGdTdT | 1238 |
| s | 542 | GCUCUAUAAACCGUGUUAGdTdT | 1239 |
| as | 560 | CUAACACGGUUUAUAGAGCdTdT | 1240 |
| s | 134 | CCUGGAUGCUGUCCGAGGCdTdT | 1241 |
| as | 152 | GCCUCGGACAGCAUCCAGGdTdT | 1242 |
| s | 119 | UCUGAUGGUCAAAGUCCUGdTdT | 1243 |
| as | 137 | CAGGACUUUGACCAUCAGAdTdT | 1244 |
| s | 241 | CUGGAGAGCUGCACGGGCUdTdT | 1245 |
| as | 259 | AGCCCGUGCAGCUCUCCAGdTdT | 1246 |
| s | 544 | UCUAUAAACCGUGUUAGCAdTdT | 1247 |
| as | 562 | UGCUAACACGGUUUAUAGAdTdT | 1248 |
| s | 530 | AACAGUGUUCUUGCUCUAUdTdT | 1249 |
| as | 548 | AUAGAGCAAGAACACUGUUdTdT | 1250 |
| s | 118 | CUCUGAUGGUCAAAGUCCUdTdT | 1251 |
| as | 136 | AGGACUUUGACCAUCAGAGdTdT | 1252 |
| s | 140 | UGCUGUCCGAGGCAGCCCUdTdT | 1253 |
| as | 158 | AGGGCUGCCUCGGACAGCAdTdT | 1254 |
| s | 239 | GUCUGGAGAGCUGCACGGGdTdT | 1255 |
| as | 257 | CCCGUGCAGCUCUCCAGACdTdT | 1256 |
| s | 531 | ACAGUGUUCUUGCUCUAUAdTdT | 1257 |
| as | 549 | UAUAGAGCAAGAACACUGUdTdT | 1258 |

TABLE 6-continued

Sense and antisense strand sequences for rat TTR dsRNAs

| Strand | Position | Sequence | SEQ ID NO |
|---|---|---|---|
| s | 117 | CCUCUGAUGGUCAAAGUCCdTdT | 1259 |
| as | 135 | GGACUUUGACCAUCAGAGGdTdT | 1260 |
| s | 131 | AGUCCUGGAUGCUGUCCGAdTdT | 1261 |
| as | 149 | UCGGACAGCAUCCAGGACUdTdT | 1262 |
| s | 217 | UUGCCUCUGGGAAGACCGCdTdT | 1263 |
| as | 235 | GCGGUCUUCCCAGAGGCAAdTdT | 1264 |
| s | 242 | UGGAGAGCUGCACGGGCUCdTdT | 1265 |
| as | 260 | GAGCCCGUGCAGCUCUCCAdTdT | 1266 |
| s | 244 | GAGAGCUGCACGGGCUCACdTdT | 1267 |
| as | 262 | GUGAGCCCGUGCAGCUCUCdTdT | 1268 |
| s | 246 | GAGCUGCACGGGCUCACCAdTdT | 1269 |
| as | 264 | UGGUGAGCCCGUGCAGCUCdTdT | 1270 |
| s | 399 | UACACCAUCGCAGCCCUGCdTdT | 1271 |
| as | 417 | GCAGGGCUGCGAUGGUGUAdTdT | 1272 |
| s | 132 | GUCCUGGAUGCUGUCCGAdTdT | 1273 |
| as | 150 | CUCGGACAGCAUCCAGGACdTdT | 1274 |
| s | 245 | AGAGCUGCACGGGCUCACCdTdT | 1275 |
| as | 263 | GGUGAGCCCGUGCAGCUCUdTdT | 1276 |

Strand:
s = sense;
as = antisense;
Position: position of 5' base on transcript (NM_012681.1, SEQ ID NO: 1330)

TABLE 7

Chemically modified sense and antisense strand sequences for rat TTR dsRNAs

| Strand | Oligo # | Position | Sequence (5' to 3') | SEQ ID NO: |
|---|---|---|---|---|
| s | A-32159 | 115 | GuccucuGAuGGucAAAGudTdT | 1277 |
| as | A-32160 | 133 | ACUUUGACcAUcAGAGGACdTdT | 1278 |
| s | A-32745 | 537 | uucuuGcucuAuAAAccGudTdT | 1279 |
| as | A-32746 | 555 | ACGGUUuAuAGAGcAAGAAdTdT | 1280 |
| s | A-32747 | 543 | cucuAuAAAccGuGuuAGcdTdT | 1281 |
| as | A-32748 | 561 | GCuAAcACGGUUuAuAGAGdTdT | 1282 |
| s | A-32749 | 392 | ucGccAcuAcAccAucGcAdTdT | 1283 |
| as | A-32750 | 410 | UGCGAUGGUGuAGUGGCGAdTdT | 1284 |
| s | A-32751 | 538 | ucuuGcucuAuAAAccGudTdT | 1285 |
| as | A-32752 | 556 | cACGGUUuAuAGAGcAAGAdTdT | 1286 |
| s | A-32753 | 541 | uGcucuAuAAAccGuGuuAdTdT | 1287 |
| as | A-32754 | 559 | uAAcACGGUUuAuAGAGcAdTdT | 1288 |
| s | A-32755 | 532 | cAGuGuucuuGcucuAuAAdTdT | 1289 |

TABLE 7-continued

Chemically modified sense and antisense strand sequences for rat TTR dsRNAs

| Strand | Oligo # | Position | Sequence (5' to 3') | SEQ ID NO: |
|---|---|---|---|---|
| as | A-32756 | 550 | UuAuAGAGcAAGAAcACUGdTdT | 1290 |
| s  | A-32757 | 542 | GcucuAuAAAccGuGuuAGdTdT | 1291 |
| as | A-32758 | 560 | CuAAcACGGUUuAuAGAGCdTdT | 1292 |
| s  | A-32759 | 134 | ccuGGAuGcuGuccGAGGcdTdT | 1293 |
| as | A-32760 | 152 | GCCUCGGAcAGcAUCcAGGdTdT | 1294 |
| s  | A-32761 | 119 | ucuGAuGGucAAAGuccuGdTdT | 1295 |
| as | A-32762 | 137 | cAGGACUUUGACcAUcAGAdTdT | 1296 |
| s  | A-32763 | 241 | cuGGAGAGcuGcAcGGGcudTdT | 1297 |
| as | A-32764 | 259 | AGCCCGUGcAGCUCUCcAGdTdT | 1298 |
| s  | A-32765 | 544 | ucuAuAAAccGuGuuAGcAdTdT | 1299 |
| as | A-32766 | 562 | UGCuAAcACGGUUuAuAGAdTdT | 1300 |
| s  | A-32767 | 530 | AAcAGuGuucuuGcucuAudTdT | 1301 |
| as | A-32768 | 548 | AuAGAGcAAGAAcACUGUUdTdT | 1302 |
| s  | A-32769 | 118 | cucuGAuGGucAAAGuccudTdT | 1303 |
| as | A-32770 | 136 | AGGACUUUGACcAUcAGAGdTdT | 1304 |
| s  | A-32771 | 140 | uGcuGuccGAGGcAGcccudTdT | 1305 |
| as | A-32772 | 158 | AGGGCUGCCUCGGAcAGcAdTdT | 1306 |
| s  | A-32773 | 239 | GucuGGAGAGcuGcAcGGGdTdT | 1307 |
| as | A-32774 | 257 | CCCGUGcAGCUCUCcAGACdTdT | 1308 |
| s  | A-32775 | 531 | AcAGuGuucuuGcucuAuAdTdT | 1309 |
| as | A-32776 | 549 | uAuAGAGcAAGAAcACUGUdTdT | 1310 |
| s  | A-32777 | 117 | ccucuGAuGGucAAAGuccdTdT | 1311 |
| as | A-32778 | 135 | GGACUUUGACcAUcAGAGGdTdT | 1312 |
| s  | A-32779 | 131 | AGuccuGGAuGcuGuccGAdTdT | 1313 |
| as | A-32780 | 149 | UCGGAcAGcAUCcAGGACUdTdT | 1314 |
| s  | A-32781 | 217 | uuGccucuGGGAAGAccGcdTdT | 1315 |
| as | A-32782 | 235 | GCGGUCUUCCcAGAGGcAAdTdT | 1316 |
| s  | A-32783 | 242 | uGGAGAGcuGcAcGGGcucdTdT | 1317 |
| as | A-32784 | 260 | GAGCCCGUGcAGCUCUCcAdTdT | 1318 |
| s  | A-32785 | 244 | GAGAGcuGcAcGGGcucAcdTdT | 1319 |
| as | A-32786 | 262 | GUGAGCCCGUGcAGCUCUCdTdT | 1320 |
| s  | A-32787 | 246 | GAGcuGcAcGGGcucAccAdTdT | 1321 |
| as | A-32788 | 264 | UGGUGAGCCCGUGcAGCUCdTdT | 1322 |
| s  | A-32791 | 399 | uAcAccAucGcAGcccuGcdTdT | 1323 |
| as | A-32792 | 417 | GcAGGGCUGCGAUGGUGuAdTdT | 1324 |
| s  | A-32793 | 132 | GuccuGGAuGcuGuccGAGdTdT | 1325 |
| as | A-32794 | 150 | CUCGGAcAGcAUCcAGGACdTdT | 1326 |

TABLE 7-continued

Chemically modified sense and antisense
strand sequences for rat TTR dsRNAs

| Strand | Oligo # | Position | Sequence (5' to 3') | SEQ ID NO: |
|---|---|---|---|---|
| s | A-32795 | 245 | AGAGcuGcAcGGGcucAccdTdT | 1327 |
| as | A-32796 | 263 | GGUGAGCCCGUGcAGCUCUdTdT | 1328 |

See Table 5 for duplex # (dsRNA name).
Strand:
s = sense;
as = antisense;
Position: position of 5' base on transcript (NM_012681.1, SEQ ID NO: 1330)

Synthesis of TTR Sequences

TTR sequences were synthesized on MerMade 192 synthesizer at 1 µmol scale. For all the sequences in the list, 'endolight' chemistry was applied as detailed below.

All pyrimidines (cytosine and uridine) in the sense strand were replaced with corresponding 2'-O-Methyl bases (2' O-Methyl C and 2'-O-Methyl U)

In the antisense strand, pyrimidines adjacent to (towards 5' position) ribo A nucleoside were replaced with their corresponding 2-O-Methyl nucleosides A two base dTdT extension at 3' end of both sense and antisense sequences was introduced The sequence file was converted to a text file to make it compatible for loading in the MerMade 192 synthesis software The synthesis of TTR sequences used solid supported oligonucleotide synthesis using phosphoramidite chemistry. The synthesis of the above sequences was performed at 1 um scale in 96 well plates. The amidite solutions were prepared at 0.1M concentration and ethyl thio tetrazole (0.6M in Acetonitrile) was used as activator.

The synthesized sequences were cleaved and deprotected in 96 well plates, using methylamine in the first step and triethylamine.3HF in the second step. The crude sequences thus obtained were precipitated using acetone: ethanol mix and the pellet were re-suspended in 0.5M sodium acetate buffer. Samples from each sequence were analyzed by LC-MS and the resulting mass data confirmed the identity of the sequences. A selected set of samples were also analyzed by IEX chromatography.

The next step in the process was purification. All sequences were purified on an AKTA explorer purification system using Source 15Q column. A single peak corresponding to the full length sequence was collected in the eluent and was subsequently analyzed for purity by ion exchange chromatography.

The purified sequences were desalted on a Sephadex G25 column using AKTA purifier. The desalted TTR sequences were analyzed for concentration and purity. The single strands were then annealed to form TTR-dsRNA.

Example 2B

In Vitro Screening of TTR siRNAs for mRNA Suppression

Human TTR targeting dsRNAs (Table 2) were assayed for inhibition of endogenous TTR expression in HepG2 and Hep3B cells, using qPCR (real time PCR) and bDNA (branched DNA) assays to quantify TTR mRNA. Rodent TTR targeting dsRNA (Table 5) were synthesized and assayed for inhibition of endogenous TTR expression using bDNA assays in H.4.II.E cells. Results from single dose assays were used to select a subset of TTR dsRNA duplexes for dose response experiments to calculate IC50's. IC50 results were used to select TTR dsRNAs for further testing.

Cell Culture and Transfections:

The hepatocyte cell lines HepG2, Hep3B and H.4.II.E cells (ATCC, Manassas, Va.) were grown to near confluence at 37° C. in an atmosphere of 5% $CO_2$ in Dulbecco's modified Eagle's medium (ATCC) supplemented with 10% FBS, streptomycin, and glutamine (ATCC) before being released from the plate by trypsinization. H.4.II.E cells were also grown in Earle's minimal essential medium. Reverse transfection was carried out by adding 5 µl of Opti-MEM to 5 µl of siRNA duplexes per well into a 96-well plate along with 10 µl of Opti-MEM plus 0.2 µl of Lipofectamine RNAiMax per well (Invitrogen, Carlsbad Calif. cat #13778-150) and incubated at room temperature for 15 minutes. 80 µl of complete growth media without antibiotics containing $4 \times 10^4$ (HepG2), $2 \times 10^4$ (Hep3B) or $2 \times 10^4$ (H.4.II.E) cells were then added. Cells were incubated for 24 hours prior to RNA purification. Single dose experiments were performed at 10 nM final duplex concentration and dose response experiments were done with 10, 1, 0.5, 0.1, 0.05, 0.01, 0.005, 0.001, 0.0005, 0.0001, 0.00005, 0.00001 nM.

Total RNA Isolation Using MagMAX-96 Total RNA Isolation Kit (Applied Biosystems, Foster City Calif., Part #: AM1830):

Cells were harvested and lysed in 140 µl of Lysis/Binding Solution then mixed for 1 minute at 850 rpm using and Eppendorf Thermomixer (the mixing speed was the same throughout the process). Twenty micro liters of magnetic beads were added into cell-lysate and mixed for 5 minutes. Magnetic beads were captured using magnetic stand and the supernatant was removed without disturbing the beads. After removing supernatant, magnetic beads were washed with Wash Solution 1 (isopropanol added) and mixed for 1 minute. Beads were captured again and supernatant removed. Beads were then washed with 150 µl Wash Solution 2 (Ethanol added), captured and supernatant was removed. 50 µl of DNase mixture (MagMax turbo DNase Buffer and Turbo DNase) was then added to the beads and they were mixed for 10 to 15 minutes. After mixing, 100 µl of RNA Rebinding Solution was added and mixed for 3 minutes. Supernatant was removed and magnetic beads were washed again with 150 µl Wash Solution 2 and mixed for 1 minute and supernatant was removed completely. The magnetic beads were mixed for 2 minutes to dry before RNA it was eluted with 50 µl of water.

cDNA Synthesis Using ABI High Capacity cDNA Reverse Transcription Kit (Applied Biosystems, Foster City, Calif., Cat #4368813):

A master mix of 2 μl 10× Buffer, 0.8 μl 25× dNTPs, 2 μl Random primers, 1 μl Reverse Transcriptase, 1 μl RNase inhibitor and 3.2 μl of H2O per reaction were added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real time PCR:

2 μl of cDNA was added to a master mix of 1 μl 18S TaqMan Probe (Applied Biosystems Cat #4319413E), 1 μl TTR TaqMan probe (Applied Biosystems cat # HS00174914 M1) and 10 μl TaqMan Universal PCR Master Mix (Applied Biosystems Cat #4324018) per well in a MicroAmp Optical 96 well plate (Applied Biosystems cat #4326659). Real time PCR was done in an ABI 7000 Prism or an ABI 7900HT Real Time PCR system (Applied Biosystems) using the ΔΔ Ct(RQ) assay. All reactions were done in triplicate.

Real time data were analyzed using the ΔΔ Ct method and normalized to assays performed from cells transfected with 10 nM BlockIT fluorescent Oligo (Invitrogen Cat #2013) or 10 nM AD-1955 (a control duplex that targets the non-mammalian luciferase gene) to calculate fold change.

Branched DNA Assays-QuantiGene 1.0 (Panomics, Fremont, Calif. Cat #: QG0004)-Used to Screen Rodent Specific Duplexes H.4.II.E cells (ATCC) were transfected with 10 nM siRNA. After removing media, H.4.II.E were lysed in 100 ul of Diluted Lysis Mixture (a mixture of 1 volume of Lysis mixture, 2 volume of nuclease-free water and 10 ul of Proteinase-K per ml for the final concentration of 20 mg/ml) then incubated at 65° C. for 35 minutes. Then, 80 μl of Working Probe Set (a mixture of TTR or GAPDH probe) and 20 ul of cell-lysate were added into the Capture Plate. Capture Plates were incubated at 53° C.±1° C. overnight (approximately 16-20 hrs). Capture Plates were washed 3 times with 1× Wash Buffer (a mixture of nuclease-free water, Buffer Component 1 and Wash Buffer Component 2), then dried by centrifuging for 1 minute at 1000 rpm. 100 μl of Amplifier Working Reagent was added into the Capture Plate, which was then sealed and incubated for 1 hour at 46° C.±1° C. Wash and dry steps were repeated after 1 hour of incubation and 100 μl of Label Solution Reagent was added. The plate was then washed, dried and 100 μl Substrate (a mixture of Lithium Lauryl Sulfate and Substrate solution) was added. Capture Plates were placed in the incubator for 30 minutes at 46° C.±1° C. Capture Plates were then removed from the incubator and incubated at room temperature for 30 minutes. Finally, the Capture Plates were read using the Victor Luminometer (Perkin Elmer, Waltham, Mass.).

Branched DNA Assays-QuantiGene 2.0 (Panomics Cat #: QS0011): Used to Screen all Other Duplexes After a 24 hour incubation at the dose or doses stated, media was removed and cells were lysed in 100 ul Lysis Mixture (1 volume lysis mixture, 2 volumes nuclease-free water and 10 μl of Proteinase-K/ml for a final concentration of 20 mg/ml) then incubated at 65° C. for 35 minutes. 20 μl Working Probe Set (TTR probe for gene target and GAPDH for endogenous control) and 80 μl of cell-lysate were then added to the Capture Plates. Capture Plates were incubated at 55° C.±1° C. (approx. 16-20 hrs). The next day, the Capture Plates were washed 3 times with 1× Wash Buffer (nuclease-free water, Buffer Component 1 and Wash Buffer Component 2), then dried by centrifuging for 1 minute at 240 g. 100 μl of pre-Amplifier Working Reagent was added to the Capture Plates, which were sealed with aluminum foil and incubated for 1 hour at 55° C.±1° C. Following a 1 hour incubation, the wash step was repeated, then 100 μl Amplifier Working Reagent was added. After 1 hour, the wash and dry steps were repeated, and 100 μl Label Probe was added. Capture plates were incubated 50° C.±1° C. for 1 hour. The plates were then washed with 1× Wash Buffer and dried, and then 100 μl Substrate was added to the Capture Plates. Capture Plates were read using the SpectraMax Luminometer (Molecular Devices, Sunnyvale, Calif.) following 5 to 15 minutes incubation.

bDNA Data Analysis:

bDNA data were analyzed by (i) subtracting the average background from each triplicate sample, (ii) averaging the resultant triplicate GAPDH (control probe) and TTR (experimental probe) values, and then (iii) taking the ratio: (experimental probe-background)/(control probe-background).

Results

A summary of the single dose and IC50 results for TTR-dsRNAs (TTR siRNAs) are presented below in Table 8. Single dose results are expressed as % TTR mRNA relative to control, assayed in HepG2 cells. IC50s were determined in HepG2 and/or Hep3B cells, as indicated.

TABLE 8

Single dose and IC50 results of in vitro screens of TTR siRNAs

| | Single Dose at 10 nM % relative to control | IC50 (nM) | | | |
|---|---|---|---|---|---|
| | HepG2 | HepG2 | | Hep3B | |
| Duplex # | qPCR | bDNA | qPCR | bDNA | qPCR | bDNA |
| AD-18243 | 50.35 | 141.53 | ND | ND | ND | ND |
| AD-18244 | 64.26 | 158.55 | ND | ND | ND | ND |
| AD-18245 | 56.89 | 107.22 | ND | ND | ND | ND |
| AD-18246 | 10.53 | 32.51* | 0.265 | 0.086 | ND | ND |
| AD-18247 | 125.56 | 69.57 | ND | ND | ND | ND |
| AD-18248 | 127.78 | 66.97 | ND | ND | ND | ND |
| AD-18249 | 48.77 | 48.76 | ND | ND | ND | ND |
| AD-18250 | 96.94 | 86.42 | ND | ND | ND | ND |
| AD-18251 | 170.41 | 129.15 | ND | ND | ND | ND |
| AD-18252 | 73.52 | 81.90 | ND | ND | ND | ND |
| AD-18253 | 25.25 | 61.25 | ND | ND | ND | ND |
| AD-18254 | 95.13 | 103.96 | ND | ND | ND | ND |
| AD-18255 | 119.46 | ND | ND | ND | ND | ND |
| AD-18256 | 42.64 | 95.67 | ND | ND | ND | ND |
| AD-18257 | 146.25 | 141.75 | ND | ND | ND | ND |
| AD-18258 | 10.20 | 13.41* | 0.007 | 0.005 | 0.004 | 0.005 |
| AD-18259 | 9.30 | 20.91* | 0.102 | 0.005 | ND | ND |
| AD-18260 | 125.37 | 81.36 | ND | ND | ND | ND |
| AD-18261 | 14.27 | 19.40* | 0.210 | ND | ND | ND |
| AD-18262 | 84.95 | 104.05 | ND | ND | ND | ND |
| AD-18263 | 16.32 | 23.25* | 0.110 | ND | ND | ND |
| AD-18264 | 104.18 | 83.69 | ND | ND | ND | ND |
| AD-18265 | 41.62 | 64.87 | ND | ND | ND | ND |
| AD-18266 | 39.98 | 110.53 | ND | ND | ND | ND |
| AD-18267 | 149.64 | ND | ND | ND | ND | ND |
| AD-18268 | 152.93 | 174.04 | ND | ND | ND | ND |
| AD-18269 | 37.27 | 92.28 | ND | ND | ND | ND |
| AD-18270 | 99.44 | 164.75 | ND | ND | ND | ND |
| AD-18271 | 18.89 | 28.33* | 0.503 | 0.004 | ND | ND |
| AD-18272 | 128.32 | 132.58 | ND | ND | ND | ND |
| AD-18273 | 115.78 | 201.95 | ND | ND | ND | ND |

TABLE 8-continued

Single dose and IC50 results of in vitro screens of TTR siRNAs

| Duplex # | Single Dose at 10 nM % relative to control HepG2 qPCR | HepG2 bDNA | IC50 (nM) HepG2 qPCR | HepG2 bDNA | Hep3B qPCR | Hep3B bDNA |
|---|---|---|---|---|---|---|
| AD-18274 | 8.97 | 20.04* | 0.009 | 0.176 | 0.036 | 0.012 |
| AD-18275 | 4.09 | 22.25* | 0.026 | 0.118 | ND | ND |
| AD-18276 | 19.73 | 45.22* | 0.198 | 0.677 | ND | ND |
| AD-18277 | 10.55 | 26.31* | 0.121 | 0.426 | ND | ND |
| AD-18278 | 108.86 | 116.26 | ND | ND | ND | ND |
| AD-18279 | 66.59 | ND | ND | ND | ND | ND |
| AD-18280 | 103.26 | 170.52 | ND | ND | ND | ND |
| AD-18281 | 87.98 | 123.88 | ND | ND | ND | ND |
| AD-18282 | 82.47 | 140.32 | ND | ND | ND | ND |
| AD-18283 | 106.54 | 182.78 | ND | ND | ND | ND |
| AD-18284 | 106.93 | 151.78 | ND | ND | ND | ND |
| AD-18285 | 26.58 | 60.05* | ND | 0.089 | ND | ND |
| AD-18286 | 109.95 | 173.66 | ND | ND | ND | ND |
| AD-18287 | 54.23 | 155.45 | ND | ND | ND | ND |
| AD-18288 | 73.52 | 174.09 | ND | ND | ND | ND |
| AD-18289 | 103.36 | 174.76 | ND | ND | ND | ND |
| AD-18290 | 17.06 | 52.04* | 1.253 | 0.181 | ND | ND |
| AD-18291 | 7.71 | 169.29* | 1.304 | 0.019 | ND | ND |
| AD-18292 | 7.51 | 210.03* | 0.604 | 0.005 | ND | ND |
| AD-18293 | 3.61 | 62.53* | 0.078 | 0.003 | ND | ND |
| AD-18294 | 111.53 | 107.56 | ND | ND | ND | ND |
| AD-18295 | 115.88 | 105.37 | ND | ND | ND | ND |
| AD-18296 | 57.03 | 38.03 | ND | ND | ND | ND |
| AD-18297 | 87.69 | 73.87 | ND | ND | ND | ND |
| AD-18298 | 10.39 | 7.25* | 0.455 | 0.008 | ND | ND |
| AD-18299 | 18.79 | 18.06* | 0.895 | 0.014 | ND | ND |
| AD-18300 | 108.70 | ND | ND | ND | ND | ND |
| AD-18301 | 114.22 | 70.50 | ND | ND | ND | ND |
| AD-18302 | 116.19 | 122.40 | ND | ND | ND | ND |
| AD-18303 | 124.89 | ND | ND | ND | ND | ND |
| AD-18304 | 132.99 | 89.54 | ND | ND | ND | ND |
| AD-18305 | 153.10 | ND | ND | ND | ND | ND |
| AD-18306 | 159.22 | ND | ND | ND | ND | ND |
| AD-18307 | 116.83 | 84.57 | ND | ND | ND | ND |
| AD-18308 | 156.72 | 87.80 | ND | ND | ND | ND |
| AD-18309 | 113.22 | 101.97 | ND | ND | ND | ND |
| AD-18310 | 132.33 | ND | ND | ND | ND | ND |
| AD-18311 | 161.68 | 92.92 | ND | ND | ND | ND |
| AD-18312 | 103.01 | 71.17 | ND | ND | ND | ND |
| AD-18313 | 120.65 | 53.26 | ND | ND | ND | ND |
| AD-18314 | 116.33 | ND | ND | ND | ND | ND |
| AD-18315 | 115.13 | ND | ND | ND | ND | ND |
| AD-18316 | 118.73 | 122.34 | ND | ND | ND | ND |
| AD-18317 | 114.03 | 121.10 | ND | ND | ND | ND |
| AD-18318 | 80.85 | 122.57 | ND | ND | ND | ND |
| AD-18319 | 119.14 | 148.87 | ND | ND | ND | ND |
| AD-18320 | 22.86 | 55.43* | ND | 0.023 | 0.403 | ND |
| AD-18321 | 6.44 | 31.56* | 0.001 | 0.033 | ND | ND |
| AD-18322 | 54.21 | 100.46 | ND | ND | ND | ND |
| AD-18323 | 6.37 | 28.71* | 0.005 | 0.023 | ND | ND |
| AD-18324 | 2.53 | 15.98* | 0.002 | 0.006 | 0.005 | 0.014 |
| AD-18325 | 2.52 | 11.96* | 0.001 | 0.016 | ND | ND |
| AD-18326 | 18.34 | 43.16* | 0.025 | 0.186 | ND | ND |
| AD-18327 | 18.28 | 13.90* | 0.044 | 0.215 | ND | ND |
| AD-18328 | 4.53 | 26.04* | 0.003 | 0.004 | 0.006 | 0.006 |
| AD-18329 | 96.93 | 131.54 | ND | ND | ND | ND |
| AD-18330 | 11.80 | 45.18* | 0.0004 | 0.010 | 0.020 | ND |
| AD-18331 | 117.77 | 163.07 | ND | ND | ND | ND |
| AD-18332 | 11.53 | 35.09* | 0.001 | 0.076 | 0.065 | ND |
| AD-18333 | 12.24 | 46.94* | 0.001 | 0.115 | 0.075 | ND |
| AD-18334 | 16.27 | 55.28* | 0.0004 | 0.181 | 1.071 | ND |
| AD-18335 | 53.52 | 112.80 | ND | ND | ND | ND |
| AD-18336 | 6.39 | 33.00* | 0.001 | 0.112 | 0.081 | ND |
| AD-18337 | 51.77 | 105.33 | ND | ND | ND | ND |
| AD-18338 | 48.21 | 102.86 | ND | ND | ND | ND |
| AD-18339 | 6.48 | 26.56* | 0.004 | 0.002 | 0.018 | 0.029 |
| AD-18340 | 4.53 | 30.76* | 0.002 | 0.002 | ND | ND |
| AD-18341 | 31.27 | 100.41 | ND | ND | ND | ND |
| AD-18342 | 7.60 | 42.89* | ND | 0.016 | 0.076 | ND |
| AD-18343 | 3.42 | 17.45* | ND | 0.001 | ND | ND |
| AD-18344 | 75.08 | 134.31 | ND | ND | ND | ND |
| AD-18345 | 13.62 | 42.75* | 0.002 | 0.013 | ND | ND |
| AD-18346 | 59.25 | 121.10 | ND | ND | ND | ND |
| AD-18347 | 91.23 | 139.54 | ND | ND | ND | ND |
| AD-18348 | 89.95 | 159.29 | ND | ND | ND | ND |
| AD-18349 | 108.01 | 144.96 | ND | ND | ND | ND |
| AD-18350 | 123.65 | 125.87 | ND | ND | ND | ND |
| AD-18351 | 108.36 | 104.02 | ND | ND | ND | ND |
| AD-18352 | 87.82 | 128.72 | ND | ND | ND | ND |
| AD-18353 | 14.40 | 65.77 | 0.012 | 0.027 | ND | ND |
| AD-18354 | 99.27 | 123.53 | ND | ND | ND | ND |
| AD-18355 | 135.04 | 150.88 | ND | ND | ND | ND |
| AD-18356 | 100.76 | 178.96 | ND | ND | ND | ND |
| AD-18357 | 125.30 | 162.85 | ND | ND | ND | ND |
| AD-18358 | 103.15 | 136.01 | ND | ND | ND | ND |
| AD-18359 | 34.74 | 140.48 | ND | ND | ND | ND |
| AD-18360 | 103.86 | 146.86 | ND | ND | ND | ND |
| AD-18361 | 105.74 | 152.74 | ND | ND | ND | ND |
| AD-18362 | 106.96 | 188.22 | ND | ND | ND | ND |
| AD-18363 | 124.22 | 58.46 | ND | ND | ND | ND |
| AD-18364 | 113.75 | 66.87 | ND | ND | ND | ND |
| AD-18446 | 29.73 | 13.30 | ND | ND | ND | ND |
| AD-18447 | 109.74 | 53.63 | ND | ND | ND | ND |
| AD-18448 | 22.96 | 8.81 | ND | ND | ND | ND |
| AD-18449 | 112.59 | 50.11 | ND | ND | ND | ND |
| AD-18450 | 89.41 | 34.89 | ND | ND | ND | ND |
| AD-18451 | 74.35 | 23.88 | ND | ND | ND | ND |
| AD-18452 | 125.25 | 54.86 | ND | ND | ND | ND |
| AD-18453 | 126.98 | 56.31 | ND | ND | ND | ND |
| AD-18454 | 113.88 | 52.48 | ND | ND | ND | ND |
| AD-18455 | 163.00 | 48.89 | ND | ND | ND | ND |
| AD-18456 | 15.70 | 10.52 | ND | ND | ND | ND |
| AD-18457 | 12.86 | 8.22 | ND | ND | ND | ND |
| AD-18458 | 13.00 | 7.00 | ND | ND | ND | ND |
| AD-18459 | 14.41 | 10.72 | ND | ND | ND | ND |
| AD-18460 | 121.16 | 74.87 | ND | ND | ND | ND |
| AD-18461 | 100.53 | 71.87 | ND | ND | ND | ND |
| AD-18462 | 47.75 | 29.35 | ND | ND | ND | ND |
| AD-18463 | 58.98 | 44.79 | ND | ND | ND | ND |

ND: no data;

*indicates result that represents average of two experiments.

The dose response data used to identify the IC50 for 5 TTR-dsRNAs (AD-18258, AD-18274, AD-18324, AD-18328, and AD-18339), are presented in detail below in Table 9. All 5 siRNAs were determined to have pM IC50s. The IC50 data for dsRNAs in Table 8 is a summary of the data presented in Table 9 below.

TABLE 9

Dose response data for 5 TTR-dsRNAs

| Cell type | Detection method | % inhibition relative to control AD-1955 Dose of duplex (nM) | | | | | | | | | | | | IC50 (nM) |
|---|---|---|---|---|---|---|---|---|---|---|---|---|---|---|
| | | 10 | 1 | 0.5 | 0.1 | 0.05 | 0.01 | 0.005 | 0.001 | 0.0005 | 0.0001 | 0.00005 | 0.00001 | |
| Duplex AD-18258 | | | | | | | | | | | | | | |
| HepG2 | qPCR | 14.4 | 14.1 | 16.2 | 23.9 | 27.26 | 40.19 | 68.46 | 78.1 | 74.48 | 104.37 | 98.28 | 113.68 | 0.007 |
| HepG2 | bDNA | 14.3 | 14.5 | 11.1 | 12.8 | 18.82 | 19.77 | 51.21 | 56.03 | 63.63 | 58.35 | 43.64 | 51.05 | 0.005 |
| Hep3B | qPCR | 11.9 | 8.62 | 12.4 | 16.4 | 28.35 | 30.49 | 58.36 | 54.57 | 81.26 | 89.43 | 81.85 | 101.87 | 0.004 |
| Hep3B | bDNA | 7.65 | 7.5 | 11.3 | 12.6 | 28.85 | 27.89 | 64.57 | 73.48 | 72.03 | 91.44 | 86.71 | 89.31 | 0.005 |
| Duplex AD-18274 | | | | | | | | | | | | | | |
| HepG2 | qPCR | 6.68 | 8.45 | 11.7 | 24.2 | 42.08 | 49.89 | 56.95 | 62.99 | 64.47 | 54.92 | 67.39 | 72.67 | 0.009 |
| HepG2 | bDNA | 27.5 | 69 | 25.2 | 34.2 | 73.03 | 103.4 | 121.57 | 97.31 | 154.93 | 156.7 | Nd | 152.25 | 0.176 |
| Hep3B | qPCR | 7.58 | 17 | 15.6 | 43.9 | 42.22 | 60.55 | 78.8 | 77.81 | 79.97 | 85.84 | 86.13 | 83.99 | 0.036 |
| Hep3B | bDNA | 3.77 | 4.92 | 7.51 | 15 | 35.21 | 51.66 | 72.45 | 70.12 | 78.31 | 77.52 | 90.72 | 83.01 | 0.012 |
| Duplex AD-18324 | | | | | | | | | | | | | | |
| HepG2 | qPCR | 2.07 | 2.27 | 2.74 | 6.36 | 8.18 | 15.23 | 28.82 | 52.79 | 90.86 | 94.72 | 116.07 | 98.97 | 0.002 |
| HepG2 | bDNA | 14.5 | 7.88 | 11.8 | 15.9 | 17.2 | 46.44 | 40.4 | 91.86 | 0 | 95.57 | 0 | 52.15 | 0.006 |
| Hep3B | qPCR | 2.07 | 3.48 | 5.76 | 16.2 | 18.73 | 44.54 | 49.77 | 68.88 | 63.48 | 76.61 | 74.7 | 77.83 | 0.005 |
| Hep3B | bDNA | 3.48 | 3.8 | 5.15 | 15.2 | 30.84 | 55.36 | 74.75 | 99.39 | 88.89 | 110.83 | 96.55 | 110.26 | 0.014 |
| Duplex AD-18328 | | | | | | | | | | | | | | |
| HepG2 | qPCR | 5.85 | 3.97 | 3.32 | 5.62 | 8 | 16.75 | 55.01 | 39.76 | 122.41 | 102.37 | 114.02 | 124.09 | 0.003 |
| HepG2 | bDNA | 12.3 | 10.7 | 10.7 | 11.9 | 20.06 | 25 | 69.52 | 57.29 | 112.28 | 98.14 | 142.26 | 148.92 | 0.004 |
| Hep3B | qPCR | 3.17 | 5.52 | 11.7 | 13.8 | 27.68 | 39.58 | 61.21 | 61.87 | 90.51 | 87.56 | 106.03 | 108.72 | 0.006 |
| Hep3B | bDNA | 3.08 | 3.66 | 4.19 | 7.25 | 21.05 | 22.1 | 73.74 | 63.19 | 105.55 | 96.27 | 105.97 | 96.46 | 0.006 |
| Duplex AD-18339 | | | | | | | | | | | | | | |
| HepG2 | qPCR | 6.27 | 7.28 | Nd | 11 | 15.25 | 38.69 | 38.78 | 71.7 | 84.09 | 62.2 | 75.61 | 85.46 | 0.004 |
| HepG2 | bDNA | 15.1 | 8.14 | 5.13 | 6.89 | 12.17 | 32.14 | 42.98 | 64.01 | 60.76 | 79.95 | 81.97 | 95.43 | 0.002 |
| Hep3B | qPCR | 8.3 | 9.47 | 13.2 | 34.5 | 44.54 | 77.38 | 81.04 | 81.41 | 93.95 | 81.04 | 75.61 | 78.28 | 0.018 |
| Hep3B | bDNA | 10.5 | 9.43 | 11.7 | 27.1 | 44.88 | 72.32 | 79.88 | 79.6 | 87.46 | 96.53 | 95.13 | 89.88 | 0.029 |

A summary of the single dose results for rodent specific TTR-dsRNAs (TTR siRNAs) are presented below in Table 10. Single dose results are expressed as % TTR mRNA relative to control, assayed in rat H.4.II.E cells, after transfection of rodent specific TTR siRNAs at 10 nM. These results show that some rodent specific TTR siRNAs are effective in suppressing endogenous rat TTR mRNA in vitro.

TABLE 10

Single dose results of in vitro screen of rodent specific TTR-dsRNAs (TTR siRNAs)

| Duplex # | % Relative to control at 10 nM |
|---|---|
| AD-18529 | 19.83 |
| AD-18530 | 44.49 |
| AD-18531 | 6.01 |
| AD-18532 | 24.06 |
| AD-18533 | 37.78 |
| AD-18534 | 8.19 |
| AD-18535 | 10.18 |
| AD-18536 | 16.13 |
| AD-18537 | 15.88 |
| AD-18538 | 19.93 |
| AD-18539 | 49.24 |
| AD-18540 | 2.99 |
| AD-18541 | 1.32 |
| AD-18542 | 6.3 |
| AD-18543 | 16.46 |
| AD-18544 | 17.55 |
| AD-18545 | 3.53 |
| AD-18546 | 2.75 |
| AD-18547 | 7.01 |
| AD-18548 | 5.02 |
| AD-18549 | 1.61 |
| AD-18550 | 9.58 |
| AD-18551 | 7.74 |
| AD-18552 | 3.74 |
| AD-18553 | 50.39 |
| AD-18554 | 111.06 |

Example 3

In Vitro Assay of TTR siRNAs for Induction of TNF-α and IFN-α Secretion

To evaluate potential for immunostimulation, TTR siRNAs were assayed in vitro for induction of TNF-α and IFN-α secretion.

Human PBMC were isolated from freshly collected buffy coats obtained from healthy donors (Research Blood Components, Inc., Boston, Mass.) by a standard Ficoll-Hypaque density centrifugation. Freshly isolated cells ($1\times10^5$/well/100 µl) were seeded in 96-well plates and cultured in RPMI 1640 GlutaMax medium (Invitrogen) supplemented with 10% heat-inactivated fetal bovine serum and 1% antibiotic/antimycotic (Invitrogen).

siRNAs were transfected into PBMC using DOTAP transfection reagent (Roche Applied Science). The DOTAP was first diluted in Opti-MEM (Invitrogen) for 5 minutes before mixing with an equal volume of Opti-MEM containing the siRNA. siRNA/DOTAP complexes were incubated as specified by the manufacturer's instructions and subsequently added to PBMC (50 μl/well) which were then cultured for 24 hours. Positive and negative control siRNAs were included in all assays. AD-5048 was used as a positive control siRNA. AD-5048 corresponds to a sequence that targets human Apolipoprotein B (Soutschek et al., 2004) and elicits secretion of both IFN-α and TNF-α in this assay. AD-1955, which does not elicit IFN-α and TNF-α secretion in this assay, was used as a negative control siRNA. All siRNAs were used at a final concentration of 133 nM. The ratio of RNA to transfection reagent was 16.5 pmoles per μg of DOTAP.

Cytokines were detected and quantified in culture supernatants with a commercially available ELISA kit for IFN-α (BMS216INST) and TNF-α (BMS223INST), both from Bender MedSystems (Vienna, Austria). TTR siRNA cytokine induction is expressed as percent IFN-α or TNF-α produced relative to the positive control siRNA AD-5048.

IFN-α and TNF-α stimulation results for a number of TTR siRNAs are presented in FIG. 1 (mean of quadruplicate wells±SD) and below in Table 11 (percentage compared with AD-5048). None of the TTR siRNAs evaluated induced significant TNF-α or IFN-α secretion by cultured human PBMCs.

TABLE 11

IFN-α and TNF-α stimulation results for TTR siRNAs

| Duplex # | IFN-α (% of AD-5048) | TNF-α (% of AD-5048) |
|---|---|---|
| AD-18246 | 0 | 4 |
| AD-18258 | 0 | 0 |
| AD-18259 | 0 | 0 |
| AD-18261 | 0 | 0 |
| AD-18263 | 0 | 0 |
| AD-18271 | 0 | 0 |
| AD-18274 | 2 | 1 |
| AD-18275 | 0 | 0 |
| AD-18276 | 0 | 0 |
| AD-18277 | 0 | 0 |
| AD-18285 | 0 | 0 |
| AD-18290 | 0 | 0 |
| AD-18291 | 0 | 0 |
| AD-18292 | 0 | 0 |
| AD-18293 | 0 | 0 |
| AD-18298 | 0 | 0 |
| AD-18299 | 0 | 0 |
| AD-18320 | 0 | 0 |
| AD-18321 | 0 | 0 |
| AD-18323 | 0 | 0 |
| AD-18324 | 0 | 0 |
| AD-18325 | 0 | 0 |
| AD-18326 | 0 | 0 |
| AD-18327 | 0 | 0 |
| AD-18328 | 0 | 0 |
| AD-18330 | 0 | 0 |
| AD-18332 | 1 | 0 |
| AD-18333 | 0 | 1 |
| AD-18334 | 0 | 1 |
| AD-18336 | 1 | 0 |
| AD-18339 | 0 | 0 |
| AD-18340 | 0 | 0 |
| AD-18342 | 0 | 0 |
| AD-18343 | 0 | 0 |
| AD-18345 | 0 | 0 |
| AD-18353 | 0 | 0 |
| AD-18448 | 0 | 0 |
| AD-18456 | 0 | 0 |
| AD-18457 | 0 | 0 |
| AD-18458 | 0 | 0 |
| AD-18459 | 0 | 0 |

The five lead TTR targeting dsRNAs (TTR siRNAs) were selected based on IC50s in the pM range in the human hepatocyte cell lines HepG2 and Hep3B, and the absence of immunostimulatory activity. Duplexes without any mismatches are more likely to achieve significant knockdown of the target transcript than duplexes with mismatches between the oligo and the mRNA. To better enable interpretation of cross-species toxicology data and to have the broadest applicability to human patients, duplexes that have 100% identity in orthologous genes from rat, cynomolgus monkey and human, and that do not target regions with known polymorphisms are generally preferred. The five lead compounds were selected based on IC50 in hepatocyte cell lines in the pM range, the absence of immunostimulatory activity, specificity to the human TTR transcripts, and absence of known polymorphisms (mutations) in the region of the mRNA targeted by the duplex. In the case of TTR, no 19 base oligos were found with complete identity in human, rat and cynomolgus monkey. A summary of these data are presented in Table 12, which also includes information on known TTR mutations in the region targeted by the duplex and cross-species reactivity.

TABLE 12

Summary of data for five most potent TTR dsRNAs.

| Duplex # | IC50 (qPCR): nM HepG2 | IC50 (bDNA): nM HepG2 | IFNa/TNFa | Mutations not covered | Cross-species reactivity |
|---|---|---|---|---|---|
| AD-18258 | 0.007 | 0.005 | Negative | None (non-coding region) | Cyno: 1 mismatch @ position 14 A to G Rat: no homology at any position |
| AD-18274 | 0.009 | 0.176 | Negative | Lys70Asn; Val71Ala; Ile73Val; Asp74His | Cyno: no mismatch Rat: no homology at any position |
| AD-18324 | 0.002 | 0.006 | Negative | None (non-coding region) | Cyno: no mismatch Rat: no homology at any position |
| AD-18328 | 0.003 | 0.004 | Negative | None (non-coding region) | Cyno: no mismatch Rat: 7 mismatches |
| AD-18339 | 0.004 | 0.002 | Negative | None (non-coding region) | None |

Example 4

Figure 2A:
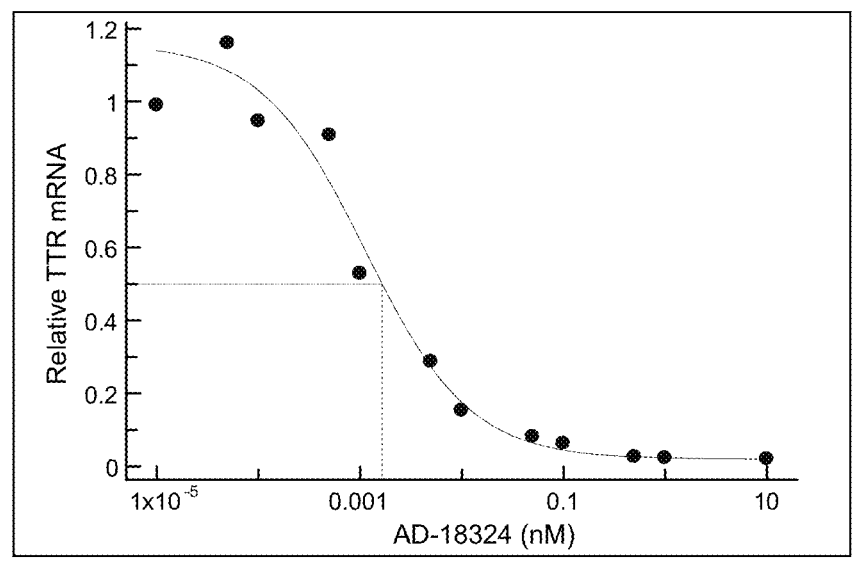
FIGS. 2A and 2B are dose response curves for AD-18324 and AD-18328, respectively, in HepG2 cells.
Figure 2B:
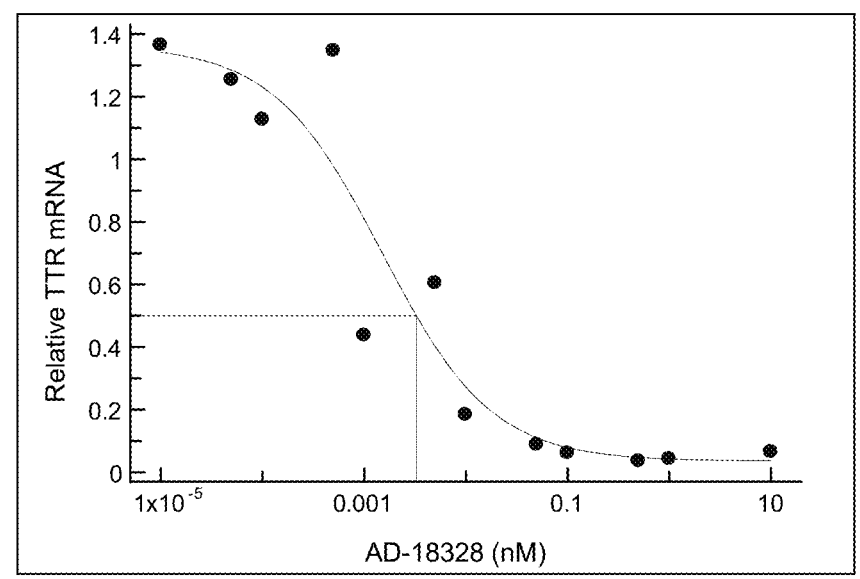

In Vivo Reduction of Liver TTR mRNA and Plasma TTR Protein by LNP01-18324, LNP01-18328 and LNP01-18246 in Transgenic Mice Two TTR siRNAs, AD-18324 and AD-18328, were chosen for in vivo evaluation. These duplexes exhibited potent dose-dependent silencing in vitro in hepatocyte cell lines (e.g. HepG2). FIG. 2A and FIG. 2B show the dose responses in HepG2 cells after transfection with AD-18324 (FIG. 2A) or AD-18328 (FIG. 2B) where the doses are expressed in nM on the x-axis and the responses are expressed as fraction TTR mRNA remaining relative to control, on the y-axis. In HepG2 cells, the IC50s of AD-18324 and AD-18328 were determined to be 2 pM and 3 pM, respectively. The TTR target sites for both lead dsRNA candidates are in the 3' untranslated region of the TTR mRNA, in a region where there are no reported mutations in the literature.

The sequences of each strand of the two lead candidates are reproduced below from the Tables. Strand: s=sense; as=antisense; Position: position of 5' base on transcript NM_000371.2.

| Duplex # | Strand | Oligo # | Position* | Sequence 5' to 3' | SEQ ID NO: |
|---|---|---|---|---|---|
| AD-18324 | s | A-32337 | 509 | GGAuuucAuGuAAccAAGAdTdT | 1001 |
| AD-18324 | as | A-32338 | 527 | UCUUGGUuAcAUGAAAUCCdTdT | 1002 |
| AD-18328 | s | A-32345 | 518 | GuAAccAAGAGuAuuccAudTdT | 1009 |
| AD-18328 | as | A-32346 | 536 | AUGGAAuACUCUUGGUuACdTdT | 1010 |

Figure 3:
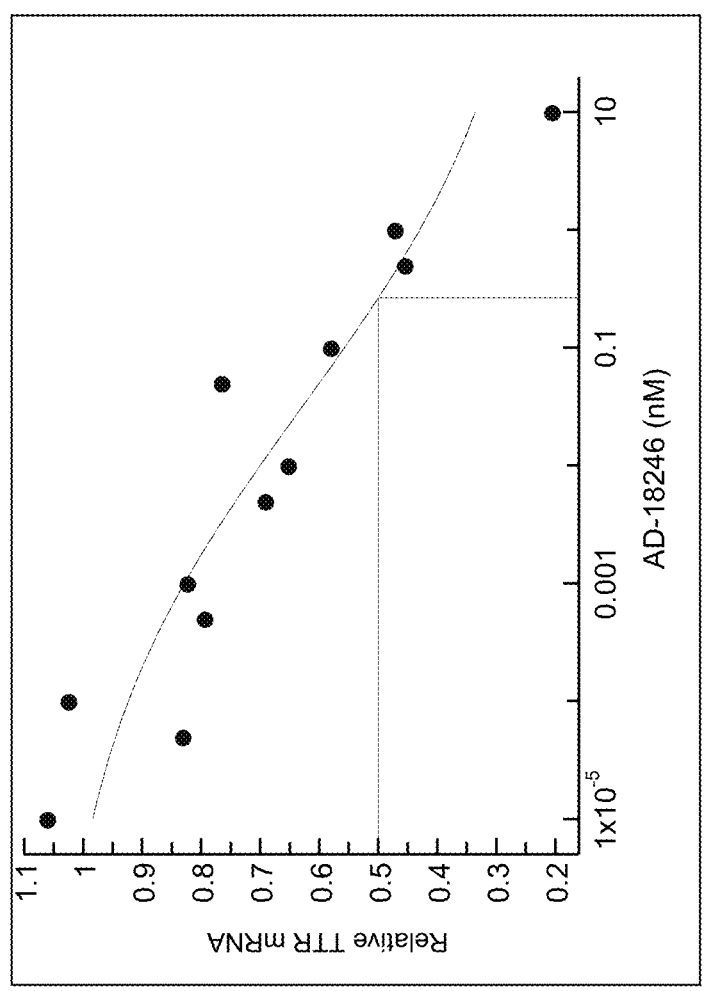
FIG. 3 is a dose response curve for AD-18246 in HepG2 cells.

In addition, a rodent cross-reactive TTR dsRNA, AD-18246, was chosen for further evaluation in vivo. AD-18246 targets a sequence beginning at position 88 of the open reading frame, where there are three mutations reported in the literature. A dose response curve for AD-18246 in HepG2 cells is shown in FIG. 3. AD-18246 is substantially less potent than AD-18324 and AD-18328; the IC50 of AD-18246 was determined to be 265 pM.

AD-18324, AD-18328, and AD-18246 were administered to transgenic mice after formulation in LNP01. 3-5 month old H129-mTTR-KO/iNOS-KO/hTTR transgenic mice (mouse transthyretin knock-out/inducible nitric oxide synthase knock-out/human transthyretin transgenic) were intravenously (IV) administered 200 μl of LNP01-formulated transthyretin-specific siRNA (AD-18324, AD-18328, or AD-18246), LNP01-formulated control siRNA targeting the non-mammalian luciferase gene (AD-1955) or PBS via the tail vein at concentrations of 1.0 mg/kg, 3.0 mg/kg, or 6.0 mg/kg for siRNAs AD-18324 and AD-18328, 3.0 mg/kg for siRNA AD-18246, and 6.0 mg/kg for siRNA AD-1955. LNP01 is a lipidoid formulation comprised of ND98, Cholesterol, and PEG-Ceramide C16.

After approximately forty-hours, mice were anesthetized with 200 μl of ketamine, and then exsanguinated by severing the right caudal artery. Whole blood was isolated and plasma was isolated and stored at −80° C. until assaying. Liver tissue was collected, flash-frozen and stored at −80° C. until processing.

Efficacy of treatment was evaluated by (i) measurement of TTR mRNA in liver at 48 hours post-dose, and (ii) measurement of TTR protein in plasma at prebleed and at 48 hours post-dose. TTR liver mRNA levels were assayed utilizing the Branched DNA assays-QuantiGene 2.0 (Panomics cat #: QS0011). Briefly, mouse liver samples were ground and tissue lysates were prepared. Liver lysis mixture (a mixture of 1 volume of lysis mixture, 2 volume of nuclease-free water and 10 ul of Proteinase-K/ml for a final concentration of 20 mg/ml) was incubated at 65° C. for 35 minutes. 20 μl of Working Probe Set (TTR probe for gene target and GAPDH for endogenous control) and 80 ul of tissue-lysate were then added into the Capture Plate. Capture Plates were incubated at 55° C.±1° C. (aprx. 16-20 hrs). The next day, the Capture Plate were washed 3 times with 1× Wash Buffer (nuclease-free water, Buffer Component 1 and Wash Buffer Component 2), then dried by centrifuging for 1 minute at 240 g. 100 ul of pre-Amplifier Working Reagent was added into the Capture Plate, which was sealed with aluminum foil and incubated for 1 hour at 55° C.±1° C.

Following 1 hour incubation, the wash step was repeated, then 100 μl of Amplifier Working Reagent was added. After 1 hour, the wash and dry steps were repeated, and 100 μl of Label Probe was added. Capture plates were incubated 50° C.±1° C. for 1 hour. The plate was then washed with 1× Wash Buffer, dried and 100 μl Substrate was added into the Capture Plate. Capture Plates were read using the SpectraMax Luminometer following a 5 to 15 minute incubation. bDNA data were analyzed by subtracting the average background from each triplicate sample, averaging the resultant triplicate GAPDH (control probe) and TTR (experimental probe) values, and then computing the ratio: (experimental probe-background)/(control probe-background).

TTR plasma levels were assayed utilizing the commercially available kit "AssayMax Human Prealbumin ELISA Kit" (AssayPro, St. Charles, Mo., Catalog # EP3010-1) according to manufacturer's guidelines. Briefly, mouse plasma was diluted 1:10,000 in 1× mix diluents and added to pre-coated plates along with kit standards, and incubated for 2 hours at room temperature followed by 5× washes with kit wash buffer. Fifty microliters of biotinylated prealbumin antibody was added to each well and incubated for 1 hr at room temperature, followed by 5× washes with wash buffer. Fifty microliters of streptavidin-peroxidase conjugate was added to each well and plates were incubated for 30 minutes at room temperature followed by washing as previously described. The reaction was developed by the addition of 50 μl/well of chromogen substrate and incubation for 10 minutes at room temperature with stopping of reaction by the addition of 50 μl/well of stop solution. Absorbance at 450 nm was read on a Versamax microplate reader (Molecular Devices, Sunnyvale, Calif.) and data were analyzed utilizing the Softmax 4.6 software package (Molecular Devices).

Figure 4A:
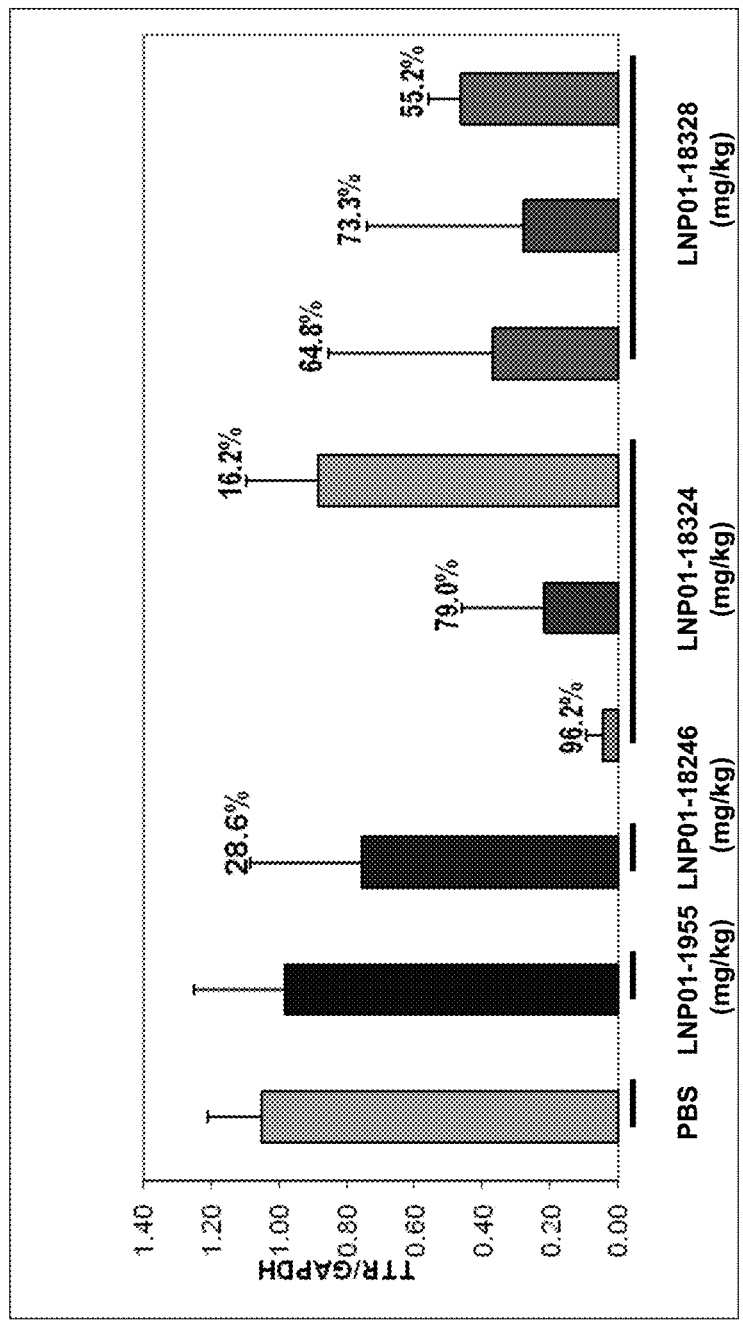
FIG. 4A and FIG. 4B show inhibition of liver mRNA and plasma protein levels, respectively, in transgenic H129-mTTR-KO/iNOS-KO/hTTR mice by an intravenous bolus administration of TTR-dsRNA (AD-18324, AD-18328 and AD-18246) formulated in LNP01.
Figure 4B:
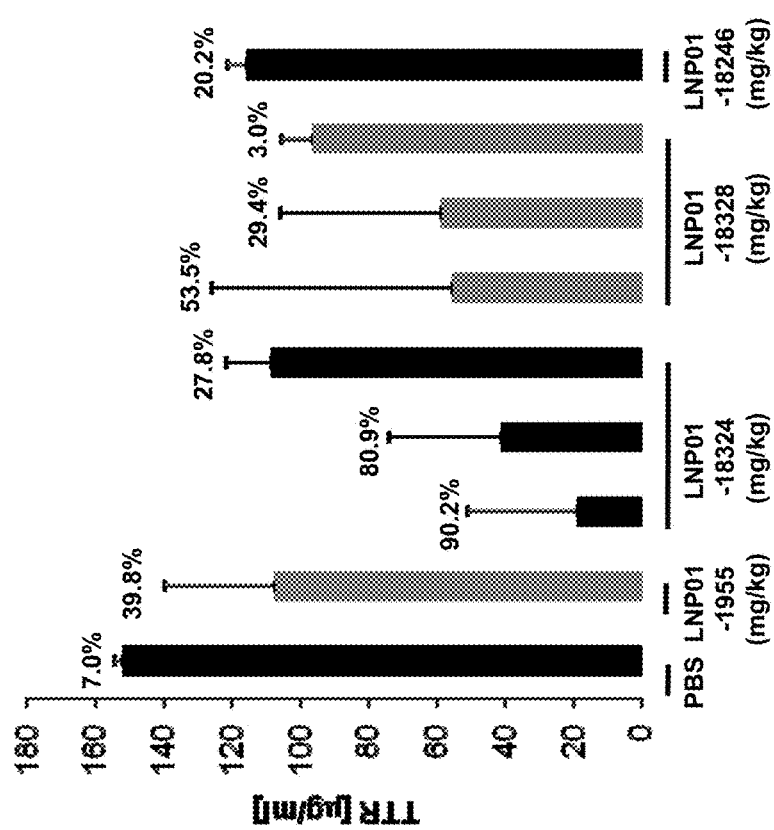

LNP01-18324 and LNP01-18328 were found to reduce liver TTR mRNA (FIG. 4A) and plasma TTR protein (FIG. 4B) levels in a dose-dependent manner with IV bolus administration. The mRNA ED50 of LNP01-18328 was determined to be ~1 mg/kg whereas the ED50 of LNP01-18324 was determined to be ~2 mg/kg. The effects of LNP01-18324 and LNP01-18328 were specific, because the control, LNP01-1955 at 6 mg/kg, did not significantly affect liver TTR mRNA levels, as compared with the PBS group. LNP01-18324 and LNP01-18328 reduced plasma TTR protein levels relative to the PBS group, with potencies that were similar to those on TTR mRNA levels. At 3 mg/kg, LNP01-18246 reduced liver TTR mRNA levels to a lessor extent than 3 mg/kg LNP01-18324 or LNP01-18328.

These results demonstrate that LNP01-18324 and LNP01-18328, administered by IV bolus, substantially reduce human TTR mRNA expressed by the transgenic mouse liver, which results in reduction of human TTR protein in the circulation.

Example 5

In Vivo Reduction of Wild-Type TTR mRNA in the Non-Human Primate Liver by SNALP-18324 and SNALP-18328

To evaluate the efficacy of TTR siRNAs AD-18324 and AD-18328 in non-human primates on liver TTR mRNA levels, the siRNAs were formulated in SNALP and administered by 15-minute IV infusion. Cynomolgus monkeys (*Macaca fascicularis*) (2 to 5 kg, 3 animals per group) were administered 15-minute IV infusions of SNALP-18324 (0.3, 1.0 or 3.0 mg/kg), SNALP-18328 (0.3, 1 or 3 mg/kg), or SNALP-1955 (3 mg/kg, with negative control siRNA AD-1955 which targets the non-mammalian gene luciferase). At forty-eight hours post-dosing, monkeys were anesthetized with sodium pentobarbital and exsanguinated. Liver tissue for TTR mRNA determination was collected, flash-frozen, and stored at −80° C. until processing.

TTR mRNA levels in the liver were assayed utilizing a custom designed Branched DNA assay, utilizing the QuantiGene1.0 technology. Briefly, monkey liver samples were ground and tissue lysates were prepared. Liver lysis mixture (1 volume lysis mixture, 2 volume nuclease-free water, and 10 µl of Proteinase-K/ml for a final concentration of 20 mg/ml) was incubated at 65° C. for 35 minutes. 20 µl Working Probe Set (TTR probe for gene target and GAPDH for endogenous control) and 80 µl tissue-lysate were then added into the Capture Plate. Capture Plates were incubated at 55° C.±1° C. (approx. 16-20 hrs). The next day, the Capture Plates were washed three times with 1× Wash Buffer (nuclease-free water, Buffer Component 1 and Wash Buffer Component 2), then dried by centrifuging for 1 minute at 240 g. 100 µl of pre-Amplifier Working Reagent was added into the Capture Plate, which was sealed with aluminum foil and incubated for 1 hour at 55° C.±1° C. Following a 1-hour incubation, the wash step was repeated, and then 100 µl Amplifier Working Reagent was added. After 1 hour, the wash and dry steps were repeated, and 100 µl Label Probe was added. Capture plates were incubated 50° C.±1° C. for 1 hour. The plates were then washed with 1× Wash Buffer and dried, and then 100 µl Substrate was added into the Capture Plate. Capture Plates were read using the SpectraMax Luminometer following a 5 to 15 minute incubation. bDNA data were analyzed by (i) subtracting the average background from each triplicate sample, (ii) averaging the resultant GAPDH (control probe) and TTR (experimental probe) values, and then (iii) taking the ratio: (experimental probe-background)/(control probe-background).

Figure 5:
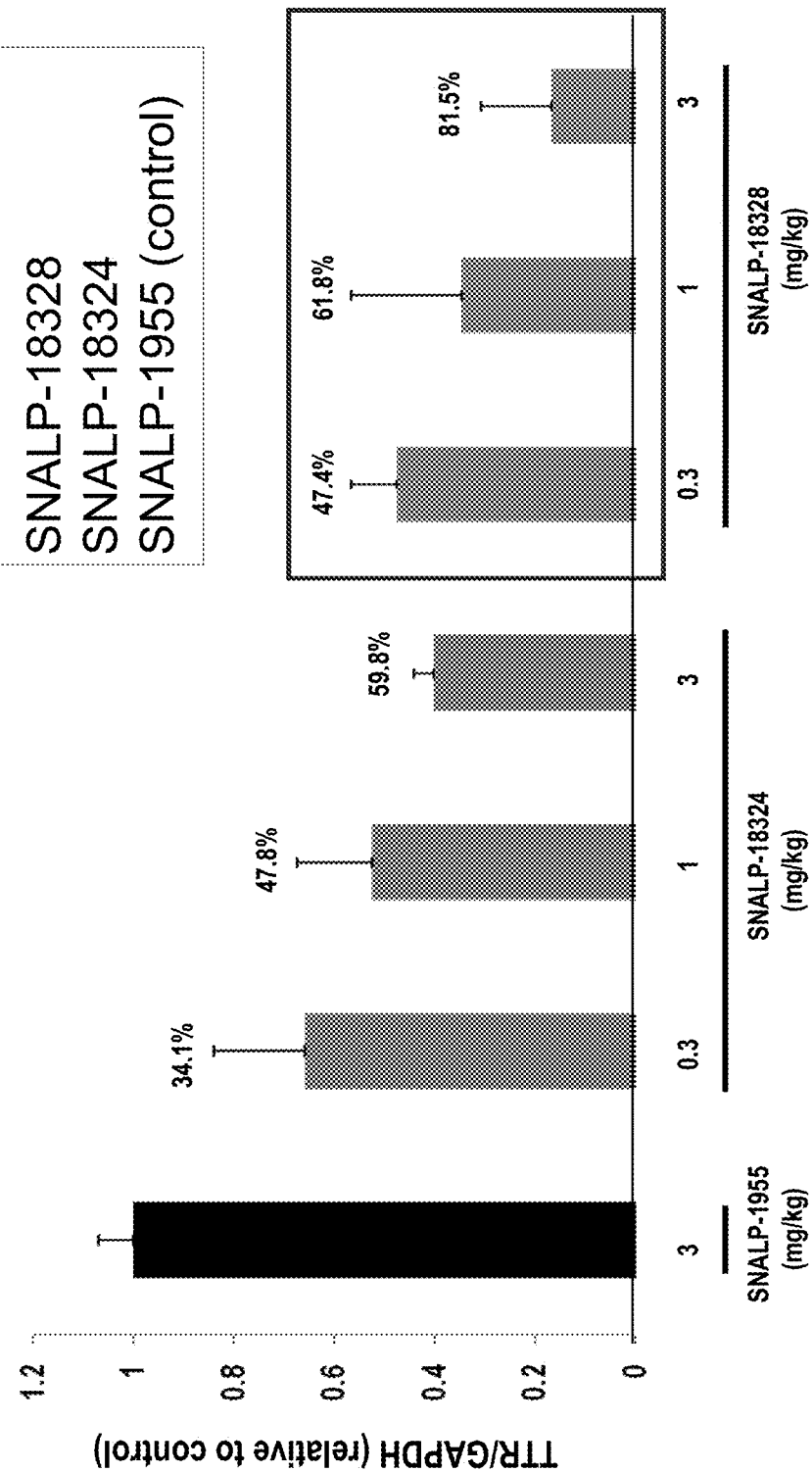
FIG. 5 is a graph summarizing the measurements of TTR mRNA levels in livers of non-human primates following 15-minute intravenous infusion of TTR-dsRNA (AD-18324 and AD-18328) formulated in SNALP.

The results are shown in FIG. 5. SNALP-18324 and SNALP-18328 reduced TTR mRNA levels in the liver in a dose-dependent manner, compared to the negative control SNALP-1955. The mRNA ED50s of SNALP-18328 and SNALP-18324 were determined to be ~0.3 and ~1 mg/kg, respectively.

These results demonstrate that SNALP-18324 and SNALP-18328 are effective in suppressing wild-type TTR mRNA in non-human primate liver when administered by IV infusion.

Example 6

In Vivo Reduction of Mutant (V30M) TTR mRNA and Protein by SNALP-18328 in the Transgenic Mouse To evaluate the efficacy of TTR siRNA AD-18328 on mutant (V30M) TTR mRNA in the liver and mutant (V30M) TTR protein in the serum, AD-18328 was formulated in SNALP and administered by IV bolus to V30M hTTR transgenic mice. 8 to 12-week old V30M hTTR transgenic mice (5 animals/group) were intravenously (IV) administered 200 µl SNALP-18328 (0.03, 0.3 or 3 mg/kg), SNALP-1955 (3 mg/kg, with negative control siRNA AD-1955 which targets the non-mammalian gene luciferase), or PBS. Mice used were the *Mus musculus* strain H129-hTTR KO from Institute of Molecular and Cellular Biology, Porto, Portugal. Briefly, hTTR H129 transgenic mice were crossed with a H129 endogenous TTR KO mice (null mice to generate the H129-hTTR transgenic mice, in a null mouse TTR background (Maeda, S., (2003), Use of genetically altered mice to study the role of serum amyloid P component in amyloid deposition. Amyloid Suppl. 1, 17-20.).

At 48 hrs post-injection, animals in all five treatment groups were given a lethal dose of ketamine/xylazine. Serum samples were collected and stored at −80° C. until analysis. Liver tissue was collected, flash-frozen and stored at −80° C. until processing.

For TTR mRNA quantitation, frozen liver tissue was ground into powder, and lysates were prepared. TTR mRNA levels relative to those of GAPDH mRNA were determined in the lysates by using a branched DNA assay (QuantiGene Reagent System, Panomics, Fremont, Calif.). Briefly, the QuantiGene assay (Genospectra) was used to quantify mRNA levels in tissue sample lysates according to the manufacturer's instructions. The mean level of TTR mRNA was normalized to the mean level of GAPDH mRNA for each sample. Group means of the normalized values were then further normalized to the mean value for the PBS treated group, to obtain the relative level of TTR mRNA expression.

For TTR protein quantitation, serum was assayed using the AssayPro (St. Charles, Mo.) Assaymax PreAlbumin ELISA Kit according to the manufacturer's protocol.

Figure 6A:
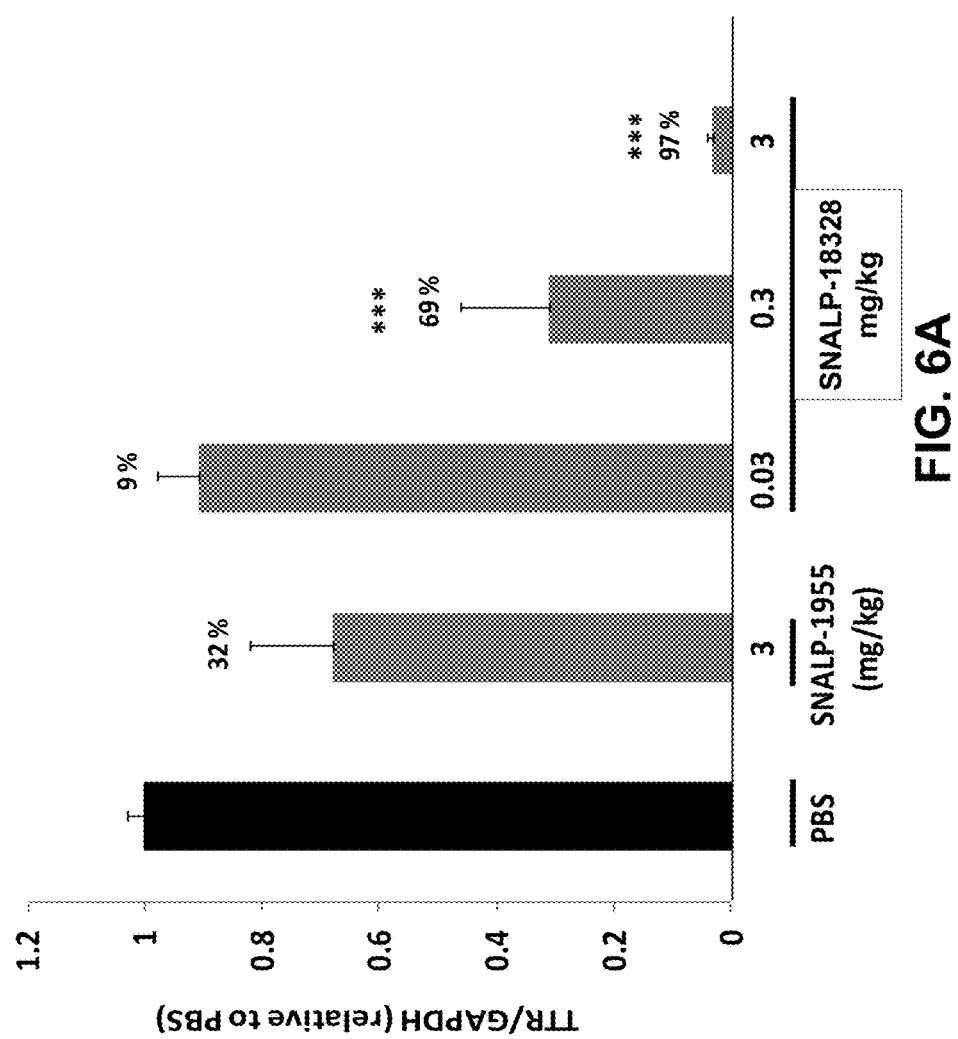

The results are shown in FIG. 6A and FIG. 6B for liver mRNA and serum protein, respectively. SNALP-18328 treated V30M hTTR transgenic mice had a dose-dependent and significant decrease in liver TTR mRNA levels relative to the PBS control group, reaching a maximum reduction of 97% ($p<0.001$) at 3 mg/kg SNALP-18328, and a 50% reduction (ED50) at ~0.15 mg/kg SNALP-18328. Serum TTR protein was also suppressed in a dose-dependent manner, with a maximum reduction of serum TTR protein of 99% ($p<0.01$) (relative to pre-dose levels) at 3 mg/kg SNALP-18328, consistent with the reduction in TTR mRNA levels. SNALP-1955 at 3 mg/kg did not have a statistically significant effect on either TTR mRNA or protein levels, compared to PBS.

These results demonstrate that SNALP-18328, when administered IV, is active in suppressing mutant V30M TTR mRNA in the transgenic mouse liver, which results in reduction of mutant V30M TTR protein in the circulation.

Example 7

Durability of TTR mRNA and Protein Suppression by SNALP-18328 in the Transgenic Mouse To evaluate the durability of TTR mRNA and protein suppression by SNALP-18328, AD-18328 was formulated in SNALP and administered by IV bolus to V30M hTTR transgenic mice. At various timepoints post-dose, liver TTR mRNA levels and serum TTR protein levels were quantified. 8- to 12-week old V30M hTTR transgenic mice (4 animals/ group) were intravenously (IV) administered 200 µl SNALP-18328 (1 mg/kg) or SNALP-1955 (1 mg/kg, with negative control siRNA AD-1955 which targets the non-mammalian gene luciferase). Mice used were *Mus musculus* strain H129-hTTR KO from Institute of Molecular and Cellular Biology, Porto, Portugal. Briefly, hTTR H129 transgenic mice were crossed with a H129 endogenous TTR KO mice (null mice to generate the H129-hTTR transgenic mice, in a null mouse TTR background (Maeda, S., (2003), Use of genetically altered mice to study the role of serum amyloid P component in amyloid deposition. Amyloid Suppl. 1, 17-20). Days 3, 8, 15, or 22 post-dose, animals in both treatment groups were given a lethal dose of ketamine/xylazine. Serum samples were collected and stored at −80° C. until analysis. Liver tissue was collected, flash-frozen and stored at −80° C. until processing.

For TTR mRNA quantitation, frozen liver tissue was ground into powder, and lysates were prepared. TTR mRNA levels relative to those of GAPDH mRNA were determined in the lysates by using a branched DNA assay (QuantiGene Reagent System, Panomics, Fremont, Calif.). Briefly, the QuantiGene assay (Genospectra) was used to quantify mRNA levels in tissue sample lysates according to the manufacturer's instructions. The mean level of TTR mRNA was normalized to the mean level of GAPDH mRNA for each sample. Group means of the normalized values were then further normalized to the mean value for the PBS treated group, to obtain the relative level of TTR mRNA expression.

For TTR protein quantitation, serum was assayed using the AssayPro (St. Charles, Mo.) Assaymax PreAlbumin ELISA Kit according to the manufacturer's protocol.

Figure 7B:
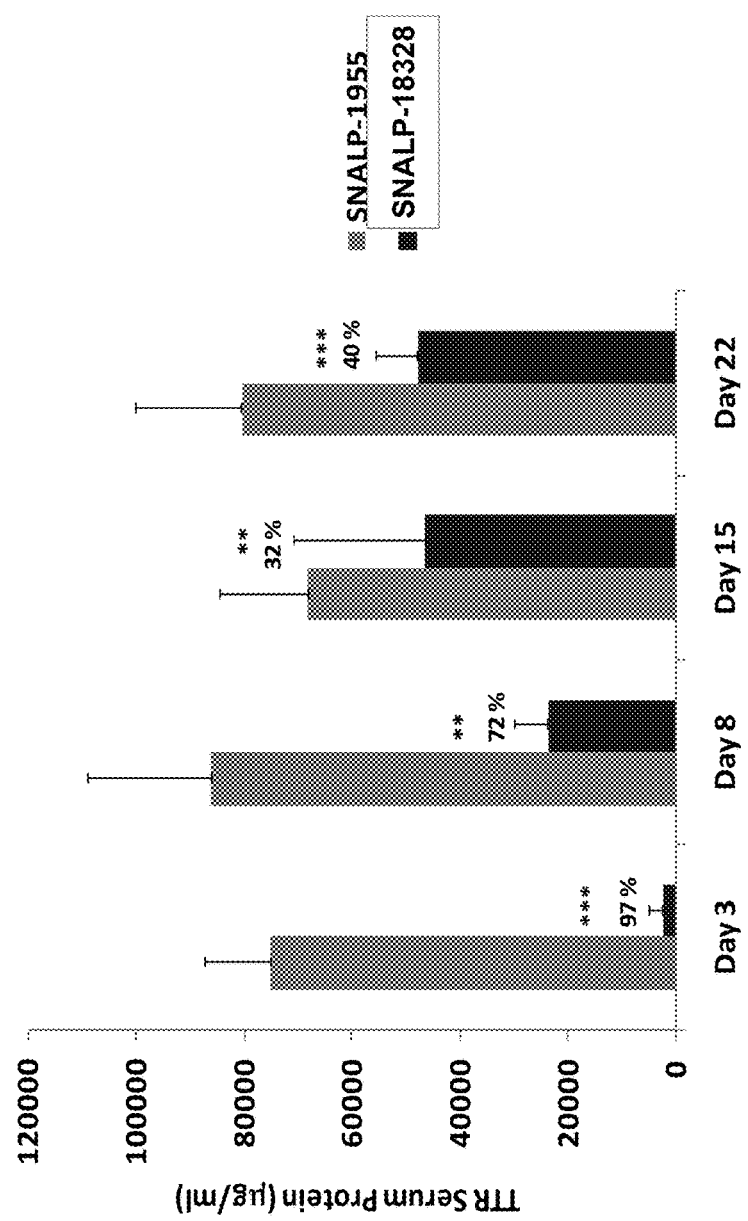

The results are shown in FIG. 7A and FIG. 7B for liver mRNA and serum protein, respectively. A single IV bolus administration of SNALP-18328 in the hTTR V30M transgenic mouse resulted in durable inhibition of TTR mRNA levels in the liver and TTR protein levels in the serum. Compared to the control group (1 mg/ml SNALP-1955), a single IV administration of SNALP-18328 at 1 mg/kg significantly reduced relative TTR mRNA levels on Days 3, 8, 15 and 22 post-dose by 96% ($p<0.001$), 90% ($p<0.001$), 82% ($p<0.001$) and 73% ($p<0.001$), respectively, and did not return to baseline levels at termination of the study (Day 22 post-dose). Protein levels also decreased with a maximum reduction of serum TTR of 97% ($p<0.001$) (relative to SNALP-1955) at Day 3 post-dose. At Days 8, 15, and 22 post-dose, TTR protein levels were suppressed by 72% ($p<0.05$), 32% ($p<0.05$), and 40% ($p<0.001$), respectively, relative to SNALP-1955.

These results demonstrate that a single IV administration of SNALP-18328 produces durable suppression of target liver mRNA and serum protein levels in the V30M hTTR transgenic mouse, with significant reductions of both liver TTR mRNA and serum TTR protein at 22 days post-dose.

Example 8

Durability of Serum TTR Protein Suppression by SNALP-18328 in the Non-Human Primate To evaluate the durability of serum TTR protein suppression by SNALP-18328, AD-18328 was formulated in SNALP and administered by IV infusion to non-human primates. At various timepoints post-dose, serum TTR protein levels were quantified.

Cynomolgus monkeys (*Macaca fascicularis*) (n=5 animals/group for SNALP-18328 groups and n=3 animals/group for SNALP-1955 and PBS groups) were administered a 15-minute IV infusion of SNALP-18328 (0.3, 1 or 3 mg/kg), SNALP-1955 (3 mg/kg) with negative control siRNA AD-1955 which targets the non-mammalian gene luciferase), or PBS. At Days 0, 1, 2, 3, 4, 5, 7, 10, and 14 of the dosing phase, serum samples were collected and stored at −80° C. until analysis.

Western blot analysis was used to evaluate TTR protein levels in serum samples. Serum samples from each group were pooled and diluted 1:1 with Laemmli sample buffer (β-mercaptoethanol was added at a 1:20 dilution). The samples were heated at 95° C. for 10 minutes. 12.5 µl of each sample was loaded in each lane of a 10-20% Criterion (Biorad, Hercules, Calif.) prep gel and separated by SDS-PAGE at 120V for 1.5 hrs, then transferred to a nitrocellulose membrane using a semi-dry system at 15V for 1 hour. The membrane was blocked overnight at 4° C. in LiCOR (Lincoln, Nebr.) blocking buffer diluted 1:1 with 1×PBS. The blot was probed first with primary antibodies (goat anti-TTR from Santa Cruz (Santa Cruz, Calif.) at a dilution of 1:1000 diluted in LiCOR blocking buffer/PBS on a rocker for 1 hr at room temperature. Blots were washed 4× with PBS+0.2% Tween 20 (10 minutes per wash). The fluorescent labeled secondary antibodies (anti-goat 680 nm from Invitrogen (Carlsbad, Calif.) were added at a dilution of 1:10,000 in LiCOR blocking buffer/PBS and the blot was incubated for 1 hour at room temperature. After incubation, blots were washed 4× with PBS+0.2% Tween 20 followed by one wash with 1×PBS. The Li-COR's Odyssey Infrared Imaging System was used to detect the protein bands. TTR monomer migrates at 15 kDa.

Figure 8:
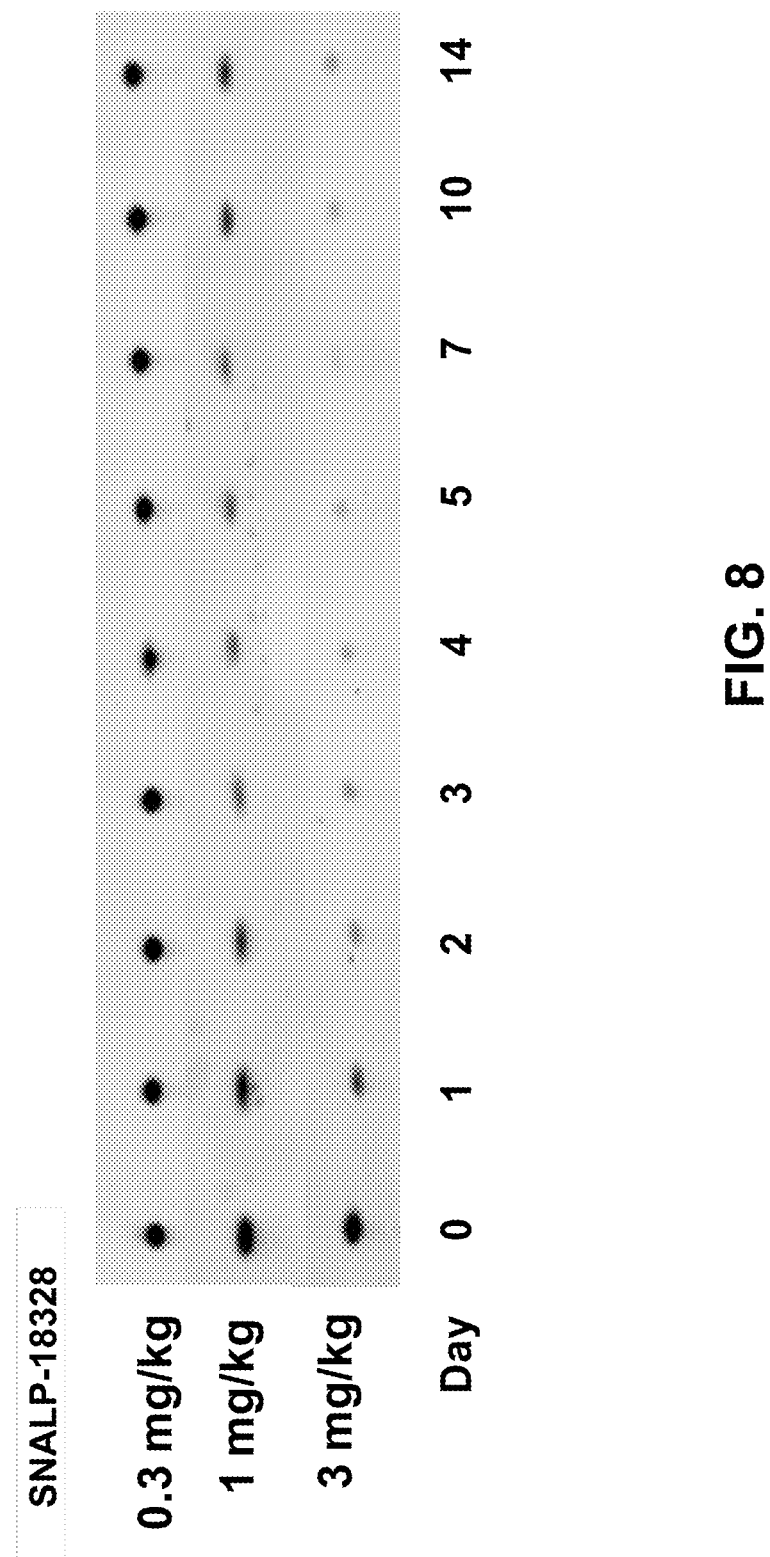
FIG. 8 shows the timecourse of TTR serum protein levels in non-human primates over 14 days following a single 15-minute intravenous infusion of SNALP-18328.

The results are shown in FIG. 8. Serum TTR protein levels showed a dose-dependent reduction with 1 or 3 mg/kg SNALP-18328, as compared to pre-dose (Day 0) levels. The duration of suppression, following a single IV administration of SNALP-18328 is at least 14 days after 1 or 3 mg/kg SNALP-18328 treatment.

These results demonstrate that a single IV administration of SNALP-18328 produces durable suppression of TTR protein in the circulation in the non-human primate (*Macaca fascicularis*), with significant reduction of TTR protein at 14 days post-dose.

Example 9

In Vivo Reduction of Mutant (V30M) TTR in Peripheral Tissues by SNALP-18328 in the Transgenic Mouse To evaluate the efficacy of SNALP-18328 in reducing TTR in peripheral tissues, hTTR V30M/HSF-1 knock-out mice were evaluated with immunohistochemical staining for TTR. Two-month old hTTR V30M/HSF-1 knock-out mice (Maeda, S., (2003), Use of genetically altered mice to study the role of serum amyloid P component in amyloid deposition. *Amyloid Suppl.* 1, 17-20) were administered an IV bolus of 3 mg/kg SNALP-18328 (12 animals), 3 mg/kg SNALP-1955 (with negative control siRNA AD-1955 which targets the non-mammalian gene luciferase, 4 animals), or PBS (4 animals) once every two weeks for a total of four doses on days 0, 14, 28, and 42. TTR liver mRNA levels and TTR-immunoreactivity in multiple peripheral tissues were evaluated at 8 weeks post-first dose on day 56.

Mice were anesthetised with 1 mg/kg medetomidine, and given a lethal dose of ketamine. Tissues and organs of interest were collected. For immunohistochemistry, esophagus (E), stomach (S), intestine (duodenum (I1) and colon (I4)), nerve (N) and dorsal root ganglia (D) were fixed in neutral buffered formalin and embedded in paraffin. For TTR detection, rabbit anti-human TTR primary antibody (1:1000, DAKO, Denmark), and anti-rabbit biotin-conjugated secondary antibody (1:20 Sigma, USA) were followed by extravidin labelling (1:20, Sigma, USA) in order to stain for the TTR protein. The reaction was developed with 3-amino-9-ethyl carbaxole, AEC (Sigma, USA). Semi-quantitative analysis of immunohistochemical slides was performed using Scion image quant program that measures the area occupied by the substrate reaction color and normalizes this value to the total image area. Mean values of % occupied area are displayed with the corresponding standard deviation. Each animal tissue was evaluated in four different areas. The presence of human TTR in parasympathetic ganglia of the stomach and intestine was studied by double immunofluorescent staining with rabbit anti-human TTR (1:1000, DAKO, Denmark) and mouse anti-PGP9.5 (1:40, Serotec, USA) as the primary antibodies; secondary antibodies were, respectively: anti-rabbit Alexa Fluor 488 (Molecular probes, UK) and goat anti-mouse Alexa Fluor 568 (Molecular probes, UK). Slides were mounted with vectashield (Vector) and visualized in a Zeiss Cell Observer System microscope (Carl Zeiss, Germany) equipped with filters for FITC and rhodamine.

Figure 9:
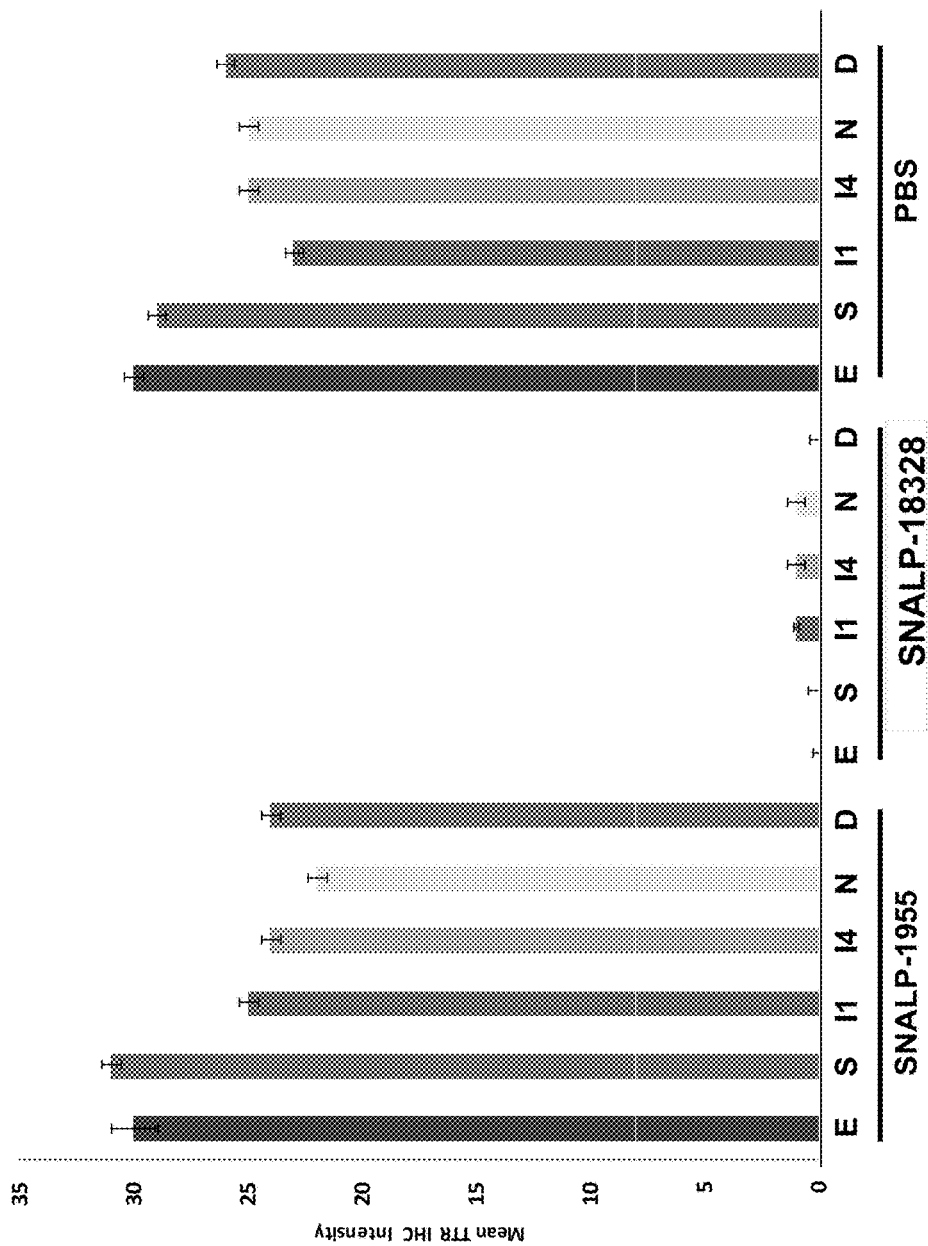
FIG. 9 shows reduction of TTR-immunoreactivity in various tissues of human V30M TTR/HSF-1 knock-out mice following intravenous bolus administration of SNALP-18328. E, esophagus; S, stomach; I1, intestine/duodenum; I4, intestine/colon; N, nerve; D, dorsal root ganglia.

The results are graphed in FIG. 9. In contrast with PBS and SNALP-1955 treated animals, SNALP-18328 treated animals had a significant reduction of TTR-immunoreactivity in all tissues examined (esophagus (E), stomach (S), intestine (duodenum (I1) and colon (I4)), nerve (N) and dorsal root ganglia (D).

These results demonstrate that SNALP-18328 administration to hTTR V30M/HSF-1 knock-out mice causes a significant reduction of TTR protein in peripheral tissues and organs, including esophagus, stomach, intestine (duodenum and colon), nerve, and dorsal root ganglion.

Example 10

In Vivo Reduction of Wild-Type TTR mRNA in the Non-Human Primate Liver by XTC-SNALP-18328

To evaluate the efficacy of the novel lipid nanoparticle formulation XTC-SNALP for delivery of siRNA in non-human primate, TTR siRNA AD-18328 was formulated in XTC-SNALP (XTC-SNALP-18328) and administered by 15-minute IV infusion, and liver TTR mRNA was quantified. Cynomolgus monkeys (*Macaca fascicularis*) were administered 15-minute IV infusions of XTC-SNALP-18328 (0.03, 0.1, 0.3 or 1 mg/kg) or XTC-SNALP-1955 (1 mg/kg, with negative control siRNA AD-1955 which targets the non-mammalian gene luciferase). At forty-eight hours post-dosing, monkeys were anesthetized with sodium pentobarbital and exsanguinated. Liver tissue for TTR mRNA determination was collected, flash-frozen, and stored at −80° C. until processing. Methods used for TTR mRNA quantitation in liver tissue were similar to those described in Example 5 above.

Figure 10:
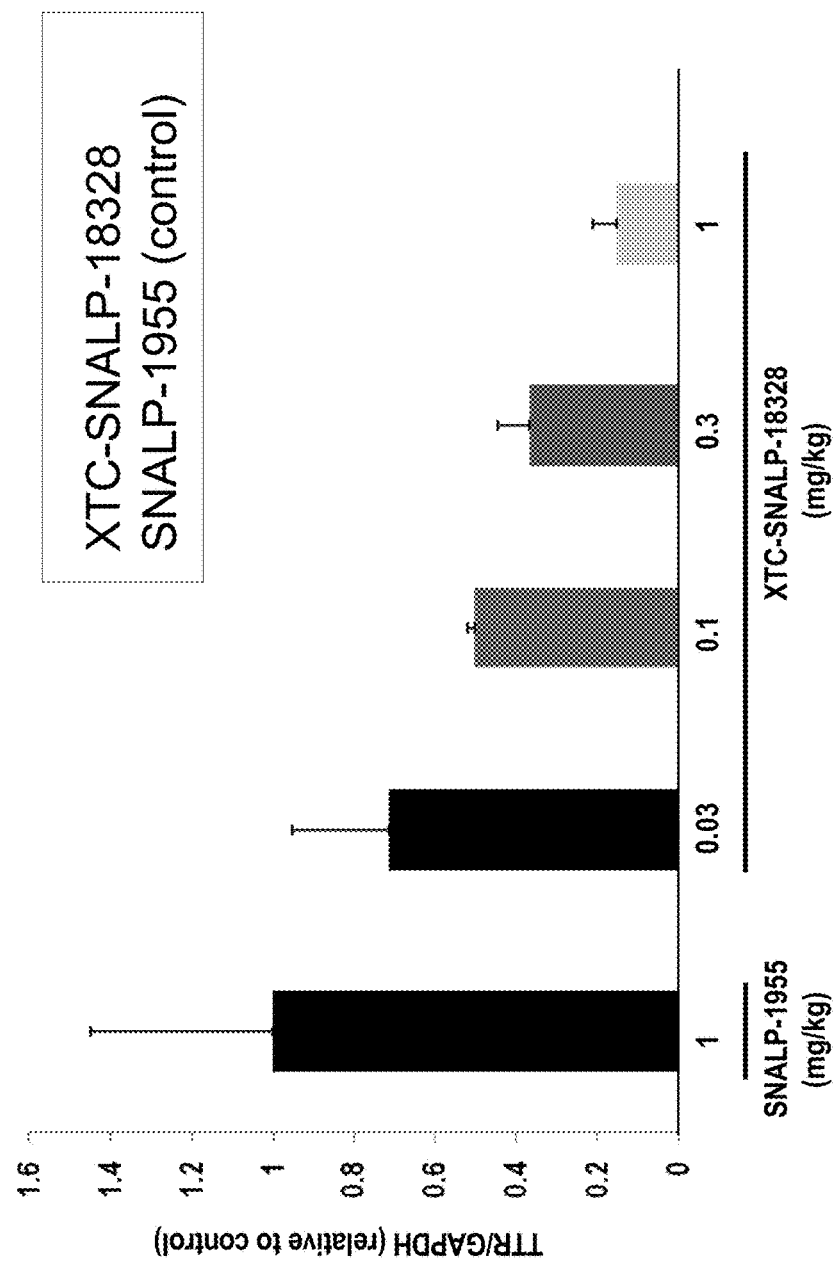
FIG. 10 shows the measurements of TTR mRNA levels in livers of non-human primates following 15-minute intravenous infusion of XTC-SNALP-18328.

The results are shown in FIG. 10. XTC-SNALP-18328 reduced TTR mRNA levels in the liver in a dose-dependent manner, compared to the negative control XTC-SNALP-1955. The mRNA ED50 was determined to be ~0.1 mg/kg XTC-SNALP-18328.

These results demonstrate that XTC-SNALP-18328 is effective in suppressing wild-type TTR mRNA in non-human primate liver when administered by IV infusion.

Example 11

In Vivo Reduction of Wild-Type TTR mRNA in the Non-Human Primate Liver by LNP09-18328 and LNP11-18328

To evaluate the efficacy of two novel lipid nanoparticle formulations, LNP09 and LNP11, for delivery of siRNA in non-human primate, TTR siRNA AD-18328 was formulated in LNP09 (LNP09-18328) or LNP11 (LNP11-18328), and administered by 15-minute IV infusion, and liver TTR mRNA and serum TTR protein levels were assayed. Cynomolgus monkeys (*Macaca fascicularis*) were administered 15-minute IV infusions of LNP09-18328 (0.03, 0.1, or 0.3 mg/kg), LNP11-18328 (0.03, 0.1, or 0.3 mg/kg), or PBS. Liver biopsy samples were collected at 48 hrs post-dosing, flash-frozen, and stored at −80° C. until processing. Serum was collected before dosing (pre-bleed), and on Days 1, 2, 4, 7, 14, 21 and 28 post-dosing and stored at −80° C. until processing. Methods used for TTR mRNA quantitation in liver tissue and serum TTR protein evaluation were similar to those described in Examples 5 and 8 above.

Figure 11B:
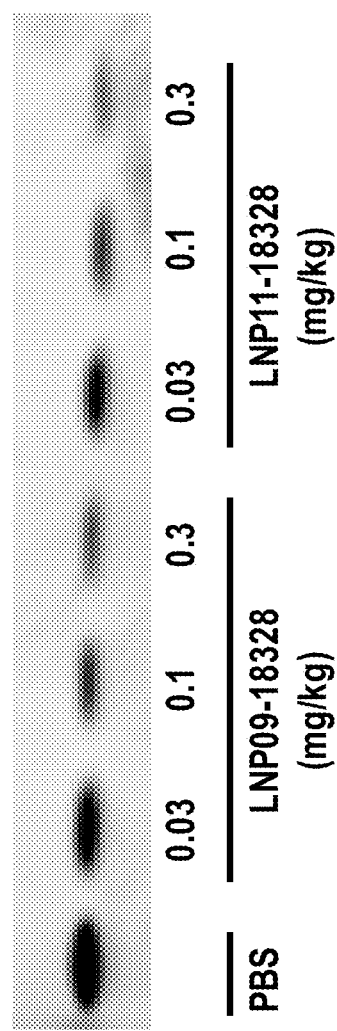
Figure 11C:
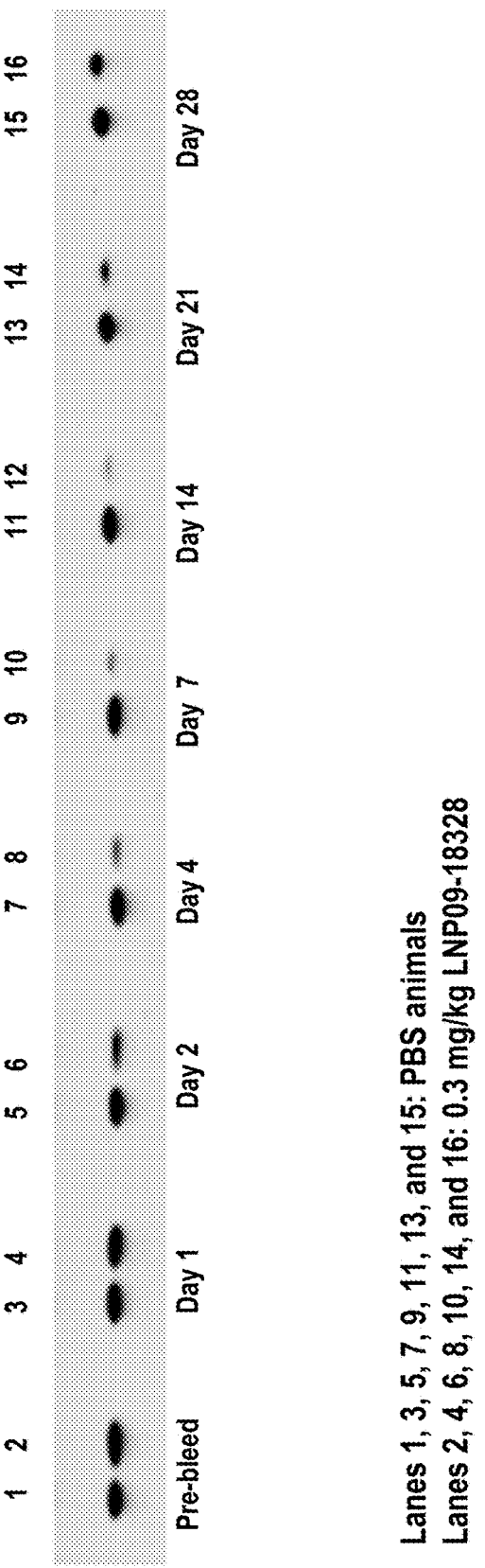
FIG. 11C shows the timecourse of TTR serum protein levels over 28 days following a 15-minute intravenous infusion of 0.3 mg/kg LNP09-18328, as compared to the PBS control group.

The results are shown in FIG. 11A for mRNA, and in FIG. 11B and FIG. 11C for protein. LNP09-18328 and LNP11-18328 treated animals showed a dose-dependent decrease in TTR mRNA levels in the liver, reaching a maximum reduction at 0.3 mg/kg of ~85% (LNP09-18328) and ~90% (LNP11-18328) mRNA relative to the PBS control. The mRNA ED50 was determined to be ~0.02 mg/kg for both LNP09-18328 and LNP11-18328. At Day 7 post-dosing, serum samples also exhibited a dose-dependent reduction of TTR protein for 0.1 and 0.3 mg/kg LNP09-18328 and LNP11-18328, compared to PBS control levels. FIG. 11C shows a decrease in TTR protein levels with a 0.3 mg/kg dose of LNP09-18328 that persisted over at least 28 days post-dosing, as compared to the PBS control group and as compared with the pre-bleed samples.

These results demonstrate that LNP09-18328 and LNP11-18328 are effective in suppressing wild-type TTR mRNA in non-human primate liver and wild-type TTR protein in the circulation, when administered by IV infusion. Furthermore, the suppression with LN09-18328 is durable, persisting for at least 28 days following the IV infusion.

Example 12

Synthesis of TTR Tiled Sequences

A set of TTR duplexes ("tiled duplexes") were designed that targeted the TTR gene near the target region of AD-18328, which targets the human TTR gene starting at nucleotide 628 of NM_000371.3.

Figure 14:
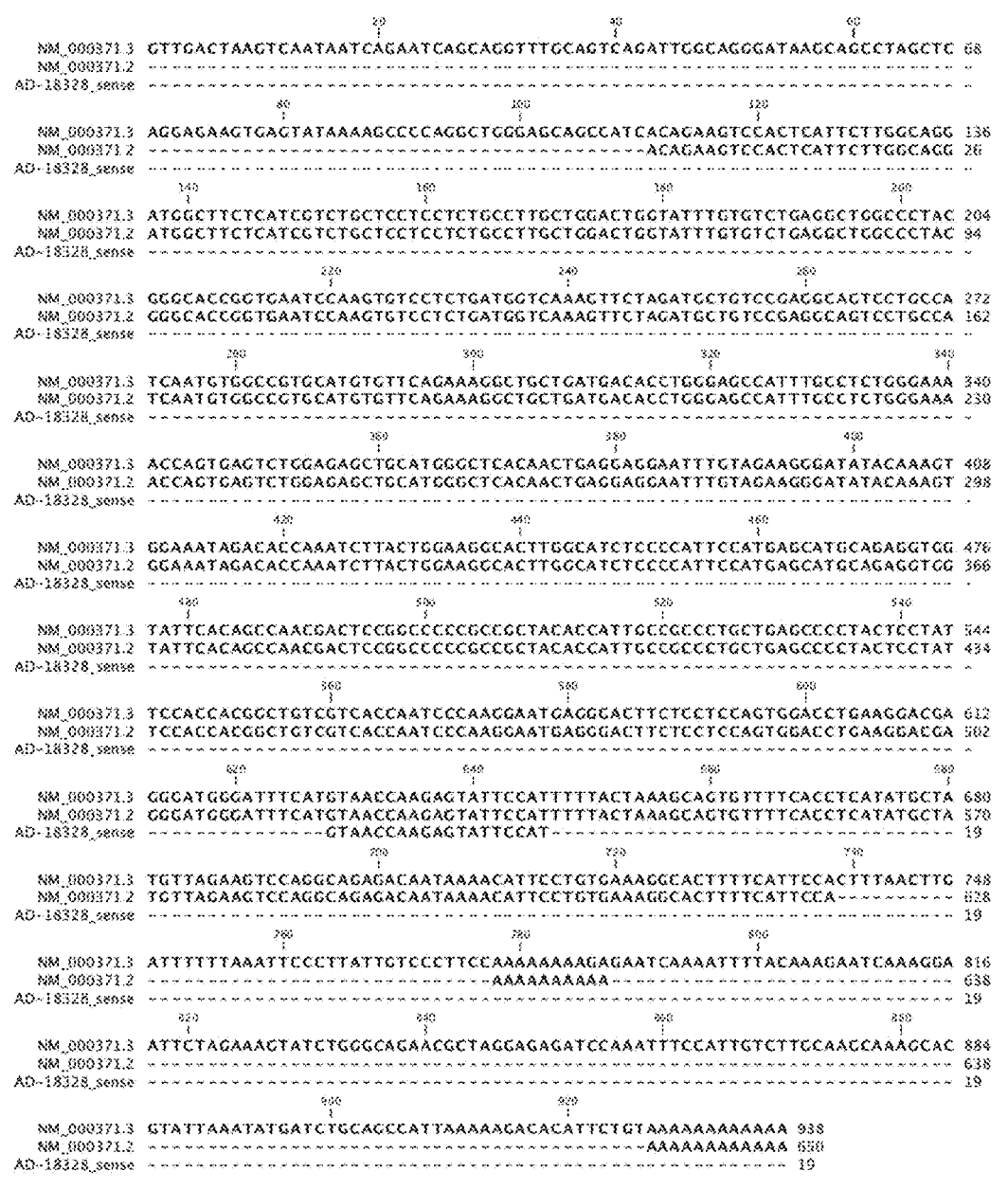

In the examples below, the numbering representing the position of the 5' base of an siRNA on the transcript is based on NM_000371.3 (FIG. 12; SEQ ID NO:1331). In the examples shown above, the numbering for siRNA targeting human siRNA was based on NM_000371.2 (FIG. 13A). NM_000371.3 extends the sequence of the 5' UTR by 110 bases compared to NM_000371.2, as shown in FIG. 14. Thus, as an example, the starting position of AD-18328 is 628 on NM_000371.3 and 518 on NM_000371.2 (FIG. 14).

TTR tiled sequences were synthesized on MerMade 192 synthesizer at 1 umol scale. For all the sequences in the list, 'endolight' chemistry was applied as detailed below.

All pyrimidines (cytosine and uridine) in the sense strand contained 2'-O-Methyl bases (2' O-Methyl C and 2'-O-Methyl U)

In the antisense strand, pyrimidines adjacent to (towards 5' position) ribo A nucleoside were replaced with their corresponding 2-O-Methyl nucleosides A two base dTdT extension at 3' end of both sense and anti sense sequences was introduced The sequence file was converted to a text file to make it compatible for loading in the MerMade 192 synthesis software Synthesis, Cleavage and Deprotection:

The synthesis of TTR sequences used solid supported oligonucleotide synthesis using phosphoramidite chemistry. The synthesis of the sequences was performed at 1 um scale in 96 well plates. The amidite solutions were prepared at 0.1M concentration and ethyl thio tetrazole (0.6M in Acetonitrile) was used as activator. The synthesized sequences were cleaved and deprotected in 96 well plates, using methylamine in the first step and fluoride reagent in the second step. The crude sequences were precipitated using acetone:ethanol (80:20) mix and the pellet were re-suspended in 0.2M sodium acetate buffer. Samples from each sequence were analyzed by LC-MS to confirm the identity, UV for quantification and a selected set of samples by IEX chromatography to determine purity.

Purification and Desalting:

TTR tiled sequences were purified on AKTA explorer purification system using Source 15Q column. A column temperature of 65 C was maintained during purification. Sample injection and collection was performed in 96 well (1.8 mL-deep well) plates. A single peak corresponding to the full length sequence was collected in the eluent. The purified sequences were desalted on a Sephadex G25 column using AKTA purifier. The desalted TTR sequences were analyzed for concentration (by UV measurement at A260) and purity (by ion exchange HPLC). The single strands were then submitted for annealing.

TTR Single Strands and Duplexes:

A detailed list of TTR tiled duplexes and corresponding single strands (sense and antisense) are shown in the table below (Table 13).

TABLE 13

TTR tiled duplexes and corresponding single strands

| Duplex # | Position | Oligo # | Strand | Sequence (5' to 3") | SEQ ID NO: |
|---|---|---|---|---|---|
| AD-18323 | 618 | A-32335 | S | GGGAuuuCAuGuAAccAAGdTdT | 1332 |
| | | A-32336 | AS | CUUGGUuAcAUGAAAUCCCdTdT | 1333 |
| AD-18324 | 619 | A-32337 | S | GGAuuuCAuGuAAccAAGAdTdT | 1334 |
| | | A-32338 | AS | UCUUGGUuAcAUGAAAUCCdTdT | 1335 |
| AD-23000 | 620 | A-42927 | S | GAuuuCAuGuAAccAAGAGdTdT | 1336 |
| | | A-42928 | AS | CUCUUGGUuAcAUGAAAUCdTdT | 1337 |
| AD-23001 | 621 | A-42929 | S | AuuuCAuGuAAccAAGAGudTdT | 1338 |
| | | A-42930 | AS | ACUCUUGGUuAcAUGAAAUdTdT | 1339 |
| AD-23002 | 622 | A-42931 | S | uuuCAuGuAAccAAGAGuAdTdT | 1340 |
| | | A-42932 | AS | uACUCUUGGUuAcAUGAAAdTdT | 1341 |
| AD-23003 | 623 | A-42933 | S | uuCAuGuAAccAAGAGuAudTdT | 1342 |
| | | A-42934 | AS | AuACUCUUGGUuAcAUGAAdTdT | 1343 |
| AD-18325 | 624 | A-32339 | S | uCAuGuAAccAAGAGuAuudTdT | 1344 |
| | | A-32340 | AS | AAuACUCUUGGUuAcAUGAdTdT | 1345 |
| AD-23004 | 625 | A-42935 | S | cAuGuAAccAAGAGuAuucdTdT | 1346 |
| | | A-42936 | AS | GAAuACUCUUGGUuAcAUGdTdT | 1347 |
| AD-18326 | 626 | A-32341 | S | AuGuAAccAAGAGuAuuccdTdT | 1348 |
| | | A-32342 | AS | GGAAuACUCUUGGUuAcAUdTdT | 1349 |
| AD-18327 | 627 | A-32343 | S | uGuAAccAAGAGuAuuccAdTdT | 1350 |
| | | A-32344 | AS | UGGAAuACUCUUGGUuAcAdTdT | 1351 |
| AD-23005 | 628 | A-42937 | S | uAAccAAGAGuAuuccAuudTdT | 1352 |
| | | A-42938 | AS | AAUGGAAuACUCUUGGUuAdTdT | 1353 |
| AD-23006 | 629 | A-42939 | S | AAccAAGAGuAuuccAuuudTdT | 1354 |
| | | A-42940 | AS | AAAUGGAAuACUCUUGGUUdTdT | 1355 |
| AD-23007 | 631 | A-42941 | S | AccAAGAGuAuuccAuuuudTdT | 1356 |
| | | A-42942 | AS | AAAAUGGAAuACUCUUGGUdTdT | 1357 |
| AD-23008 | 632 | A-42943 | S | ccAAGAGuAuuccAuuuuudTdT | 1358 |
| | | A-42944 | AS | AAAAAUGGAAuACUCUUGGdTdT | 1359 |
| AD-23009 | 633 | A-42945 | S | cAAGAGuAuuccAuuuuuAdTdT | 1360 |
| | | A-42946 | AS | uAAAAAUGGAAuACUCUUGdTdT | 1361 |
| AD-23010 | 634 | A-42947 | S | AAGAGuAuuccAuuuuuAcdTdT | 1362 |
| | | A-42948 | AS | GuAAAAAUGGAAuACUCUUdTdT | 1363 |

TABLE 13-continued

TTR tiled duplexes and corresponding single strands

| Duplex # | Position | Oligo # | Strand | Sequence (5' to 3") | SEQ ID NO: |
|---|---|---|---|---|---|
| AD-23011 | 635 | A-42949 | S | AGAGuAuccAuuuuuAcudTdT | 1364 |
|  |  | A-42950 | AS | AGuAAAAAUGGAAuACUCUdTdT | 1365 |
| AD-23012 | 636 | A-42951 | S | GAGuAuccAuuuuuAcuAdTdT | 1366 |
|  |  | A-42952 | AS | uAGuAAAAAUGGAAuACUCdTdT | 1367 |
| AD-23013 | 637 | A-42953 | S | AGuAuccAuuuuuAcuAAdTdT | 1368 |
|  |  | A-42954 | AS | UuAGuAAAAAUGGAAuACUdTdT | 1369 |
| AD-23014 | 638 | A-42955 | S | GuAuccAuuuuuAcuAAdTdT | 1370 |
|  |  | A-42956 | AS | UUuAGuAAAAAUGGAAuACdTdT | 1371 |
| AD-23015 | 639 | A-42957 | S | uAuccAuuuuuAcuAAAGdTdT | 1372 |
|  |  | A-42958 | AS | CUUuAGuAAAAAUGGAAuAdTdT | 1373 |
| AD-23016 | 640 | A-42959 | S | AuccAuuuuuAcuAAAGcdTdT | 1374 |
|  |  | A-42960 | AS | GCUUuAGuAAAAAUGGAAUdTdT | 1375 |
| AD-23017 | 641 | A-42961 | S | uccAuuuuuAcuAAAGcAdTdT | 1376 |
|  |  | A-42962 | AS | UGCUUuAGuAAAAAUGGAAdTdT | 1377 |
| AD-23018 | 642 | A-42963 | S | uccAuuuuuAcuAAAGcAGdTdT | 1378 |
|  |  | A-42964 | AS | CUGCUUuAGuAAAAAUGGAdTdT | 1379 |
| AD-23019 | 643 | A-42965 | S | ccAuuuuuAcuAAAGcAGudTdT | 1380 |
|  |  | A-42966 | AS | ACUGCUUuAGuAAAAAUGGdTdT | 1381 |
| AD-23020 | 644 | A-42967 | S | cAuuuuuAcuAAAGcAGuGdTdT | 1382 |
|  |  | A-42968 | AS | cACUGCUUuAGuAAAAAUGdTdT | 1383 |
| AD-23021 | 645 | A-42969 | S | AuuuuuAcuAAAGcAGuGudTdT | 1384 |
|  |  | A-42970 | AS | AcACUGCUUuAGuAAAAAUdTdT | 1385 |
| AD-23022 | 646 | A-42971 | S | uuuuuAcuAAAGcAGuGuudTdT | 1386 |
|  |  | A-42972 | AS | AAcACUGCUUuAGuAAAAAdTdT | 1387 |
| AD-23023 | 647 | A-42973 | S | uuuuAcuAAAGcAGuGuuudTdT | 1388 |
|  |  | A-42974 | AS | AAAcACUGCUUuAGuAAAAdTdT | 1389 |
| AD-23024 | 648 | A-42975 | S | uuuAcuAAAGcAGuGuuuudTdT | 1390 |
|  |  | A-42976 | AS | AAAAcACUGCUUuAGuAAAdTdT | 1391 |
| AD-23025 | 649 | A-42977 | S | uuAcuAAAGcAGuGuuuucdTdT | 1392 |
|  |  | A-42978 | AS | GAAAAcACUGCUUuAGuAAdTdT | 1393 |
| AD-23026 | 650 | A-42979 | S | uAcuAAAGcAGuGuuuucAdTdT | 1394 |
|  |  | A-42980 | AS | UGAAAAcACUGCUUuAGuAdTdT | 1395 |
| AD-23027 | 651 | A-42981 | S | AcuAAAGcAGuGuuuucAcdTdT | 1396 |
|  |  | A-42982 | AS | GUGAAAAcACUGCUUuAGUdTdT | 1397 |
| AD-23028 | 652 | A-42983 | S | cuAAAGcAGuGuuuucAccdTdT | 1398 |
|  |  | A-42984 | AS | GGUGAAAAcACUGCUUuAGdTdT | 1399 |
| AD-18330 | 653 | A-32349 | S | uAAAGcAGuGuuuucAccudTdT | 1400 |
|  |  | A-32350 | AS | AGGUGAAAAcACUGCUUuAGdTdT | 1401 |
| AD-23029 | 654 | A-42985 | S | AAAGcAGuGuuuucAccucdTdT | 1402 |
|  |  | A-42986 | AS | GAGGUGAAAAcACUGCUUUdTdT | 1403 |
| AD-23030 | 655 | A-42987 | S | AAGcAGuGuuuucAccucAdTdT | 1404 |
|  |  | A-42988 | AS | UGAGGUGAAAAcACUGCUUdTdT | 1405 |
| AD-23031 | 656 | A-42989 | S | AGcAGuGuuuucAccucAudTdT | 1406 |
|  |  | A-42990 | AS | AUGAGGUGAAAAcACUGCUdTdT | 1407 |
| AD-18328 | 628 | A-32345 | S | GuAAccAAGAGuAuuccAudTdT | 1408 |
|  |  | A-32346 | AS | AUGGAAuACUCUUGGUuACdTdT | 1409 |

Strand:
s = sense;
as = antisense;
Position: position of 5' base on transcript (NM_000371.3, SEQ ID NO: 1331).

Example 13

In Vitro Screening of TTR Tiled siRNAs

Tiled TTR duplexes were assayed in Hep3B cells for inhibition of endogenous TTR expression using real time PCR assays.

Cell culture and transfection: Hep3B cells (ATCC, Manassas, Va.) were grown to near confluence at 37° C. in an atmosphere of 5% $CO_2$ in Eagle's Minimum Essential Medium (EMEM, ATCC) supplemented with 10% FBS, streptomycin, and glutamine (ATCC) before being released from the plate by trypsinization. Reverse transfection was carried out by adding 5 µl of Opti-MEM to 5 µl of each siRNA in individual wells of a 96-well plate. To this 10 µl of Opti-MEM plus 0.2 µl of Lipofectamine RNAiMax was added per well (Invitrogen, Carlsbad Calif. cat #13778-150) and the mixture was incubated at room temperature for 15 minutes. 80 µl of complete growth media described above, but without antibiotic containing $2.0 \times 10^4$ Hep3B cells were then added. Cells were incubated for 24 hours prior to RNA purification. Experiments were performed at 0.1 or 10 nM final duplex concentration.

Total RNA isolation using MagMAX-96 Total RNA Isolation Kit (Applied Biosystems, Foster City Calif., part #: AM1830): Cells were harvested and lysed in 140 µl of Lysis/Binding Solution then mixed for 1 minute at 850 rpm using and Eppendorf Thermomixer (the mixing speed was the same throughout the process). Twenty micro liters of magnetic beads and Lysis/Binding Enhancer mixture were added into cell-lysate and mixed for 5 minutes. Magnetic beads were captured using magnetic stand and the supernatant was removed without disturbing the beads. After removing supernatant, magnetic beads were washed with Wash Solution 1 (isopropanol added) and mixed for 1 minute. Beads were capture again and supernatant removed. Beads were then washed with 150 µl Wash Solution 2 (Ethanol added), captured and supernatant was removed. 50 µl of DNase mixture (MagMax turbo DNase Buffer and Turbo DNase) was then added to the beads and they were mixed for 10 to 15 minutes. After mixing, 100 µl of RNA Rebinding Solution was added and mixed for 3 minutes. Supernatant was removed and magnetic beads were washed again with 150 µl Wash Solution 2 and mixed for 1 minute and supernatant was removed completely. The magnetic beads were mixed for 2 minutes to dry before RNA was eluted with 50 µl of water.

cDNA synthesis using ABI High capacity cDNA reverse transcription kit (Applied Biosystems, Foster City, Calif., Cat #4368813): A master mix of 2 µl 10× Buffer, 0.8 µl 25× dNTPs, 2 µl Random primers, 1 µl Reverse Transcriptase, 1 µl RNase inhibitor and 3.2 µl of H2O per reaction were added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Real time PCR: 2 µl of cDNA were added to a master mix containing 0.5 µl GAPDH TaqMan Probe (Applied Biosystems Cat #4326317E), 0.5 µl TTR TaqMan probe (Applied Biosystems cat #HS00174914 M1) and 10 µl Roche Probes Master Mix (Roche Cat #04887301001) per well in a LightCycler 480 384 well plate (Roche cat #0472974001). Real time PCR was done in a LightCycler 480 Real Time PCR machine (Roche). Each duplex was tested in two independent transfections and each transfection was assayed in duplicate.

Real time data were analyzed using the ΔΔCt method. Each sample was normalized to GAPDH expression and knockdown was assessed relative to cells transfected with the non-targeting duplex AD-1955. Table 14 shows the knockdown of TTR using the siRNAs. Data are expressed as the percent of message remaining relative to cells targeted with AD-1955.

Many but not all tiled TTR-dsRNAs, targeting TTR near the target of AD-18328, reduced TTR mRNA by at least 70% when transfected into Hep3B cells at 0.1 nM.

TABLE 14

Inhibition of TTR by tiled dsRNA targeting TTR near target of AD-18328.

| Duplex # | % message remaining 0.1 nM | % SD 0.1 nM | % message remaining 10 nM | % SD 10 nM |
|---|---|---|---|---|
| AD-18323 | 6.7 | 1.90 | 1.7 | 0.02 |
| AD-18324 | 1.8 | 0.58 | 0.9 | 0.10 |
| AD-23000 | 5.5 | 0.93 | 2.1 | 0.87 |
| AD-23001 | 15.2 | 4.89 | 4.9 | 1.74 |
| AD-23002 | 3.1 | 1.12 | 1.4 | 0.55 |
| AD-23003 | 17.3 | 3.13 | 1.7 | 0.06 |
| AD-18325 | 1.5 | 0.27 | 1.4 | 0.66 |
| AD-23004 | 9.0 | 0.15 | 10.5 | 0.96 |
| AD-18326 | 22.0 | 1.85 | 7.6 | 0.78 |
| AD-18327 | 11.6 | 2.64 | 9.6 | 1.67 |
| AD-18328 | 1.1 | 0.70 | 0.6 | 0.16 |
| AD-23005 | 0.8 | 0.31 | 0.6 | 0.21 |
| AD-23006 | 1.5 | 0.46 | 1.2 | 0.43 |
| AD-23007 | 2.4 | 0.91 | 1.9 | 0.46 |
| AD-23008 | 0.6 | 0.10 | 0.8 | 0.26 |
| AD-23009 | 1.0 | 0.13 | 0.9 | 0.22 |
| AD-23010 | 60.1 | 15.66 | 66.2 | 22.71 |
| AD-23011 | 56.5 | 16.99 | 53.6 | 4.70 |
| AD-23012 | 7.7 | 2.36 | 7.7 | 3.25 |
| AD-23013 | 7.0 | 0.64 | 8.0 | 1.06 |
| AD-23014 | 0.7 | 0.01 | 0.6 | 0.10 |
| AD-23015 | 15.4 | 0.25 | 16.5 | 7.07 |
| AD-23016 | 27.1 | 0.37 | 6.7 | 1.80 |
| AD-23017 | 4.5 | 1.26 | 1.4 | 0.40 |
| AD-23018 | 44.6 | 9.45 | 7.5 | 1.09 |
| AD-23019 | 2.2 | 0.68 | 0.8 | 0.10 |
| AD-23020 | 52.7 | 6.45 | 29.7 | 1.17 |
| AD-23021 | 95.4 | 16.16 | 45.0 | 3.00 |
| AD-23022 | 70.1 | 3.01 | 60.8 | 12.11 |
| AD-23023 | 2.7 | 1.12 | 1.8 | 0.07 |
| AD-23024 | 1.7 | 0.30 | 1.8 | 0.33 |
| AD-23025 | 64.2 | 13.21 | 10.5 | 1.34 |
| AD-23026 | 1.9 | 0.15 | 1.9 | 0.78 |
| AD-23027 | 2.5 | 0.21 | 1.6 | 0.49 |
| AD-23028 | 6.7 | 4.41 | 1.2 | 0.50 |
| AD-18330 | 6.0 | 0.56 | 5.7 | 1.15 |
| AD-23029 | 4.5 | 0.47 | 1.6 | 0.10 |
| AD-23030 | 3.9 | 0.25 | 3.3 | 0.84 |
| AD-23031 | 3.4 | 0.78 | 1.7 | 0.02 |

Example 14

Evaluation of Infusion Duration on Efficacy of a Single Intravenous Administration of SNALP-18534 in Sprague-Dawley Rats Objectives To determine the effect of infusion duration on efficacy of a single IV infusion of SNALP-18534 on liver TTR mRNA levels in Sprague-Dawley rats.

TABLE 15

Abbreviations and definitions used

| | |
|---|---|
| SNALP-18534 | Rodent transthyretin specific siRNA formulated in SNALP |

TABLE 15-continued

Abbreviations and definitions used

| | |
|---|---|
| SNALP-1955 | Non-mammalian luciferase specific siRNA formulated in SNALP |

The sequences of the sense and antisense strands of AD-18534 are reproduced below from the tables above:

| Strand | Oligo # | Position | Sequence 5' to 3' | SEQ ID NO: |
|---|---|---|---|---|
| s | A-32755 | 532 | cAGuGuucuuGc ucuAuAAdTdT | 1289 |
| as | A-32756 | 550 | UuAuAGAGcAAG AAcACUGdTdT | 1290 |

Study Materials
Test Article(s)

SNALP-18534 is comprised of an siRNA targeting rodent TTR mRNA (AD-18534), formulated in stable nucleic acid lipid particles (SNALP) for delivery to target tissues. The SNALP formulation (lipid particle) consists of a novel aminolipid (DLinDMA), a PEGylated lipid (mPEG2000-C-DMA), a neutral lipid (DPPC) and cholesterol. The ratio of lipid:nucleic acid in the SNALP formulation is approximately 5.8:1 (w:w). SNALP-1955 contains an siRNA targeting the non-mammalian luciferase mRNA, is formulated with the identical lipid particle as SNALP-18534, and serves as a non-pharmacologically active control. Dose levels are expressed as mg/kg based on the weight of siRNA content.

Study Design & Procedures
Animals and Test Article Administration:

The study was comprised of 9 groups of Sprague-Dawley rats (4 males/group). The animals were allowed to have at least a 2 day acclimation period before the study and all animals were 7 weeks old at the initiation of dosing. The dose administered was calculated based upon body weight data collected prior to dosing on Day 1. The test and control articles were administered as a single 15-minute, 1-hour, 2-hour, or 3-hour IV infusion via the tail vein using a 24G ¾" cannula sealed with a Baxter Injection Site septum connected via 27G Terumo butterfly needle to a Baxter AS40A Syringe Pump. The dose volume was 3 ml/kg, the infusion rate was 12 ml/kg/hr, and animals were freely moving in the cages during dosing. Rats were divided into nine treatment groups and administered a single IV infusion of SNALP-18534, SNALP-1955, or PBS as shown in Table 16:

TABLE 16

Test Animal Dosage Groups

| Group | N | Test Article | Infusion Duration | Dose |
|---|---|---|---|---|
| A | 4 | PBS | 15 minute | — |
| B | 4 | PBS | 3 hour | — |
| C | 4 | SNALP-1955 | 1 hour | 1 mg/kg |
| D | 4 | SNALP-1955 | 2 hour | 1 mg/kg |
| E | 4 | SNALP-1955 | 3 hour | 1 mg/kg |
| F | 4 | SNALP-18534 | 15 minute | 1 mg/kg |
| G | 4 | SNALP-18534 | 1 hour | 1 mg/kg |
| H | 4 | SNALP-18534 | 2 hour | 1 mg/kg |
| I | 4 | SNALP-18534 | 3 hour | 1 mg/kg |

Tissue Collection and RNA Isolation:

On Day 0, animals were anesthetized by isofluorane inhalation and pre-dosing blood samples were collected into serum separator tubes by retro-orbital bleed. The blood samples were allowed to clot at room temperature for approximately 30 minutes prior to centrifugation at 4° C. Serum samples were then stored at −80° C. until analysis was performed. On Day 3, animals in all nine treatment groups were given a lethal dose of ketamine/xylazine. Blood was collected via caudal vena cava into serum separation tubes, and then allowed to clot at room temperature for approximately 30 minutes prior to centrifugation at 4° C. Serum samples were stored at −80° C. until analysis was performed. Liver tissue was harvested and snap frozen on dry ice. Frozen liver tissue was ground and tissue lysates were prepared for liver mRNA quantitation.

TTR mRNA Quantitation:

TTR mRNA levels relative to those of GAPDH mRNA were determined in the lysates by using a branched DNA assay (QuantiGene Reagent System, Panomics, Fremont, Calif.). Briefly, the QuantiGene assay (Genospectra) was used to quantify mRNA levels in tissue sample lysates according to the manufacturer's instructions. The mean level of TTR mRNA was normalized to the mean level of GAPDH mRNA for each sample.

To obtain the relative level of TTR mRNA expression, group mean values for SNALP-1955 and SNALP-18534 treated groups with 15-minute, 1 hour and 2 hour infusion durations were then normalized to the mean value for the PBS treated group with 15-minute infusion whereas group mean values for SNALP-1955 and SNALP-18534 treated groups with 3 hour infusion duration were then normalized to the mean value for the PBS treated group with 3 hour infusion duration.

Results

Figure 16:
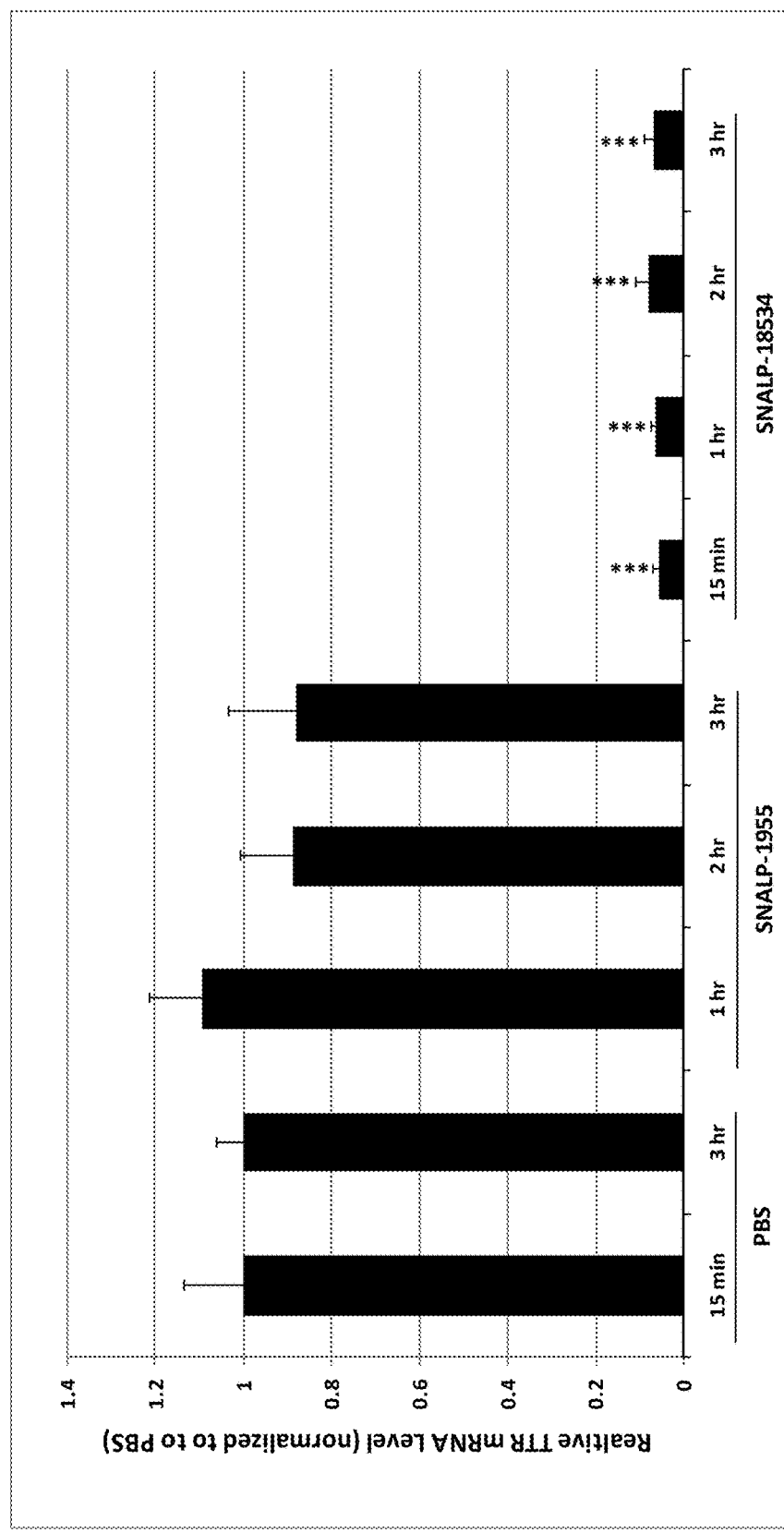
FIG. 16 shows reduction of TTR mRNA levels in the liver with SNALP-18534 with different infusion durations. Groups of animals (n=4/group) were administered 1 mg/kg SNALP-18534 via a 15-minute, or 1, 2, or 3 hour infusion. Forty-eight hours later, rats were euthanized and livers harvested. TTR and GAPDH mRNA levels were measured from liver lysates using the Quantigene bDNA assay. The ratio of TTR to GAPDH mRNA levels was calculated for each animal. Group means were determined and normalized to a PBS control group, and then plotted. Error bars represent standard deviations. (***p<0.001, One-way ANOVA with Bonferroni post-hoc test, relative to PBS).

As shown in FIG. 16, a single IV infusion of 1 mg/kg SNALP-18534 with different infusion durations of 15 minutes to 3 hours results in comparable inhibition of liver TTR mRNA levels measured two days after dosing. A single IV infusion of 1 mg/kg SNALP-18534 also showed durable TTR downregulation over 29 days following a single 15 minute IV infusion, as compared to SNALP-1955 control (data not shown). Compared to the PBS-treated group, a single 15-minute, 1-hour, 2-hour, or 3-hour IV infusion of SNALP-18534 at 1 mg/kg significantly reduced relative TTR mRNA expression levels by 94% ($p<0.001$), 94% ($p<0.001$), 92% ($p<0.001$) and 93% ($p<0.001$), respectively. Specificity of SNALP-18534 activity is demonstrated by lack of significant target inhibition by SNALP-1955 administration via 1-hour, 2-hour, or 3-hour IV infusion at the same dose level.

Conclusions

This study demonstrates that varying the infusion duration from 15 minutes to up to 3 hours does not affect the efficacy of a single IV administration of 1 mg/kg SNALP-18534 in rats, as assessed by reduction of TTR mRNA levels in the liver.

Example 15

In Vivo Reduction of Wild-Type TTR mRNA in the Rat Liver by LNP07-18534 and LNP08-18534

To evaluate the efficacy of 2 novel lipid nanoparticle formulations, LNP07 and LNP08, for delivery of siRNA in the rat, the rodent-specific TTR siRNA, AD-18534, was formulated in LNP07 (LNP07-18534) or LNP08 (LNP08-18534), and administered by 15-minute IV infusion, and liver TTR mRNA was quantified. Sprague-Dawley rats (4 animals per group) were administered 15-minute IV infusions of LNP07-18534 (0.03, 0.1, 0.3 or 1 mg/kg), LNP08-18534 (0.01, 0.03 or 0.1 mg/kg), or LNP07-1955 (1 mg/kg) or LNP08-1955 (0.1 mg/kg) containing the negative control siRNA AD-1955 which targets the non-mammalian gene luciferase. Forty-eight hours later, animals were euthanized and liver tissue was collected, flash-frozen and stored at −80° C. until processing.

For TTR mRNA quantitation, frozen liver tissue was ground into powder, and lysates were prepared. TTR mRNA levels relative to those of GAPDH mRNA were determined in the lysates by using a branched DNA assay (QuantiGene Reagent System, Panomics, Fremont, Calif.). Briefly, the QuantiGene assay (Genospectra) was used to quantify mRNA levels in tissue sample lysates according to the manufacturer's instructions. The mean level of TTR mRNA was normalized to the mean level of GAPDH mRNA for each sample. Group means of the normalized values were then further normalized to the mean value for the PBS treated group, to obtain the relative level of TTR mRNA expression.

Figure 17:
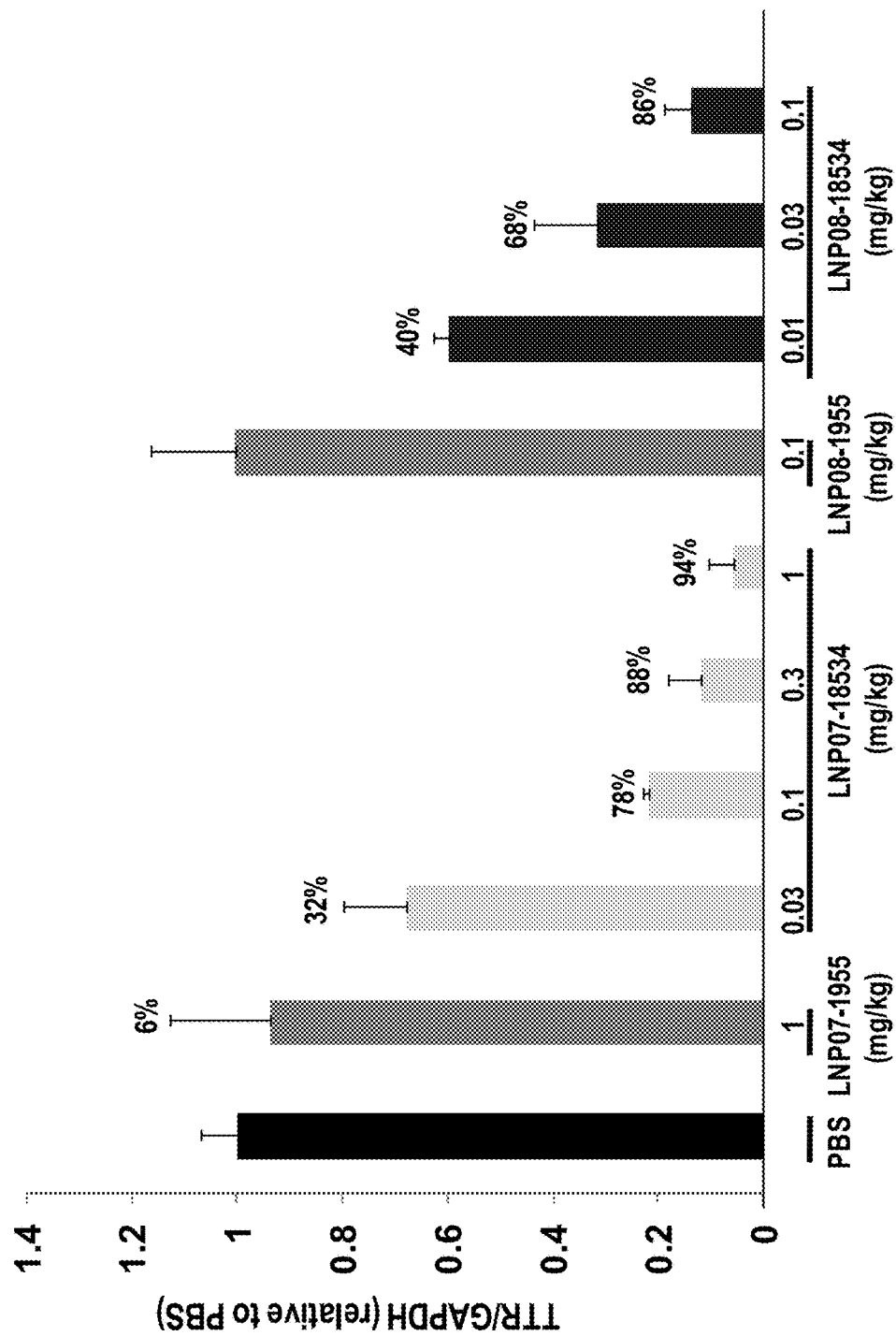
FIG. 17 shows the measurements of TTR mRNA levels in livers of rats following 15-minute intravenous infusion of LNP07-18534 or LNP08-18534.

The results are shown in FIG. 17. LNP07-18534 reduced TTR mRNA levels in the liver in a dose-dependent manner, with 94% suppression of TTR mRNA at 1 mg/kg. The effect was specific, since the negative control LNP07-1955 at 1 mg/kg did not significantly affect TTR mRNA levels compared to the PBS control. The mRNA ED50 was determined to be ~0.05 mg/kg LNP07-18534. LNP08-18534 reduced TTR mRNA levels in the liver in a dose-dependent manner, with 86% suppression of TTR mRNA at 0.1 mg/kg. The effect was specific, since the negative control LNP08-1955 at 0.1 mg/kg did not significantly affect TTR mRNA levels compared to the PBS control. The mRNA ED50 was determined to be ~0.02 mg/kg LNP08-18534.

These results demonstrate that LNP07-18534 and LNP08-18534 are effective in suppressing wild-type TTR mRNA in the rat liver when administered by IV infusion, and that LNP07 and LNP08 are effective formulations for delivering siRNA to the liver.

Example 16

Reduction of TTR Liver mRNA by a Single Intravenous Administration of LNP09-18534 or LNP11-18534 in Sprague-Dawley Rats Objective:

To evaluate the efficacy of two novel lipid nanoparticle (LNP) formulations for delivery of the rodent TTR-specific siRNA, AD-18534 in the Sprague-Dawley rat for reducing endogenous (wild type) liver TTR mRNA levels. Rats were intravenously dosed via a 15 minute infusion with either 0.01, 0.03, 0.1, or 0.3 mg/kg LNP09-18534, LNP11-18534, or phosphate buffered saline (PBS) and TTR liver mRNA levels were assayed at 48 hrs post-treatment.

Material and Methods:

LNP09 formulation: (XTC/DSPC/Chol/PEG$_{2000}$-C-14)=50/10/38.5/1.5 mol %; Lipid: siRNA~11:1. LNP11 formulation: (MC3/DSPC/Chol/PEG$_{2000}$-C14)=50/10/38.5/1.5 mol %; Lipid:siRNA~11.1

Tissue collection and RNA isolation: On Day 3, animals in all treatment groups were given a lethal dose of ketamine/xylazine. Blood was collected via caudal vena cava into serum separation tubes, and then allowed to clot at room temperature for approximately 30 minutes prior to centrifugation at 4° C. Serum samples were stored at −80° C. until for future analysis. Liver tissues were harvested and snap frozen on dry ice. Frozen liver tissue was ground and tissue lysates were prepared for liver mRNA quantitation.

TTR mRNA Quantitation: TTR mRNA levels relative to those of GAPDH mRNA were determined in the lysates by using a branched DNA assay (QuantiGene Reagent System, Panomics, Fremont, Calif.). Briefly, the QuantiGene assay (Genospectra) was used to quantify mRNA levels in tissue sample lysates according to the manufacturer's instructions. The mean level of TTR mRNA was normalized to the mean level of GAPDH mRNA for each sample. Group mean values were then normalized to the mean value for the PBS treated group, to obtain the relative level of TTR mRNA expression.

Figure 18:
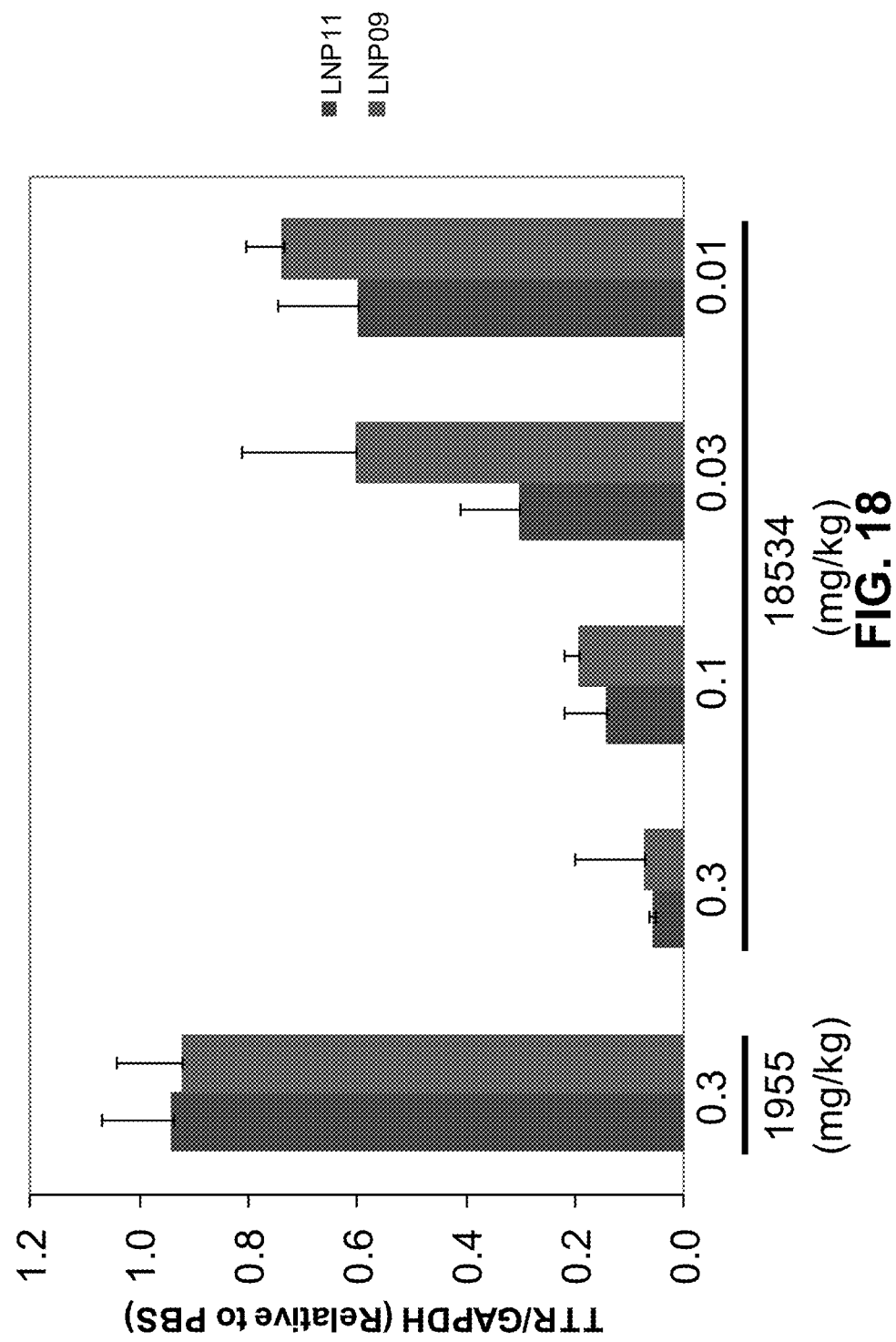
FIG. 18 shows in vivo inhibition of endogenous TTR mRNA levels in livers of Sprague-Dawley Rats following a 15-min IV infusion of LNP09-18534 or LNP11-18534. Groups of animals (n=4/group) were intravenously administered 0.01, 0.03, 0.1, or 0.3 mg/kg LNP09-18534, LNP-11-18534; or PBS via a 15-minute infusion. Forty-eight hours later, animals were euthanized and livers harvested. TTR and GAPDH mRNA levels were measured from liver biopsy lysates using the Quantigene bDNA assay. The ratio of TTR to GAPDH mRNA levels was calculated for each animal. Group means were determined, normalized to the PBS control group, and then plotted. Error bars represent standard deviations.

Results:

As shown in FIG. 18, in contrast with PBS treated animals, LNP09-18534 and LNP11-18534 treated animals had a significant dose-dependent decrease in TTR mRNA levels in the liver, reaching maximum reduction of ~90% mRNA reduction for both LNP09 and LNP11 formulated groups, relative to PBC control group at 0.3 mg/kg, and a dose achieving 50% reduction (ED$_{50}$) of <0.03 mg/kg for LNP11-18534 and <0.1 mg/kg for LNP09-18534.

Conclusions

This study demonstrates that a single 15 minute IV infusion of LNP09-18534 or LNP11-18534 in Sprague-Dawley rats results in a dose-dependent reduction of liver TTR mRNA. These data demonstrate the efficacy of LNP09-18328 and LNP11-18328 in reducing endogenously expressed (wild type) TTR mRNA with ED50 levels of <0.03 and <0.1 mg/kg for LNP11-18534 and LNP09-18534, respectively.

Example 17

Inhibition of TTR in Humans

A human subject is treated with a dsRNA targeted to a TTR gene to inhibit expression of the TTR gene to treat a condition.

A subject in need of treatment is selected or identified. The subject can have a liver disorder, transthyretin amyloidosis, and/or a transplanted liver.

The identification of the subject can occur in a clinical setting, or elsewhere, e.g., in the subject's home through the subject's own use of a self-testing kit.

At time zero, a suitable first dose of an anti-TTR siRNA is administered to the subject. The dsRNA is formulated as described herein. After a period of time following the first dose, e.g., 7 days, 14 days, and 21 days, the subject's condition is evaluated, e.g., by measuring liver function. This measurement can be accompanied by a measurement of TTR expression in said subject, and/or the products of the successful siRNA-targeting of TTR mRNA. Other relevant criteria can also be measured. The number and strength of doses are adjusted according to the subject's needs.

After treatment, the subject's tumor growth rate is lowered relative to the rate existing prior to the treatment, or relative to the rate measured in a similarly afflicted but untreated subject.

The invention claimed is:

1. A pharmaceutical composition comprising a double-stranded ribonucleic acid (dsRNA) for inhibiting expression of transthyretin (TTR), wherein the dsRNA comprises a sense strand and an antisense strand, wherein the antisense strand is 19, 20, 21, 22, 23, or 24 nucleotides in length and comprises AUGGAAUACUCUUGGUUACNN (SEQ ID NO:450) and the sense strand of the dsRNA is 19, 20, 21, 22, 23, or 24 nucleotides in length and comprises a region complementary to the antisense strand, wherein the dsRNA comprises at least one chemically modified nucleotide and administration of 10 nM of the dsRNA to a HepG2 cell results in at least 80% inhibition of TTR mRNA expression as measured by a real time PCR assay.

2. A pharmaceutical composition comprising a double-stranded ribonucleic acid (dsRNA) for inhibiting expression of transthyretin (TTR), wherein the dsRNA comprises a sense strand and an antisense strand, wherein the antisense strand is 19, 20, 21, 22, 23, or 24 nucleotides in length and comprises AUGGAAUACUCUUGGUUACNN (SEQ ID NO:450) and the sense strand of the dsRNA is 19, 20, 21, 22, 23, or 24 nucleotides in length, and comprises a region complementary to the antisense strand, wherein the dsRNA comprises at least one chemically modified nucleotide and wherein the pharmaceutical composition has an ED50 in humans of less than 0.03 mg dsRNA/kg.

3. A pharmaceutical composition comprising a double-stranded ribonucleic acid (dsRNA) for inhibiting expression of transthyretin (TTR), wherein the dsRNA comprises a sense strand and an antisense strand, wherein the antisense strand comprises AUGGAAUACUCUUGGUUACNN (SEQ ID NO:450) and the sense strand of the dsRNA is 19, 20, 21, 22, 23, or 24 nucleotides in length, and comprises a region complementary to the antisense strand, wherein the dsRNA comprises at least one chemically modified nucleotide and wherein the pharmaceutical composition reduces human serum TTR protein by at least 50%, as compared prior to treatment, at a dose of less than 0.03 mg dsRNA/kg.

4. A pharmaceutical composition comprising a double-stranded ribonucleic acid (dsRNA) for inhibiting expression of transthyretin (TTR), wherein the dsRNA comprises a sense strand and an antisense strand, wherein the antisense strand comprises AUGGAAUACUCUUGGUUACNN (SEQ ID NO:450) and the sense strand of the dsRNA is 19, 20, 21, 22, 23, or 24 nucleotides in length, wherein the dsRNA comprises at least one chemically modified nucleotide and wherein the pharmaceutical composition reduces human serum TTR protein by at least 70%, as compared to prior to treatment, at a dose of 0.3 mg dsRNA/kg.

5. The pharmaceutical composition of claim 1, wherein the at least one chemically modified nucleotide is selected from the group of a 2'-O-methyl modified nucleotide, a nucleotide comprising a 5'-phosphorothioate group.

6. The pharmaceutical composition of claim 1, wherein the nucleotide sequence of the sense strand comprises GUAACCAAGAGUAUUCCAUNN (SEQ ID NO:449).

7. The pharmaceutical composition of claim 1, wherein the nucleotide sequence of the antisense strand comprises AUGGAAUACUCUUGGUUACdTdT (SEQ ID NO:730).

8. The pharmaceutical composition of claim 1, wherein the nucleotide sequence of the sense strand comprises GUAACCAAGAGUAUUCCAUdTdT (SEQ ID NO: 729).

9. The pharmaceutical composition of claim 7, wherein the nucleotide sequence of the sense strand comprises GUAACCAAGAGUAUUCCAUdTdT (SEQ ID NO: 729).

10. The pharmaceutical composition of claim 1, wherein the antisense strand consists of AUGGAAuACUCUUG-GUuACdTdT (SEQ ID NO:1010), wherein A is adenosine, C is cytidine, G is guanosine, U is uridine, a is 2'-O-methyladenosine, c is 2'-O-methylcytidine, g is 2'-O-methylguanosine, u is 2'-O-methyluridine and dT is 2'-deoxythymidine.

11. The pharmaceutical composition of claim 1, wherein the sense strand consists of GuAAccAAGAGuAuuc-cAudTdT (SEQ ID NO: 1009), wherein A is adenosine, C is cytidine, G is guanosine, U is uridine, a is 2'-O-methyladenosine, c is 2'-O-methylcytidine, g is 2'-O-methylguanosine, u is 2'-O-methyluridine and dT is 2'-deoxythymidine.

12. The pharmaceutical composition of claim 1, wherein the sense strand is 21 nucleotides in length.

13. The pharmaceutical composition of claim 2, wherein the sense strand is 21 nucleotides in length.

14. The pharmaceutical composition of claim 3, wherein the sense strand is 21 nucleotides in length.

15. The pharmaceutical composition of claim 4, wherein the sense strand is 21 nucleotides in length.

16. The pharmaceutical composition of claim 1, wherein the antisense strand comprises 4 modified ribonucleotides.

17. The pharmaceutical composition of claim 1, wherein the sense strand comprises 11 modified ribonucleotides.

18. The pharmaceutical composition of claim 1, wherein administration of the dsRNA to a cell results in at least 90% inhibition of TTR mRNA expression as measured by a real time PCR assay, wherein the cell is a HepG2 cell, and wherein the concentration of the dsRNA is 10 nM.

19. The pharmaceutical composition of claim 1, wherein the dsRNA is formulated in a lipid formulation.

20. The pharmaceutical composition of claim 19 wherein the dsRNA is formulated in a LNP formulation.

21. The pharmaceutical composition of claim 20, wherein the dsRNA is formulated in a LNP11 formulation comprising MC3/DSPC/Chol/PEG$_{2000}$-C14 in a ratio of about 50/10/38.5/1.5 mol %.

22. The pharmaceutical composition of claim 21, wherein the dsRNA is formulated in a LNP11 formulation comprising MC3/DSPC/Chol/PEG$_{2000}$-C14 in a ratio of about 50/10/38.5/1.5 mol % and a lipid:siRNA ratio of about 11:1.

23. A method of inhibiting TTR expression in a mammalian cell, the method comprising: (a) contacting the cell with the pharmaceutical composition of claim 1 and (b) maintaining the cell produced in step (a) for a time sufficient to obtain degradation of the mRNA transcript of a TTR gene, thereby inhibiting expression of the TTR gene in the cell.

24. A method of treating a transthyretin amyloidosis comprising administering to a human subject with transthyretin amyloidosis the pharmaceutical composition of claim 1.

25. The method of claim 24, wherein the dsRNA is administered at not more than a 2 week interval or not more than a 3 week interval or not more than a 4 week interval.

26. The method of claim 24, wherein the dsRNA is administered every 3 to 4 weeks.

27. The method of claim 24, wherein the dsRNA is administered at a dose of 0.3 mg/kg.

28. The method of claim 24, wherein the subject suffers from at least one symptom of TTR amyloidosis selected from the group consisting of polyneuropathy, cardiomyopathy, gastrointestinal dysfunction and weight loss.

29. The method of claim 24, wherein the method reduces serum TTR protein by at least 70% as compared to prior to treatment or reduces serum TTR protein by at least 80% as compared to prior to treatment.

30. A method of treating a subject with hereditary transthyretin mediated amyloidosis comprising administering via intravenous infusion to a human in need of such treatment 0.3 mg dsRNA/kg every three weeks, wherein the dsRNA comprises a sense strand and an antisense strand, the sense strand consisting of the nucleotide sequence GuAAccAAGAGuAuuccAudTdT (SEQ ID NO: 1009) and the antisense strand consisting of the nucleotide sequence AUGGAAuACUCUUGGUuACdTdT (SEQ ID NO: 1010), wherein A is adenosine, C is cytidine, G is guanosine, U is uridine, a is 2'-O-methyladenosine, c is 2'-O-methylcytidine, g is 2'-O-methylguanosine, u is 2'-O-methyluridine and dT is 2'-deoxythymidine, and wherein the dsRNA is in a lipid nanoparticle formulation comprising MC3/DSPC/cholesterol/PEG-DMG at a ratio of about 50/10/38.5/1.5 mol %.

31. A pharmaceutical composition comprising a double-stranded ribonucleic acid (dsRNA) for inhibiting the expression of transthyretin (TTR), wherein the dsRNA comprises a sense strand and an antisense strand, wherein the antisense strand consists of the nucleotide sequence AUGGAAuACUCUUGGUuACdTdT (SEQ ID NO:1010), wherein A is adenosine, C is cytidine, G is guanosine, U is uridine, a is 2'-O-methyladenosine, c is 2'-O-methylcytidine, g is 2'-O-methylguanosine, u is 2'-O-methyluridine and dT is 2'-deoxythymidine, and the sense strand consists of GuAAcAAGAGuAuuccAudTdT (SEQ ID NO: 1009), wherein A is adenosine, C is cytidine, G is guanosine, U is uridine, a is 2'-O-methyladenosine, c is 2'-O-methylcytidine, g is 2'-O-methylguanosine, u is 2'-O-methyluridine and dT is 2'-deoxythymidine.

32. The pharmaceutical composition of claim 31, wherein at least one nucleotide comprises a 5'-phosphorothioate group.

33. The pharmaceutical composition of claim 31, wherein administration of the dsRNA to a cell results in at least 90% inhibition of TTR mRNA expression as measured by a real time PCR assay, wherein the cell is a HepG2 cell, and wherein the concentration of the dsRNA is 10 nM.

34. The pharmaceutical composition of claim 32, wherein administration of the dsRNA to a cell results in at least 90% inhibition of TTR mRNA expression as measured by a real time PCR assay, wherein the cell is a HepG2 cell, and wherein the concentration of the dsRNA is 10 nM.

35. The pharmaceutical composition of claim 31, wherein the dsRNA is formulated in a lipid formulation.

36. The pharmaceutical composition of claim 32, wherein the dsRNA is formulated in a lipid formulation.

37. The pharmaceutical composition of claim 33, wherein the dsRNA is formulated in a lipid formulation.

38. The pharmaceutical composition of claim 34, wherein the dsRNA is formulated in a lipid formulation.

39. The pharmaceutical composition of claim 35, wherein the dsRNA is formulated in a LNP formulation.

40. The pharmaceutical composition of claim 36, wherein the dsRNA is formulated in a LNP formulation.

41. The pharmaceutical composition of claim 37, wherein the dsRNA is formulated in a LNP formulation.

42. The pharmaceutical composition of claim 38, wherein the dsRNA is formulated in a LNP formulation.

43. The pharmaceutical composition of claim 39, wherein the dsRNA is formulated in a LNP11 formulation comprising MC3/DSPC/Chol/PEG$_{2000}$-C14 in a ratio of about 50/10/38.5/1.5 mol %.

44. The pharmaceutical composition of claim 40, wherein the dsRNA is formulated in a LNP11 formulation comprising MC3/DSPC/Chol/PEG$_{2000}$-C14 in a ratio of about 50/10/38.5/1.5 mol %.

45. The pharmaceutical composition of claim 41, wherein the dsRNA is formulated in a LNP11 formulation comprising MC3/DSPC/Chol/PEG$_{2000}$-C14 in a ratio of about 50/10/38.5/1.5 mol %.

46. The pharmaceutical composition of claim 42, wherein the dsRNA is formulated in a LNP11 formulation comprising MC3/DSPC/Chol/PEG$_{2000}$-C14 in a ratio of about 50/10/38.5/1.5 mol %.

47. A method of inhibiting TTR expression in a mammalian cell, the method comprising: (a) contacting the cell with the pharmaceutical composition of claim 31 and (b) maintaining the cell produced in step (a) for a time sufficient to obtain degradation of the mRNA transcript of a TTR gene, thereby inhibiting expression of the TTR gene in the cell.

48. A method of treating a transthyretin amyloidosis comprising administering to a human subject with transthyretin amyloidosis the pharmaceutical composition of claim 31.

49. The method of claim 48, wherein the dsRNA is administered at not more than a 2 week interval or not more than a 3 week interval or not more than a 4 week interval.

50. The method of claim 48, wherein the dsRNA is administered every 3 to 4 weeks.

51. The method of claim 48, wherein the dsRNA is administered at a dose of 0.3 mg/kg.

52. The method of claim 48, wherein the subject suffers from at least one symptom of TTR amyloidosis selected from the group consisting of polyneuropathy, cardiomyopathy, gastrointestinal dysfunction and weight loss.

53. The method of claim 48, wherein the method reduces serum TTR protein by at least 70% as compared to prior to treatment or by at least 80% as compared to prior to treatment.

\* \* \* \* \*